US010267809B2

(12) United States Patent
Karsdal et al.

(10) Patent No.: US 10,267,809 B2
(45) Date of Patent: Apr. 23, 2019

(54) BIOCHEMICAL MARKERS FOR CVD RISK ASSESSMENT

(71) Applicants: Morten Karsdal, Copenhagen (DK); Natasha Barascuk Michaelsen, Gentofte (DK); Per Qvist, Copenhagen (DK)

(72) Inventors: Morten Karsdal, Copenhagen (DK); Natasha Barascuk Michaelsen, Gentofte (DK); Per Qvist, Copenhagen (DK)

(73) Assignee: Nordic Bioscience A/S, Herlev (DK)

( * ) Notice: Subject to any disclaimer, the term of this patent is extended or adjusted under 35 U.S.C. 154(b) by 0 days.

(21) Appl. No.: 15/173,852

(22) Filed: Jun. 6, 2016

(65) Prior Publication Data

US 2016/0282362 A1    Sep. 29, 2016

Related U.S. Application Data

(63) Continuation of application No. 12/740,648, filed as application No. PCT/EP2008/064946 on Nov. 4, 2008, now Pat. No. 9,359,633.

(30) Foreign Application Priority Data

Nov. 5, 2007   (GB) .................................. 0721713.6
Nov. 20, 2007  (GB) .................................. 0722748.1
Feb. 15, 2008  (GB) .................................. 0802814.4

(51) Int. Cl.
| | |
|---|---|
| *G01N 31/00* | (2006.01) |
| *G01N 33/53* | (2006.01) |
| *G01N 33/68* | (2006.01) |
| *C07K 14/775* | (2006.01) |
| *C12Q 1/37* | (2006.01) |
| *G01N 33/542* | (2006.01) |
| *C07K 14/77* | (2006.01) |
| *C07K 14/78* | (2006.01) |
| *G01N 33/577* | (2006.01) |

(52) U.S. Cl.
CPC ......... *G01N 33/6878* (2013.01); *C07K 14/77* (2013.01); *C07K 14/775* (2013.01); *C07K 14/78* (2013.01); *C12Q 1/37* (2013.01); *G01N 33/542* (2013.01); *G01N 33/577* (2013.01); *G01N 33/6893* (2013.01); *G01N 2800/32* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 9,206,464 | B2 * | 12/2015 | Veidal | C12Q 1/37 |
| 9,359,633 | B2 * | 6/2016 | Karsdal | C07K 14/775 |
| 9,404,932 | B2 * | 8/2016 | Veidal | C07K 14/78 |
| 9,459,260 | B2 * | 10/2016 | Leeming | G01N 33/564 |
| 9,500,659 | B2 * | 11/2016 | Leeming | C07K 16/18 |
| 9,606,130 | B2 * | 3/2017 | Veidal | C12Q 1/37 |
| 9,733,260 | B2 * | 8/2017 | Michaelsen | C12Q 1/37 |
| 9,880,177 | B2 * | 1/2018 | Veidal | C12Q 1/37 |
| 9,891,234 | B2 * | 2/2018 | Michaelsen | G01N 33/6893 |

OTHER PUBLICATIONS

Veidal et al., (Disease Markeres; 28, pp. 15-28, 2010).*
Tascilar et al. (Annals of Oncology 10,Suppl. 4:S107-S110, 1999).*
Tockman et al. (Cancer Research 52:2711s-2718s, 1992).*

* cited by examiner

*Primary Examiner* — Lisa V Cook
(74) *Attorney, Agent, or Firm* — Benjamin Aaron Adler

(57) ABSTRACT

Provided is a method of bioassay for the quantification of N- or C-terminal neo-epitope biomarkers formed by cleavage of a CRP, ApoE, lumican, versican, perlecan, decorin, biglycan or elastin by a proteinase. The method includes contacting a biofluid sample with an antibody reactive with the neo-epitope biomarker and determining the level of binding of the antibody to the biomarker in the sample. The assay is predictive of risk of cardiovascular disease events.

8 Claims, 6 Drawing Sheets

Specification includes a Sequence Listing.

```
                          SEQUENCE LISTING

<160> NUMBER OF SEQ ID NOS: 844

<210> SEQ ID NO 1
<211> LENGTH: 3396
<212> TYPE: PRT
<213> ORGANISM: Homo sapiens

<400> SEQUENCE: 1

Met Phe Ile Asn Ile Lys Ser Ile Leu Trp Met Cys Ser Thr Leu Ile
1               5                   10                  15

Val Thr His Ala Leu His Lys Val Lys Val Gly Lys Ser Pro Pro Val
            20                  25                  30

Arg Gly Ser Leu Ser Gly Lys Val Ser Leu Pro Cys His Phe Ser Thr
        35                  40                  45

Met Pro Thr Leu Pro Pro Ser Tyr Asn Thr Ser Glu Phe Leu Arg Ile
    50                  55                  60

Lys Trp Ser Lys Ile Glu Val Asp Lys Asn Gly Lys Asp Leu Lys Glu
65                  70                  75                  80

Thr Thr Val Leu Val Ala Gln Asn Gly Asn Ile Lys Ile Gly Gln Asp
                85                  90                  95

Tyr Lys Gly Arg Val Ser Val Pro Thr His Pro Glu Ala Val Gly Asp
            100                 105                 110

Ala Ser Leu Thr Val Val Lys Leu Leu Ala Ser Asp Ala Gly Leu Tyr
        115                 120                 125

Arg Cys Asp Val Met Tyr Gly Ile Glu Asp Thr Gln Asp Thr Val Ser
    130                 135                 140

Leu Thr Val Asp Gly Val Val Phe His Tyr Arg Ala Ala Thr Ser Arg
145                 150                 155                 160

Tyr Thr Leu Asn Phe Glu Ala Ala Gln Lys Ala Cys Leu Asp Val Gly
                165                 170                 175

Ala Val Ile Ala Thr Pro Glu Gln Leu Phe Ala Ala Tyr Glu Asp Gly
            180                 185                 190

Phe Glu Gln Cys Asp Ala Gly Trp Leu Ala Asp Gln Thr Val Arg Tyr
        195                 200                 205

Pro Ile Arg Ala Pro Arg Val Gly Cys Tyr Gly Asp Lys Met Gly Lys
    210                 215                 220

Ala Gly Val Arg Thr Tyr Gly Phe Arg Ser Pro Gln Glu Thr Tyr Asp
225                 230                 235                 240

Val Tyr Cys Tyr Val Asp His Leu Asp Gly Asp Val Phe His Leu Thr
                245                 250                 255

Val Pro Ser Lys Phe Thr Phe Glu Glu Ala Ala Lys Glu Cys Glu Asn
            260                 265                 270

Gln Asp Ala Arg Leu Ala Thr Val Gly Glu Leu Gln Ala Ala Trp Arg
        275                 280                 285

Asn Gly Phe Asp Gln Cys Asp Tyr Gly Trp Leu Ser Asp Ala Ser Val
    290                 295                 300

Arg His Pro Val Thr Val Ala Arg Ala Gln Cys Gly Gly Gly Leu Leu
305                 310                 315                 320

Gly Val Arg Thr Leu Tyr Arg Phe Glu Asn Gln Thr Gly Phe Pro Pro
```

```
                    325                 330                 335
Pro Asp Ser Arg Phe Asp Ala Tyr Cys Phe Lys Pro Lys Glu Ala Thr
                340                 345                 350
Thr Ile Asp Leu Ser Ile Leu Ala Glu Thr Ala Ser Pro Ser Leu Ser
                355                 360                 365
Lys Glu Pro Gln Met Val Ser Asp Arg Thr Thr Pro Ile Ile Pro Leu
            370                 375                 380
Val Asp Glu Leu Pro Val Ile Pro Thr Glu Phe Pro Pro Val Gly Asn
385                 390                 395                 400
Ile Val Ser Phe Glu Gln Lys Ala Thr Val Gln Pro Gln Ala Ile Thr
                405                 410                 415
Asp Ser Leu Ala Thr Lys Leu Pro Thr Pro Thr Gly Ser Thr Lys Lys
            420                 425                 430
Pro Trp Asp Met Asp Asp Tyr Ser Pro Ser Ala Ser Gly Pro Leu Gly
        435                 440                 445
Lys Leu Asp Ile Ser Glu Ile Lys Glu Glu Val Leu Gln Ser Thr Thr
        450                 455                 460
Gly Val Ser His Tyr Ala Thr Asp Ser Trp Asp Gly Val Val Glu Asp
465                 470                 475                 480
Lys Gln Thr Gln Glu Ser Val Thr Gln Ile Glu Gln Ile Glu Val Gly
                485                 490                 495
Pro Leu Val Thr Ser Met Glu Ile Leu Lys His Ile Pro Ser Lys Glu
                500                 505                 510
Phe Pro Val Thr Glu Thr Pro Leu Val Thr Ala Arg Met Ile Leu Glu
            515                 520                 525
Ser Lys Thr Glu Lys Lys Met Val Ser Thr Val Ser Glu Leu Val Thr
            530                 535                 540
Thr Gly His Tyr Gly Phe Thr Leu Gly Glu Glu Asp Asp Glu Asp Arg
545                 550                 555                 560
Thr Leu Thr Val Gly Ser Asp Glu Ser Thr Leu Ile Phe Asp Gln Ile
                565                 570                 575
Pro Glu Val Ile Thr Val Ser Lys Thr Ser Glu Asp Thr Ile His Thr
            580                 585                 590
His Leu Glu Asp Leu Glu Ser Val Ser Ala Ser Thr Thr Val Ser Pro
        595                 600                 605
Leu Ile Met Pro Asp Asn Asn Gly Ser Ser Met Asp Asp Trp Glu Glu
        610                 615                 620
Arg Gln Thr Ser Gly Arg Ile Thr Glu Glu Phe Leu Gly Lys Tyr Leu
625                 630                 635                 640
Ser Thr Thr Pro Phe Pro Ser Gln His Arg Thr Glu Ile Glu Leu Phe
                645                 650                 655
Pro Tyr Ser Gly Asp Lys Ile Leu Val Glu Gly Ile Ser Thr Val Ile
            660                 665                 670
Tyr Pro Ser Leu Gln Thr Glu Met Thr His Arg Arg Glu Arg Thr Glu
        675                 680                 685
Thr Leu Ile Pro Glu Met Arg Thr Asp Thr Tyr Thr Asp Glu Ile Gln
        690                 695                 700
Glu Glu Ile Thr Lys Ser Pro Phe Met Gly Lys Thr Glu Glu Val
705                 710                 715                 720
Phe Ser Gly Met Lys Leu Ser Thr Ser Leu Ser Glu Pro Ile His Val
                725                 730                 735
Thr Glu Ser Ser Val Glu Met Thr Lys Ser Phe Asp Phe Pro Thr Leu
            740                 745                 750
```

```
Ile Thr Lys Leu Ser Ala Glu Pro Thr Glu Val Arg Asp Met Glu Glu
            755                 760                 765
Asp Phe Thr Ala Thr Pro Gly Thr Thr Lys Tyr Asp Glu Asn Ile Thr
    770                 775                 780
Thr Val Leu Leu Ala His Gly Thr Leu Ser Val Glu Ala Ala Thr Val
785                 790                 795                 800
Ser Lys Trp Ser Trp Asp Glu Asp Asn Thr Thr Ser Lys Pro Leu Glu
                805                 810                 815
Ser Thr Glu Pro Ser Ala Ser Ser Lys Leu Pro Pro Ala Leu Leu Thr
                820                 825                 830
Thr Val Gly Met Asn Gly Lys Asp Lys Asp Ile Pro Ser Phe Thr Glu
                835                 840                 845
Asp Gly Ala Asp Glu Phe Thr Leu Ile Pro Asp Ser Thr Gln Lys Gln
    850                 855                 860
Leu Glu Glu Val Thr Asp Glu Asp Ile Ala Ala His Gly Lys Phe Thr
865                 870                 875                 880
Ile Arg Phe Gln Pro Thr Thr Ser Thr Gly Ile Ala Glu Lys Ser Thr
                885                 890                 895
Leu Arg Asp Ser Thr Thr Glu Glu Lys Val Pro Pro Ile Thr Ser Thr
                900                 905                 910
Glu Gly Gln Val Tyr Ala Thr Met Glu Gly Ser Ala Leu Gly Glu Val
            915                 920                 925
Glu Asp Val Asp Leu Ser Lys Pro Val Ser Thr Val Pro Gln Phe Ala
    930                 935                 940
His Thr Ser Glu Val Glu Gly Leu Ala Phe Val Ser Tyr Ser Ser Thr
945                 950                 955                 960
Gln Glu Pro Thr Thr Tyr Val Asp Ser Ser His Thr Ile Pro Leu Ser
                965                 970                 975
Val Ile Pro Lys Thr Asp Trp Gly Val Leu Val Pro Ser Val Pro Ser
                980                 985                 990
Glu Asp Glu Val Leu Gly Glu Pro Ser Gln Asp Ile Leu Val Ile Asp
    995                 1000                1005
Gln Thr Arg Leu Glu Ala Thr Ile Ser Pro Glu Thr Met Arg Thr
    1010                1015                1020
Thr Lys Ile Thr Glu Gly Thr Gln Glu Glu Phe Pro Trp Lys
1025                1030                1035
Glu Gln Thr Ala Glu Lys Pro Val Pro Ala Leu Ser Ser Thr Ala
    1040                1045                1050
Trp Thr Pro Lys Glu Ala Val Thr Pro Leu Asp Glu Gln Glu Gly
1055                1060                1065
Asp Gly Ser Ala Tyr Thr Val Ser Glu Asp Glu Leu Leu Thr Gly
    1070                1075                1080
Ser Glu Arg Val Pro Val Leu Glu Thr Thr Pro Val Gly Lys Ile
1085                1090                1095
Asp His Ser Val Ser Tyr Pro Pro Gly Ala Val Thr Glu His Lys
1100                1105                1110
Val Lys Thr Asp Glu Val Val Thr Leu Thr Pro Arg Ile Gly Pro
1115                1120                1125
Lys Val Ser Leu Ser Pro Gly Pro Glu Gln Lys Tyr Glu Thr Glu
1130                1135                1140
Gly Ser Ser Thr Thr Gly Phe Thr Ser Ser Leu Ser Pro Phe Ser
1145                1150                1155
```

```
Thr His Ile Thr Gln Leu Met Glu Glu Thr Thr Thr Glu Lys Thr
1160                 1165                 1170

Ser Leu Glu Asp Ile Asp Leu Gly Ser Gly Leu Phe Glu Lys Pro
1175                 1180                 1185

Lys Ala Thr Glu Leu Ile Glu Phe Ser Thr Ile Lys Val Thr Val
1190                 1195                 1200

Pro Ser Asp Ile Thr Thr Ala Phe Ser Ser Val Asp Arg Leu His
1205                 1210                 1215

Thr Thr Ser Ala Phe Lys Pro Ser Ser Ala Ile Thr Lys Lys Pro
1220                 1225                 1230

Pro Leu Ile Asp Arg Glu Pro Gly Glu Glu Thr Thr Ser Asp Met
1235                 1240                 1245

Val Ile Ile Gly Glu Ser Thr Ser His Val Pro Pro Thr Thr Leu
1250                 1255                 1260

Glu Asp Ile Val Ala Lys Glu Thr Glu Thr Asp Ile Asp Arg Glu
1265                 1270                 1275

Tyr Phe Thr Thr Ser Ser Pro Pro Ala Thr Gln Pro Thr Arg Pro
1280                 1285                 1290

Pro Thr Val Glu Asp Lys Glu Ala Phe Gly Pro Gln Ala Leu Ser
1295                 1300                 1305

Thr Pro Gln Pro Pro Ala Ser Thr Lys Phe His Pro Asp Ile Asn
1310                 1315                 1320

Val Tyr Ile Ile Glu Val Arg Glu Asn Lys Thr Gly Arg Met Ser
1325                 1330                 1335

Asp Leu Ser Val Ile Gly His Pro Ile Asp Ser Glu Ser Lys Glu
1340                 1345                 1350

Asp Glu Pro Cys Ser Glu Glu Thr Asp Pro Val His Asp Leu Met
1355                 1360                 1365

Ala Glu Ile Leu Pro Glu Phe Pro Asp Ile Ile Glu Ile Asp Leu
1370                 1375                 1380

Tyr His Ser Glu Glu Asn Glu Glu Glu Glu Glu Cys Ala Asn
1385                 1390                 1395

Ala Thr Asp Val Thr Thr Thr Pro Ser Val Gln Tyr Ile Asn Gly
1400                 1405                 1410

Lys His Leu Val Thr Thr Val Pro Lys Asp Pro Glu Ala Ala Glu
1415                 1420                 1425

Ala Arg Arg Gly Gln Phe Glu Ser Val Ala Pro Ser Gln Asn Phe
1430                 1435                 1440

Ser Asp Ser Ser Glu Ser Asp Thr His Pro Phe Val Ile Ala Lys
1445                 1450                 1455

Thr Glu Leu Ser Thr Ala Val Gln Pro Asn Glu Ser Thr Glu Thr
1460                 1465                 1470

Thr Glu Ser Leu Glu Val Thr Trp Lys Pro Glu Thr Tyr Pro Glu
1475                 1480                 1485

Thr Ser Glu His Phe Ser Gly Gly Glu Pro Asp Val Phe Pro Thr
1490                 1495                 1500

Val Pro Phe His Glu Glu Phe Glu Ser Gly Thr Ala Lys Lys Gly
1505                 1510                 1515

Ala Glu Ser Val Thr Glu Arg Asp Thr Glu Val Gly His Gln Ala
1520                 1525                 1530

His Glu His Thr Glu Pro Val Ser Leu Phe Pro Glu Glu Ser Ser
1535                 1540                 1545

Gly Glu Ile Ala Ile Asp Gln Glu Ser Gln Lys Ile Ala Phe Ala
```

```
            1550                1555                1560

Arg Ala Thr Glu Val Thr Phe Gly Glu Val Glu Lys Ser Thr
1565                1570                1575

Ser Val Thr Tyr Thr Pro Thr Ile Val Pro Ser Ser Ala Ser Ala
1580                1585                1590

Tyr Val Ser Glu Glu Glu Ala Val Thr Leu Ile Gly Asn Pro Trp
1595                1600                1605

Pro Asp Asp Leu Leu Ser Thr Lys Glu Ser Trp Val Glu Ala Thr
1610                1615                1620

Pro Arg Gln Val Val Glu Leu Ser Gly Ser Ser Ser Ile Pro Ile
1625                1630                1635

Thr Glu Gly Ser Gly Glu Ala Glu Glu Asp Glu Asp Thr Met Phe
1640                1645                1650

Thr Met Val Thr Asp Leu Ser Gln Arg Asn Thr Thr Asp Thr Leu
1655                1660                1665

Ile Thr Leu Asp Thr Ser Arg Ile Ile Thr Glu Ser Phe Phe Glu
1670                1675                1680

Val Pro Ala Thr Thr Ile Tyr Pro Val Ser Glu Gln Pro Ser Ala
1685                1690                1695

Lys Val Val Pro Thr Lys Phe Val Ser Glu Thr Asp Thr Ser Glu
1700                1705                1710

Trp Ile Ser Ser Thr Thr Val Glu Glu Lys Lys Arg Lys Glu Glu
1715                1720                1725

Glu Gly Thr Thr Gly Thr Ala Ser Thr Phe Glu Val Tyr Ser Ser
1730                1735                1740

Thr Gln Arg Ser Asp Gln Leu Ile Leu Pro Phe Glu Leu Glu Ser
1745                1750                1755

Pro Asn Val Ala Thr Ser Ser Asp Ser Gly Thr Arg Lys Ser Phe
1760                1765                1770

Met Ser Leu Thr Thr Pro Thr Gln Ser Glu Arg Glu Met Thr Asp
1775                1780                1785

Ser Thr Pro Val Phe Thr Glu Thr Asn Thr Leu Glu Asn Leu Gly
1790                1795                1800

Ala Gln Thr Thr Glu His Ser Ser Ile His Gln Pro Gly Val Gln
1805                1810                1815

Glu Gly Leu Thr Thr Leu Pro Arg Ser Pro Ala Ser Val Phe Met
1820                1825                1830

Glu Gln Gly Ser Gly Glu Ala Ala Ala Asp Pro Glu Thr Thr Thr
1835                1840                1845

Val Ser Ser Phe Ser Leu Asn Val Glu Tyr Ala Ile Gln Ala Glu
1850                1855                1860

Lys Glu Val Ala Gly Thr Leu Ser Pro His Val Glu Thr Thr Phe
1865                1870                1875

Ser Thr Glu Pro Thr Gly Leu Val Leu Ser Thr Val Met Asp Arg
1880                1885                1890

Val Val Ala Glu Asn Ile Thr Gln Thr Ser Arg Glu Ile Val Ile
1895                1900                1905

Ser Glu Arg Leu Gly Glu Pro Asn Tyr Gly Ala Glu Ile Arg Gly
1910                1915                1920

Phe Ser Thr Gly Phe Pro Leu Glu Glu Asp Phe Ser Gly Asp Phe
1925                1930                1935

Arg Glu Tyr Ser Thr Val Ser His Pro Ile Ala Lys Glu Glu Thr
1940                1945                1950
```

```
Val Met Met Glu Gly Ser Gly Asp Ala Ala Phe Arg Asp Thr Gln
1955                1960                1965
Thr Ser Pro Ser Thr Val Pro Thr Ser Val His Ile Ser His Ile
1970                1975                1980
Ser Asp Ser Glu Gly Pro Ser Ser Thr Met Val Ser Thr Ser Ala
1985                1990                1995
Phe Pro Trp Glu Glu Phe Thr Ser Ser Ala Glu Gly Ser Gly Glu
2000                2005                2010
Gln Leu Val Thr Val Ser Ser Ser Val Val Pro Val Leu Pro Ser
2015                2020                2025
Ala Val Gln Lys Phe Ser Gly Thr Ala Ser Ser Ile Ile Asp Glu
2030                2035                2040
Gly Leu Gly Glu Val Gly Thr Val Asn Glu Ile Asp Arg Arg Ser
2045                2050                2055
Thr Ile Leu Pro Thr Ala Glu Val Glu Gly Thr Lys Ala Pro Val
2060                2065                2070
Glu Lys Glu Glu Val Lys Val Ser Gly Thr Val Ser Thr Asn Phe
2075                2080                2085
Pro Gln Thr Ile Glu Pro Ala Lys Leu Trp Ser Arg Gln Glu Val
2090                2095                2100
Asn Pro Val Arg Gln Glu Ile Glu Ser Glu Thr Thr Ser Glu Glu
2105                2110                2115
Gln Ile Gln Glu Glu Lys Ser Phe Glu Ser Pro Gln Asn Ser Pro
2120                2125                2130
Ala Thr Glu Gln Thr Ile Phe Asp Ser Gln Thr Phe Thr Glu Thr
2135                2140                2145
Glu Leu Lys Thr Thr Asp Tyr Ser Val Leu Thr Thr Lys Lys Thr
2150                2155                2160
Tyr Ser Asp Asp Lys Glu Met Lys Glu Glu Asp Thr Ser Leu Val
2165                2170                2175
Asn Met Ser Thr Pro Asp Pro Asp Ala Asn Gly Leu Glu Ser Tyr
2180                2185                2190
Thr Thr Leu Pro Glu Ala Thr Glu Lys Ser His Phe Phe Leu Ala
2195                2200                2205
Thr Ala Leu Val Thr Glu Ser Ile Pro Ala Glu His Val Val Thr
2210                2215                2220
Asp Ser Pro Ile Lys Lys Glu Glu Ser Thr Lys His Phe Pro Lys
2225                2230                2235
Gly Met Arg Pro Thr Ile Gln Glu Ser Asp Thr Glu Leu Leu Phe
2240                2245                2250
Ser Gly Leu Gly Ser Gly Glu Glu Val Leu Pro Thr Leu Pro Thr
2255                2260                2265
Glu Ser Val Asn Phe Thr Glu Val Glu Gln Ile Asn Asn Thr Leu
2270                2275                2280
Tyr Pro His Thr Ser Gln Val Glu Ser Thr Ser Ser Asp Lys Ile
2285                2290                2295
Glu Asp Phe Asn Arg Met Glu Asn Val Ala Lys Glu Val Gly Pro
2300                2305                2310
Leu Val Ser Gln Thr Asp Ile Phe Glu Gly Ser Gly Ser Val Thr
2315                2320                2325
Ser Thr Thr Leu Ile Glu Ile Leu Ser Asp Thr Gly Ala Glu Gly
2330                2335                2340
```

```
Pro Thr Val Ala Pro Leu Pro Phe Ser Thr Asp Ile Gly His Pro
2345                2350                2355

Gln Asn Gln Thr Val Arg Trp Ala Glu Glu Ile Gln Thr Ser Arg
2360                2365                2370

Pro Gln Thr Ile Thr Glu Gln Asp Ser Asn Lys Asn Ser Ser Thr
2375                2380                2385

Ala Glu Ile Asn Glu Thr Thr Thr Ser Ser Thr Asp Phe Leu Ala
2390                2395                2400

Arg Ala Tyr Gly Phe Glu Met Ala Lys Glu Phe Val Thr Ser Ala
2405                2410                2415

Pro Lys Pro Ser Asp Leu Tyr Tyr Glu Pro Ser Gly Glu Gly Ser
2420                2425                2430

Gly Glu Val Asp Ile Val Asp Ser Phe His Thr Ser Ala Thr Thr
2435                2440                2445

Gln Ala Thr Arg Gln Glu Ser Ser Thr Thr Phe Val Ser Asp Gly
2450                2455                2460

Ser Leu Glu Lys His Pro Glu Val Pro Ser Ala Lys Ala Val Thr
2465                2470                2475

Ala Asp Gly Phe Pro Thr Val Ser Val Met Leu Pro Leu His Ser
2480                2485                2490

Glu Gln Asn Lys Ser Ser Pro Asp Pro Thr Ser Thr Leu Ser Asn
2495                2500                2505

Thr Val Ser Tyr Glu Arg Ser Thr Asp Gly Ser Phe Gln Asp Arg
2510                2515                2520

Phe Arg Glu Phe Glu Asp Ser Thr Leu Lys Pro Asn Arg Lys Lys
2525                2530                2535

Pro Thr Glu Asn Ile Ile Ile Asp Leu Asp Lys Glu Asp Lys Asp
2540                2545                2550

Leu Ile Leu Thr Ile Thr Glu Ser Thr Ile Leu Glu Ile Leu Pro
2555                2560                2565

Glu Leu Thr Ser Asp Lys Asn Thr Ile Ile Asp Ile Asp His Thr
2570                2575                2580

Lys Pro Val Tyr Glu Asp Ile Leu Gly Met Gln Thr Asp Ile Asp
2585                2590                2595

Thr Glu Val Pro Ser Glu Pro His Asp Ser Asn Asp Glu Ser Asn
2600                2605                2610

Asp Asp Ser Thr Gln Val Gln Glu Ile Tyr Glu Ala Ala Val Asn
2615                2620                2625

Leu Ser Leu Thr Glu Glu Thr Phe Glu Gly Ser Ala Asp Val Leu
2630                2635                2640

Ala Ser Tyr Thr Gln Ala Thr His Asp Glu Ser Met Thr Tyr Glu
2645                2650                2655

Asp Arg Ser Gln Leu Asp His Met Gly Phe His Phe Thr Thr Gly
2660                2665                2670

Ile Pro Ala Pro Ser Thr Glu Thr Glu Leu Asp Val Leu Leu Pro
2675                2680                2685

Thr Ala Thr Ser Leu Pro Ile Pro Arg Lys Ser Ala Thr Val Ile
2690                2695                2700

Pro Glu Ile Glu Gly Ile Lys Ala Glu Ala Lys Ala Leu Asp Asp
2705                2710                2715

Met Phe Glu Ser Ser Thr Leu Ser Asp Gly Gln Ala Ile Ala Asp
2720                2725                2730

Gln Ser Glu Ile Ile Pro Thr Leu Gly Gln Phe Glu Arg Thr Gln
```

-continued

```
            2735                2740                 2745
Glu Glu Tyr Glu Asp Lys Lys His Ala Gly Pro Ser Phe Gln Pro
2750                2755                 2760

Glu Phe Ser Ser Gly Ala Glu Glu Ala Leu Val Asp His Thr Pro
2765                2770                 2775

Tyr Leu Ser Ile Ala Thr Thr His Leu Met Asp Gln Ser Val Thr
2780                2785                 2790

Glu Val Pro Asp Val Met Glu Gly Ser Asn Pro Pro Tyr Tyr Thr
2795                2800                 2805

Asp Thr Thr Leu Ala Val Ser Thr Phe Ala Lys Leu Ser Ser Gln
2810                2815                 2820

Thr Pro Ser Ser Pro Leu Thr Ile Tyr Ser Gly Ser Glu Ala Ser
2825                2830                 2835

Gly His Thr Glu Ile Pro Gln Pro Ser Ala Leu Pro Gly Ile Asp
2840                2845                 2850

Val Gly Ser Ser Val Met Ser Pro Gln Asp Ser Phe Lys Glu Ile
2855                2860                 2865

His Val Asn Ile Glu Ala Thr Phe Lys Pro Ser Ser Glu Glu Tyr
2870                2875                 2880

Leu His Ile Thr Glu Pro Pro Ser Leu Ser Pro Asp Thr Lys Leu
2885                2890                 2895

Glu Pro Ser Glu Asp Asp Gly Lys Pro Glu Leu Leu Glu Glu Met
2900                2905                 2910

Glu Ala Ser Pro Thr Glu Leu Ile Ala Val Glu Gly Thr Glu Ile
2915                2920                 2925

Leu Gln Asp Phe Gln Asn Lys Thr Asp Gly Gln Val Ser Gly Glu
2930                2935                 2940

Ala Ile Lys Met Phe Pro Thr Ile Lys Thr Pro Glu Ala Gly Thr
2945                2950                 2955

Val Ile Thr Thr Ala Asp Glu Ile Glu Leu Glu Gly Ala Thr Gln
2960                2965                 2970

Trp Pro His Ser Thr Ser Ala Ser Ala Thr Tyr Gly Val Glu Ala
2975                2980                 2985

Gly Val Val Pro Trp Leu Ser Pro Gln Thr Ser Glu Arg Pro Thr
2990                2995                 3000

Leu Ser Ser Ser Pro Glu Ile Asn Pro Glu Thr Gln Ala Ala Leu
3005                3010                 3015

Ile Arg Gly Gln Asp Ser Thr Ile Ala Ala Ser Glu Gln Gln Val
3020                3025                 3030

Ala Ala Arg Ile Leu Asp Ser Asn Asp Gln Ala Thr Val Asn Pro
3035                3040                 3045

Val Glu Phe Asn Thr Glu Val Ala Thr Pro Pro Phe Ser Leu Leu
3050                3055                 3060

Glu Thr Ser Asn Glu Thr Asp Phe Leu Ile Gly Ile Asn Glu Glu
3065                3070                 3075

Ser Val Glu Gly Thr Ala Ile Tyr Leu Pro Gly Pro Asp Arg Cys
3080                3085                 3090

Lys Met Asn Pro Cys Leu Asn Gly Gly Thr Cys Tyr Pro Thr Glu
3095                3100                 3105

Thr Ser Tyr Val Cys Thr Cys Val Pro Gly Tyr Ser Gly Asp Gln
3110                3115                 3120

Cys Glu Leu Asp Phe Asp Glu Cys His Ser Asn Pro Cys Arg Asn
3125                3130                 3135
```

-continued

Gly Ala Thr Cys Val Asp Gly Phe Asn Thr Phe Arg Cys Leu Cys
3140                3145                3150

Leu Pro Ser Tyr Val Gly Ala Leu Cys Glu Gln Asp Thr Glu Thr
3155                3160                3165

Cys Asp Tyr Gly Trp His Lys Phe Gln Gly Gln Cys Tyr Lys Tyr
3170                3175                3180

Phe Ala His Arg Arg Thr Trp Asp Ala Ala Glu Arg Glu Cys Arg
3185                3190                3195

Leu Gln Gly Ala His Leu Thr Ser Ile Leu Ser His Glu Glu Gln
3200                3205                3210

Met Phe Val Asn Arg Val Gly His Asp Tyr Gln Trp Ile Gly Leu
3215                3220                3225

Asn Asp Lys Met Phe Glu His Asp Phe Arg Trp Thr Asp Gly Ser
3230                3235                3240

Thr Leu Gln Tyr Glu Asn Trp Arg Pro Asn Gln Pro Asp Ser Phe
3245                3250                3255

Phe Ser Ala Gly Glu Asp Cys Val Val Ile Ile Trp His Glu Asn
3260                3265                3270

Gly Gln Trp Asn Asp Val Pro Cys Asn Tyr His Leu Thr Tyr Thr
3275                3280                3285

Cys Lys Lys Gly Thr Val Ala Cys Gly Gln Pro Pro Val Val Glu
3290                3295                3300

Asn Ala Lys Thr Phe Gly Lys Met Lys Pro Arg Tyr Glu Ile Asn
3305                3310                3315

Ser Leu Ile Arg Tyr His Cys Lys Asp Gly Phe Ile Gln Arg His
3320                3325                3330

Leu Pro Thr Ile Arg Cys Leu Gly Asn Gly Arg Trp Ala Ile Pro
3335                3340                3345

Lys Ile Thr Cys Met Asn Pro Ser Ala Tyr Gln Arg Thr Tyr Ser
3350                3355                3360

Met Lys Tyr Phe Lys Asn Ser Ser Ser Ala Lys Asp Asn Ser Ile
3365                3370                3375

Asn Thr Ser Lys His Asp His Arg Trp Ser Arg Arg Trp Gln Glu
3380                3385                3390

Ser Arg Arg
3395

<210> SEQ ID NO 2
<211> LENGTH: 338
<212> TYPE: PRT
<213> ORGANISM: Homo sapiens

<400> SEQUENCE: 2

Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
                20                  25                  30

Ser Ser Pro Asn Cys Ala Pro Glu Cys Asn Cys Pro Glu Ser Tyr Pro
            35                  40                  45

Ser Ala Met Tyr Cys Asp Glu Leu Lys Leu Lys Ser Val Pro Met Val
        50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile

```
                    85                  90                  95
Leu Asp His Asn Leu Leu Glu Asn Ser Lys Ile Lys Gly Arg Val Phe
                100                 105                 110

Ser Lys Leu Lys Gln Leu Lys Lys Leu His Ile Asn His Asn Asn Leu
            115                 120                 125

Thr Glu Ser Val Gly Pro Leu Pro Lys Ser Leu Glu Asp Leu Gln Leu
        130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
                180                 185                 190

Phe Asn Gln Ile Ala Arg Leu Pro Ser Gly Leu Pro Val Ser Leu Leu
                195                 200                 205

Thr Leu Tyr Leu Asp Asn Asn Lys Ile Ser Asn Ile Pro Asp Glu Tyr
        210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
                260                 265                 270

Asn Glu Asn Leu Glu Asn Tyr Tyr Leu Glu Val Asn Gln Leu Glu Lys
            275                 280                 285

Phe Asp Ile Lys Ser Phe Cys Lys Ile Leu Gly Pro Leu Ser Tyr Ser
290                 295                 300

Lys Ile Lys His Leu Arg Leu Asp Gly Asn Arg Ile Ser Glu Thr Ser
305                 310                 315                 320

Leu Pro Pro Asp Met Tyr Glu Cys Leu Arg Val Ala Asn Glu Val Thr
                325                 330                 335

Leu Asn

<210> SEQ ID NO 3
<211> LENGTH: 4391
<212> TYPE: PRT
<213> ORGANISM: Homo sapiens

<400> SEQUENCE: 3

Met Gly Trp Arg Ala Pro Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Asp Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
                100                 105                 110

Glu Ala Val Val Asp Thr Leu Glu Ser Glu Tyr Leu Lys Ile Pro Gly
```

```
              115                 120                 125
Asp Gln Val Val Ser Val Val Phe Ile Lys Glu Leu Asp Gly Trp Val
    130                 135                 140
Phe Val Glu Leu Asp Val Gly Ser Glu Gly Asn Ala Asp Gly Ala Gln
145                 150                 155                 160
Ile Gln Glu Met Leu Leu Arg Val Ile Ser Gly Ser Val Ala Ser
                165                 170                 175
Tyr Val Thr Ser Pro Gln Gly Phe Gln Phe Arg Arg Leu Gly Thr Val
            180                 185                 190
Pro Gln Phe Pro Arg Ala Cys Thr Glu Ala Glu Phe Ala Cys His Ser
        195                 200                 205
Tyr Asn Glu Cys Val Ala Leu Glu Tyr Arg Cys Asp Arg Pro Asp
    210                 215                 220
Cys Arg Asp Met Ser Asp Glu Leu Asn Cys Glu Pro Val Leu Gly
225                 230                 235                 240
Ile Ser Pro Thr Phe Ser Leu Leu Val Glu Thr Thr Ser Leu Pro Pro
                245                 250                 255
Arg Pro Glu Thr Thr Ile Met Arg Gln Pro Pro Val Thr His Ala Pro
            260                 265                 270
Gln Pro Leu Leu Pro Gly Ser Val Arg Pro Leu Pro Cys Gly Pro Gln
        275                 280                 285
Glu Ala Ala Cys Arg Asn Gly His Cys Ile Pro Arg Asp Tyr Leu Cys
    290                 295                 300
Asp Gly Gln Glu Asp Cys Glu Asp Gly Ser Asp Glu Leu Asp Cys Gly
305                 310                 315                 320
Pro Pro Pro Pro Cys Glu Pro Asn Glu Phe Pro Cys Gly Asn Gly His
                325                 330                 335
Cys Ala Leu Lys Leu Trp Arg Cys Asp Gly Asp Phe Asp Cys Glu Asp
            340                 345                 350
Arg Thr Asp Glu Ala Asn Cys Pro Thr Lys Arg Pro Glu Glu Val Cys
        355                 360                 365
Gly Pro Thr Gln Phe Arg Cys Val Ser Thr Asn Met Cys Ile Pro Ala
    370                 375                 380
Ser Phe His Cys Asp Glu Glu Ser Asp Cys Pro Asp Arg Ser Asp Glu
385                 390                 395                 400
Phe Gly Cys Met Pro Pro Gln Val Thr Pro Pro Arg Glu Ser Ile
                405                 410                 415
Gln Ala Ser Arg Gly Gln Thr Val Thr Phe Thr Cys Val Ala Ile Gly
            420                 425                 430
Val Pro Thr Pro Ile Ile Asn Trp Arg Leu Asn Trp Gly His Ile Pro
        435                 440                 445
Ser His Pro Arg Val Thr Val Thr Ser Glu Gly Gly Arg Gly Thr Leu
    450                 455                 460
Ile Ile Arg Asp Val Lys Glu Ser Asp Gln Gly Ala Tyr Thr Cys Glu
465                 470                 475                 480
Ala Met Asn Ala Arg Gly Met Val Phe Gly Ile Pro Asp Gly Val Leu
                485                 490                 495
Glu Leu Val Pro Gln Arg Gly Pro Cys Pro Asp Gly His Phe Tyr Leu
            500                 505                 510
Glu His Ser Ala Ala Cys Leu Pro Cys Phe Cys Phe Gly Ile Thr Ser
        515                 520                 525
Val Cys Gln Ser Thr Arg Arg Phe Arg Asp Gln Ile Arg Leu Arg Phe
    530                 535                 540
```

```
Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
    610                 615                 620

Gly Met Leu Glu Pro Val Gln Arg Pro Asp Val Val Leu Val Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750

Pro Gly Gly Pro Tyr Leu Gly Thr Cys Ser Gly Cys Ser Cys Asn Gly
        755                 760                 765

His Ala Ser Ser Cys Asp Pro Val Tyr Gly His Cys Leu Asn Cys Gln
    770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
        835                 840                 845

Arg Arg Cys Glu Ser Cys Ala Pro Gly Tyr Glu Gly Asn Pro Ile Gln
    850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
            900                 905                 910

Leu Ser Thr Arg Asn Pro Asp Gly Cys Leu Lys Cys Phe Cys Met Gly
        915                 920                 925

Val Ser Arg His Cys Thr Ser Ser Trp Ser Arg Ala Gln Leu His
    930                 935                 940

Gly Ala Ser Glu Glu Pro Gly His Phe Ser Leu Thr Asn Ala Ala Ser
945                 950                 955                 960
```

```
Thr His Thr Thr Asn Glu Gly Ile Phe Ser Pro Thr Pro Gly Glu Leu
            965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
            995                1000                1005

Leu Arg Phe Thr Val Thr Gln Arg Ser Gln Pro Gly Ser Thr Pro
        1010                1015                1020

Leu His Gly Gln Pro Leu Val Val Leu Gly Asn Asn Ile Ile
1025                1030                1035

Leu Glu His His Val Ala Gln Glu Pro Ser Pro Gly Gln Pro Ser
1040                1045                1050

Thr Phe Ile Val Pro Phe Arg Glu Gln Ala Trp Gln Arg Pro Asp
1055                1060                1065

Gly Gln Pro Ala Thr Arg Glu His Leu Leu Met Ala Leu Ala Gly
1070                1075                1080

Ile Asp Thr Leu Leu Ile Arg Ala Ser Tyr Ala Gln Gln Pro Ala
1085                1090                1095

Glu Ser Arg Val Ser Gly Ile Ser Met Asp Val Ala Val Pro Glu
1100                1105                1110

Glu Thr Gly Gln Asp Pro Ala Leu Glu Val Glu Gln Cys Ser Cys
1115                1120                1125

Pro Pro Gly Tyr Arg Gly Pro Ser Cys Gln Asp Cys Asp Thr Gly
1130                1135                1140

Tyr Thr Arg Thr Pro Ser Gly Leu Tyr Leu Gly Thr Cys Glu Arg
1145                1150                1155

Cys Ser Cys His Gly His Ser Glu Ala Cys Glu Pro Glu Thr Gly
1160                1165                1170

Ala Cys Gln Gly Cys Gln His His Thr Glu Gly Pro Arg Cys Glu
1175                1180                1185

Gln Cys Gln Pro Gly Tyr Tyr Gly Asp Ala Gln Arg Gly Thr Pro
1190                1195                1200

Gln Asp Cys Gln Leu Cys Pro Cys Tyr Gly Asp Pro Ala Ala Gly
1205                1210                1215

Gln Ala Ala His Thr Cys Phe Leu Asp Thr Asp Gly His Pro Thr
1220                1225                1230

Cys Asp Ala Cys Ser Pro Gly His Ser Gly Arg His Cys Glu Arg
1235                1240                1245

Cys Ala Pro Gly Tyr Tyr Gly Asn Pro Ser Gln Gly Gln Pro Cys
1250                1255                1260

Gln Arg Asp Ser Gln Val Pro Gly Pro Ile Gly Cys Asn Cys Asp
1265                1270                1275

Pro Gln Gly Ser Val Ser Ser Gln Cys Asp Ala Ala Gly Gln Cys
1280                1285                1290

Gln Cys Lys Ala Gln Val Glu Gly Leu Thr Cys Ser His Cys Arg
1295                1300                1305

Pro His His Phe His Leu Ser Ala Ser Asn Pro Asp Gly Cys Leu
1310                1315                1320

Pro Cys Phe Cys Met Gly Ile Thr Gln Gln Cys Ala Ser Ser Ala
1325                1330                1335

Tyr Thr Arg His Leu Ile Ser Thr His Phe Ala Pro Gly Asp Phe
1340                1345                1350

Gln Gly Phe Ala Leu Val Asn Pro Gln Arg Asn Ser Arg Leu Thr
```

-continued

```
            1355                1360                1365
Gly Glu Phe Thr Val Glu Pro Val Pro Glu Gly Ala Gln Leu Ser
1370                1375                1380
Phe Gly Asn Phe Ala Gln Leu Gly His Glu Ser Phe Tyr Trp Gln
1385                1390                1395
Leu Pro Glu Thr Tyr Gln Gly Asp Lys Val Ala Ala Tyr Gly Gly
1400                1405                1410
Lys Leu Arg Tyr Thr Leu Ser Tyr Thr Ala Gly Pro Gln Gly Ser
1415                1420                1425
Pro Leu Ser Asp Pro Asp Val Gln Ile Thr Gly Asn Asn Ile Met
1430                1435                1440
Leu Val Ala Ser Gln Pro Ala Leu Gln Gly Pro Glu Arg Arg Ser
1445                1450                1455
Tyr Glu Ile Met Phe Arg Glu Glu Phe Trp Arg Arg Pro Asp Gly
1460                1465                1470
Gln Pro Ala Thr Arg Glu His Leu Leu Met Ala Leu Ala Asp Leu
1475                1480                1485
Asp Glu Leu Leu Ile Arg Ala Thr Phe Ser Ser Val Pro Leu Val
1490                1495                1500
Ala Ser Ile Ser Ala Val Ser Leu Glu Val Ala Gln Pro Gly Pro
1505                1510                1515
Ser Asn Arg Pro Arg Ala Leu Glu Val Glu Glu Cys Arg Cys Pro
1520                1525                1530
Pro Gly Tyr Ile Gly Leu Ser Cys Gln Asp Cys Ala Pro Gly Tyr
1535                1540                1545
Thr Arg Thr Gly Ser Gly Leu Tyr Leu Gly His Cys Glu Leu Cys
1550                1555                1560
Glu Cys Asn Gly His Ser Asp Leu Cys His Pro Glu Thr Gly Ala
1565                1570                1575
Cys Ser Gln Cys Gln His Asn Ala Ala Gly Glu Phe Cys Glu Leu
1580                1585                1590
Cys Ala Pro Gly Tyr Tyr Gly Asp Ala Thr Ala Gly Thr Pro Glu
1595                1600                1605
Asp Cys Gln Pro Cys Ala Cys Pro Leu Thr Asn Pro Glu Asn Met
1610                1615                1620
Phe Ser Arg Thr Cys Glu Ser Leu Gly Ala Gly Gly Tyr Arg Cys
1625                1630                1635
Thr Ala Cys Glu Pro Gly Tyr Thr Gly Gln Tyr Cys Glu Gln Cys
1640                1645                1650
Gly Pro Gly Tyr Val Gly Asn Pro Ser Val Gln Gly Gly Gln Cys
1655                1660                1665
Leu Pro Glu Thr Asn Gln Ala Pro Leu Val Val Glu Val His Pro
1670                1675                1680
Ala Arg Ser Ile Val Pro Gln Gly Gly Ser His Ser Leu Arg Cys
1685                1690                1695
Gln Val Ser Gly Ser Pro Pro His Tyr Phe Tyr Trp Ser Arg Glu
1700                1705                1710
Asp Gly Arg Pro Val Pro Ser Gly Thr Gln Arg His Gln Gly
1715                1720                1725
Ser Glu Leu His Phe Pro Ser Val Gln Pro Ser Asp Ala Gly Val
1730                1735                1740
Tyr Ile Cys Thr Cys Arg Asn Leu His Gln Ser Asn Thr Ser Arg
1745                1750                1755
```

```
Ala Glu Leu Leu Val Thr Glu Ala Pro Ser Lys Pro Ile Thr Val
1760                1765                1770

Thr Val Glu Glu Gln Arg Ser Gln Ser Val Arg Pro Gly Ala Asp
1775                1780                1785

Val Thr Phe Ile Cys Thr Ala Lys Ser Lys Ser Pro Ala Tyr Thr
1790                1795                1800

Leu Val Trp Thr Arg Leu His Asn Gly Lys Leu Pro Thr Arg Ala
1805                1810                1815

Met Asp Phe Asn Gly Ile Leu Thr Ile Arg Asn Val Gln Leu Ser
1820                1825                1830

Asp Ala Gly Thr Tyr Val Cys Thr Gly Ser Asn Met Phe Ala Met
1835                1840                1845

Asp Gln Gly Thr Ala Thr Leu His Val Gln Ala Ser Gly Thr Leu
1850                1855                1860

Ser Ala Pro Val Val Ser Ile His Pro Pro Gln Leu Thr Val Gln
1865                1870                1875

Pro Gly Gln Leu Ala Glu Phe Arg Cys Ser Ala Thr Gly Ser Pro
1880                1885                1890

Thr Pro Thr Leu Glu Trp Thr Gly Gly Pro Gly Gly Gln Leu Pro
1895                1900                1905

Ala Lys Ala Gln Ile His Gly Gly Ile Leu Arg Leu Pro Ala Val
1910                1915                1920

Glu Pro Thr Asp Gln Ala Gln Tyr Leu Cys Arg Ala His Ser Ser
1925                1930                1935

Ala Gly Gln Gln Val Ala Arg Ala Val Leu His Val His Gly Gly
1940                1945                1950

Gly Gly Pro Arg Val Gln Val Ser Pro Glu Arg Thr Gln Val His
1955                1960                1965

Ala Gly Arg Thr Val Arg Leu Tyr Cys Arg Ala Ala Gly Val Pro
1970                1975                1980

Ser Ala Thr Ile Thr Trp Arg Lys Glu Gly Gly Ser Leu Pro Pro
1985                1990                1995

Gln Ala Arg Ser Glu Arg Thr Asp Ile Ala Thr Leu Leu Ile Pro
2000                2005                2010

Ala Ile Thr Thr Ala Asp Ala Gly Phe Tyr Leu Cys Val Ala Thr
2015                2020                2025

Ser Pro Ala Gly Thr Ala Gln Ala Arg Ile Gln Val Val Val Leu
2030                2035                2040

Ser Ala Ser Asp Ala Ser Pro Pro Pro Val Lys Ile Glu Ser Ser
2045                2050                2055

Ser Pro Ser Val Thr Glu Gly Gln Thr Leu Asp Leu Asn Cys Val
2060                2065                2070

Val Ala Gly Ser Ala His Ala Gln Val Thr Trp Tyr Arg Arg Gly
2075                2080                2085

Gly Ser Leu Pro Pro His Thr Gln Val His Gly Ser Arg Leu Arg
2090                2095                2100

Leu Pro Gln Val Ser Pro Ala Asp Ser Gly Glu Tyr Val Cys Arg
2105                2110                2115

Val Glu Asn Gly Ser Gly Pro Lys Glu Ala Ser Ile Thr Val Ser
2120                2125                2130

Val Leu His Gly Thr His Ser Gly Pro Ser Tyr Thr Pro Val Pro
2135                2140                2145
```

-continued

Gly Ser Thr Arg Pro Ile Arg Ile Glu Pro Ser Ser Ser His Val
2150              2155              2160

Ala Glu Gly Gln Thr Leu Asp Leu Asn Cys Val Val Pro Gly Gln
2165              2170              2175

Ala His Ala Gln Val Thr Trp His Lys Arg Gly Gly Ser Leu Pro
2180              2185              2190

Ala Arg His Gln Thr His Gly Ser Leu Leu Arg Leu His Gln Val
2195              2200              2205

Thr Pro Ala Asp Ser Gly Glu Tyr Val Cys His Val Val Gly Thr
2210              2215              2220

Ser Gly Pro Leu Glu Ala Ser Val Leu Val Thr Ile Glu Ala Ser
2225              2230              2235

Val Ile Pro Gly Pro Ile Pro Pro Val Arg Ile Glu Ser Ser Ser
2240              2245              2250

Ser Thr Val Ala Glu Gly Gln Thr Leu Asp Leu Ser Cys Val Val
2255              2260              2265

Ala Gly Gln Ala His Ala Gln Val Thr Trp Tyr Lys Arg Gly Gly
2270              2275              2280

Ser Leu Pro Ala Arg His Gln Val Arg Gly Ser Arg Leu Tyr Ile
2285              2290              2295

Phe Gln Ala Ser Pro Ala Asp Ala Gly Gln Tyr Val Cys Arg Ala
2300              2305              2310

Ser Asn Gly Met Glu Ala Ser Ile Thr Val Thr Val Thr Gly Thr
2315              2320              2325

Gln Gly Ala Asn Leu Ala Tyr Pro Ala Gly Ser Thr Gln Pro Ile
2330              2335              2340

Arg Ile Glu Pro Ser Ser Ser Gln Val Ala Glu Gly Gln Thr Leu
2345              2350              2355

Asp Leu Asn Cys Val Val Pro Gly Gln Ser His Ala Gln Val Thr
2360              2365              2370

Trp His Lys Arg Gly Gly Ser Leu Pro Val Arg His Gln Thr His
2375              2380              2385

Gly Ser Leu Leu Arg Leu Tyr Gln Ala Ser Pro Ala Asp Ser Gly
2390              2395              2400

Glu Tyr Val Cys Arg Val Leu Gly Ser Ser Val Pro Leu Glu Ala
2405              2410              2415

Ser Val Leu Val Thr Ile Glu Pro Ala Gly Ser Val Pro Ala Leu
2420              2425              2430

Gly Val Thr Pro Thr Val Arg Ile Glu Ser Ser Ser Ser Gln Val
2435              2440              2445

Ala Glu Gly Gln Thr Leu Asp Leu Asn Cys Leu Val Ala Gly Gln
2450              2455              2460

Ala His Ala Gln Val Thr Trp His Lys Arg Gly Gly Ser Leu Pro
2465              2470              2475

Ala Arg His Gln Val His Gly Ser Arg Leu Arg Leu Leu Gln Val
2480              2485              2490

Thr Pro Ala Asp Ser Gly Glu Tyr Val Cys Arg Val Val Gly Ser
2495              2500              2505

Ser Gly Thr Gln Glu Ala Ser Val Leu Val Thr Ile Gln Gln Arg
2510              2515              2520

Leu Ser Gly Ser His Ser Gln Gly Val Ala Tyr Pro Val Arg Ile
2525              2530              2535

Glu Ser Ser Ser Ala Ser Leu Ala Asn Gly His Thr Leu Asp Leu

```
                2540                2545                    2550
Asn Cys     Leu Val Ala Ser Gln    Ala Pro His Thr Ile    Thr Trp Tyr
2555                        2560                 2565

Lys Arg     Gly Gly Ser Leu Pro    Ser Arg His Gln Ile    Val Gly Ser
2570                        2575                 2580

Arg Leu     Arg Ile Pro Gln Val    Thr Pro Ala Asp Ser    Gly Glu Tyr
2585                        2590                 2595

Val Cys     His Val Ser Asn Gly    Ala Gly Ser Arg Glu    Thr Ser Leu
2600                        2605                 2610

Ile Val     Thr Ile Gln Gly Ser    Gly Ser Ser His Val    Pro Ser Val
2615                        2620                 2625

Ser Pro     Pro Ile Arg Ile Glu    Ser Ser Ser Pro Thr    Val Val Glu
2630                        2635                 2640

Gly Gln     Thr Leu Asp Leu Asn    Cys Val Val Ala Arg    Gln Pro Gln
2645                        2650                 2655

Ala Ile     Ile Thr Trp Tyr Lys    Arg Gly Gly Ser Leu    Pro Ser Arg
2660                        2665                 2670

His Gln     Thr His Gly Ser His    Leu Arg Leu His Gln    Met Ser Val
2675                        2680                 2685

Ala Asp     Ser Gly Glu Tyr Val    Cys Arg Ala Asn Asn    Asn Ile Asp
2690                        2695                 2700

Ala Leu     Glu Ala Ser Ile Val    Ile Ser Val Ser Pro    Ser Ala Gly
2705                        2710                 2715

Ser Pro     Ser Ala Pro Gly Ser    Ser Met Pro Ile Arg    Ile Glu Ser
2720                        2725                 2730

Ser Ser     Ser His Val Ala Glu    Gly Glu Thr Leu Asp    Leu Asn Cys
2735                        2740                 2745

Val Val     Pro Gly Gln Ala His    Ala Gln Val Thr Trp    His Lys Arg
2750                        2755                 2760

Gly Gly     Ser Leu Pro Ser His    His Gln Thr Arg Gly    Ser Arg Leu
2765                        2770                 2775

Arg Leu     His His Val Ser Pro    Ala Asp Ser Gly Glu    Tyr Val Cys
2780                        2785                 2790

Arg Val     Met Gly Ser Ser Gly    Pro Leu Glu Ala Ser    Val Leu Val
2795                        2800                 2805

Thr Ile     Glu Ala Ser Gly Ser    Ser Ala Val His Val    Pro Ala Pro
2810                        2815                 2820

Gly Gly     Ala Pro Pro Ile Arg    Ile Glu Pro Ser Ser    Ser Arg Val
2825                        2830                 2835

Ala Glu     Gly Gln Thr Leu Asp    Leu Lys Cys Val Val    Pro Gly Gln
2840                        2845                 2850

Ala His     Ala Gln Val Thr Trp    His Lys Arg Gly Gly    Asn Leu Pro
2855                        2860                 2865

Ala Arg     His Gln Val His Gly    Pro Leu Leu Arg Leu    Asn Gln Val
2870                        2875                 2880

Ser Pro     Ala Asp Ser Gly Glu    Tyr Ser Cys Gln Val    Thr Gly Ser
2885                        2890                 2895

Ser Gly     Thr Leu Glu Ala Ser    Val Leu Val Thr Ile    Glu Pro Ser
2900                        2905                 2910

Ser Pro     Gly Pro Ile Pro Ala    Pro Gly Leu Ala Gln    Pro Ile Tyr
2915                        2920                 2925

Ile Glu     Ala Ser Ser Ser His    Val Thr Glu Gly Gln    Thr Leu Asp
2930                        2935                 2940
```

```
Leu Asn Cys Val Val Pro Gly Gln Ala His Ala Gln Val Thr Trp
2945                2950                2955
Tyr Lys Arg Gly Gly Ser Leu Pro Ala Arg His Gln Thr His Gly
2960                2965                2970
Ser Gln Leu Arg Leu His Leu Val Ser Pro Ala Asp Ser Gly Glu
2975                2980                2985
Tyr Val Cys Arg Ala Ala Ser Gly Pro Gly Pro Glu Gln Glu Ala
2990                2995                3000
Ser Phe Thr Val Thr Val Pro Pro Ser Glu Gly Ser Ser Tyr Arg
3005                3010                3015
Leu Arg Ser Pro Val Ile Ser Ile Asp Pro Pro Ser Ser Thr Val
3020                3025                3030
Gln Gln Gly Gln Asp Ala Ser Phe Lys Cys Leu Ile His Asp Gly
3035                3040                3045
Ala Ala Pro Ile Ser Leu Glu Trp Lys Thr Arg Asn Gln Glu Leu
3050                3055                3060
Glu Asp Asn Val His Ile Ser Pro Asn Gly Ser Ile Ile Thr Ile
3065                3070                3075
Val Gly Thr Arg Pro Ser Asn His Gly Thr Tyr Arg Cys Val Ala
3080                3085                3090
Ser Asn Ala Tyr Gly Val Ala Gln Ser Val Val Asn Leu Ser Val
3095                3100                3105
His Gly Pro Pro Thr Val Ser Val Leu Pro Glu Gly Pro Val Trp
3110                3115                3120
Val Lys Val Gly Lys Ala Val Thr Leu Glu Cys Val Ser Ala Gly
3125                3130                3135
Glu Pro Arg Ser Ser Ala Arg Trp Thr Arg Ile Ser Ser Thr Pro
3140                3145                3150
Ala Lys Leu Glu Gln Arg Thr Tyr Gly Leu Met Asp Ser His Ala
3155                3160                3165
Val Leu Gln Ile Ser Ser Ala Lys Pro Ser Asp Ala Gly Thr Tyr
3170                3175                3180
Val Cys Leu Ala Gln Asn Ala Leu Gly Thr Ala Gln Lys Gln Val
3185                3190                3195
Glu Val Ile Val Asp Thr Gly Ala Met Ala Pro Gly Ala Pro Gln
3200                3205                3210
Val Gln Ala Glu Glu Ala Glu Leu Thr Val Glu Ala Gly His Thr
3215                3220                3225
Ala Thr Leu Arg Cys Ser Ala Thr Gly Ser Pro Ala Pro Thr Ile
3230                3235                3240
His Trp Ser Lys Leu Arg Ser Pro Leu Pro Trp Gln His Arg Leu
3245                3250                3255
Glu Gly Asp Thr Leu Ile Ile Pro Arg Val Ala Gln Gln Asp Ser
3260                3265                3270
Gly Gln Tyr Ile Cys Asn Ala Thr Ser Pro Ala Gly His Ala Glu
3275                3280                3285
Ala Thr Ile Ile Leu His Val Glu Ser Pro Pro Tyr Ala Thr Thr
3290                3295                3300
Val Pro Glu His Ala Ser Val Gln Ala Gly Glu Thr Val Gln Leu
3305                3310                3315
Gln Cys Leu Ala His Gly Thr Pro Pro Leu Thr Phe Gln Trp Ser
3320                3325                3330
```

```
Arg Val  Gly Ser Ser Leu Pro  Gly Arg Ala Thr Ala  Arg Asn Glu
3335             3340                3345

Leu Leu  His Phe Glu Arg Ala  Ala Pro Glu Asp Ser  Gly Arg Tyr
3350             3355                3360

Arg Cys  Arg Val Thr Asn Lys  Val Gly Ser Ala Glu  Ala Phe Ala
3365             3370                3375

Gln Leu  Leu Val Gln Gly Pro  Pro Gly Ser Leu Pro  Ala Thr Ser
3380             3385                3390

Ile Pro  Ala Gly Ser Thr Pro  Thr Val Gln Val Thr  Pro Gln Leu
3395             3400                3405

Glu Thr  Lys Ser Ile Gly Ala  Ser Val Glu Phe His  Cys Ala Val
3410             3415                3420

Pro Ser  Asp Arg Gly Thr Gln  Leu Arg Trp Phe Lys  Glu Gly Gly
3425             3430                3435

Gln Leu  Pro Pro Gly His Ser  Val Gln Asp Gly Val  Leu Arg Ile
3440             3445                3450

Gln Asn  Leu Asp Gln Ser Cys  Gln Gly Thr Tyr Ile  Cys Gln Ala
3455             3460                3465

His Gly  Pro Trp Gly Lys Ala  Gln Ala Ser Ala Gln  Leu Val Ile
3470             3475                3480

Gln Ala  Leu Pro Ser Val Leu  Ile Asn Ile Arg Thr  Ser Val Gln
3485             3490                3495

Thr Val  Val Val Gly His Ala  Val Glu Phe Glu Cys  Leu Ala Leu
3500             3505                3510

Gly Asp  Pro Lys Pro Gln Val  Thr Trp Ser Lys Val  Gly Gly His
3515             3520                3525

Leu Arg  Pro Gly Ile Val Gln  Ser Gly Gly Val Val  Arg Ile Ala
3530             3535                3540

His Val  Glu Leu Ala Asp Ala  Gly Gln Tyr Arg Cys  Thr Ala Thr
3545             3550                3555

Asn Ala  Ala Gly Thr Thr Gln  Ser His Val Leu Leu  Leu Val Gln
3560             3565                3570

Ala Leu  Pro Gln Ile Ser Met  Pro Gln Glu Val Arg  Val Pro Ala
3575             3580                3585

Gly Ser  Ala Ala Val Phe Pro  Cys Ile Ala Ser Gly  Tyr Pro Thr
3590             3595                3600

Pro Asp  Ile Ser Trp Ser Lys  Leu Asp Gly Ser Leu  Pro Pro Asp
3605             3610                3615

Ser Arg  Leu Glu Asn Asn Met  Leu Met Leu Pro Ser  Val Arg Pro
3620             3625                3630

Gln Asp  Ala Gly Thr Tyr Val  Cys Thr Ala Thr Asn  Arg Gln Gly
3635             3640                3645

Lys Val  Lys Ala Phe Ala His  Leu Gln Val Pro Glu  Arg Val Val
3650             3655                3660

Pro Tyr  Phe Thr Gln Thr Pro  Tyr Ser Phe Leu Pro  Leu Pro Thr
3665             3670                3675

Ile Lys  Asp Ala Tyr Arg Lys  Phe Glu Ile Lys Ile  Thr Phe Arg
3680             3685                3690

Pro Asp  Ser Ala Asp Gly Met  Leu Leu Tyr Asn Gly  Gln Lys Arg
3695             3700                3705

Val Pro  Gly Ser Pro Thr Asn  Leu Ala Asn Arg Gln  Pro Asp Phe
3710             3715                3720

Ile Ser  Phe Gly Leu Val Gly  Gly Arg Pro Glu Phe  Arg Phe Asp
```

```
                3725                    3730                    3735
Ala Gly Ser Gly Met Ala Thr Ile Arg His Pro Thr Pro Leu Ala
3740                    3745                    3750

Leu Gly His Phe His Thr Val Thr Leu Leu Arg Ser Leu Thr Gln
3755                    3760                    3765

Gly Ser Leu Ile Val Gly Asp Leu Ala Pro Val Asn Gly Thr Ser
3770                    3775                    3780

Gln Gly Lys Phe Gln Gly Leu Asp Leu Asn Glu Glu Leu Tyr Leu
3785                    3790                    3795

Gly Gly Tyr Pro Asp Tyr Gly Ala Ile Pro Lys Ala Gly Leu Ser
3800                    3805                    3810

Ser Gly Phe Ile Gly Cys Val Arg Glu Leu Arg Ile Gln Gly Glu
3815                    3820                    3825

Glu Ile Val Phe His Asp Leu Asn Leu Thr Ala His Gly Ile Ser
3830                    3835                    3840

His Cys Pro Thr Cys Arg Asp Arg Pro Cys Gln Asn Gly Gly Gln
3845                    3850                    3855

Cys His Asp Ser Glu Ser Ser Ser Tyr Val Cys Val Cys Pro Ala
3860                    3865                    3870

Gly Phe Thr Gly Ser Arg Cys Glu His Ser Gln Ala Leu His Cys
3875                    3880                    3885

His Pro Glu Ala Cys Gly Pro Asp Ala Thr Cys Val Asn Arg Pro
3890                    3895                    3900

Asp Gly Arg Gly Tyr Thr Cys Arg Cys His Leu Gly Arg Ser Gly
3905                    3910                    3915

Leu Arg Cys Glu Glu Gly Val Thr Val Thr Pro Ser Leu Ser
3920                    3925                    3930

Gly Ala Gly Ser Tyr Leu Ala Leu Pro Ala Leu Thr Asn Thr His
3935                    3940                    3945

His Glu Leu Arg Leu Asp Val Glu Phe Lys Pro Leu Ala Pro Asp
3950                    3955                    3960

Gly Val Leu Leu Phe Ser Gly Gly Lys Ser Gly Pro Val Glu Asp
3965                    3970                    3975

Phe Val Ser Leu Ala Met Val Gly Gly His Leu Glu Phe Arg Tyr
3980                    3985                    3990

Glu Leu Gly Ser Gly Leu Ala Val Leu Arg Ser Ala Glu Pro Leu
3995                    4000                    4005

Ala Leu Gly Arg Trp His Arg Val Ser Ala Glu Arg Leu Asn Lys
4010                    4015                    4020

Asp Gly Ser Leu Arg Val Asn Gly Gly Arg Pro Val Leu Arg Ser
4025                    4030                    4035

Ser Pro Gly Lys Ser Gln Gly Leu Asn Leu His Thr Leu Leu Tyr
4040                    4045                    4050

Leu Gly Gly Val Glu Pro Ser Val Pro Leu Ser Pro Ala Thr Asn
4055                    4060                    4065

Met Ser Ala His Phe Arg Gly Cys Val Gly Glu Val Ser Val Asn
4070                    4075                    4080

Gly Lys Arg Leu Asp Leu Thr Tyr Ser Phe Leu Gly Ser Gln Gly
4085                    4090                    4095

Ile Gly Gln Cys Tyr Asp Ser Ser Pro Cys Glu Arg Gln Pro Cys
4100                    4105                    4110

Gln His Gly Ala Thr Cys Met Pro Ala Gly Glu Tyr Glu Phe Gln
4115                    4120                    4125
```

```
Cys Leu Cys Arg Asp Gly Phe Lys Gly Asp Leu Cys Glu His Glu
4130                4135                4140

Glu Asn Pro Cys Gln Leu Arg Glu Pro Cys Leu His Gly Gly Thr
4145                4150                4155

Cys Gln Gly Thr Arg Cys Leu Cys Leu Pro Gly Phe Ser Gly Pro
4160                4165                4170

Arg Cys Gln Gln Gly Ser Gly His Gly Ile Ala Glu Ser Asp Trp
4175                4180                4185

His Leu Glu Gly Ser Gly Gly Asn Asp Ala Pro Gly Gln Tyr Gly
4190                4195                4200

Ala Tyr Phe His Asp Asp Gly Phe Leu Ala Phe Pro Gly His Val
4205                4210                4215

Phe Ser Arg Ser Leu Pro Glu Val Pro Glu Thr Ile Glu Leu Glu
4220                4225                4230

Val Arg Thr Ser Thr Ala Ser Gly Leu Leu Leu Trp Gln Gly Val
4235                4240                4245

Glu Val Gly Glu Ala Gly Gln Gly Lys Asp Phe Ile Ser Leu Gly
4250                4255                4260

Leu Gln Asp Gly His Leu Val Phe Arg Tyr Gln Leu Gly Ser Gly
4265                4270                4275

Glu Ala Arg Leu Val Ser Glu Asp Pro Ile Asn Asp Gly Glu Trp
4280                4285                4290

His Arg Val Thr Ala Leu Arg Glu Gly Arg Arg Gly Ser Ile Gln
4295                4300                4305

Val Asp Gly Glu Glu Leu Val Ser Gly Arg Ser Pro Gly Pro Asn
4310                4315                4320

Val Ala Val Asn Ala Lys Gly Ser Val Tyr Ile Gly Gly Ala Pro
4325                4330                4335

Asp Val Ala Thr Leu Thr Gly Gly Arg Phe Ser Ser Gly Ile Thr
4340                4345                4350

Gly Cys Val Lys Asn Leu Val Leu His Ser Ala Arg Pro Gly Ala
4355                4360                4365

Pro Pro Pro Gln Pro Leu Asp Leu Gln His Arg Ala Gln Ala Gly
4370                4375                4380

Ala Asn Thr Arg Pro Cys Pro Ser
4385                4390

<210> SEQ ID NO 4
<211> LENGTH: 368
<212> TYPE: PRT
<213> ORGANISM: Homo sapiens

<400> SEQUENCE: 4

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
                20                  25                  30

Pro Phe Met Met Asn Asp Glu Glu Ala Ser Gly Ala Asp Thr Ser Gly
            35                  40                  45

Val Leu Asp Pro Asp Ser Val Thr Pro Thr Tyr Ser Ala Met Cys Pro
        50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
```

```
                    85                  90                  95

Leu Gln Asn Asn Asp Ile Ser Glu Leu Arg Lys Asp Phe Lys Gly
                100                 105                 110

Leu Gln His Leu Tyr Ala Leu Val Leu Val Asn Asn Lys Ile Ser Lys
                115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
                180                 185                 190

Asn Pro Leu Glu Asn Ser Gly Phe Glu Pro Gly Ala Phe Asp Gly Leu
                195                 200                 205

Lys Leu Asn Tyr Leu Arg Ile Ser Glu Ala Lys Leu Thr Gly Ile Pro
                210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
                260                 265                 270

Leu Ser Phe Leu Pro Thr Leu Arg Glu Leu His Leu Asp Asn Asn Lys
                275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
                340                 345                 350

Arg Cys Val Thr Asp Arg Leu Ala Ile Gln Phe Gly Asn Tyr Lys Lys
                355                 360                 365

<210> SEQ ID NO 5
<211> LENGTH: 359
<212> TYPE: PRT
<213> ORGANISM: Homo sapiens

<400> SEQUENCE: 5

Met Lys Ala Thr Ile Ile Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
                35                  40                  45

Ser Leu Gly Pro Val Cys Pro Phe Arg Cys Gln Cys His Leu Arg Val
                50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95
```

```
Lys Asp Gly Asp Phe Lys Asn Leu Lys Asn Leu His Ala Leu Ile Leu
                100                 105                 110

Val Asn Asn Lys Ile Ser Lys Val Ser Pro Gly Ala Phe Thr Pro Leu
            115                 120                 125

Val Lys Leu Glu Arg Leu Tyr Leu Ser Lys Asn Gln Leu Lys Glu Leu
        130                 135                 140

Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
                165                 170                 175

Ile Val Ile Glu Leu Gly Thr Asn Pro Leu Lys Ser Ser Gly Ile Glu
            180                 185                 190

Asn Gly Ala Phe Gln Gly Met Lys Lys Leu Ser Tyr Ile Arg Ile Ala
        195                 200                 205

Asp Thr Asn Ile Thr Ser Ile Pro Gln Gly Leu Pro Pro Ser Leu Thr
210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Pro Gly Gly Leu
        275                 280                 285

Ala Glu His Lys Tyr Ile Gln Val Val Tyr Leu His Asn Asn Asn Ile
290                 295                 300

Ser Val Val Gly Ser Ser Asp Phe Cys Pro Pro Gly His Asn Thr Lys
305                 310                 315                 320

Lys Ala Ser Tyr Ser Gly Val Ser Leu Phe Ser Asn Pro Val Gln Tyr
                325                 330                 335

Trp Glu Ile Gln Pro Ser Thr Phe Arg Cys Val Tyr Val Arg Ser Ala
            340                 345                 350

Ile Gln Leu Gly Asn Tyr Lys
        355

<210> SEQ ID NO 6
<211> LENGTH: 24
<212> TYPE: PRT
<213> ORGANISM: Homo sapiens

<400> SEQUENCE: 6

Lys Ser Val Pro Lys Glu Ile Ser Pro Asp Thr Thr Leu Leu Asp Leu
1               5                   10                  15

Gln Asn Asn Asp Ile Ser Glu Leu
            20

<210> SEQ ID NO 7
<211> LENGTH: 25
<212> TYPE: PRT
<213> ORGANISM: Homo sapiens

<400> SEQUENCE: 7

Leu Lys Ser Val Pro Lys Glu Ile Ser Pro Asp Thr Thr Leu Leu Asp
1               5                   10                  15

Leu Gln Asn Asn Asp Ile Ser Glu Leu
            20                  25
```

<210> SEQ ID NO 8
<211> LENGTH: 25
<212> TYPE: PRT
<213> ORGANISM: Homo sapiens

<400> SEQUENCE: 8

Glu Asn Ser Gly Phe Glu Pro Gly Ala Phe Asp Gly Leu Lys Leu Asn
1               5                   10                  15
Tyr Leu Arg Ile Ser Glu Ala Lys Leu
            20                  25

<210> SEQ ID NO 9
<211> LENGTH: 26
<212> TYPE: PRT
<213> ORGANISM: Homo sapiens

<400> SEQUENCE: 9

Gly Leu Lys Ser Val Pro Lys Glu Ile Ser Pro Asp Thr Thr Leu Leu
1               5                   10                  15
Asp Leu Gln Asn Asn Asp Ile Ser Glu Leu
            20                  25

<210> SEQ ID NO 10
<211> LENGTH: 20
<212> TYPE: PRT
<213> ORGANISM: Homo sapiens

<400> SEQUENCE: 10

Tyr Leu Arg Ile Ser Glu Ala Lys Leu Thr Gly Ile Pro Lys Asp Leu
1               5                   10                  15
Pro Glu Thr Leu
            20

<210> SEQ ID NO 11
<211> LENGTH: 26
<212> TYPE: PRT
<213> ORGANISM: Homo sapiens

<400> SEQUENCE: 11

Gly Leu Lys Ser Val Pro Lys Glu Ile Ser Pro Asp Thr Thr Leu Leu
1               5                   10                  15
Asp Leu Gln Asn Asn Asp Ile Ser Glu Leu
            20                  25

<210> SEQ ID NO 12
<211> LENGTH: 26
<212> TYPE: PRT
<213> ORGANISM: Homo sapiens

<400> SEQUENCE: 12

Leu Thr Gly Ile Pro Lys Asp Leu Pro Glu Thr Leu Asn Glu Leu His
1               5                   10                  15
Leu Asp His Asn Lys Ile Gln Ala Ile Glu
            20                  25

<210> SEQ ID NO 13
<211> LENGTH: 22
<212> TYPE: PRT
<213> ORGANISM: Homo sapiens

<400> SEQUENCE: 13

Lys Arg Ile Ser Glu Ala Lys Leu Thr Gly Ile Pro Lys Asp Leu Pro

```
                1               5                   10                  15

Glu Thr Leu Asn Glu Leu
            20

<210> SEQ ID NO 14
<211> LENGTH: 14
<212> TYPE: PRT
<213> ORGANISM: Homo sapiens

<400> SEQUENCE: 14

Gln Ala Ile Glu Leu Glu Asp Leu Leu Arg Tyr Ser Lys Leu
1               5                   10

<210> SEQ ID NO 15
<211> LENGTH: 12
<212> TYPE: PRT
<213> ORGANISM: Homo sapiens

<400> SEQUENCE: 15

Gln Ala Ile Glu Leu Glu Asp Leu Leu Arg Tyr Ser
1               5                   10

<210> SEQ ID NO 16
<211> LENGTH: 19
<212> TYPE: PRT
<213> ORGANISM: Homo sapiens

<400> SEQUENCE: 16

Ser Glu Ala Lys Leu Thr Gly Ile Pro Lys Asp Leu Pro Glu Thr Leu
1               5                   10                  15

Asn Glu Leu

<210> SEQ ID NO 17
<211> LENGTH: 25
<212> TYPE: PRT
<213> ORGANISM: Homo sapiens

<400> SEQUENCE: 17

Leu Lys Ala Val Pro Lys Glu Ile Ser Pro Asp Thr Thr Leu Leu Asp
1               5                   10                  15

Leu Gln Asn Asn Asp Ile Ser Glu Leu
            20                  25

<210> SEQ ID NO 18
<211> LENGTH: 18
<212> TYPE: PRT
<213> ORGANISM: Homo sapiens

<400> SEQUENCE: 18

Thr Leu Leu Asp Leu Gln Asn Asn Asp Ile Ser Glu Leu Arg Lys Asp
1               5                   10                  15

Asp Phe

<210> SEQ ID NO 19
<211> LENGTH: 12
<212> TYPE: PRT
<213> ORGANISM: Homo sapiens

<400> SEQUENCE: 19

Ala Ile Glu Leu Glu Asp Leu Leu Arg Tyr Ser Lys
1               5                   10
```

<210> SEQ ID NO 20
<211> LENGTH: 15
<212> TYPE: PRT
<213> ORGANISM: Homo sapiens

<400> SEQUENCE: 20

Glu Asn Ser Gly Phe Glu Pro Gly Ala Phe Asp Gly Leu Lys Leu
1               5                   10                  15

<210> SEQ ID NO 21
<211> LENGTH: 13
<212> TYPE: PRT
<213> ORGANISM: Homo sapiens

<400> SEQUENCE: 21

Met Ile Val Ile Glu Leu Gly Thr Asn Pro Leu Lys Ser
1               5                   10

<210> SEQ ID NO 22
<211> LENGTH: 13
<212> TYPE: PRT
<213> ORGANISM: Homo sapiens

<400> SEQUENCE: 22

Met Ile Val Ile Glu Leu Gly Thr Asn Pro Leu Lys Ser
1               5                   10

<210> SEQ ID NO 23
<211> LENGTH: 17
<212> TYPE: PRT
<213> ORGANISM: Homo sapiens

<400> SEQUENCE: 23

Glu Leu His Leu Asp Gly Asn Lys Ile Ser Arg Val Asp Ala Ala Ser
1               5                   10                  15

Leu

<210> SEQ ID NO 24
<211> LENGTH: 18
<212> TYPE: PRT
<213> ORGANISM: Homo sapiens

<400> SEQUENCE: 24

Leu Val Asn Asn Lys Ile Ser Lys Val Ser Pro Gly Ala Phe Thr Pro
1               5                   10                  15

Leu Val

<210> SEQ ID NO 25
<211> LENGTH: 26
<212> TYPE: PRT
<213> ORGANISM: Homo sapiens

<400> SEQUENCE: 25

Ala Leu Ile Leu Val Asn Asn Lys Ile Ser Lys Val Ser Pro Gly Ala
1               5                   10                  15

Phe Thr Pro Leu Val Lys Leu Glu Arg Leu
            20                  25

<210> SEQ ID NO 26
<211> LENGTH: 17
<212> TYPE: PRT
<213> ORGANISM: Homo sapiens

<400> SEQUENCE: 26

-continued

Phe Ser Asn Pro Val Gln Tyr Trp Glu Ile Gln Pro Ser Thr Phe Arg
1               5                   10                  15
Cys

<210> SEQ ID NO 27
<211> LENGTH: 15
<212> TYPE: PRT
<213> ORGANISM: Homo sapiens

<400> SEQUENCE: 27

Lys Ser Ser Gly Ile Glu Asn Gly Ala Phe Gln Gly Met Lys Lys
1               5                   10                  15

<210> SEQ ID NO 28
<211> LENGTH: 18
<212> TYPE: PRT
<213> ORGANISM: Homo sapiens

<400> SEQUENCE: 28

Lys Ser Ser Gly Ile Glu Asn Gly Ala Phe Gln Gly Met Lys Lys Leu
1               5                   10                  15
Ser Tyr

<210> SEQ ID NO 29
<211> LENGTH: 13
<212> TYPE: PRT
<213> ORGANISM: Homo sapiens

<400> SEQUENCE: 29

Asn Lys Ile Thr Glu Ile Lys Asp Gly Asp Phe Lys Asn
1               5                   10

<210> SEQ ID NO 30
<211> LENGTH: 17
<212> TYPE: PRT
<213> ORGANISM: Homo sapiens

<400> SEQUENCE: 30

Gln Gly Leu Pro Pro Ser Leu Thr Glu Leu His Leu Asp Gly Asn Lys
1               5                   10                  15
Ile

<210> SEQ ID NO 31
<211> LENGTH: 12
<212> TYPE: PRT
<213> ORGANISM: Homo sapiens

<400> SEQUENCE: 31

Lys Leu Leu Ala Ser Asp Ala Gly Leu Tyr Arg Cys
1               5                   10

<210> SEQ ID NO 32
<211> LENGTH: 13
<212> TYPE: PRT
<213> ORGANISM: Homo sapiens

<400> SEQUENCE: 32

Leu Ala Thr Val Gly Glu Leu Gln Ala Ala Trp Arg Asn
1               5                   10

<210> SEQ ID NO 33
<211> LENGTH: 15

```
<212> TYPE: PRT
<213> ORGANISM: Homo sapiens

<400> SEQUENCE: 33

Lys Glu Thr Thr Val Leu Val Ala Gln Asn Gly Asn Ile Lys Ile
1               5                   10                  15

<210> SEQ ID NO 34
<211> LENGTH: 12
<212> TYPE: PRT
<213> ORGANISM: Homo sapiens

<400> SEQUENCE: 34

Ser Leu Glu Asp Leu Gln Leu Thr His Asn Lys Ile
1               5                   10

<210> SEQ ID NO 35
<211> LENGTH: 13
<212> TYPE: PRT
<213> ORGANISM: Homo sapiens

<400> SEQUENCE: 35

Arg Leu Lys Glu Asp Ala Val Ser Ala Ala Phe Lys Gly
1               5                   10

<210> SEQ ID NO 36
<211> LENGTH: 16
<212> TYPE: PRT
<213> ORGANISM: Homo sapiens

<400> SEQUENCE: 36

Arg Ser Ile Glu Tyr Ser Pro Gln Leu Glu Asp Ala Gly Ser Arg Glu
1               5                   10                  15

<210> SEQ ID NO 37
<211> LENGTH: 12
<212> TYPE: PRT
<213> ORGANISM: Homo sapiens

<400> SEQUENCE: 37

Arg Leu Glu Gly Asp Thr Leu Ile Ile Pro Arg Val
1               5                   10

<210> SEQ ID NO 38
<211> LENGTH: 15
<212> TYPE: PRT
<213> ORGANISM: Homo sapiens

<400> SEQUENCE: 38

Glu Val Ser Glu Ala Val Val Glu Lys Leu Glu Pro Glu Tyr Arg
1               5                   10                  15

<210> SEQ ID NO 39
<211> LENGTH: 16
<212> TYPE: PRT
<213> ORGANISM: Homo sapiens

<400> SEQUENCE: 39

Arg Glu Val Ser Glu Ala Val Val Glu Lys Leu Glu Pro Glu Tyr Arg
1               5                   10                  15

<210> SEQ ID NO 40
<211> LENGTH: 12
<212> TYPE: PRT
<213> ORGANISM: Homo sapiens
```

```
<400> SEQUENCE: 40

Arg Ser Ile Glu Tyr Ser Pro Gln Leu Glu Asp Ala
1               5                   10

<210> SEQ ID NO 41
<211> LENGTH: 22
<212> TYPE: PRT
<213> ORGANISM: Homo sapiens

<400> SEQUENCE: 41

Ser Val Pro Lys Glu Ile Ser Pro Asp Thr Thr Leu Leu Asp Leu Gln
1               5                   10                  15

Asn Asn Asp Ile Ser Glu
            20

<210> SEQ ID NO 42
<211> LENGTH: 23
<212> TYPE: PRT
<213> ORGANISM: Homo sapiens

<400> SEQUENCE: 42

Lys Ser Val Pro Lys Glu Ile Ser Pro Asp Thr Thr Leu Leu Asp Leu
1               5                   10                  15

Gln Asn Asn Asp Ile Ser Glu
            20

<210> SEQ ID NO 43
<211> LENGTH: 23
<212> TYPE: PRT
<213> ORGANISM: Homo sapiens

<400> SEQUENCE: 43

Asn Ser Gly Phe Glu Pro Gly Ala Phe Asp Gly Leu Lys Leu Asn Tyr
1               5                   10                  15

Leu Arg Ile Ser Glu Ala Lys
            20

<210> SEQ ID NO 44
<211> LENGTH: 24
<212> TYPE: PRT
<213> ORGANISM: Homo sapiens

<400> SEQUENCE: 44

Leu Lys Ser Val Pro Lys Glu Ile Ser Pro Asp Thr Thr Leu Leu Asp
1               5                   10                  15

Leu Gln Asn Asn Asp Ile Ser Glu
            20

<210> SEQ ID NO 45
<211> LENGTH: 18
<212> TYPE: PRT
<213> ORGANISM: Homo sapiens

<400> SEQUENCE: 45

Leu Arg Ile Ser Glu Ala Lys Leu Thr Gly Ile Pro Lys Asp Leu Pro
1               5                   10                  15

Glu Thr

<210> SEQ ID NO 46
<211> LENGTH: 24
<212> TYPE: PRT
```

<213> ORGANISM: Homo sapiens

<400> SEQUENCE: 46

Leu Lys Ser Val Pro Lys Glu Ile Ser Pro Asp Thr Thr Leu Leu Asp
1               5                   10                  15
Leu Gln Asn Asn Asp Ile Ser Glu
            20

<210> SEQ ID NO 47
<211> LENGTH: 26
<212> TYPE: PRT
<213> ORGANISM: Homo sapiens

<400> SEQUENCE: 47

Leu Thr Gly Ile Pro Lys Asp Leu Pro Glu Thr Leu Asn Glu Leu His
1               5                   10                  15
Leu Asp His Asn Lys Ile Gln Ala Ile Glu
            20                  25

<210> SEQ ID NO 48
<211> LENGTH: 11
<212> TYPE: PRT
<213> ORGANISM: Homo sapiens

<400> SEQUENCE: 48

Ile Val Ile Glu Leu Gly Thr Asn Pro Leu Lys
1               5                   10

<210> SEQ ID NO 49
<211> LENGTH: 10
<212> TYPE: PRT
<213> ORGANISM: Homo sapiens

<400> SEQUENCE: 49

Leu Leu Ala Ser Asp Ala Gly Leu Tyr Arg
1               5                   10

<210> SEQ ID NO 50
<211> LENGTH: 12
<212> TYPE: PRT
<213> ORGANISM: Homo sapiens

<400> SEQUENCE: 50

Leu Ala Thr Val Gly Glu Leu Gln Ala Ala Trp Arg
1               5                   10

<210> SEQ ID NO 51
<211> LENGTH: 13
<212> TYPE: PRT
<213> ORGANISM: Homo sapiens

<400> SEQUENCE: 51

Glu Thr Thr Val Leu Val Ala Gln Asn Gly Asn Ile Lys
1               5                   10

<210> SEQ ID NO 52
<211> LENGTH: 11
<212> TYPE: PRT
<213> ORGANISM: Homo sapiens

<400> SEQUENCE: 52

Ser Leu Glu Asp Leu Gln Leu Thr His Asn Lys
1               5                   10

<210> SEQ ID NO 53
<211> LENGTH: 11
<212> TYPE: PRT
<213> ORGANISM: Homo sapiens

<400> SEQUENCE: 53

Leu Lys Glu Asp Ala Val Ser Ala Ala Phe Lys
1               5                   10

<210> SEQ ID NO 54
<211> LENGTH: 14
<212> TYPE: PRT
<213> ORGANISM: Homo sapiens

<400> SEQUENCE: 54

Ser Ile Glu Tyr Ser Pro Gln Leu Glu Asp Ala Gly Ser Arg
1               5                   10

<210> SEQ ID NO 55
<211> LENGTH: 10
<212> TYPE: PRT
<213> ORGANISM: Homo sapiens

<400> SEQUENCE: 55

Leu Glu Gly Asp Thr Leu Ile Ile Pro Arg
1               5                   10

<210> SEQ ID NO 56
<211> LENGTH: 20
<212> TYPE: PRT
<213> ORGANISM: Homo sapiens

<400> SEQUENCE: 56

Arg Ile Ser Glu Ala Lys Leu Thr Gly Ile Pro Lys Asp Leu Pro Glu
1               5                   10                  15

Thr Leu Asn Glu
            20

<210> SEQ ID NO 57
<211> LENGTH: 12
<212> TYPE: PRT
<213> ORGANISM: Homo sapiens

<400> SEQUENCE: 57

Ala Ile Glu Leu Glu Asp Leu Leu Arg Tyr Ser Lys
1               5                   10

<210> SEQ ID NO 58
<211> LENGTH: 10
<212> TYPE: PRT
<213> ORGANISM: Homo sapiens

<400> SEQUENCE: 58

Ala Ile Glu Leu Glu Asp Leu Leu Arg Tyr
1               5                   10

<210> SEQ ID NO 59
<211> LENGTH: 17
<212> TYPE: PRT
<213> ORGANISM: Homo sapiens

<400> SEQUENCE: 59

Glu Ala Lys Leu Thr Gly Ile Pro Lys Asp Leu Pro Glu Thr Leu Asn
1               5                   10                  15

Glu

<210> SEQ ID NO 60
<211> LENGTH: 24
<212> TYPE: PRT
<213> ORGANISM: Homo sapiens

<400> SEQUENCE: 60

Leu Lys Ala Val Pro Lys Glu Ile Ser Pro Asp Thr Thr Leu Leu Asp
1               5                   10                  15

Leu Gln Asn Asn Asp Ile Ser Glu
            20

<210> SEQ ID NO 61
<211> LENGTH: 16
<212> TYPE: PRT
<213> ORGANISM: Homo sapiens

<400> SEQUENCE: 61

Leu Leu Asp Leu Gln Asn Asn Asp Ile Ser Glu Leu Arg Lys Asp Asp
1               5                   10                  15

<210> SEQ ID NO 62
<211> LENGTH: 10
<212> TYPE: PRT
<213> ORGANISM: Homo sapiens

<400> SEQUENCE: 62

Ile Glu Leu Glu Asp Leu Leu Arg Tyr Ser
1               5                   10

<210> SEQ ID NO 63
<211> LENGTH: 13
<212> TYPE: PRT
<213> ORGANISM: Homo sapiens

<400> SEQUENCE: 63

Asn Ser Gly Phe Glu Pro Gly Ala Phe Asp Gly Leu Lys
1               5                   10

<210> SEQ ID NO 64
<211> LENGTH: 14
<212> TYPE: PRT
<213> ORGANISM: Homo sapiens

<400> SEQUENCE: 64

Asp Glu Ala Ser Gly Ile Gly Pro Glu Val Pro Asp Asp Arg
1               5                   10

<210> SEQ ID NO 65
<211> LENGTH: 15
<212> TYPE: PRT
<213> ORGANISM: Homo sapiens

<400> SEQUENCE: 65

Leu His Leu Asp Gly Asn Lys Ile Ser Arg Val Asp Ala Ala Ser
1               5                   10                  15

<210> SEQ ID NO 66
<211> LENGTH: 16
<212> TYPE: PRT
<213> ORGANISM: Homo sapiens

<400> SEQUENCE: 66

-continued

Val Asn Asn Lys Ile Ser Lys Val Ser Pro Gly Ala Phe Thr Pro Leu
1               5                   10                  15

<210> SEQ ID NO 67
<211> LENGTH: 24
<212> TYPE: PRT
<213> ORGANISM: Homo sapiens

<400> SEQUENCE: 67

Leu Ile Leu Val Asn Asn Lys Ile Ser Lys Val Ser Pro Gly Ala Phe
1               5                   10                  15

Thr Pro Leu Val Lys Leu Glu Arg
            20

<210> SEQ ID NO 68
<211> LENGTH: 15
<212> TYPE: PRT
<213> ORGANISM: Homo sapiens

<400> SEQUENCE: 68

Ser Asn Pro Val Gln Tyr Trp Glu Ile Gln Pro Ser Thr Phe Arg
1               5                   10                  15

<210> SEQ ID NO 69
<211> LENGTH: 13
<212> TYPE: PRT
<213> ORGANISM: Homo sapiens

<400> SEQUENCE: 69

Ser Ser Gly Ile Glu Asn Gly Ala Phe Gln Gly Met Lys
1               5                   10

<210> SEQ ID NO 70
<211> LENGTH: 16
<212> TYPE: PRT
<213> ORGANISM: Homo sapiens

<400> SEQUENCE: 70

Ser Ser Gly Ile Glu Asn Gly Ala Phe Gln Gly Met Lys Lys Leu Ser
1               5                   10                  15

<210> SEQ ID NO 71
<211> LENGTH: 11
<212> TYPE: PRT
<213> ORGANISM: Homo sapiens

<400> SEQUENCE: 71

Lys Ile Thr Glu Ile Lys Asp Gly Asp Phe Lys
1               5                   10

<210> SEQ ID NO 72
<211> LENGTH: 15
<212> TYPE: PRT
<213> ORGANISM: Homo sapiens

<400> SEQUENCE: 72

Gly Leu Pro Pro Ser Leu Thr Glu Leu His Leu Asp Gly Asn Lys
1               5                   10                  15

<210> SEQ ID NO 73
<211> LENGTH: 14
<212> TYPE: PRT
<213> ORGANISM: Homo sapiens

```
<400> SEQUENCE: 73

Val Ser Glu Ala Val Val Glu Lys Leu Glu Pro Glu Tyr Arg
1               5                   10

<210> SEQ ID NO 74
<211> LENGTH: 15
<212> TYPE: PRT
<213> ORGANISM: Homo sapiens

<400> SEQUENCE: 74

Glu Val Ser Glu Ala Val Val Glu Lys Leu Glu Pro Glu Tyr Arg
1               5                   10                  15

<210> SEQ ID NO 75
<211> LENGTH: 17
<212> TYPE: PRT
<213> ORGANISM: Homo sapiens

<400> SEQUENCE: 75

Ser Ile Glu Tyr Ser Pro Gln Leu Glu Asp Ala Ser Ala Lys Glu Phe
1               5                   10                  15

Arg

<210> SEQ ID NO 76
<211> LENGTH: 6
<212> TYPE: PRT
<213> ORGANISM: Homo sapiens

<400> SEQUENCE: 76

Ser Val Pro Lys Glu Ile
1               5

<210> SEQ ID NO 77
<211> LENGTH: 6
<212> TYPE: PRT
<213> ORGANISM: Homo sapiens

<400> SEQUENCE: 77

Asn Ser Gly Phe Glu Pro
1               5

<210> SEQ ID NO 78
<211> LENGTH: 6
<212> TYPE: PRT
<213> ORGANISM: Homo sapiens

<400> SEQUENCE: 78

Leu Lys Ser Val Pro Lys
1               5

<210> SEQ ID NO 79
<211> LENGTH: 6
<212> TYPE: PRT
<213> ORGANISM: Homo sapiens

<400> SEQUENCE: 79

Leu Arg Ile Ser Glu Ala
1               5

<210> SEQ ID NO 80
<211> LENGTH: 6
<212> TYPE: PRT
<213> ORGANISM: Homo sapiens
```

```
<400> SEQUENCE: 80

Gly Leu Lys Leu Asn Tyr
1               5

<210> SEQ ID NO 81
<211> LENGTH: 6
<212> TYPE: PRT
<213> ORGANISM: Homo sapiens

<400> SEQUENCE: 81

Leu Lys Ser Val Pro Lys
1               5

<210> SEQ ID NO 82
<211> LENGTH: 6
<212> TYPE: PRT
<213> ORGANISM: Homo sapiens

<400> SEQUENCE: 82

Gln Cys Ser Asp Leu Gly
1               5

<210> SEQ ID NO 83
<211> LENGTH: 6
<212> TYPE: PRT
<213> ORGANISM: Homo sapiens

<400> SEQUENCE: 83

Leu Thr Gly Ile Pro Lys
1               5

<210> SEQ ID NO 84
<211> LENGTH: 6
<212> TYPE: PRT
<213> ORGANISM: Homo sapiens

<400> SEQUENCE: 84

Arg Ile Ser Glu Ala Lys
1               5

<210> SEQ ID NO 85
<211> LENGTH: 6
<212> TYPE: PRT
<213> ORGANISM: Homo sapiens

<400> SEQUENCE: 85

Ala Ile Glu Leu Glu Asp
1               5

<210> SEQ ID NO 86
<211> LENGTH: 6
<212> TYPE: PRT
<213> ORGANISM: Homo sapiens

<400> SEQUENCE: 86

Glu Ala Lys Leu Thr Gly
1               5

<210> SEQ ID NO 87
<211> LENGTH: 6
<212> TYPE: PRT
<213> ORGANISM: Homo sapiens

<400> SEQUENCE: 87
```

Leu Lys Ala Val Pro Lys
1               5

<210> SEQ ID NO 88
<211> LENGTH: 6
<212> TYPE: PRT
<213> ORGANISM: Homo sapiens

<400> SEQUENCE: 88

Leu Leu Asp Leu Gln Asn
1               5

<210> SEQ ID NO 89
<211> LENGTH: 6
<212> TYPE: PRT
<213> ORGANISM: Homo sapiens

<400> SEQUENCE: 89

Ile Glu Leu Glu Asp Leu
1               5

<210> SEQ ID NO 90
<211> LENGTH: 6
<212> TYPE: PRT
<213> ORGANISM: Homo sapiens

<400> SEQUENCE: 90

Asn Ser Gly Phe Glu Pro
1               5

<210> SEQ ID NO 91
<211> LENGTH: 6
<212> TYPE: PRT
<213> ORGANISM: Homo sapiens

<400> SEQUENCE: 91

Ile Val Ile Glu Leu Gly
1               5

<210> SEQ ID NO 92
<211> LENGTH: 6
<212> TYPE: PRT
<213> ORGANISM: Homo sapiens

<400> SEQUENCE: 92

Asn Gly Leu Asn Gln Met
1               5

<210> SEQ ID NO 93
<211> LENGTH: 6
<212> TYPE: PRT
<213> ORGANISM: Homo sapiens

<400> SEQUENCE: 93

Asp Glu Ala Ser Gly Ile
1               5

<210> SEQ ID NO 94
<211> LENGTH: 6
<212> TYPE: PRT
<213> ORGANISM: Homo sapiens

<400> SEQUENCE: 94

Leu His Leu Asp Gly Asn
1               5

```
<210> SEQ ID NO 95
<211> LENGTH: 6
<212> TYPE: PRT
<213> ORGANISM: Homo sapiens

<400> SEQUENCE: 95

Val Asn Asn Lys Ile Ser
1               5

<210> SEQ ID NO 96
<211> LENGTH: 6
<212> TYPE: PRT
<213> ORGANISM: Homo sapiens

<400> SEQUENCE: 96

Leu Ile Leu Val Asn Asn
1               5

<210> SEQ ID NO 97
<211> LENGTH: 6
<212> TYPE: PRT
<213> ORGANISM: Homo sapiens

<400> SEQUENCE: 97

Ser Asn Pro Val Gln Tyr
1               5

<210> SEQ ID NO 98
<211> LENGTH: 6
<212> TYPE: PRT
<213> ORGANISM: Homo sapiens

<400> SEQUENCE: 98

Ser Ser Gly Ile Glu Asn
1               5

<210> SEQ ID NO 99
<211> LENGTH: 6
<212> TYPE: PRT
<213> ORGANISM: Homo sapiens

<400> SEQUENCE: 99

Lys Ile Thr Glu Ile Lys
1               5

<210> SEQ ID NO 100
<211> LENGTH: 6
<212> TYPE: PRT
<213> ORGANISM: Homo sapiens

<400> SEQUENCE: 100

Gly Leu Pro Pro Ser Leu
1               5

<210> SEQ ID NO 101
<211> LENGTH: 6
<212> TYPE: PRT
<213> ORGANISM: Homo sapiens

<400> SEQUENCE: 101

Leu Leu Ala Ser Asp Ala
1               5
```

```
<210> SEQ ID NO 102
<211> LENGTH: 6
<212> TYPE: PRT
<213> ORGANISM: Homo sapiens

<400> SEQUENCE: 102

Leu Ala Thr Val Gly Glu
1               5

<210> SEQ ID NO 103
<211> LENGTH: 6
<212> TYPE: PRT
<213> ORGANISM: Homo sapiens

<400> SEQUENCE: 103

Glu Thr Thr Val Leu Val
1               5

<210> SEQ ID NO 104
<211> LENGTH: 6
<212> TYPE: PRT
<213> ORGANISM: Homo sapiens

<400> SEQUENCE: 104

Ser Leu Thr Val Val Lys
1               5

<210> SEQ ID NO 105
<211> LENGTH: 6
<212> TYPE: PRT
<213> ORGANISM: Homo sapiens

<400> SEQUENCE: 105

Glu Asn Gln Asp Ala Arg
1               5

<210> SEQ ID NO 106
<211> LENGTH: 6
<212> TYPE: PRT
<213> ORGANISM: Homo sapiens

<400> SEQUENCE: 106

Asn Gly Phe Asp Gln Cys
1               5

<210> SEQ ID NO 107
<211> LENGTH: 6
<212> TYPE: PRT
<213> ORGANISM: Homo sapiens

<400> SEQUENCE: 107

Ser Leu Glu Asp Leu Gln
1               5

<210> SEQ ID NO 108
<211> LENGTH: 6
<212> TYPE: PRT
<213> ORGANISM: Homo sapiens

<400> SEQUENCE: 108

Leu Lys Glu Asp Ala Val
1               5

<210> SEQ ID NO 109
<211> LENGTH: 6
```

```
<212> TYPE: PRT
<213> ORGANISM: Homo sapiens

<400> SEQUENCE: 109

His Leu Gln His Asn Arg
1               5

<210> SEQ ID NO 110
<211> LENGTH: 6
<212> TYPE: PRT
<213> ORGANISM: Homo sapiens

<400> SEQUENCE: 110

Leu Gln His Asn Arg Leu
1               5

<210> SEQ ID NO 111
<211> LENGTH: 6
<212> TYPE: PRT
<213> ORGANISM: Homo sapiens

<400> SEQUENCE: 111

Ser Ile Glu Tyr Ser Pro
1               5

<210> SEQ ID NO 112
<211> LENGTH: 6
<212> TYPE: PRT
<213> ORGANISM: Homo sapiens

<400> SEQUENCE: 112

Leu Val Asn Phe Thr Arg
1               5

<210> SEQ ID NO 113
<211> LENGTH: 6
<212> TYPE: PRT
<213> ORGANISM: Homo sapiens

<400> SEQUENCE: 113

Val Ser Glu Ala Val Val
1               5

<210> SEQ ID NO 114
<211> LENGTH: 6
<212> TYPE: PRT
<213> ORGANISM: Homo sapiens

<400> SEQUENCE: 114

Glu Val Ser Glu Ala Val
1               5

<210> SEQ ID NO 115
<211> LENGTH: 6
<212> TYPE: PRT
<213> ORGANISM: Homo sapiens

<400> SEQUENCE: 115

Ser Ile Glu Tyr Ser Pro
1               5

<210> SEQ ID NO 116
<211> LENGTH: 6
<212> TYPE: PRT
<213> ORGANISM: Homo sapiens
```

```
<400> SEQUENCE: 116

Asn Asn Asp Ile Ser Glu
1               5

<210> SEQ ID NO 117
<211> LENGTH: 6
<212> TYPE: PRT
<213> ORGANISM: Homo sapiens

<400> SEQUENCE: 117

Arg Ile Ser Glu Ala Lys
1               5

<210> SEQ ID NO 118
<211> LENGTH: 6
<212> TYPE: PRT
<213> ORGANISM: Homo sapiens

<400> SEQUENCE: 118

Leu Arg Lys Asp Asp Phe
1               5

<210> SEQ ID NO 119
<211> LENGTH: 6
<212> TYPE: PRT
<213> ORGANISM: Homo sapiens

<400> SEQUENCE: 119

Lys Asp Leu Pro Glu Thr
1               5

<210> SEQ ID NO 120
<211> LENGTH: 6
<212> TYPE: PRT
<213> ORGANISM: Homo sapiens

<400> SEQUENCE: 120

Leu Asn Glu Leu His Leu
1               5

<210> SEQ ID NO 121
<211> LENGTH: 6
<212> TYPE: PRT
<213> ORGANISM: Homo sapiens

<400> SEQUENCE: 121

Tyr Trp Glu Val Gln Pro
1               5

<210> SEQ ID NO 122
<211> LENGTH: 6
<212> TYPE: PRT
<213> ORGANISM: Homo sapiens

<400> SEQUENCE: 122

Lys Ile Gln Ala Ile Glu
1               5

<210> SEQ ID NO 123
<211> LENGTH: 6
<212> TYPE: PRT
<213> ORGANISM: Homo sapiens

<400> SEQUENCE: 123
```

Pro Glu Thr Leu Asn Glu
1               5

<210> SEQ ID NO 124
<211> LENGTH: 6
<212> TYPE: PRT
<213> ORGANISM: Homo sapiens

<400> SEQUENCE: 124

Leu Leu Arg Tyr Ser Lys
1               5

<210> SEQ ID NO 125
<211> LENGTH: 6
<212> TYPE: PRT
<213> ORGANISM: Homo sapiens

<400> SEQUENCE: 125

Glu Asp Leu Leu Arg Tyr
1               5

<210> SEQ ID NO 126
<211> LENGTH: 6
<212> TYPE: PRT
<213> ORGANISM: Homo sapiens

<400> SEQUENCE: 126

Asn Asn Asp Ile Ser Glu
1               5

<210> SEQ ID NO 127
<211> LENGTH: 6
<212> TYPE: PRT
<213> ORGANISM: Homo sapiens

<400> SEQUENCE: 127

Glu Leu Arg Lys Asp Asp
1               5

<210> SEQ ID NO 128
<211> LENGTH: 6
<212> TYPE: PRT
<213> ORGANISM: Homo sapiens

<400> SEQUENCE: 128

Asp Leu Leu Arg Tyr Ser
1               5

<210> SEQ ID NO 129
<211> LENGTH: 6
<212> TYPE: PRT
<213> ORGANISM: Homo sapiens

<400> SEQUENCE: 129

Ala Phe Asp Gly Leu Lys
1               5

<210> SEQ ID NO 130
<211> LENGTH: 6
<212> TYPE: PRT
<213> ORGANISM: Homo sapiens

<400> SEQUENCE: 130

Gly Thr Asn Pro Leu Lys

```
1               5

<210> SEQ ID NO 131
<211> LENGTH: 6
<212> TYPE: PRT
<213> ORGANISM: Homo sapiens

<400> SEQUENCE: 131

Ser Ser Gly Ile Glu Asn
1               5

<210> SEQ ID NO 132
<211> LENGTH: 6
<212> TYPE: PRT
<213> ORGANISM: Homo sapiens

<400> SEQUENCE: 132

Glu Val Pro Asp Asp Arg
1               5

<210> SEQ ID NO 133
<211> LENGTH: 6
<212> TYPE: PRT
<213> ORGANISM: Homo sapiens

<400> SEQUENCE: 133

Arg Val Asp Ala Ala Ser
1               5

<210> SEQ ID NO 134
<211> LENGTH: 6
<212> TYPE: PRT
<213> ORGANISM: Homo sapiens

<400> SEQUENCE: 134

Gly Ala Phe Thr Pro Leu
1               5

<210> SEQ ID NO 135
<211> LENGTH: 6
<212> TYPE: PRT
<213> ORGANISM: Homo sapiens

<400> SEQUENCE: 135

Leu Val Lys Leu Glu Arg
1               5

<210> SEQ ID NO 136
<211> LENGTH: 6
<212> TYPE: PRT
<213> ORGANISM: Homo sapiens

<400> SEQUENCE: 136

Gln Pro Ser Thr Phe Arg
1               5

<210> SEQ ID NO 137
<211> LENGTH: 6
<212> TYPE: PRT
<213> ORGANISM: Homo sapiens

<400> SEQUENCE: 137

Ala Phe Gln Gly Met Lys
1               5
```

<210> SEQ ID NO 138
<211> LENGTH: 6
<212> TYPE: PRT
<213> ORGANISM: Homo sapiens

<400> SEQUENCE: 138

Gly Met Lys Lys Leu Ser
1               5

<210> SEQ ID NO 139
<211> LENGTH: 6
<212> TYPE: PRT
<213> ORGANISM: Homo sapiens

<400> SEQUENCE: 139

Lys Asp Gly Asp Phe Lys
1               5

<210> SEQ ID NO 140
<211> LENGTH: 6
<212> TYPE: PRT
<213> ORGANISM: Homo sapiens

<400> SEQUENCE: 140

His Leu Asp Gly Asn Lys
1               5

<210> SEQ ID NO 141
<211> LENGTH: 6
<212> TYPE: PRT
<213> ORGANISM: Homo sapiens

<400> SEQUENCE: 141

Cys Asp Val Met Tyr Gly
1               5

<210> SEQ ID NO 142
<211> LENGTH: 6
<212> TYPE: PRT
<213> ORGANISM: Homo sapiens

<400> SEQUENCE: 142

Asn Gly Phe Asp Gln Cys
1               5

<210> SEQ ID NO 143
<211> LENGTH: 6
<212> TYPE: PRT
<213> ORGANISM: Homo sapiens

<400> SEQUENCE: 143

Gln Asn Gly Ile Asn Lys
1               5

<210> SEQ ID NO 144
<211> LENGTH: 6
<212> TYPE: PRT
<213> ORGANISM: Homo sapiens

<400> SEQUENCE: 144

Ile Gly Gln Asp Tyr Lys
1               5

<210> SEQ ID NO 145

```
<211> LENGTH: 6
<212> TYPE: PRT
<213> ORGANISM: Homo sapiens

<400> SEQUENCE: 145

Gln Leu Thr His Asn Lys
1               5

<210> SEQ ID NO 146
<211> LENGTH: 6
<212> TYPE: PRT
<213> ORGANISM: Homo sapiens

<400> SEQUENCE: 146

Val Ser Ala Ala Phe Lys
1               5

<210> SEQ ID NO 147
<211> LENGTH: 6
<212> TYPE: PRT
<213> ORGANISM: Homo sapiens

<400> SEQUENCE: 147

Gly Leu Lys Ser Leu Glu
1               5

<210> SEQ ID NO 148
<211> LENGTH: 6
<212> TYPE: PRT
<213> ORGANISM: Homo sapiens

<400> SEQUENCE: 148

Glu Asp Ala Gly Ser Arg
1               5

<210> SEQ ID NO 149
<211> LENGTH: 6
<212> TYPE: PRT
<213> ORGANISM: Homo sapiens

<400> SEQUENCE: 149

Glu Phe Arg Glu Val Ser
1               5

<210> SEQ ID NO 150
<211> LENGTH: 6
<212> TYPE: PRT
<213> ORGANISM: Homo sapiens

<400> SEQUENCE: 150

Val Ala Gln Gln Asp Ser
1               5

<210> SEQ ID NO 151
<211> LENGTH: 6
<212> TYPE: PRT
<213> ORGANISM: Homo sapiens

<400> SEQUENCE: 151

Leu Glu Pro Glu Tyr Arg
1               5

<210> SEQ ID NO 152
<211> LENGTH: 6
<212> TYPE: PRT
```

<213> ORGANISM: Homo sapiens

<400> SEQUENCE: 152

Ser Ala Lys Glu Phe Arg
1               5

<210> SEQ ID NO 153
<211> LENGTH: 1466
<212> TYPE: PRT
<213> ORGANISM: Homo sapiens

<400> SEQUENCE: 153

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu

```
                340             345             350
Val Gly Pro Ala Gly Ser Pro Gly Ser Asn Gly Ala Pro Gly Gln Arg
            355             360             365
Gly Glu Pro Gly Pro Gln Gly His Ala Gly Ala Gln Gly Pro Pro Gly
        370             375             380
Pro Pro Gly Ile Asn Gly Ser Pro Gly Gly Lys Gly Glu Met Gly Pro
385             390             395             400
Ala Gly Ile Pro Gly Ala Pro Gly Leu Met Gly Ala Arg Gly Pro Pro
            405             410             415
Gly Pro Ala Gly Ala Asn Gly Ala Pro Gly Leu Arg Gly Gly Ala Gly
        420             425             430
Glu Pro Gly Lys Asn Gly Ala Lys Gly Glu Pro Gly Pro Arg Gly Glu
        435             440             445
Arg Gly Glu Ala Gly Ile Pro Gly Val Pro Gly Ala Lys Gly Glu Asp
        450             455             460
Gly Lys Asp Gly Ser Pro Gly Glu Pro Gly Ala Asn Gly Leu Pro Gly
465             470             475             480
Ala Ala Gly Glu Arg Gly Ala Pro Gly Phe Arg Gly Pro Ala Gly Pro
            485             490             495
Asn Gly Ile Pro Gly Glu Lys Gly Pro Ala Gly Glu Arg Gly Ala Pro
            500             505             510
Gly Pro Ala Gly Pro Arg Gly Ala Ala Gly Glu Pro Gly Arg Asp Gly
        515             520             525
Val Pro Gly Gly Pro Gly Met Arg Gly Met Pro Gly Ser Pro Gly Gly
        530             535             540
Pro Gly Ser Asp Gly Lys Pro Gly Pro Pro Gly Ser Gln Gly Glu Ser
545             550             555             560
Gly Arg Pro Gly Pro Pro Gly Pro Ser Gly Pro Arg Gly Gln Pro Gly
            565             570             575
Val Met Gly Phe Pro Gly Pro Lys Gly Asn Asp Gly Ala Pro Gly Lys
        580             585             590
Asn Gly Glu Arg Gly Gly Pro Gly Gly Pro Gly Pro Gln Gly Pro Pro
        595             600             605
Gly Lys Asn Gly Glu Thr Gly Pro Gln Gly Pro Pro Gly Pro Thr Gly
        610             615             620
Pro Gly Gly Asp Lys Gly Asp Thr Gly Pro Pro Gly Pro Gln Gly Leu
625             630             635             640
Gln Gly Leu Pro Gly Thr Gly Gly Pro Pro Gly Glu Asn Gly Lys Pro
            645             650             655
Gly Glu Pro Gly Pro Lys Gly Asp Ala Gly Ala Pro Gly Ala Pro Gly
            660             665             670
Gly Lys Gly Asp Ala Gly Ala Pro Gly Glu Arg Gly Pro Pro Gly Leu
        675             680             685
Ala Gly Ala Pro Gly Leu Arg Gly Gly Ala Gly Pro Pro Gly Pro Glu
        690             695             700
Gly Gly Lys Gly Ala Ala Gly Pro Pro Gly Pro Pro Gly Ala Ala Gly
705             710             715             720
Thr Pro Gly Leu Gln Gly Met Pro Gly Glu Arg Gly Gly Leu Gly Ser
            725             730             735
Pro Gly Pro Lys Gly Asp Lys Gly Glu Pro Gly Gly Pro Gly Ala Asp
            740             745             750
Gly Val Pro Gly Lys Asp Gly Pro Arg Gly Pro Thr Gly Pro Ile Gly
        755             760             765
```

```
Pro Pro Gly Pro Ala Gly Gln Pro Gly Asp Lys Gly Glu Gly Gly Ala
        770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
            805                 810                 815

Gln Asn Gly Glu Pro Gly Gly Lys Gly Glu Arg Gly Ala Pro Gly Glu
            820                 825                 830

Lys Gly Glu Gly Gly Pro Pro Gly Val Ala Gly Pro Pro Gly Gly Ser
            835                 840                 845

Gly Pro Ala Gly Pro Pro Gly Pro Gln Gly Val Lys Gly Glu Arg Gly
            850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
            885                 890                 895

Gly Ser Pro Gly Lys Asp Gly Pro Pro Gly Pro Ala Gly Asn Thr Gly
            900                 905                 910

Ala Pro Gly Ser Pro Gly Val Ser Gly Pro Lys Gly Asp Ala Gly Gln
            915                 920                 925

Pro Gly Glu Lys Gly Ser Pro Gly Ala Gln Gly Pro Pro Gly Ala Pro
            930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
            980                 985                 990

Gly Pro Pro Gly Pro Gln Gly Leu Pro Gly Leu Ala Gly Thr Ala Gly
            995                 1000                1005

Glu Pro Gly Arg Asp Gly Asn Pro Gly Ser Asp Gly Leu Pro Gly
        1010                1015                1020

Arg Asp Gly Ser Pro Gly Gly Lys Gly Asp Arg Gly Glu Asn Gly
1025                1030                1035

Ser Pro Gly Ala Pro Gly Ala Pro Gly His Pro Gly Pro Pro Gly
1040                1045                1050

Pro Val Gly Pro Ala Gly Lys Ser Gly Asp Arg Gly Glu Ser Gly
1055                1060                1065

Pro Ala Gly Pro Ala Gly Ala Pro Gly Pro Ala Gly Ser Arg Gly
1070                1075                1080

Ala Pro Gly Pro Gln Gly Pro Arg Gly Asp Lys Gly Glu Thr Gly
1085                1090                1095

Glu Arg Gly Ala Ala Gly Ile Lys Gly His Arg Gly Phe Pro Gly
1100                1105                1110

Asn Pro Gly Ala Pro Gly Ser Pro Gly Pro Ala Gly Gln Gln Gly
1115                1120                1125

Ala Ile Gly Ser Pro Gly Pro Ala Gly Pro Arg Gly Pro Val Gly
1130                1135                1140

Pro Ser Gly Pro Pro Gly Lys Asp Gly Thr Ser Gly His Pro Gly
1145                1150                1155

Pro Ile Gly Pro Pro Gly Pro Arg Gly Asn Arg Gly Glu Arg Gly
1160                1165                1170
```

```
Ser Glu Gly Ser Pro Gly His Pro Gly Gln Pro Gly Pro Pro Gly
1175                1180                1185

Pro Pro Gly Ala Pro Gly Pro Cys Cys Gly Gly Val Gly Ala Ala
1190                1195                1200

Ala Ile Ala Gly Ile Gly Gly Glu Lys Ala Gly Gly Phe Ala Pro
1205                1210                1215

Tyr Tyr Gly Asp Glu Pro Met Asp Phe Lys Ile Asn Thr Asp Glu
1220                1225                1230

Ile Met Thr Ser Leu Lys Ser Val Asn Gly Gln Ile Glu Ser Leu
1235                1240                1245

Ile Ser Pro Asp Gly Ser Arg Lys Asn Pro Ala Arg Asn Cys Arg
1250                1255                1260

Asp Leu Lys Phe Cys His Pro Glu Leu Lys Ser Gly Glu Tyr Trp
1265                1270                1275

Val Asp Pro Asn Gln Gly Cys Lys Leu Asp Ala Ile Lys Val Phe
1280                1285                1290

Cys Asn Met Glu Thr Gly Glu Thr Cys Ile Ser Ala Asn Pro Leu
1295                1300                1305

Asn Val Pro Arg Lys His Trp Trp Thr Asp Ser Ser Ala Glu Lys
1310                1315                1320

Lys His Val Trp Phe Gly Glu Ser Met Asp Gly Gly Phe Gln Phe
1325                1330                1335

Ser Tyr Gly Asn Pro Glu Leu Pro Glu Asp Val Leu Asp Val Gln
1340                1345                1350

Leu Ala Phe Leu Arg Leu Leu Ser Ser Arg Ala Ser Gln Asn Ile
1355                1360                1365

Thr Tyr His Cys Lys Asn Ser Ile Ala Tyr Met Asp Gln Ala Ser
1370                1375                1380

Gly Asn Val Lys Lys Ala Leu Lys Leu Met Gly Ser Asn Glu Gly
1385                1390                1395

Glu Phe Lys Ala Glu Gly Asn Ser Lys Phe Thr Tyr Thr Val Leu
1400                1405                1410

Glu Asp Gly Cys Thr Lys His Thr Gly Glu Trp Ser Lys Thr Val
1415                1420                1425

Phe Glu Tyr Arg Thr Arg Lys Ala Val Arg Leu Pro Ile Val Asp
1430                1435                1440

Ile Ala Pro Tyr Asp Ile Gly Gly Pro Asp Gln Glu Phe Gly Val
1445                1450                1455

Asp Val Gly Pro Val Cys Phe Leu
1460                1465

<210> SEQ ID NO 154
<211> LENGTH: 20
<212> TYPE: PRT
<213> ORGANISM: Homo sapiens

<400> SEQUENCE: 154

Ala Gly Ile Pro Gly Ala Pro Gly Leu Met Gly Ala Arg Gly Pro Pro
1               5                   10                  15

Gly Pro Ala Gly
            20

<210> SEQ ID NO 155
<211> LENGTH: 19
<212> TYPE: PRT
<213> ORGANISM: Homo sapiens
```

<400> SEQUENCE: 155

Lys Gly Asp Pro Gly Pro Pro Gly Ile Pro Gly Arg Asn Gly Asp Pro
1               5                   10                  15

Gly Ile Pro

<210> SEQ ID NO 156
<211> LENGTH: 20
<212> TYPE: PRT
<213> ORGANISM: Homo sapiens

<400> SEQUENCE: 156

Gly Leu Ala Gly Pro Pro Gly Met Pro Gly Pro Arg Gly Ser Pro Gly
1               5                   10                  15

Pro Gln Gly Val
            20

<210> SEQ ID NO 157
<211> LENGTH: 21
<212> TYPE: PRT
<213> ORGANISM: Homo sapiens

<400> SEQUENCE: 157

Gly Glu Arg Gly Leu Pro Gly Pro Pro Gly Ile Lys Gly Pro Ala Gly
1               5                   10                  15

Ile Pro Gly Phe Pro
            20

<210> SEQ ID NO 158
<211> LENGTH: 22
<212> TYPE: PRT
<213> ORGANISM: Homo sapiens

<400> SEQUENCE: 158

Gly Ile Ala Gly Ile Thr Gly Ala Arg Gly Leu Ala Gly Pro Pro Gly
1               5                   10                  15

Met Pro Gly Pro Arg Gly
            20

<210> SEQ ID NO 159
<211> LENGTH: 23
<212> TYPE: PRT
<213> ORGANISM: Homo sapiens

<400> SEQUENCE: 159

Gly Ile Lys Gly His Arg Gly Phe Pro Gly Asn Pro Gly Ala Pro Gly
1               5                   10                  15

Ser Pro Gly Pro Ala Gly Gln
            20

<210> SEQ ID NO 160
<211> LENGTH: 23
<212> TYPE: PRT
<213> ORGANISM: Homo sapiens

<400> SEQUENCE: 160

Ala Arg Gly Leu Ala Gly Pro Pro Gly Met Pro Gly Pro Arg Gly Ser
1               5                   10                  15

Pro Gly Pro Gln Gly Val Lys
            20

-continued

<210> SEQ ID NO 161
<211> LENGTH: 25
<212> TYPE: PRT
<213> ORGANISM: Homo sapiens

<400> SEQUENCE: 161

Ile Thr Gly Ala Arg Gly Leu Ala Gly Pro Pro Gly Met Pro Gly Pro
1               5                   10                  15

Arg Gly Ser Pro Gly Pro Gln Gly Val
            20                  25

<210> SEQ ID NO 162
<211> LENGTH: 26
<212> TYPE: PRT
<213> ORGANISM: Homo sapiens

<400> SEQUENCE: 162

Ile Thr Gly Ala Arg Gly Leu Ala Gly Pro Pro Gly Met Pro Gly Pro
1               5                   10                  15

Arg Gly Ser Pro Gly Pro Gln Gly Val Lys
            20                  25

<210> SEQ ID NO 163
<211> LENGTH: 26
<212> TYPE: PRT
<213> ORGANISM: Homo sapiens

<400> SEQUENCE: 163

Gly Ile Thr Gly Ala Arg Gly Leu Ala Gly Pro Pro Gly Met Pro Gly
1               5                   10                  15

Pro Arg Gly Ser Pro Gly Pro Gln Gly Val
            20                  25

<210> SEQ ID NO 164
<211> LENGTH: 26
<212> TYPE: PRT
<213> ORGANISM: Homo sapiens

<400> SEQUENCE: 164

Gly Val Lys Gly Glu Ser Gly Lys Pro Gly Ala Asn Gly Leu Ser Gly
1               5                   10                  15

Glu Arg Gly Pro Pro Gly Pro Gln Gly Leu
            20                  25

<210> SEQ ID NO 165
<211> LENGTH: 26
<212> TYPE: PRT
<213> ORGANISM: Homo sapiens

<400> SEQUENCE: 165

Gly Ser Arg Gly Ala Pro Gly Pro Gln Gly Pro Arg Gly Asp Lys Gly
1               5                   10                  15

Glu Thr Gly Glu Arg Gly Ala Ala Gly Ile
            20                  25

<210> SEQ ID NO 166
<211> LENGTH: 28
<212> TYPE: PRT
<213> ORGANISM: Homo sapiens

<400> SEQUENCE: 166

Pro Lys Gly Asp Ala Gly Gln Pro Gly Glu Lys Gly Ser Pro Gly Ala
1               5                   10                  15

Gln Gly Pro Pro Gly Ala Pro Gly Pro Leu Gly Ile
            20                  25

<210> SEQ ID NO 167
<211> LENGTH: 27
<212> TYPE: PRT
<213> ORGANISM: Homo sapiens

<400> SEQUENCE: 167

Gly Ile Thr Gly Ala Arg Gly Leu Ala Gly Pro Pro Gly Met Pro Gly
1               5                   10                  15

Pro Arg Gly Ser Pro Gly Pro Gln Gly Val Lys
            20                  25

<210> SEQ ID NO 168
<211> LENGTH: 32
<212> TYPE: PRT
<213> ORGANISM: Homo sapiens

<400> SEQUENCE: 168

Gly Leu Arg Gly Gly Ala Gly Pro Pro Gly Pro Glu Gly Gly Lys Gly
1               5                   10                  15

Ala Ala Gly Pro Pro Gly Pro Pro Gly Ala Ala Gly Thr Pro Gly Leu
            20                  25                  30

<210> SEQ ID NO 169
<211> LENGTH: 35
<212> TYPE: PRT
<213> ORGANISM: Homo sapiens

<400> SEQUENCE: 169

Gly His Ala Gly Ala Gln Gly Pro Pro Gly Pro Pro Gly Ile Asn Gly
1               5                   10                  15

Ser Pro Gly Gly Lys Gly Glu Met Gly Pro Ala Gly Ile Pro Gly Ala
            20                  25                  30

Pro Gly Leu
        35

<210> SEQ ID NO 170
<211> LENGTH: 48
<212> TYPE: PRT
<213> ORGANISM: Homo sapiens

<400> SEQUENCE: 170

Ala Gly Lys Ser Gly Asp Arg Gly Glu Ser Gly Pro Ala Gly Pro Ala
1               5                   10                  15

Gly Ala Pro Gly Pro Ala Gly Ser Arg Gly Ala Pro Gly Pro Gln Gly
            20                  25                  30

Pro Arg Gly Asp Lys Gly Glu Thr Gly Glu Arg Gly Ala Ala Gly Ile
        35                  40                  45

<210> SEQ ID NO 171
<211> LENGTH: 50
<212> TYPE: PRT
<213> ORGANISM: Homo sapiens

<400> SEQUENCE: 171

Gly Leu Gln Gly Leu Pro Gly Thr Gly Gly Pro Pro Gly Glu Asn Gly
1               5                   10                  15

Lys Pro Gly Glu Pro Gly Pro Lys Gly Asp Ala Gly Ala Pro Gly Ala
            20                  25                  30

```
Pro Gly Gly Lys Gly Asp Ala Gly Ala Pro Gly Glu Arg Gly Pro Pro
        35                  40                  45
Gly Leu
    50

<210> SEQ ID NO 172
<211> LENGTH: 21
<212> TYPE: PRT
<213> ORGANISM: Homo sapiens

<400> SEQUENCE: 172

Gly Glu Arg Gly Leu Pro Gly Pro Pro Gly Ile Lys Gly Pro Ala Gly
1               5                   10                  15

Ile Pro Gly Phe Pro
            20

<210> SEQ ID NO 173
<211> LENGTH: 24
<212> TYPE: PRT
<213> ORGANISM: Homo sapiens

<400> SEQUENCE: 173

Ala Val Gly Gly Leu Ala Gly Tyr Pro Gly Pro Ala Gly Pro Pro Gly
1               5                   10                  15

Pro Pro Gly Pro Pro Gly Thr Ser
            20

<210> SEQ ID NO 174
<211> LENGTH: 24
<212> TYPE: PRT
<213> ORGANISM: Homo sapiens

<400> SEQUENCE: 174

Lys Asp Gly Thr Ser Gly His Pro Gly Pro Ile Gly Pro Pro Gly Pro
1               5                   10                  15

Arg Gly Asn Arg Gly Glu Arg Gly
            20

<210> SEQ ID NO 175
<211> LENGTH: 29
<212> TYPE: PRT
<213> ORGANISM: Homo sapiens

<400> SEQUENCE: 175

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser
            20                  25

<210> SEQ ID NO 176
<211> LENGTH: 29
<212> TYPE: PRT
<213> ORGANISM: Homo sapiens

<400> SEQUENCE: 176

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 177
```

```
<211> LENGTH: 31
<212> TYPE: PRT
<213> ORGANISM: Homo sapiens

<400> SEQUENCE: 177

Ala Pro Gly Ala Pro Gly Gly Lys Gly Asp Ala Gly Ala Pro Gly Glu
1               5                   10                  15

Arg Gly Pro Pro Gly Leu Ala Gly Ala Pro Gly Leu Arg Gly Gly
            20                  25                  30

<210> SEQ ID NO 178
<211> LENGTH: 32
<212> TYPE: PRT
<213> ORGANISM: Homo sapiens

<400> SEQUENCE: 178

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser Pro Gly Ser
            20                  25                  30

<210> SEQ ID NO 179
<211> LENGTH: 22
<212> TYPE: PRT
<213> ORGANISM: Homo sapiens

<400> SEQUENCE: 179

Ala Ile Gly Ser Pro Gly Pro Ala Gly Pro Arg Gly Pro Val Gly Pro
1               5                   10                  15

Ser Gly Pro Pro Gly Lys
            20

<210> SEQ ID NO 180
<211> LENGTH: 23
<212> TYPE: PRT
<213> ORGANISM: Homo sapiens

<400> SEQUENCE: 180

Gly Ala Ile Gly Ser Pro Gly Pro Ala Gly Pro Arg Gly Pro Val Gly
1               5                   10                  15

Pro Ser Gly Pro Pro Gly Lys
            20

<210> SEQ ID NO 181
<211> LENGTH: 15
<212> TYPE: PRT
<213> ORGANISM: Homo sapiens

<400> SEQUENCE: 181

Pro Ala Gly Gln Gln Gly Ala Ile Gly Ser Pro Gly Pro Ala Gly
1               5                   10                  15

<210> SEQ ID NO 182
<211> LENGTH: 20
<212> TYPE: PRT
<213> ORGANISM: Homo sapiens

<400> SEQUENCE: 182

Gly Gly Pro Pro Gly Val Ala Gly Pro Pro Gly Gly Ser Gly Pro Ala
1               5                   10                  15

Gly Pro Pro Gly
            20
```

<210> SEQ ID NO 183
<211> LENGTH: 19
<212> TYPE: PRT
<213> ORGANISM: Homo sapiens

<400> SEQUENCE: 183

Leu Ala Gly Pro Pro Gly Met Pro Gly Pro Arg Gly Ser Pro Gly
1               5                   10                  15

Gln Gly Val

<210> SEQ ID NO 184
<211> LENGTH: 19
<212> TYPE: PRT
<213> ORGANISM: Homo sapiens

<400> SEQUENCE: 184

Gly Leu Ser Gly Glu Arg Gly Pro Pro Gly Pro Gln Gly Leu Pro Gly
1               5                   10                  15

Leu Ala Gly

<210> SEQ ID NO 185
<211> LENGTH: 21
<212> TYPE: PRT
<213> ORGANISM: Homo sapiens

<400> SEQUENCE: 185

Arg Gly Leu Ala Gly Pro Pro Gly Met Pro Gly Pro Arg Gly Ser Pro
1               5                   10                  15

Gly Pro Gln Gly Val
            20

<210> SEQ ID NO 186
<211> LENGTH: 21
<212> TYPE: PRT
<213> ORGANISM: Homo sapiens

<400> SEQUENCE: 186

Gly Leu Ala Gly Pro Pro Gly Met Pro Gly Pro Arg Gly Ser Pro Gly
1               5                   10                  15

Pro Gln Gly Val Lys
            20

<210> SEQ ID NO 187
<211> LENGTH: 22
<212> TYPE: PRT
<213> ORGANISM: Homo sapiens

<400> SEQUENCE: 187

Arg Gly Leu Ala Gly Pro Pro Gly Met Pro Gly Pro Arg Gly Ser Pro
1               5                   10                  15

Gly Pro Gln Gly Val Lys
            20

<210> SEQ ID NO 188
<211> LENGTH: 21
<212> TYPE: PRT
<213> ORGANISM: Homo sapiens

<400> SEQUENCE: 188

Gly Pro Gln Gly Pro Pro Gly Lys Asn Gly Glu Thr Gly Pro Gln Gly
1               5                   10                  15

```
Pro Pro Gly Pro Thr
            20

<210> SEQ ID NO 189
<211> LENGTH: 22
<212> TYPE: PRT
<213> ORGANISM: Homo sapiens

<400> SEQUENCE: 189

Gly Val Lys Gly Glu Arg Gly Ser Pro Gly Gly Pro Gly Ala Ala Gly
1               5                   10                  15

Phe Pro Gly Ala Arg Gly
            20

<210> SEQ ID NO 190
<211> LENGTH: 22
<212> TYPE: PRT
<213> ORGANISM: Homo sapiens

<400> SEQUENCE: 190

Ala Arg Gly Leu Ala Gly Pro Pro Gly Met Pro Gly Pro Arg Gly Ser
1               5                   10                  15

Pro Gly Pro Gln Gly Val
            20

<210> SEQ ID NO 191
<211> LENGTH: 23
<212> TYPE: PRT
<213> ORGANISM: Homo sapiens

<400> SEQUENCE: 191

Asn Gly Leu Ser Gly Glu Arg Gly Pro Pro Gly Pro Gln Gly Leu Pro
1               5                   10                  15

Gly Leu Ala Gly Thr Ala Gly
            20

<210> SEQ ID NO 192
<211> LENGTH: 24
<212> TYPE: PRT
<213> ORGANISM: Homo sapiens

<400> SEQUENCE: 192

Ala Val Gly Gly Leu Ala Gly Tyr Pro Gly Pro Ala Gly Pro Pro Gly
1               5                   10                  15

Pro Pro Gly Pro Pro Gly Thr Ser
            20

<210> SEQ ID NO 193
<211> LENGTH: 24
<212> TYPE: PRT
<213> ORGANISM: Homo sapiens

<400> SEQUENCE: 193

Gly Ser Pro Gly Gly Lys Gly Glu Met Gly Pro Ala Gly Ile Pro Gly
1               5                   10                  15

Ala Pro Gly Leu Met Gly Ala Arg
            20

<210> SEQ ID NO 194
<211> LENGTH: 24
<212> TYPE: PRT
<213> ORGANISM: Homo sapiens
```

-continued

```
<400> SEQUENCE: 194

Thr Gly Ala Arg Gly Leu Ala Gly Pro Pro Gly Met Pro Gly Pro Arg
1               5                   10                  15

Gly Ser Pro Gly Pro Gln Gly Val
            20

<210> SEQ ID NO 195
<211> LENGTH: 25
<212> TYPE: PRT
<213> ORGANISM: Homo sapiens

<400> SEQUENCE: 195

Val Lys Gly Glu Ser Gly Lys Pro Gly Ala Asn Gly Leu Ser Gly Glu
1               5                   10                  15

Arg Gly Pro Pro Gly Pro Gln Gly Leu
            20                  25

<210> SEQ ID NO 196
<211> LENGTH: 53
<212> TYPE: PRT
<213> ORGANISM: Homo sapiens

<400> SEQUENCE: 196

Gly Val Lys Gly Glu Arg Gly Ser Pro Gly Gly Pro Gly Ala Ala Gly
1               5                   10                  15

Phe Pro Gly Ala Arg Gly Leu Pro Gly Pro Pro Gly Ser Asn Gly Asn
            20                  25                  30

Pro Gly Pro Pro Gly Pro Ser Gly Ser Pro Gly Lys Asp Gly Pro Pro
        35                  40                  45

Gly Pro Ala Gly Asn
        50

<210> SEQ ID NO 197
<211> LENGTH: 32
<212> TYPE: PRT
<213> ORGANISM: Homo sapiens

<400> SEQUENCE: 197

Gly Ser Pro Gly Ala Gln Gly Pro Pro Gly Ala Pro Gly Pro Leu Gly
1               5                   10                  15

Ile Ala Gly Ile Thr Gly Ala Arg Gly Leu Ala Gly Pro Pro Gly Met
            20                  25                  30

<210> SEQ ID NO 198
<211> LENGTH: 32
<212> TYPE: PRT
<213> ORGANISM: Homo sapiens

<400> SEQUENCE: 198

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

<210> SEQ ID NO 199
<211> LENGTH: 32
<212> TYPE: PRT
<213> ORGANISM: Homo sapiens

<400> SEQUENCE: 199

Arg Gly Ala Pro Gly Glu Lys Gly Glu Gly Gly Pro Pro Gly Val Ala
```

```
                1               5                   10                  15
Gly Pro Pro Gly Gly Ser Gly Pro Ala Gly Pro Pro Gly Pro Gln Gly
            20                  25                  30

<210> SEQ ID NO 200
<211> LENGTH: 29
<212> TYPE: PRT
<213> ORGANISM: Homo sapiens

<400> SEQUENCE: 200

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 201
<211> LENGTH: 14
<212> TYPE: PRT
<213> ORGANISM: Homo sapiens

<400> SEQUENCE: 201

Gly Ile Lys Gly Pro Ala Gly Ile Pro Gly Phe Pro Gly Met
1               5                   10

<210> SEQ ID NO 202
<211> LENGTH: 14
<212> TYPE: PRT
<213> ORGANISM: Homo sapiens

<400> SEQUENCE: 202

Gly Gln Pro Gly Val Met Gly Phe Pro Gly Pro Lys Gly Asn
1               5                   10

<210> SEQ ID NO 203
<211> LENGTH: 16
<212> TYPE: PRT
<213> ORGANISM: Homo sapiens

<400> SEQUENCE: 203

Gly Ile Lys Gly Pro Ala Gly Ile Pro Gly Phe Pro Gly Met Lys Gly
1               5                   10                  15

<210> SEQ ID NO 204
<211> LENGTH: 17
<212> TYPE: PRT
<213> ORGANISM: Homo sapiens

<400> SEQUENCE: 204

Gly Ile Lys Gly Pro Ala Gly Ile Pro Gly Phe Pro Gly Met Lys Gly
1               5                   10                  15

His

<210> SEQ ID NO 205
<211> LENGTH: 19
<212> TYPE: PRT
<213> ORGANISM: Homo sapiens

<400> SEQUENCE: 205

Ile Pro Gly Ala Pro Gly Leu Met Gly Ala Arg Gly Pro Pro Gly Pro
1               5                   10                  15

Ala Gly Ala
```

```
<210> SEQ ID NO 206
<211> LENGTH: 19
<212> TYPE: PRT
<213> ORGANISM: Homo sapiens

<400> SEQUENCE: 206

Gly Glu Arg Gly Leu Pro Gly Pro Pro Gly Ile Lys Gly Pro Ala Gly
1               5                   10                  15

Ile Pro Gly

<210> SEQ ID NO 207
<211> LENGTH: 20
<212> TYPE: PRT
<213> ORGANISM: Homo sapiens

<400> SEQUENCE: 207

Gly Ile Pro Gly Ala Pro Gly Leu Met Gly Ala Arg Gly Pro Pro Gly
1               5                   10                  15

Pro Ala Gly Ala
            20

<210> SEQ ID NO 208
<211> LENGTH: 20
<212> TYPE: PRT
<213> ORGANISM: Homo sapiens

<400> SEQUENCE: 208

Gly Phe Arg Gly Pro Ala Gly Pro Asn Gly Ile Pro Gly Glu Lys Gly
1               5                   10                  15

Pro Ala Gly Glu
            20

<210> SEQ ID NO 209
<211> LENGTH: 20
<212> TYPE: PRT
<213> ORGANISM: Homo sapiens

<400> SEQUENCE: 209

Pro Gly Ile Pro Gly Gln Pro Gly Ser Pro Gly Ser Pro Gly Pro Pro
1               5                   10                  15

Gly Ile Cys Glu
            20

<210> SEQ ID NO 210
<211> LENGTH: 21
<212> TYPE: PRT
<213> ORGANISM: Homo sapiens

<400> SEQUENCE: 210

Gly Glu Arg Gly Leu Pro Gly Pro Pro Gly Ile Lys Gly Pro Ala Gly
1               5                   10                  15

Ile Pro Gly Phe Pro
            20

<210> SEQ ID NO 211
<211> LENGTH: 23
<212> TYPE: PRT
<213> ORGANISM: Homo sapiens

<400> SEQUENCE: 211

Ala Val Gly Gly Leu Ala Gly Tyr Pro Gly Pro Ala Gly Pro Pro Gly
1               5                   10                  15
```

```
Pro Pro Gly Pro Pro Gly Thr
            20

<210> SEQ ID NO 212
<211> LENGTH: 23
<212> TYPE: PRT
<213> ORGANISM: Homo sapiens

<400> SEQUENCE: 212

Gly Val Lys Gly Glu Arg Gly Ser Pro Gly Gly Pro Gly Ala Ala Gly
1               5                   10                  15

Phe Pro Gly Ala Arg Gly Leu
            20

<210> SEQ ID NO 213
<211> LENGTH: 26
<212> TYPE: PRT
<213> ORGANISM: Homo sapiens

<400> SEQUENCE: 213

Gly Asp Ala Gly Ala Pro Gly Ala Pro Gly Gly Lys Gly Asp Ala Gly
1               5                   10                  15

Ala Pro Gly Glu Arg Gly Pro Pro Gly Leu
            20                  25

<210> SEQ ID NO 214
<211> LENGTH: 25
<212> TYPE: PRT
<213> ORGANISM: Homo sapiens

<400> SEQUENCE: 214

Gln Gly Pro Pro Gly Pro Thr Gly Pro Gly Gly Asp Lys Gly Asp Thr
1               5                   10                  15

Gly Pro Pro Gly Pro Gln Gly Leu Gln
            20                  25

<210> SEQ ID NO 215
<211> LENGTH: 25
<212> TYPE: PRT
<213> ORGANISM: Homo sapiens

<400> SEQUENCE: 215

Gly Ile Asn Gly Ser Pro Gly Gly Lys Gly Glu Met Gly Pro Ala Gly
1               5                   10                  15

Ile Pro Gly Ala Pro Gly Leu Met Gly
            20                  25

<210> SEQ ID NO 216
<211> LENGTH: 26
<212> TYPE: PRT
<213> ORGANISM: Homo sapiens

<400> SEQUENCE: 216

Gln Gly Pro Pro Gly Glu Pro Gly Gln Ala Gly Pro Ser Gly Pro Pro
1               5                   10                  15

Gly Pro Pro Gly Ala Ile Gly Pro Ser Gly
            20                  25

<210> SEQ ID NO 217
<211> LENGTH: 26
<212> TYPE: PRT
<213> ORGANISM: Homo sapiens
```

```
<400> SEQUENCE: 217

Pro Gly Pro Pro Gly Ile Asn Gly Ser Pro Gly Gly Lys Gly Glu Met
1               5                   10                  15

Gly Pro Ala Gly Ile Pro Gly Ala Pro Gly
            20                  25

<210> SEQ ID NO 218
<211> LENGTH: 33
<212> TYPE: PRT
<213> ORGANISM: Homo sapiens

<400> SEQUENCE: 218

Arg Gly Leu Pro Gly Pro Gly Ser Asn Gly Asn Pro Gly Pro Pro
1               5                   10                  15

Gly Pro Ser Gly Ser Pro Gly Lys Asp Gly Pro Pro Gly Pro Ala Gly
            20                  25                  30

Asn

<210> SEQ ID NO 219
<211> LENGTH: 32
<212> TYPE: PRT
<213> ORGANISM: Homo sapiens

<400> SEQUENCE: 219

Gly Lys Asn Gly Glu Thr Gly Pro Gln Gly Pro Pro Gly Pro Thr Gly
1               5                   10                  15

Pro Gly Gly Asp Lys Gly Asp Thr Gly Pro Pro Gly Pro Gln Gly Leu
            20                  25                  30

<210> SEQ ID NO 220
<211> LENGTH: 32
<212> TYPE: PRT
<213> ORGANISM: Homo sapiens

<400> SEQUENCE: 220

Gly Leu Pro Gly Ile Ala Gly Pro Arg Gly Ser Pro Gly Glu Arg Gly
1               5                   10                  15

Glu Thr Gly Pro Pro Gly Pro Ala Gly Phe Pro Gly Ala Pro Gly Gln
            20                  25                  30

<210> SEQ ID NO 221
<211> LENGTH: 35
<212> TYPE: PRT
<213> ORGANISM: Homo sapiens

<400> SEQUENCE: 221

Gly Ile Asn Gly Ser Pro Gly Gly Lys Gly Glu Met Gly Pro Ala Gly
1               5                   10                  15

Ile Pro Gly Ala Pro Gly Leu Met Gly Ala Arg Gly Pro Pro Gly Pro
            20                  25                  30

Ala Gly Ala
        35

<210> SEQ ID NO 222
<211> LENGTH: 36
<212> TYPE: PRT
<213> ORGANISM: Homo sapiens

<400> SEQUENCE: 222

Pro Gly Ile Asn Gly Ser Pro Gly Gly Lys Gly Glu Met Gly Pro Ala
1               5                   10                  15
```

-continued

Gly Ile Pro Gly Ala Pro Gly Leu Met Gly Ala Arg Gly Pro Pro Gly
            20                  25                  30

Pro Ala Gly Ala
        35

<210> SEQ ID NO 223
<211> LENGTH: 40
<212> TYPE: PRT
<213> ORGANISM: Homo sapiens

<400> SEQUENCE: 223

Pro Pro Gly Glu Asn Gly Lys Pro Gly Glu Pro Gly Pro Lys Gly Asp
1               5                   10                  15

Ala Gly Ala Pro Gly Ala Pro Gly Lys Gly Asp Ala Gly Ala Pro
            20                  25                  30

Gly Glu Arg Gly Pro Pro Gly Leu
        35                  40

<210> SEQ ID NO 224
<211> LENGTH: 38
<212> TYPE: PRT
<213> ORGANISM: Homo sapiens

<400> SEQUENCE: 224

Gly Leu Lys Gly Glu Asn Gly Leu Pro Gly Glu Asn Gly Ala Pro Gly
1               5                   10                  15

Pro Met Gly Pro Arg Gly Ala Pro Gly Glu Arg Gly Arg Pro Gly Leu
            20                  25                  30

Pro Gly Ala Ala Gly Ala
        35

<210> SEQ ID NO 225
<211> LENGTH: 41
<212> TYPE: PRT
<213> ORGANISM: Homo sapiens

<400> SEQUENCE: 225

Gly Asn Thr Gly Ala Pro Gly Ser Pro Gly Val Ser Gly Pro Lys Gly
1               5                   10                  15

Asp Ala Gly Gln Pro Gly Glu Lys Gly Ser Pro Gly Ala Gln Gly Pro
            20                  25                  30

Pro Gly Ala Pro Gly Pro Leu Gly Ile
        35                  40

<210> SEQ ID NO 226
<211> LENGTH: 41
<212> TYPE: PRT
<213> ORGANISM: Homo sapiens

<400> SEQUENCE: 226

Gly Leu Met Gly Ala Arg Gly Pro Pro Gly Pro Ala Gly Ala Asn Gly
1               5                   10                  15

Ala Pro Gly Leu Arg Gly Gly Ala Gly Glu Pro Gly Lys Asn Gly Ala
            20                  25                  30

Lys Gly Glu Pro Gly Pro Arg Gly Glu
        35                  40

<210> SEQ ID NO 227
<211> LENGTH: 50
<212> TYPE: PRT

<213> ORGANISM: Homo sapiens

<400> SEQUENCE: 227

Gly Leu Arg Gly Gly Ala Gly Pro Pro Gly Pro Glu Gly Gly Lys Gly
1               5                   10                  15
Ala Ala Gly Pro Pro Gly Pro Pro Gly Ala Ala Gly Thr Pro Gly Leu
            20                  25                  30
Gln Gly Met Pro Gly Glu Arg Gly Gly Leu Gly Ser Pro Gly Pro Lys
        35                  40                  45
Gly Asp
    50

<210> SEQ ID NO 228
<211> LENGTH: 26
<212> TYPE: PRT
<213> ORGANISM: Homo sapiens

<400> SEQUENCE: 228

Gly Gln Gln Gly Ala Ile Gly Ser Pro Gly Pro Ala Gly Pro Arg Gly
1               5                   10                  15
Pro Val Gly Pro Ser Gly Pro Pro Gly Lys
            20                  25

<210> SEQ ID NO 229
<211> LENGTH: 24
<212> TYPE: PRT
<213> ORGANISM: Homo sapiens

<400> SEQUENCE: 229

Lys Gly Asp Pro Gly Pro Pro Gly Ile Pro Gly Arg Asn Gly Asp Pro
1               5                   10                  15
Gly Ile Pro Gly Gln Pro Gly Ser
            20

<210> SEQ ID NO 230
<211> LENGTH: 26
<212> TYPE: PRT
<213> ORGANISM: Homo sapiens

<400> SEQUENCE: 230

Gly Leu Arg Gly Gly Ala Gly Pro Pro Gly Pro Glu Gly Gly Lys Gly
1               5                   10                  15
Ala Ala Gly Pro Pro Gly Pro Pro Gly Ala
            20                  25

<210> SEQ ID NO 231
<211> LENGTH: 32
<212> TYPE: PRT
<213> ORGANISM: Homo sapiens

<400> SEQUENCE: 231

Gly Lys Asn Gly Glu Thr Gly Pro Gln Gly Pro Pro Gly Pro Thr Gly
1               5                   10                  15
Pro Gly Gly Asp Lys Gly Asp Thr Gly Pro Pro Gly Pro Gln Gly Leu
            20                  25                  30

<210> SEQ ID NO 232
<211> LENGTH: 23
<212> TYPE: PRT
<213> ORGANISM: Homo sapiens

<400> SEQUENCE: 232

Gly Tyr Gln Gly Pro Pro Gly Glu Pro Gly Gln Ala Gly Pro Ser Gly
1               5                   10                  15

Pro Pro Gly Pro Pro Gly Ala
            20

<210> SEQ ID NO 233
<211> LENGTH: 20
<212> TYPE: PRT
<213> ORGANISM: Homo sapiens

<400> SEQUENCE: 233

Gly Val Ala Gly Pro Pro Gly Gly Ser Gly Pro Ala Gly Pro Pro Gly
1               5                   10                  15

Pro Gln Gly Val
            20

<210> SEQ ID NO 234
<211> LENGTH: 35
<212> TYPE: PRT
<213> ORGANISM: Homo sapiens

<400> SEQUENCE: 234

Gly Asp Lys Gly Glu Pro Gly Gly Pro Gly Ala Asp Gly Val Pro Gly
1               5                   10                  15

Lys Asp Gly Pro Arg Gly Pro Thr Gly Pro Ile Gly Pro Pro Gly Pro
            20                  25                  30

Ala Gly Gln
        35

<210> SEQ ID NO 235
<211> LENGTH: 17
<212> TYPE: PRT
<213> ORGANISM: Homo sapiens

<400> SEQUENCE: 235

Gln Gly His Ala Gly Ala Gln Gly Pro Pro Gly Pro Pro Gly Ile Asn
1               5                   10                  15

Gly

<210> SEQ ID NO 236
<211> LENGTH: 11
<212> TYPE: PRT
<213> ORGANISM: Homo sapiens

<400> SEQUENCE: 236

Ala Gly Glu Arg Gly Ala Pro Gly Pro Ala Gly
1               5                   10

<210> SEQ ID NO 237
<211> LENGTH: 11
<212> TYPE: PRT
<213> ORGANISM: Homo sapiens

<400> SEQUENCE: 237

Ala Gly Ile Pro Gly Phe Pro Gly Met Lys Gly
1               5                   10

<210> SEQ ID NO 238
<211> LENGTH: 12
<212> TYPE: PRT
<213> ORGANISM: Homo sapiens

```
<400> SEQUENCE: 238

Phe Pro Gly Met Lys Gly His Arg Gly Phe Asp Gly
1               5                   10

<210> SEQ ID NO 239
<211> LENGTH: 14
<212> TYPE: PRT
<213> ORGANISM: Homo sapiens

<400> SEQUENCE: 239

Gly Phe Pro Gly Ala Arg Gly Leu Pro Gly Pro Gly Ser
1               5                   10

<210> SEQ ID NO 240
<211> LENGTH: 15
<212> TYPE: PRT
<213> ORGANISM: Homo sapiens

<400> SEQUENCE: 240

Ala Gly Phe Pro Gly Ala Arg Gly Leu Pro Gly Pro Pro Gly Ser
1               5                   10                  15

<210> SEQ ID NO 241
<211> LENGTH: 15
<212> TYPE: PRT
<213> ORGANISM: Homo sapiens

<400> SEQUENCE: 241

Pro Pro Gly Pro Pro Gly Pro Pro Gly Thr Ser Gly His Pro Gly
1               5                   10                  15

<210> SEQ ID NO 242
<211> LENGTH: 13
<212> TYPE: PRT
<213> ORGANISM: Homo sapiens

<400> SEQUENCE: 242

Gly Phe Pro Gly Met Lys Gly His Arg Gly Phe Asp Gly
1               5                   10

<210> SEQ ID NO 243
<211> LENGTH: 17
<212> TYPE: PRT
<213> ORGANISM: Homo sapiens

<400> SEQUENCE: 243

Gln Pro Gly Asp Lys Gly Glu Gly Gly Ala Pro Gly Leu Pro Gly Ile
1               5                   10                  15

Ala

<210> SEQ ID NO 244
<211> LENGTH: 17
<212> TYPE: PRT
<213> ORGANISM: Homo sapiens

<400> SEQUENCE: 244

Arg Gly Asp Lys Gly Glu Thr Gly Glu Arg Gly Ala Ala Gly Ile Lys
1               5                   10                  15

Gly

<210> SEQ ID NO 245
<211> LENGTH: 17
<212> TYPE: PRT
```

```
<213> ORGANISM: Homo sapiens

<400> SEQUENCE: 245

Asp Gly Arg Asn Gly Glu Lys Gly Glu Thr Gly Ala Pro Gly Leu Lys
1               5                   10                  15

Gly

<210> SEQ ID NO 246
<211> LENGTH: 20
<212> TYPE: PRT
<213> ORGANISM: Homo sapiens

<400> SEQUENCE: 246

Ala Gly Gln Pro Gly Asp Lys Gly Glu Gly Gly Ala Pro Gly Leu Pro
1               5                   10                  15

Gly Ile Ala Gly
            20

<210> SEQ ID NO 247
<211> LENGTH: 19
<212> TYPE: PRT
<213> ORGANISM: Homo sapiens

<400> SEQUENCE: 247

Gly Gly Pro Pro Gly Glu Asn Gly Lys Pro Gly Glu Pro Gly Pro Lys
1               5                   10                  15

Gly Asp Ala

<210> SEQ ID NO 248
<211> LENGTH: 17
<212> TYPE: PRT
<213> ORGANISM: Homo sapiens

<400> SEQUENCE: 248

Ala Gly Ile Pro Gly Phe Pro Gly Met Lys Gly His Arg Gly Phe Asp
1               5                   10                  15

Gly

<210> SEQ ID NO 249
<211> LENGTH: 20
<212> TYPE: PRT
<213> ORGANISM: Homo sapiens

<400> SEQUENCE: 249

Arg Gly Gly Ala Gly Glu Pro Gly Lys Asn Gly Ala Lys Gly Glu Pro
1               5                   10                  15

Gly Pro Arg Gly
            20

<210> SEQ ID NO 250
<211> LENGTH: 26
<212> TYPE: PRT
<213> ORGANISM: Homo sapiens

<400> SEQUENCE: 250

Lys Gly Glu Arg Gly Ser Pro Gly Gly Pro Gly Ala Ala Gly Phe Pro
1               5                   10                  15

Gly Ala Arg Gly Leu Pro Gly Pro Pro Gly
            20                  25

<210> SEQ ID NO 251
```

```
<211> LENGTH: 27
<212> TYPE: PRT
<213> ORGANISM: Homo sapiens

<400> SEQUENCE: 251

Ile Pro Gly Val Pro Gly Ala Lys Gly Glu Asp Gly Lys Asp Gly Ser
1               5                   10                  15

Pro Gly Glu Pro Gly Ala Asn Gly Leu Pro Gly
            20                  25

<210> SEQ ID NO 252
<211> LENGTH: 28
<212> TYPE: PRT
<213> ORGANISM: Homo sapiens

<400> SEQUENCE: 252

Gly Ala Ala Gly Phe Pro Gly Ala Arg Gly Leu Pro Gly Pro Pro Gly
1               5                   10                  15

Ser Asn Gly Asn Pro Gly Pro Pro Gly Pro Ser Gly
            20                  25

<210> SEQ ID NO 253
<211> LENGTH: 26
<212> TYPE: PRT
<213> ORGANISM: Homo sapiens

<400> SEQUENCE: 253

Arg Pro Gly Pro Pro Gly Pro Ser Gly Pro Arg Gly Gln Pro Gly Val
1               5                   10                  15

Met Gly Phe Pro Gly Pro Lys Gly Asn Asp
            20                  25

<210> SEQ ID NO 254
<211> LENGTH: 29
<212> TYPE: PRT
<213> ORGANISM: Homo sapiens

<400> SEQUENCE: 254

Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly
            20                  25

<210> SEQ ID NO 255
<211> LENGTH: 26
<212> TYPE: PRT
<213> ORGANISM: Homo sapiens

<400> SEQUENCE: 255

Ala Gly Lys Asp Gly Glu Ser Gly Arg Pro Gly Arg Pro Gly Glu Arg
1               5                   10                  15

Gly Leu Pro Gly Pro Pro Gly Ile Lys Gly
            20                  25

<210> SEQ ID NO 256
<211> LENGTH: 30
<212> TYPE: PRT
<213> ORGANISM: Homo sapiens

<400> SEQUENCE: 256

Ala Gly Ala Arg Gly Asn Asp Gly Ala Arg Gly Ser Asp Gly Gln Pro
1               5                   10                  15
```

```
Gly Pro Pro Gly Pro Pro Gly Thr Ala Gly Phe Pro Gly Ser
            20                  25                  30
```

<210> SEQ ID NO 257
<211> LENGTH: 31
<212> TYPE: PRT
<213> ORGANISM: Homo sapiens

<400> SEQUENCE: 257

```
Ser Pro Gly Val Ser Gly Pro Lys Gly Asp Ala Gly Gln Pro Gly Glu
1               5                   10                  15

Lys Gly Ser Pro Gly Ala Gln Gly Pro Pro Gly Ala Pro Gly Pro
            20                  25                  30
```

<210> SEQ ID NO 258
<211> LENGTH: 32
<212> TYPE: PRT
<213> ORGANISM: Homo sapiens

<400> SEQUENCE: 258

```
Arg Gly Ser Asp Gly Gln Pro Gly Pro Pro Gly Pro Pro Gly Thr Ala
1               5                   10                  15

Gly Phe Pro Gly Ser Pro Gly Ala Lys Gly Glu Val Gly Pro Ala Gly
            20                  25                  30
```

<210> SEQ ID NO 259
<211> LENGTH: 32
<212> TYPE: PRT
<213> ORGANISM: Homo sapiens

<400> SEQUENCE: 259

```
Gln Gly Pro Pro Gly Pro Pro Gly Ile Asn Gly Ser Pro Gly Gly Lys
1               5                   10                  15

Gly Glu Met Gly Pro Ala Gly Ile Pro Gly Ala Pro Gly Leu Met Gly
            20                  25                  30
```

<210> SEQ ID NO 260
<211> LENGTH: 33
<212> TYPE: PRT
<213> ORGANISM: Homo sapiens

<400> SEQUENCE: 260

```
Ala Gly Pro Pro Gly Pro Pro Gly Pro Pro Gly Thr Ser Gly His Pro
1               5                   10                  15

Gly Ser Pro Gly Ser Pro Gly Tyr Gln Gly Pro Pro Gly Glu Pro Gly
            20                  25                  30

Gln
```

<210> SEQ ID NO 261
<211> LENGTH: 33
<212> TYPE: PRT
<213> ORGANISM: Homo sapiens

<400> SEQUENCE: 261

```
Phe Pro Gly Ala Pro Gly Gln Asn Gly Glu Pro Gly Gly Lys Gly Glu
1               5                   10                  15

Arg Gly Ala Pro Gly Glu Lys Gly Glu Gly Gly Pro Pro Gly Val Ala
            20                  25                  30

Gly
```

<210> SEQ ID NO 262

<211> LENGTH: 33
<212> TYPE: PRT
<213> ORGANISM: Homo sapiens

<400> SEQUENCE: 262

Ala Gly Phe Pro Gly Ala Pro Gly Gln Asn Gly Glu Pro Gly Lys
1               5                   10                  15
Gly Glu Arg Gly Ala Pro Gly Glu Lys Gly Glu Gly Gly Pro Pro Gly
                20                  25                  30
Val

<210> SEQ ID NO 263
<211> LENGTH: 41
<212> TYPE: PRT
<213> ORGANISM: Homo sapiens

<400> SEQUENCE: 263

Ala Gly Ala Arg Gly Asn Asp Gly Ala Arg Gly Ser Asp Gly Gln Pro
1               5                   10                  15
Gly Pro Pro Gly Pro Pro Gly Thr Ala Gly Phe Pro Gly Ser Pro Gly
                20                  25                  30
Ala Lys Gly Glu Val Gly Pro Ala Gly
        35                  40

<210> SEQ ID NO 264
<211> LENGTH: 53
<212> TYPE: PRT
<213> ORGANISM: Homo sapiens

<400> SEQUENCE: 264

Arg Gly Ala Ala Gly Glu Pro Gly Arg Asp Gly Val Pro Gly Gly Pro
1               5                   10                  15
Gly Met Arg Gly Met Pro Gly Ser Pro Gly Gly Pro Gly Ser Asp Gly
                20                  25                  30
Lys Pro Gly Pro Pro Gly Ser Gln Gly Glu Ser Gly Arg Pro Gly Pro
        35                  40                  45
Pro Gly Pro Ser Gly
    50

<210> SEQ ID NO 265
<211> LENGTH: 12
<212> TYPE: PRT
<213> ORGANISM: Homo sapiens

<400> SEQUENCE: 265

Gly Ile Ala Gly Ile Thr Gly Ala Arg Gly Leu Ala
1               5                   10

<210> SEQ ID NO 266
<211> LENGTH: 18
<212> TYPE: PRT
<213> ORGANISM: Homo sapiens

<400> SEQUENCE: 266

Ala Gly Pro Pro Gly Pro Pro Gly Ala Ala Gly Thr Pro Gly Leu Gln
1               5                   10                  15
Gly Met

<210> SEQ ID NO 267
<211> LENGTH: 18
<212> TYPE: PRT

<213> ORGANISM: Homo sapiens

<400> SEQUENCE: 267

Asn Gly Leu Ser Gly Glu Arg Gly Pro Pro Gly Pro Gln Gly Leu Pro
1               5                   10                  15

Gly Leu

<210> SEQ ID NO 268
<211> LENGTH: 20
<212> TYPE: PRT
<213> ORGANISM: Homo sapiens

<400> SEQUENCE: 268

Met Gly Ala Arg Gly Pro Pro Gly Pro Ala Gly Ala Asn Gly Ala Pro
1               5                   10                  15

Gly Leu Arg Gly
            20

<210> SEQ ID NO 269
<211> LENGTH: 20
<212> TYPE: PRT
<213> ORGANISM: Homo sapiens

<400> SEQUENCE: 269

Asn Gly Leu Ser Gly Glu Arg Gly Pro Pro Gly Pro Gln Gly Leu Pro
1               5                   10                  15

Gly Leu Ala Gly
            20

<210> SEQ ID NO 270
<211> LENGTH: 23
<212> TYPE: PRT
<213> ORGANISM: Homo sapiens

<400> SEQUENCE: 270

Gly Ile Ala Gly Ile Thr Gly Ala Arg Gly Leu Ala Gly Pro Pro Gly
1               5                   10                  15

Met Pro Gly Pro Arg Gly Ser
            20

<210> SEQ ID NO 271
<211> LENGTH: 29
<212> TYPE: PRT
<213> ORGANISM: Homo sapiens

<400> SEQUENCE: 271

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val
            20                  25

<210> SEQ ID NO 272
<211> LENGTH: 32
<212> TYPE: PRT
<213> ORGANISM: Homo sapiens

<400> SEQUENCE: 272

Arg Gly Gly Ala Gly Pro Pro Gly Pro Glu Gly Gly Lys Gly Ala Ala
1               5                   10                  15

Gly Pro Pro Gly Pro Pro Gly Ala Ala Gly Thr Pro Gly Leu Gln Gly
            20                  25                  30

<210> SEQ ID NO 273
<211> LENGTH: 30
<212> TYPE: PRT
<213> ORGANISM: Homo sapiens

<400> SEQUENCE: 273

Ser Gly Pro Lys Gly Asp Ala Gly Gln Pro Gly Glu Lys Gly Ser Pro
1               5                   10                  15

Gly Ala Gln Gly Pro Pro Gly Ala Pro Gly Pro Leu Gly Ile
            20                  25                  30

<210> SEQ ID NO 274
<211> LENGTH: 31
<212> TYPE: PRT
<213> ORGANISM: Homo sapiens

<400> SEQUENCE: 274

Gly Ile Ala Gly Ile Thr Gly Ala Arg Gly Leu Ala Gly Pro Pro Gly
1               5                   10                  15

Met Pro Gly Pro Arg Gly Ser Pro Gly Pro Gln Gly Val Lys Gly
            20                  25                  30

<210> SEQ ID NO 275
<211> LENGTH: 37
<212> TYPE: PRT
<213> ORGANISM: Homo sapiens

<400> SEQUENCE: 275

Ala Val Gly Gly Leu Ala Gly Tyr Pro Gly Pro Ala Gly Pro Pro Gly
1               5                   10                  15

Pro Pro Gly Pro Pro Gly Thr Ser Gly His Pro Gly Ser Pro Gly Ser
            20                  25                  30

Pro Gly Tyr Gln Gly
        35

<210> SEQ ID NO 276
<211> LENGTH: 40
<212> TYPE: PRT
<213> ORGANISM: Homo sapiens

<400> SEQUENCE: 276

Glu Pro Gly Pro Gln Gly His Ala Gly Ala Gln Gly Pro Pro Gly Pro
1               5                   10                  15

Pro Gly Ile Asn Gly Ser Pro Gly Gly Lys Gly Glu Met Gly Pro Ala
            20                  25                  30

Gly Ile Pro Gly Ala Pro Gly Leu
        35                  40

<210> SEQ ID NO 277
<211> LENGTH: 12
<212> TYPE: PRT
<213> ORGANISM: Homo sapiens

<400> SEQUENCE: 277

Ile Pro Gly Phe Pro Gly Met Lys Gly His Arg Gly
1               5                   10

<210> SEQ ID NO 278
<211> LENGTH: 17
<212> TYPE: PRT
<213> ORGANISM: Homo sapiens

```
<400> SEQUENCE: 278

Arg Gly Ser Pro Gly Gly Pro Gly Ala Ala Gly Phe Pro Gly Ala Arg
1               5                   10                  15

Gly

<210> SEQ ID NO 279
<211> LENGTH: 17
<212> TYPE: PRT
<213> ORGANISM: Homo sapiens

<400> SEQUENCE: 279

Lys Gly Pro Ala Gly Ile Pro Gly Phe Pro Gly Met Lys Gly His Arg
1               5                   10                  15

Gly

<210> SEQ ID NO 280
<211> LENGTH: 20
<212> TYPE: PRT
<213> ORGANISM: Homo sapiens

<400> SEQUENCE: 280

Arg Gly Leu Ala Gly Pro Pro Gly Met Pro Gly Pro Arg Gly Ser Pro
1               5                   10                  15

Gly Pro Gln Gly
            20

<210> SEQ ID NO 281
<211> LENGTH: 20
<212> TYPE: PRT
<213> ORGANISM: Homo sapiens

<400> SEQUENCE: 281

Ala Gly Ile Thr Gly Ala Arg Gly Leu Ala Gly Pro Pro Gly Met Pro
1               5                   10                  15

Gly Pro Arg Gly
            20

<210> SEQ ID NO 282
<211> LENGTH: 23
<212> TYPE: PRT
<213> ORGANISM: Homo sapiens

<400> SEQUENCE: 282

Leu Gly Ile Ala Gly Ile Thr Gly Ala Arg Gly Leu Ala Gly Pro Pro
1               5                   10                  15

Gly Met Pro Gly Pro Arg Gly
            20

<210> SEQ ID NO 283
<211> LENGTH: 23
<212> TYPE: PRT
<213> ORGANISM: Homo sapiens

<400> SEQUENCE: 283

Thr Gly Ala Arg Gly Leu Ala Gly Pro Pro Gly Met Pro Gly Pro Arg
1               5                   10                  15

Gly Ser Pro Gly Pro Gln Gly
            20

<210> SEQ ID NO 284
<211> LENGTH: 24
```

```
<212> TYPE: PRT
<213> ORGANISM: Homo sapiens

<400> SEQUENCE: 284

Gln Gly Pro Pro Gly Pro Pro Gly Ile Asn Gly Ser Pro Gly Gly Lys
1               5                   10                  15
Gly Glu Met Gly Pro Ala Gly Ile
            20

<210> SEQ ID NO 285
<211> LENGTH: 24
<212> TYPE: PRT
<213> ORGANISM: Homo sapiens

<400> SEQUENCE: 285

Leu Pro Gly Pro Pro Gly Ile Lys Gly Pro Ala Gly Ile Pro Gly Phe
1               5                   10                  15
Pro Gly Met Lys Gly His Arg Gly
            20

<210> SEQ ID NO 286
<211> LENGTH: 26
<212> TYPE: PRT
<213> ORGANISM: Homo sapiens

<400> SEQUENCE: 286

Ala Gly Ile Thr Gly Ala Arg Gly Leu Ala Gly Pro Pro Gly Met Pro
1               5                   10                  15
Gly Pro Arg Gly Ser Pro Gly Pro Gln Gly
            20                  25

<210> SEQ ID NO 287
<211> LENGTH: 26
<212> TYPE: PRT
<213> ORGANISM: Homo sapiens

<400> SEQUENCE: 287

Thr Gly Ala Arg Gly Leu Ala Gly Pro Pro Gly Met Pro Gly Pro Arg
1               5                   10                  15
Gly Ser Pro Gly Pro Gln Gly Val Lys Gly
            20                  25

<210> SEQ ID NO 288
<211> LENGTH: 26
<212> TYPE: PRT
<213> ORGANISM: Homo sapiens

<400> SEQUENCE: 288

Arg Gly Leu Pro Gly Pro Pro Gly Ile Lys Gly Pro Ala Gly Ile Pro
1               5                   10                  15
Gly Phe Pro Gly Met Lys Gly His Arg Gly
            20                  25

<210> SEQ ID NO 289
<211> LENGTH: 29
<212> TYPE: PRT
<213> ORGANISM: Homo sapiens

<400> SEQUENCE: 289

Gly Arg Pro Gly Leu Pro Gly Ala Ala Gly Ala Arg Gly Asn Asp Gly
1               5                   10                  15
Ala Arg Gly Ser Asp Gly Gln Pro Gly Pro Pro Gly Pro
```

```
                        20                  25

<210> SEQ ID NO 290
<211> LENGTH: 29
<212> TYPE: PRT
<213> ORGANISM: Homo sapiens

<400> SEQUENCE: 290

Asn Gly Ala Pro Gly Pro Met Gly Pro Arg Gly Ala Pro Gly Glu Arg
1               5                   10                  15

Gly Arg Pro Gly Leu Pro Gly Ala Ala Gly Ala Arg Gly
                20                  25

<210> SEQ ID NO 291
<211> LENGTH: 29
<212> TYPE: PRT
<213> ORGANISM: Homo sapiens

<400> SEQUENCE: 291

Ala Gly Ser Arg Gly Ala Pro Gly Pro Gln Gly Pro Arg Gly Asp Lys
1               5                   10                  15

Gly Glu Thr Gly Glu Arg Gly Ala Ala Gly Ile Lys Gly
                20                  25

<210> SEQ ID NO 292
<211> LENGTH: 32
<212> TYPE: PRT
<213> ORGANISM: Homo sapiens

<400> SEQUENCE: 292

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
                20                  25                  30

<210> SEQ ID NO 293
<211> LENGTH: 34
<212> TYPE: PRT
<213> ORGANISM: Homo sapiens

<400> SEQUENCE: 293

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
                20                  25                  30

Leu Ser

<210> SEQ ID NO 294
<211> LENGTH: 37
<212> TYPE: PRT
<213> ORGANISM: Homo sapiens

<400> SEQUENCE: 294

Pro Gly Pro Pro Gly Ser Asn Gly Asn Pro Gly Pro Pro Gly Pro Ser
1               5                   10                  15

Gly Ser Pro Gly Lys Asp Gly Pro Gly Pro Ala Gly Asn Thr Gly
                20                  25                  30

Ala Pro Gly Ser Pro
        35

<210> SEQ ID NO 295
```

```
<211> LENGTH: 35
<212> TYPE: PRT
<213> ORGANISM: Homo sapiens

<400> SEQUENCE: 295

Thr Gly Ala Arg Gly Leu Ala Gly Pro Pro Gly Met Pro Gly Pro Arg
1               5                   10                  15

Gly Ser Pro Gly Pro Gln Gly Val Lys Gly Glu Ser Gly Lys Pro Gly
            20                  25                  30

Ala Asn Gly
        35

<210> SEQ ID NO 296
<211> LENGTH: 38
<212> TYPE: PRT
<213> ORGANISM: Homo sapiens

<400> SEQUENCE: 296

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly
        35

<210> SEQ ID NO 297
<211> LENGTH: 40
<212> TYPE: PRT
<213> ORGANISM: Homo sapiens

<400> SEQUENCE: 297

Gly Gly Pro Pro Gly Val Ala Gly Pro Pro Gly Gly Ser Gly Pro Ala
1               5                   10                  15

Gly Pro Pro Gly Pro Gln Gly Val Lys Gly Glu Arg Gly Ser Pro Gly
            20                  25                  30

Gly Pro Gly Ala Ala Gly Phe Pro
        35                  40

<210> SEQ ID NO 298
<211> LENGTH: 48
<212> TYPE: PRT
<213> ORGANISM: Homo sapiens

<400> SEQUENCE: 298

Lys Ser Gly Asp Arg Gly Glu Ser Gly Pro Ala Gly Pro Ala Gly Ala
1               5                   10                  15

Pro Gly Pro Ala Gly Ser Arg Gly Ala Pro Gly Pro Gln Gly Pro Arg
            20                  25                  30

Gly Asp Lys Gly Glu Thr Gly Glu Arg Gly Ala Ala Gly Ile Lys Gly
        35                  40                  45

<210> SEQ ID NO 299
<211> LENGTH: 12
<212> TYPE: PRT
<213> ORGANISM: Homo sapiens

<400> SEQUENCE: 299

Ile Pro Gly Phe Pro Gly Met Lys Gly His Arg Gly
1               5                   10

<210> SEQ ID NO 300
```

<211> LENGTH: 14
<212> TYPE: PRT
<213> ORGANISM: Homo sapiens

<400> SEQUENCE: 300

Arg Gly Leu Ala Gly Pro Pro Gly Met Pro Gly Pro Arg Gly
1               5                   10

<210> SEQ ID NO 301
<211> LENGTH: 16
<212> TYPE: PRT
<213> ORGANISM: Homo sapiens

<400> SEQUENCE: 301

Gly Pro Gln Gly Leu Gln Gly Leu Pro Gly Thr Gly Pro Pro Gly
1               5                   10                  15

<210> SEQ ID NO 302
<211> LENGTH: 17
<212> TYPE: PRT
<213> ORGANISM: Homo sapiens

<400> SEQUENCE: 302

Lys Gly Pro Ala Gly Ile Pro Gly Phe Pro Gly Met Lys Gly His Arg
1               5                   10                  15
Gly

<210> SEQ ID NO 303
<211> LENGTH: 21
<212> TYPE: PRT
<213> ORGANISM: Homo sapiens

<400> SEQUENCE: 303

Arg Gly Leu Ala Gly Pro Pro Gly Met Pro Gly Pro Arg Gly Ser Pro
1               5                   10                  15
Gly Pro Gln Gly Val
            20

<210> SEQ ID NO 304
<211> LENGTH: 23
<212> TYPE: PRT
<213> ORGANISM: Homo sapiens

<400> SEQUENCE: 304

Gly Gly Pro Pro Gly Glu Asn Gly Lys Pro Gly Glu Pro Gly Pro Lys
1               5                   10                  15
Gly Asp Ala Gly Ala Pro Gly
            20

<210> SEQ ID NO 305
<211> LENGTH: 24
<212> TYPE: PRT
<213> ORGANISM: Homo sapiens

<400> SEQUENCE: 305

Ala Pro Gly Phe Arg Gly Pro Ala Gly Pro Asn Gly Ile Pro Gly Glu
1               5                   10                  15
Lys Gly Pro Ala Gly Glu Arg Gly
            20

<210> SEQ ID NO 306
<211> LENGTH: 27
<212> TYPE: PRT

```
<213> ORGANISM: Homo sapiens

<400> SEQUENCE: 306

Glu Lys Gly Ser Pro Gly Ala Gln Gly Pro Pro Gly Ala Pro Gly Pro
1               5                   10                  15

Leu Gly Ile Ala Gly Ile Thr Gly Ala Arg Gly
            20                  25

<210> SEQ ID NO 307
<211> LENGTH: 27
<212> TYPE: PRT
<213> ORGANISM: Homo sapiens

<400> SEQUENCE: 307

Glu Lys Gly Ser Pro Gly Ala Gln Gly Pro Pro Gly Ala Pro Gly Pro
1               5                   10                  15

Leu Gly Ile Ala Gly Ile Thr Gly Ala Arg Gly
            20                  25

<210> SEQ ID NO 308
<211> LENGTH: 26
<212> TYPE: PRT
<213> ORGANISM: Homo sapiens

<400> SEQUENCE: 308

Arg Gly Ala Pro Gly Phe Arg Gly Pro Ala Gly Pro Asn Gly Ile Pro
1               5                   10                  15

Gly Glu Lys Gly Pro Ala Gly Glu Arg Gly
            20                  25

<210> SEQ ID NO 309
<211> LENGTH: 26
<212> TYPE: PRT
<213> ORGANISM: Homo sapiens

<400> SEQUENCE: 309

Arg Gly Leu Pro Gly Pro Pro Gly Ile Lys Gly Pro Ala Gly Ile Pro
1               5                   10                  15

Gly Phe Pro Gly Met Lys Gly His Arg Gly
            20                  25

<210> SEQ ID NO 310
<211> LENGTH: 29
<212> TYPE: PRT
<213> ORGANISM: Homo sapiens

<400> SEQUENCE: 310

Arg Gly Pro Val Gly Pro Ser Gly Pro Pro Gly Lys Asp Gly Thr Ser
1               5                   10                  15

Gly His Pro Gly Pro Ile Gly Pro Pro Gly Pro Arg Gly
            20                  25

<210> SEQ ID NO 311
<211> LENGTH: 27
<212> TYPE: PRT
<213> ORGANISM: Homo sapiens

<400> SEQUENCE: 311

Ala Pro Gly Pro Gln Gly Pro Arg Gly Asp Lys Gly Glu Thr Gly Glu
1               5                   10                  15

Arg Gly Ala Ala Gly Ile Lys Gly His Arg Gly
            20                  25
```

<210> SEQ ID NO 312
<211> LENGTH: 29
<212> TYPE: PRT
<213> ORGANISM: Homo sapiens

<400> SEQUENCE: 312

Arg Gly Ala Pro Gly Pro Gln Gly Pro Arg Gly Asp Lys Gly Glu Thr
1               5                   10                  15

Gly Glu Arg Gly Ala Ala Gly Ile Lys Gly His Arg Gly
            20                  25

<210> SEQ ID NO 313
<211> LENGTH: 32
<212> TYPE: PRT
<213> ORGANISM: Homo sapiens

<400> SEQUENCE: 313

Arg Gly Phe Pro Gly Asn Pro Gly Ala Pro Gly Ser Pro Gly Pro Ala
1               5                   10                  15

Gly Gln Gln Gly Ala Ile Gly Ser Pro Gly Pro Ala Gly Pro Arg Gly
            20                  25                  30

<210> SEQ ID NO 314
<211> LENGTH: 29
<212> TYPE: PRT
<213> ORGANISM: Homo sapiens

<400> SEQUENCE: 314

Leu Pro Gly Pro Pro Gly Ile Lys Gly Pro Ala Gly Ile Pro Gly Phe
1               5                   10                  15

Pro Gly Met Lys Gly His Arg Gly Phe Asp Gly Arg Asn
            20                  25

<210> SEQ ID NO 315
<211> LENGTH: 33
<212> TYPE: PRT
<213> ORGANISM: Homo sapiens

<400> SEQUENCE: 315

Asp Ala Gly Gln Pro Gly Glu Lys Gly Ser Pro Gly Ala Gln Gly Pro
1               5                   10                  15

Pro Gly Ala Pro Gly Pro Leu Gly Ile Ala Gly Ile Thr Gly Ala Arg
            20                  25                  30

Gly

<210> SEQ ID NO 316
<211> LENGTH: 35
<212> TYPE: PRT
<213> ORGANISM: Homo sapiens

<400> SEQUENCE: 316

Arg Gly Pro Thr Gly Pro Ile Gly Pro Pro Gly Pro Ala Gly Gln Pro
1               5                   10                  15

Gly Asp Lys Gly Glu Gly Gly Ala Pro Gly Leu Pro Gly Ile Ala Gly
            20                  25                  30

Pro Arg Gly
        35

<210> SEQ ID NO 317
<211> LENGTH: 35

```
<212> TYPE: PRT
<213> ORGANISM: Homo sapiens

<400> SEQUENCE: 317

Lys Gly Asp Ala Gly Gln Pro Gly Glu Lys Gly Ser Pro Gly Ala Gln
1               5                   10                  15

Gly Pro Pro Gly Ala Pro Gly Pro Leu Gly Ile Ala Gly Ile Thr Gly
            20                  25                  30

Ala Arg Gly
        35

<210> SEQ ID NO 318
<211> LENGTH: 33
<212> TYPE: PRT
<213> ORGANISM: Homo sapiens

<400> SEQUENCE: 318

Arg Asn Gly Glu Lys Gly Glu Thr Gly Ala Pro Gly Leu Lys Gly Glu
1               5                   10                  15

Asn Gly Leu Pro Gly Glu Asn Gly Ala Pro Gly Pro Met Gly Pro Arg
            20                  25                  30

Gly

<210> SEQ ID NO 319
<211> LENGTH: 35
<212> TYPE: PRT
<213> ORGANISM: Homo sapiens

<400> SEQUENCE: 319

Ala Pro Gly Phe Arg Gly Pro Ala Gly Pro Asn Gly Ile Pro Gly Glu
1               5                   10                  15

Lys Gly Pro Ala Gly Glu Arg Gly Ala Pro Gly Pro Ala Gly Pro Arg
            20                  25                  30

Gly Ala Ala
        35

<210> SEQ ID NO 320
<211> LENGTH: 35
<212> TYPE: PRT
<213> ORGANISM: Homo sapiens

<400> SEQUENCE: 320

Arg Gly Ala Pro Gly Phe Arg Gly Pro Ala Gly Pro Asn Gly Ile Pro
1               5                   10                  15

Gly Glu Lys Gly Pro Ala Gly Glu Arg Gly Ala Pro Gly Pro Ala Gly
            20                  25                  30

Pro Arg Gly
        35

<210> SEQ ID NO 321
<211> LENGTH: 35
<212> TYPE: PRT
<213> ORGANISM: Homo sapiens

<400> SEQUENCE: 321

Arg Gly Ser Pro Gly Glu Arg Gly Glu Thr Gly Pro Pro Gly Pro Ala
1               5                   10                  15

Gly Phe Pro Gly Ala Pro Gly Gln Asn Gly Glu Pro Gly Gly Lys Gly
            20                  25                  30

Glu Arg Gly
```

<210> SEQ ID NO 322
<211> LENGTH: 38
<212> TYPE: PRT
<213> ORGANISM: Homo sapiens

<400> SEQUENCE: 322

Gly His Ala Gly Ala Gln Gly Pro Pro Gly Pro Pro Gly Ile Asn Gly
1               5                   10                  15

Ser Pro Gly Gly Lys Gly Glu Met Gly Pro Ala Gly Ile Pro Gly Ala
            20                  25                  30

Pro Gly Leu Met Gly Ala
        35

<210> SEQ ID NO 323
<211> LENGTH: 38
<212> TYPE: PRT
<213> ORGANISM: Homo sapiens

<400> SEQUENCE: 323

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

Leu Ser Gly Glu Arg Gly
        35

<210> SEQ ID NO 324
<211> LENGTH: 13
<212> TYPE: PRT
<213> ORGANISM: Homo sapiens

<400> SEQUENCE: 324

Leu Gly Ile Ala Gly Ile Thr Gly Ala Arg Gly Leu Ala
1               5                   10

<210> SEQ ID NO 325
<211> LENGTH: 12
<212> TYPE: PRT
<213> ORGANISM: Homo sapiens

<400> SEQUENCE: 325

Ile Pro Gly Phe Pro Gly Met Lys Gly His Arg Gly
1               5                   10

<210> SEQ ID NO 326
<211> LENGTH: 14
<212> TYPE: PRT
<213> ORGANISM: Homo sapiens

<400> SEQUENCE: 326

Arg Gly Leu Ala Gly Pro Pro Gly Met Pro Gly Pro Arg Gly
1               5                   10

<210> SEQ ID NO 327
<211> LENGTH: 20
<212> TYPE: PRT
<213> ORGANISM: Homo sapiens

<400> SEQUENCE: 327

Gln Gly Pro Pro Gly Ala Pro Gly Pro Leu Gly Ile Ala Gly Ile Thr
1               5                   10                  15

Gly Ala Arg Gly
        20

<210> SEQ ID NO 328
<211> LENGTH: 20
<212> TYPE: PRT
<213> ORGANISM: Homo sapiens

<400> SEQUENCE: 328

Ala Gly Ile Thr Gly Ala Arg Gly Leu Ala Gly Pro Pro Gly Met Pro
1               5                   10                  15

Gly Pro Arg Gly
        20

<210> SEQ ID NO 329
<211> LENGTH: 23
<212> TYPE: PRT
<213> ORGANISM: Homo sapiens

<400> SEQUENCE: 329

Ala Gly Ile Pro Gly Ala Pro Gly Leu Met Gly Ala Arg Gly Pro Pro
1               5                   10                  15

Gly Pro Ala Gly Ala Asn Gly
        20

<210> SEQ ID NO 330
<211> LENGTH: 24
<212> TYPE: PRT
<213> ORGANISM: Homo sapiens

<400> SEQUENCE: 330

Arg Gly Leu Ala Gly Pro Pro Gly Met Pro Gly Pro Arg Gly Ser Pro
1               5                   10                  15

Gly Pro Gln Gly Val Lys Gly Glu
        20

<210> SEQ ID NO 331
<211> LENGTH: 26
<212> TYPE: PRT
<213> ORGANISM: Homo sapiens

<400> SEQUENCE: 331

Lys Gly Ser Pro Gly Ala Gln Gly Pro Pro Gly Ala Pro Gly Pro Leu
1               5                   10                  15

Gly Ile Ala Gly Ile Thr Gly Ala Arg Gly
        20                  25

<210> SEQ ID NO 332
<211> LENGTH: 24
<212> TYPE: PRT
<213> ORGANISM: Homo sapiens

<400> SEQUENCE: 332

Leu Pro Gly Pro Pro Gly Ile Lys Gly Pro Ala Gly Ile Pro Gly Phe
1               5                   10                  15

Pro Gly Met Lys Gly His Arg Gly
        20

<210> SEQ ID NO 333
<211> LENGTH: 24
<212> TYPE: PRT
<213> ORGANISM: Homo sapiens

```
<400> SEQUENCE: 333

Lys Asp Gly Thr Ser Gly His Pro Gly Pro Ile Gly Pro Pro Gly Pro
1               5                   10                  15

Arg Gly Asn Arg Gly Glu Arg Gly
            20

<210> SEQ ID NO 334
<211> LENGTH: 26
<212> TYPE: PRT
<213> ORGANISM: Homo sapiens

<400> SEQUENCE: 334

Ala Gly Ile Thr Gly Ala Arg Gly Leu Ala Gly Pro Pro Gly Met Pro
1               5                   10                  15

Gly Pro Arg Gly Ser Pro Gly Pro Gln Gly
            20                  25

<210> SEQ ID NO 335
<211> LENGTH: 27
<212> TYPE: PRT
<213> ORGANISM: Homo sapiens

<400> SEQUENCE: 335

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys
            20                  25

<210> SEQ ID NO 336
<211> LENGTH: 32
<212> TYPE: PRT
<213> ORGANISM: Homo sapiens

<400> SEQUENCE: 336

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

<210> SEQ ID NO 337
<211> LENGTH: 34
<212> TYPE: PRT
<213> ORGANISM: Homo sapiens

<400> SEQUENCE: 337

Arg Gly Leu Ala Gly Pro Pro Gly Met Pro Gly Pro Arg Gly Ser Pro
1               5                   10                  15

Gly Pro Gln Gly Val Lys Gly Glu Ser Gly Lys Pro Gly Ala Asn Gly
            20                  25                  30

Leu Ser

<210> SEQ ID NO 338
<211> LENGTH: 37
<212> TYPE: PRT
<213> ORGANISM: Homo sapiens

<400> SEQUENCE: 338

Pro Gly Pro Pro Gly Ser Asn Gly Asn Pro Gly Pro Pro Gly Pro Ser
1               5                   10                  15

Gly Ser Pro Gly Lys Asp Gly Pro Pro Gly Pro Ala Gly Asn Thr Gly
```

```
                20                  25                  30

Ala Pro Gly Ser Pro
        35

<210> SEQ ID NO 339
<211> LENGTH: 38
<212> TYPE: PRT
<213> ORGANISM: Homo sapiens

<400> SEQUENCE: 339

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly
        35

<210> SEQ ID NO 340
<211> LENGTH: 44
<212> TYPE: PRT
<213> ORGANISM: Homo sapiens

<400> SEQUENCE: 340

Lys Ser Gly Asp Arg Gly Glu Ser Gly Pro Ala Gly Pro Ala Gly Ala
1               5                   10                  15

Pro Gly Pro Ala Gly Ser Arg Gly Ala Pro Gly Pro Gln Gly Pro Arg
            20                  25                  30

Gly Asp Lys Gly Glu Thr Gly Glu Arg Gly Ala Ala
        35                  40

<210> SEQ ID NO 341
<211> LENGTH: 53
<212> TYPE: PRT
<213> ORGANISM: Homo sapiens

<400> SEQUENCE: 341

Arg Gly Ala Pro Gly Glu Lys Gly Glu Gly Gly Pro Pro Gly Val Ala
1               5                   10                  15

Gly Pro Pro Gly Gly Ser Gly Pro Ala Gly Pro Pro Gly Pro Gln Gly
            20                  25                  30

Val Lys Gly Glu Arg Gly Ser Pro Gly Gly Pro Gly Ala Ala Gly Phe
        35                  40                  45

Pro Gly Ala Arg Gly
    50

<210> SEQ ID NO 342
<211> LENGTH: 6
<212> TYPE: PRT
<213> ORGANISM: Homo sapiens

<400> SEQUENCE: 342

Ala Ile Gly Pro Ser Gly
1               5

<210> SEQ ID NO 343
<211> LENGTH: 6
<212> TYPE: PRT
<213> ORGANISM: Homo sapiens

<400> SEQUENCE: 343

Gly Ile Pro Gly Ala Pro
```

```
1               5

<210> SEQ ID NO 344
<211> LENGTH: 6
<212> TYPE: PRT
<213> ORGANISM: Homo sapiens

<400> SEQUENCE: 344

Ile Lys Gly His Arg Gly
1               5

<210> SEQ ID NO 345
<211> LENGTH: 6
<212> TYPE: PRT
<213> ORGANISM: Homo sapiens

<400> SEQUENCE: 345

Val Lys Gly Glu Ser Gly
1               5

<210> SEQ ID NO 346
<211> LENGTH: 6
<212> TYPE: PRT
<213> ORGANISM: Homo sapiens

<400> SEQUENCE: 346

His Ala Gly Ala Gln Gly
1               5

<210> SEQ ID NO 347
<211> LENGTH: 6
<212> TYPE: PRT
<213> ORGANISM: Homo sapiens

<400> SEQUENCE: 347

Asp Gly Thr Ser Gly His
1               5

<210> SEQ ID NO 348
<211> LENGTH: 6
<212> TYPE: PRT
<213> ORGANISM: Homo sapiens

<400> SEQUENCE: 348

Ile Gly Ser Pro Gly Pro
1               5

<210> SEQ ID NO 349
<211> LENGTH: 6
<212> TYPE: PRT
<213> ORGANISM: Homo sapiens

<400> SEQUENCE: 349

Leu Ser Gly Glu Arg Gly
1               5

<210> SEQ ID NO 350
<211> LENGTH: 6
<212> TYPE: PRT
<213> ORGANISM: Homo sapiens

<400> SEQUENCE: 350

Val Lys Gly Glu Arg Gly
1               5
```

<210> SEQ ID NO 351
<211> LENGTH: 6
<212> TYPE: PRT
<213> ORGANISM: Homo sapiens

<400> SEQUENCE: 351

Gly Ala Arg Gly Leu Ala
1               5

<210> SEQ ID NO 352
<211> LENGTH: 6
<212> TYPE: PRT
<213> ORGANISM: Homo sapiens

<400> SEQUENCE: 352

Gly Ala Pro Gly Glu Lys
1               5

<210> SEQ ID NO 353
<211> LENGTH: 6
<212> TYPE: PRT
<213> ORGANISM: Homo sapiens

<400> SEQUENCE: 353

Ile Lys Gly Pro Ala Gly
1               5

<210> SEQ ID NO 354
<211> LENGTH: 6
<212> TYPE: PRT
<213> ORGANISM: Homo sapiens

<400> SEQUENCE: 354

Gly Ile Pro Gly Gln Pro
1               5

<210> SEQ ID NO 355
<211> LENGTH: 6
<212> TYPE: PRT
<213> ORGANISM: Homo sapiens

<400> SEQUENCE: 355

Gly Pro Pro Gly Pro Thr
1               5

<210> SEQ ID NO 356
<211> LENGTH: 6
<212> TYPE: PRT
<213> ORGANISM: Homo sapiens

<400> SEQUENCE: 356

Lys Asn Gly Glu Thr Gly
1               5

<210> SEQ ID NO 357
<211> LENGTH: 6
<212> TYPE: PRT
<213> ORGANISM: Homo sapiens

<400> SEQUENCE: 357

Leu Lys Gly Glu Asn Gly
1               5

<210> SEQ ID NO 358

```
<211> LENGTH: 6
<212> TYPE: PRT
<213> ORGANISM: Homo sapiens

<400> SEQUENCE: 358

Gly Asp Pro Gly Pro Pro
1               5

<210> SEQ ID NO 359
<211> LENGTH: 6
<212> TYPE: PRT
<213> ORGANISM: Homo sapiens

<400> SEQUENCE: 359

Gly Asp Pro Gly Pro Pro
1               5

<210> SEQ ID NO 360
<211> LENGTH: 6
<212> TYPE: PRT
<213> ORGANISM: Homo sapiens

<400> SEQUENCE: 360

Phe Pro Gly Ala Arg Gly
1               5

<210> SEQ ID NO 361
<211> LENGTH: 6
<212> TYPE: PRT
<213> ORGANISM: Homo sapiens

<400> SEQUENCE: 361

Gly Asp Lys Gly Glu Thr
1               5

<210> SEQ ID NO 362
<211> LENGTH: 6
<212> TYPE: PRT
<213> ORGANISM: Homo sapiens

<400> SEQUENCE: 362

Gly Gly Ala Gly Glu Pro
1               5

<210> SEQ ID NO 363

<400> SEQUENCE: 363

000

<210> SEQ ID NO 364
<211> LENGTH: 6
<212> TYPE: PRT
<213> ORGANISM: Homo sapiens

<400> SEQUENCE: 364

Gly Pro Pro Gly Pro Pro
1               5

<210> SEQ ID NO 365
<211> LENGTH: 6
<212> TYPE: PRT
<213> ORGANISM: Homo sapiens

<400> SEQUENCE: 365
```

Gly Ala Ala Gly Glu Pro
1               5

<210> SEQ ID NO 366
<211> LENGTH: 6
<212> TYPE: PRT
<213> ORGANISM: Homo sapiens

<400> SEQUENCE: 366

Gly Leu Ser Gly Glu Arg
1               5

<210> SEQ ID NO 367
<211> LENGTH: 6
<212> TYPE: PRT
<213> ORGANISM: Homo sapiens

<400> SEQUENCE: 367

Ile Ala Gly Ile Thr Gly
1               5

<210> SEQ ID NO 368
<211> LENGTH: 6
<212> TYPE: PRT
<213> ORGANISM: Homo sapiens

<400> SEQUENCE: 368

Pro Gly Phe Pro Gly Met
1               5

<210> SEQ ID NO 369
<211> LENGTH: 6
<212> TYPE: PRT
<213> ORGANISM: Homo sapiens

<400> SEQUENCE: 369

Gly Ile Ala Gly Ile Thr
1               5

<210> SEQ ID NO 370
<211> LENGTH: 6
<212> TYPE: PRT
<213> ORGANISM: Homo sapiens

<400> SEQUENCE: 370

Gly Ala Arg Gly Leu Ala
1               5

<210> SEQ ID NO 371
<211> LENGTH: 6
<212> TYPE: PRT
<213> ORGANISM: Homo sapiens

<400> SEQUENCE: 371

Gly Leu Ala Gly Pro Pro
1               5

<210> SEQ ID NO 372
<211> LENGTH: 6
<212> TYPE: PRT
<213> ORGANISM: Homo sapiens

<400> SEQUENCE: 372

Gly Pro Pro Gly Val Ala
1               5

<210> SEQ ID NO 373
<211> LENGTH: 6
<212> TYPE: PRT
<213> ORGANISM: Homo sapiens

<400> SEQUENCE: 373

Gly Pro Ala Gly Ile Pro
1               5

<210> SEQ ID NO 374
<211> LENGTH: 6
<212> TYPE: PRT
<213> ORGANISM: Homo sapiens

<400> SEQUENCE: 374

Pro Gly Pro Pro Gly Ile
1               5

<210> SEQ ID NO 375
<211> LENGTH: 6
<212> TYPE: PRT
<213> ORGANISM: Homo sapiens

<400> SEQUENCE: 375

Gly Ala Pro Gly Pro Gln
1               5

<210> SEQ ID NO 376
<211> LENGTH: 6
<212> TYPE: PRT
<213> ORGANISM: Homo sapiens

<400> SEQUENCE: 376

Gly Asp Ala Gly Gln Pro
1               5

<210> SEQ ID NO 377
<211> LENGTH: 6
<212> TYPE: PRT
<213> ORGANISM: Homo sapiens

<400> SEQUENCE: 377

His Ala Gly Ala Gln Gly
1               5

<210> SEQ ID NO 378
<211> LENGTH: 6
<212> TYPE: PRT
<213> ORGANISM: Homo sapiens

<400> SEQUENCE: 378

Gly Pro Pro Gly Ala Pro
1               5

<210> SEQ ID NO 379
<211> LENGTH: 6
<212> TYPE: PRT
<213> ORGANISM: Homo sapiens

<400> SEQUENCE: 379

Gly Leu Ala Gly Pro Pro
1               5

```
<210> SEQ ID NO 380
<211> LENGTH: 6
<212> TYPE: PRT
<213> ORGANISM: Homo sapiens

<400> SEQUENCE: 380

Ala Ile Gly Pro Ser Gly
1               5

<210> SEQ ID NO 381
<211> LENGTH: 6
<212> TYPE: PRT
<213> ORGANISM: Homo sapiens

<400> SEQUENCE: 381

Gly Pro Pro Gly Pro Ala
1               5

<210> SEQ ID NO 382
<211> LENGTH: 6
<212> TYPE: PRT
<213> ORGANISM: Homo sapiens

<400> SEQUENCE: 382

Ser Pro Gly Pro Ala Gly
1               5

<210> SEQ ID NO 383
<211> LENGTH: 6
<212> TYPE: PRT
<213> ORGANISM: Homo sapiens

<400> SEQUENCE: 383

Ala Ala Gly Thr Pro Gly
1               5

<210> SEQ ID NO 384
<211> LENGTH: 6
<212> TYPE: PRT
<213> ORGANISM: Homo sapiens

<400> SEQUENCE: 384

Thr Ser Gly His Pro Gly
1               5

<210> SEQ ID NO 385
<211> LENGTH: 6
<212> TYPE: PRT
<213> ORGANISM: Homo sapiens

<400> SEQUENCE: 385

Pro Ser Gly Pro Pro Gly
1               5

<210> SEQ ID NO 386
<211> LENGTH: 6
<212> TYPE: PRT
<213> ORGANISM: Homo sapiens

<400> SEQUENCE: 386

Pro Gly Leu Met Gly Ala
1               5

<210> SEQ ID NO 387
<211> LENGTH: 6
```

```
<212> TYPE: PRT
<213> ORGANISM: Homo sapiens

<400> SEQUENCE: 387

Ser Pro Gly Pro Gln Gly
1               5

<210> SEQ ID NO 388
<211> LENGTH: 6
<212> TYPE: PRT
<213> ORGANISM: Homo sapiens

<400> SEQUENCE: 388

Pro Pro Gly Pro Pro Gly
1               5

<210> SEQ ID NO 389
<211> LENGTH: 6
<212> TYPE: PRT
<213> ORGANISM: Homo sapiens

<400> SEQUENCE: 389

Gly Ala Ile Gly Pro Ser
1               5

<210> SEQ ID NO 390
<211> LENGTH: 6
<212> TYPE: PRT
<213> ORGANISM: Homo sapiens

<400> SEQUENCE: 390

Pro Pro Gly Pro Ala Gly
1               5

<210> SEQ ID NO 391
<211> LENGTH: 6
<212> TYPE: PRT
<213> ORGANISM: Homo sapiens

<400> SEQUENCE: 391

Ser Pro Gly Pro Lys Gly
1               5

<210> SEQ ID NO 392
<211> LENGTH: 6
<212> TYPE: PRT
<213> ORGANISM: Homo sapiens

<400> SEQUENCE: 392

Pro Pro Gly Pro Ala Gly
1               5

<210> SEQ ID NO 393
<211> LENGTH: 6
<212> TYPE: PRT
<213> ORGANISM: Homo sapiens

<400> SEQUENCE: 393

Leu Pro Gly Pro Pro Gly
1               5

<210> SEQ ID NO 394
<211> LENGTH: 6
<212> TYPE: PRT
<213> ORGANISM: Homo sapiens
```

<400> SEQUENCE: 394

Gly Ala Pro Gly Leu Lys
1               5

<210> SEQ ID NO 395
<211> LENGTH: 6
<212> TYPE: PRT
<213> ORGANISM: Homo sapiens

<400> SEQUENCE: 395

Gly Leu Pro Gly Pro Pro
1               5

<210> SEQ ID NO 396
<211> LENGTH: 6
<212> TYPE: PRT
<213> ORGANISM: Homo sapiens

<400> SEQUENCE: 396

Gly Pro Pro Gly Ile Lys
1               5

<210> SEQ ID NO 397
<211> LENGTH: 6
<212> TYPE: PRT
<213> ORGANISM: Homo sapiens

<400> SEQUENCE: 397

Gly Pro Pro Gly Val Ala
1               5

<210> SEQ ID NO 398
<211> LENGTH: 6
<212> TYPE: PRT
<213> ORGANISM: Homo sapiens

<400> SEQUENCE: 398

Thr Pro Gly Leu Gln Gly
1               5

<210> SEQ ID NO 399
<211> LENGTH: 6
<212> TYPE: PRT
<213> ORGANISM: Homo sapiens

<400> SEQUENCE: 399

Gly Thr Pro Gly Leu Gln
1               5

<210> SEQ ID NO 400
<211> LENGTH: 6
<212> TYPE: PRT
<213> ORGANISM: Homo sapiens

<400> SEQUENCE: 400

Gly Phe Pro Gly Ala Arg
1               5

<210> SEQ ID NO 401
<211> LENGTH: 6
<212> TYPE: PRT
<213> ORGANISM: Homo sapiens

<400> SEQUENCE: 401

```
Gln Pro Gly Pro Pro Gly
1               5

<210> SEQ ID NO 402
<211> LENGTH: 6
<212> TYPE: PRT
<213> ORGANISM: Homo sapiens

<400> SEQUENCE: 402

Thr Gly Ala Pro Gly Ser
1               5

<210> SEQ ID NO 403
<211> LENGTH: 6
<212> TYPE: PRT
<213> ORGANISM: Homo sapiens

<400> SEQUENCE: 403

Ser Pro Gly Pro Gln Gly
1               5

<210> SEQ ID NO 404
<211> LENGTH: 6
<212> TYPE: PRT
<213> ORGANISM: Homo sapiens

<400> SEQUENCE: 404

Gly Pro Ala Gly Pro Arg
1               5

<210> SEQ ID NO 405
<211> LENGTH: 6
<212> TYPE: PRT
<213> ORGANISM: Homo sapiens

<400> SEQUENCE: 405

Ala Pro Gly Leu Met Gly
1               5

<210> SEQ ID NO 406
<211> LENGTH: 6
<212> TYPE: PRT
<213> ORGANISM: Homo sapiens

<400> SEQUENCE: 406

Gly Asn Arg Gly Glu Arg
1               5

<210> SEQ ID NO 407
<211> LENGTH: 6
<212> TYPE: PRT
<213> ORGANISM: Homo sapiens

<400> SEQUENCE: 407

Thr Gly Ala Pro Gly Ser
1               5

<210> SEQ ID NO 408
<211> LENGTH: 6
<212> TYPE: PRT
<213> ORGANISM: Homo sapiens

<400> SEQUENCE: 408

Gly Asp Pro Gly Pro Pro
```

```
1               5

<210> SEQ ID NO 409
<211> LENGTH: 6
<212> TYPE: PRT
<213> ORGANISM: Homo sapiens

<400> SEQUENCE: 409

Arg Gly Leu Ala Gly Pro
1               5

<210> SEQ ID NO 410
<211> LENGTH: 6
<212> TYPE: PRT
<213> ORGANISM: Homo sapiens

<400> SEQUENCE: 410

Ser Arg Gly Ala Pro Gly
1               5

<210> SEQ ID NO 411
<211> LENGTH: 6
<212> TYPE: PRT
<213> ORGANISM: Homo sapiens

<400> SEQUENCE: 411

Gly Lys Ser Gly Asp Arg
1               5

<210> SEQ ID NO 412
<211> LENGTH: 6
<212> TYPE: PRT
<213> ORGANISM: Homo sapiens

<400> SEQUENCE: 412

Val Gly Gly Leu Ala Gly
1               5

<210> SEQ ID NO 413
<211> LENGTH: 6
<212> TYPE: PRT
<213> ORGANISM: Homo sapiens

<400> SEQUENCE: 413

Ala Ile Gly Ser Pro Gly
1               5

<210> SEQ ID NO 414
<211> LENGTH: 6
<212> TYPE: PRT
<213> ORGANISM: Homo sapiens

<400> SEQUENCE: 414

Gly Leu Ala Gly Pro Pro
1               5

<210> SEQ ID NO 415
<211> LENGTH: 6
<212> TYPE: PRT
<213> ORGANISM: Homo sapiens

<400> SEQUENCE: 415

Arg Gly Leu Ala Gly Pro
1               5
```

<210> SEQ ID NO 416
<211> LENGTH: 6
<212> TYPE: PRT
<213> ORGANISM: Homo sapiens

<400> SEQUENCE: 416

Lys Gly Glu Ser Gly Lys
1               5

<210> SEQ ID NO 417
<211> LENGTH: 6
<212> TYPE: PRT
<213> ORGANISM: Homo sapiens

<400> SEQUENCE: 417

Ile Ala Gly Ile Thr Gly
1               5

<210> SEQ ID NO 418
<211> LENGTH: 6
<212> TYPE: PRT
<213> ORGANISM: Homo sapiens

<400> SEQUENCE: 418

Pro Gly Ala Pro Gly Leu
1               5

<210> SEQ ID NO 419
<211> LENGTH: 6
<212> TYPE: PRT
<213> ORGANISM: Homo sapiens

<400> SEQUENCE: 419

Glu Arg Gly Leu Pro Gly
1               5

<210> SEQ ID NO 420
<211> LENGTH: 6
<212> TYPE: PRT
<213> ORGANISM: Homo sapiens

<400> SEQUENCE: 420

Ile Asn Gly Ser Pro Gly
1               5

<210> SEQ ID NO 421
<211> LENGTH: 6
<212> TYPE: PRT
<213> ORGANISM: Homo sapiens

<400> SEQUENCE: 421

Leu Pro Gly Ile Ala Gly
1               5

<210> SEQ ID NO 422
<211> LENGTH: 6
<212> TYPE: PRT
<213> ORGANISM: Homo sapiens

<400> SEQUENCE: 422

Asn Thr Gly Ala Pro Gly
1               5

<210> SEQ ID NO 423

```
<211> LENGTH: 6
<212> TYPE: PRT
<213> ORGANISM: Homo sapiens

<400> SEQUENCE: 423

Leu Arg Gly Gly Ala Gly
1               5

<210> SEQ ID NO 424
<211> LENGTH: 6
<212> TYPE: PRT
<213> ORGANISM: Homo sapiens

<400> SEQUENCE: 424

Gly His Ala Gly Ala Gln
1               5

<210> SEQ ID NO 425
<211> LENGTH: 6
<212> TYPE: PRT
<213> ORGANISM: Homo sapiens

<400> SEQUENCE: 425

Gly Phe Pro Gly Ala Arg
1               5

<210> SEQ ID NO 426
<211> LENGTH: 6
<212> TYPE: PRT
<213> ORGANISM: Homo sapiens

<400> SEQUENCE: 426

Gly Arg Asn Gly Glu Lys
1               5

<210> SEQ ID NO 427
<211> LENGTH: 6
<212> TYPE: PRT
<213> ORGANISM: Homo sapiens

<400> SEQUENCE: 427

Gly Glu Arg Gly Ser Pro
1               5

<210> SEQ ID NO 428
<211> LENGTH: 6
<212> TYPE: PRT
<213> ORGANISM: Homo sapiens

<400> SEQUENCE: 428

Gly Lys Asp Gly Glu Ser
1               5

<210> SEQ ID NO 429
<211> LENGTH: 6
<212> TYPE: PRT
<213> ORGANISM: Homo sapiens

<400> SEQUENCE: 429

Ile Ala Gly Ile Thr Gly
1               5

<210> SEQ ID NO 430
<211> LENGTH: 6
<212> TYPE: PRT
```

<213> ORGANISM: Homo sapiens

<400> SEQUENCE: 430

Gly Pro Lys Gly Asp Ala
1               5

<210> SEQ ID NO 431
<211> LENGTH: 6
<212> TYPE: PRT
<213> ORGANISM: Homo sapiens

<400> SEQUENCE: 431

Gly Ser Pro Gly Gly Pro
1               5

<210> SEQ ID NO 432
<211> LENGTH: 6
<212> TYPE: PRT
<213> ORGANISM: Homo sapiens

<400> SEQUENCE: 432

Gly Leu Pro Gly Pro Pro
1               5

<210> SEQ ID NO 433
<211> LENGTH: 6
<212> TYPE: PRT
<213> ORGANISM: Homo sapiens

<400> SEQUENCE: 433

Ser Gly Asp Arg Gly Glu
1               5

<210> SEQ ID NO 434
<211> LENGTH: 6
<212> TYPE: PRT
<213> ORGANISM: Homo sapiens

<400> SEQUENCE: 434

Gly Leu Ala Gly Pro Pro
1               5

<210> SEQ ID NO 435
<211> LENGTH: 6
<212> TYPE: PRT
<213> ORGANISM: Homo sapiens

<400> SEQUENCE: 435

Gly Ala Pro Gly Phe Arg
1               5

<210> SEQ ID NO 436
<211> LENGTH: 6
<212> TYPE: PRT
<213> ORGANISM: Homo sapiens

<400> SEQUENCE: 436

Gly Phe Pro Gly Asn Pro
1               5

<210> SEQ ID NO 437
<211> LENGTH: 6
<212> TYPE: PRT
<213> ORGANISM: Homo sapiens

```
<400> SEQUENCE: 437

Asn Gly Glu Lys Gly Glu
1               5

<210> SEQ ID NO 438
<211> LENGTH: 6
<212> TYPE: PRT
<213> ORGANISM: Homo sapiens

<400> SEQUENCE: 438

Gly Leu Ala Gly Pro Pro
1               5

<210> SEQ ID NO 439
<211> LENGTH: 6
<212> TYPE: PRT
<213> ORGANISM: Homo sapiens

<400> SEQUENCE: 439

Gly Ile Thr Gly Ala Arg
1               5

<210> SEQ ID NO 440
<211> LENGTH: 6
<212> TYPE: PRT
<213> ORGANISM: Homo sapiens

<400> SEQUENCE: 440

Asp Gly Thr Ser Gly His
1               5

<210> SEQ ID NO 441
<211> LENGTH: 6
<212> TYPE: PRT
<213> ORGANISM: Homo sapiens

<400> SEQUENCE: 441

Gly Pro Pro Gly Ser Asn
1               5

<210> SEQ ID NO 442
<211> LENGTH: 6
<212> TYPE: PRT
<213> ORGANISM: Homo sapiens

<400> SEQUENCE: 442

Asn Gly Asp Pro Gly Ile
1               5

<210> SEQ ID NO 443
<211> LENGTH: 6
<212> TYPE: PRT
<213> ORGANISM: Homo sapiens

<400> SEQUENCE: 443

Pro Gly Pro Gln Gly Val
1               5

<210> SEQ ID NO 444
<211> LENGTH: 6
<212> TYPE: PRT
<213> ORGANISM: Homo sapiens

<400> SEQUENCE: 444
```

Ile Pro Gly Ala Pro Gly
1               5

<210> SEQ ID NO 445
<211> LENGTH: 6
<212> TYPE: PRT
<213> ORGANISM: Homo sapiens

<400> SEQUENCE: 445

Ser Pro Gly Pro Gln Gly
1               5

<210> SEQ ID NO 446
<211> LENGTH: 6
<212> TYPE: PRT
<213> ORGANISM: Homo sapiens

<400> SEQUENCE: 446

Gly Ser Pro Gly Pro Ala
1               5

<210> SEQ ID NO 447
<211> LENGTH: 6
<212> TYPE: PRT
<213> ORGANISM: Homo sapiens

<400> SEQUENCE: 447

Gln Gly Pro Pro Gly Pro
1               5

<210> SEQ ID NO 448
<211> LENGTH: 6
<212> TYPE: PRT
<213> ORGANISM: Homo sapiens

<400> SEQUENCE: 448

Ile Pro Gly Phe Pro Gly
1               5

<210> SEQ ID NO 449
<211> LENGTH: 6
<212> TYPE: PRT
<213> ORGANISM: Homo sapiens

<400> SEQUENCE: 449

Gly Pro Ala Gly Ile Pro
1               5

<210> SEQ ID NO 450
<211> LENGTH: 6
<212> TYPE: PRT
<213> ORGANISM: Homo sapiens

<400> SEQUENCE: 450

Phe Pro Gly Ala Arg Gly
1               5

<210> SEQ ID NO 451
<211> LENGTH: 6
<212> TYPE: PRT
<213> ORGANISM: Homo sapiens

<400> SEQUENCE: 451

Gly Ile Pro Gly Ala Pro
1               5

<210> SEQ ID NO 452
<211> LENGTH: 6
<212> TYPE: PRT
<213> ORGANISM: Homo sapiens

<400> SEQUENCE: 452

Glu Arg Gly Pro Pro Gly
1               5

<210> SEQ ID NO 453
<211> LENGTH: 6
<212> TYPE: PRT
<213> ORGANISM: Homo sapiens

<400> SEQUENCE: 453

Pro Ser Gly Pro Pro Gly
1               5

<210> SEQ ID NO 454
<211> LENGTH: 6
<212> TYPE: PRT
<213> ORGANISM: Homo sapiens

<400> SEQUENCE: 454

Gly Pro Pro Gly Ile Asn
1               5

<210> SEQ ID NO 455
<211> LENGTH: 6
<212> TYPE: PRT
<213> ORGANISM: Homo sapiens

<400> SEQUENCE: 455

Gly Thr Ser Gly His Pro
1               5

<210> SEQ ID NO 456
<211> LENGTH: 6
<212> TYPE: PRT
<213> ORGANISM: Homo sapiens

<400> SEQUENCE: 456

Gly Leu Pro Gly Ile Ala
1               5

<210> SEQ ID NO 457
<211> LENGTH: 6
<212> TYPE: PRT
<213> ORGANISM: Homo sapiens

<400> SEQUENCE: 457

Gly Ala Asn Gly Leu Pro
1               5

<210> SEQ ID NO 458
<211> LENGTH: 6
<212> TYPE: PRT
<213> ORGANISM: Homo sapiens

<400> SEQUENCE: 458

Thr Ala Gly Phe Pro Gly
1               5

```
<210> SEQ ID NO 459
<211> LENGTH: 6
<212> TYPE: PRT
<213> ORGANISM: Homo sapiens

<400> SEQUENCE: 459

Glu Gly Gly Pro Pro Gly
1               5

<210> SEQ ID NO 460
<211> LENGTH: 6
<212> TYPE: PRT
<213> ORGANISM: Homo sapiens

<400> SEQUENCE: 460

Pro Gln Gly Leu Pro Gly
1               5

<210> SEQ ID NO 461
<211> LENGTH: 6
<212> TYPE: PRT
<213> ORGANISM: Homo sapiens

<400> SEQUENCE: 461

Ala Pro Gly Pro Leu Gly
1               5

<210> SEQ ID NO 462
<211> LENGTH: 6
<212> TYPE: PRT
<213> ORGANISM: Homo sapiens

<400> SEQUENCE: 462

Gly Ser Pro Gly Pro Gln
1               5

<210> SEQ ID NO 463
<211> LENGTH: 6
<212> TYPE: PRT
<213> ORGANISM: Homo sapiens

<400> SEQUENCE: 463

Gly Ala Ala Gly Ala Arg
1               5

<210> SEQ ID NO 464
<211> LENGTH: 6
<212> TYPE: PRT
<213> ORGANISM: Homo sapiens

<400> SEQUENCE: 464

Gly Val Lys Gly Glu Arg
1               5

<210> SEQ ID NO 465
<211> LENGTH: 6
<212> TYPE: PRT
<213> ORGANISM: Homo sapiens

<400> SEQUENCE: 465

Gly Asp Ala Gly Ala Pro
1               5

<210> SEQ ID NO 466
<211> LENGTH: 6
```

```
<212> TYPE: PRT
<213> ORGANISM: Homo sapiens

<400> SEQUENCE: 466

Arg Gly Phe Asp Gly Arg
1               5

<210> SEQ ID NO 467
<211> LENGTH: 6
<212> TYPE: PRT
<213> ORGANISM: Homo sapiens

<400> SEQUENCE: 467

Gly Leu Ser Gly Glu Arg
1               5

<210> SEQ ID NO 468
<211> LENGTH: 6
<212> TYPE: PRT
<213> ORGANISM: Homo sapiens

<400> SEQUENCE: 468

Gly Ser Pro Gly Pro Gln
1               5

<210> SEQ ID NO 469
<211> LENGTH: 6
<212> TYPE: PRT
<213> ORGANISM: Homo sapiens

<400> SEQUENCE: 469

Gly Val Lys Gly Glu Arg
1               5

<210> SEQ ID NO 470
<211> LENGTH: 6
<212> TYPE: PRT
<213> ORGANISM: Homo sapiens

<400> SEQUENCE: 470

Leu Ala Gly Pro Pro Gly
1               5

<210> SEQ ID NO 471
<211> LENGTH: 6
<212> TYPE: PRT
<213> ORGANISM: Homo sapiens

<400> SEQUENCE: 471

Thr Gly Ala Arg Gly Leu
1               5

<210> SEQ ID NO 472
<211> LENGTH: 6
<212> TYPE: PRT
<213> ORGANISM: Homo sapiens

<400> SEQUENCE: 472

Lys Gly Asp Ala Gly Gln
1               5

<210> SEQ ID NO 473
<211> LENGTH: 6
<212> TYPE: PRT
<213> ORGANISM: Homo sapiens
```

<400> SEQUENCE: 473

Leu Gln Gly Leu Pro Gly
1               5

<210> SEQ ID NO 474
<211> LENGTH: 6
<212> TYPE: PRT
<213> ORGANISM: Homo sapiens

<400> SEQUENCE: 474

Ile Ala Gly Ile Thr Gly
1               5

<210> SEQ ID NO 475
<211> LENGTH: 6
<212> TYPE: PRT
<213> ORGANISM: Homo sapiens

<400> SEQUENCE: 475

Ala Gly Gln Gln Gly Ala
1               5

<210> SEQ ID NO 476
<211> LENGTH: 6
<212> TYPE: PRT
<213> ORGANISM: Homo sapiens

<400> SEQUENCE: 476

Leu Ala Gly Pro Pro Gly
1               5

<210> SEQ ID NO 477
<211> LENGTH: 6
<212> TYPE: PRT
<213> ORGANISM: Homo sapiens

<400> SEQUENCE: 477

Gly Leu Ser Gly Glu Arg
1               5

<210> SEQ ID NO 478
<211> LENGTH: 6
<212> TYPE: PRT
<213> ORGANISM: Homo sapiens

<400> SEQUENCE: 478

Val Lys Gly Glu Arg Gly
1               5

<210> SEQ ID NO 479
<211> LENGTH: 6
<212> TYPE: PRT
<213> ORGANISM: Homo sapiens

<400> SEQUENCE: 479

Ile Lys Gly Pro Ala Gly
1               5

<210> SEQ ID NO 480
<211> LENGTH: 6
<212> TYPE: PRT
<213> ORGANISM: Homo sapiens

<400> SEQUENCE: 480

```
Glu Arg Gly Leu Pro Gly
1               5

<210> SEQ ID NO 481
<211> LENGTH: 6
<212> TYPE: PRT
<213> ORGANISM: Homo sapiens

<400> SEQUENCE: 481

Val Gly Gly Leu Ala Gly
1               5

<210> SEQ ID NO 482
<211> LENGTH: 6
<212> TYPE: PRT
<213> ORGANISM: Homo sapiens

<400> SEQUENCE: 482

Gly Pro Pro Gly Glu Pro
1               5

<210> SEQ ID NO 483
<211> LENGTH: 6
<212> TYPE: PRT
<213> ORGANISM: Homo sapiens

<400> SEQUENCE: 483

Ile Asn Gly Ser Pro Gly
1               5

<210> SEQ ID NO 484
<211> LENGTH: 6
<212> TYPE: PRT
<213> ORGANISM: Homo sapiens

<400> SEQUENCE: 484

Leu Met Gly Ala Arg Gly
1               5

<210> SEQ ID NO 485

<400> SEQUENCE: 485

000

<210> SEQ ID NO 486
<211> LENGTH: 6
<212> TYPE: PRT
<213> ORGANISM: Homo sapiens

<400> SEQUENCE: 486

Gly Glu Arg Gly Ala Pro
1               5

<210> SEQ ID NO 487
<211> LENGTH: 6
<212> TYPE: PRT
<213> ORGANISM: Homo sapiens

<400> SEQUENCE: 487

Pro Gly Pro Pro Gly Pro
1               5

<210> SEQ ID NO 488
```

```
<211> LENGTH: 6
<212> TYPE: PRT
<213> ORGANISM: Homo sapiens

<400> SEQUENCE: 488

Gly Gln Pro Gly Asp Lys
1               5

<210> SEQ ID NO 489
<211> LENGTH: 6
<212> TYPE: PRT
<213> ORGANISM: Homo sapiens

<400> SEQUENCE: 489

Pro Gly Val Pro Gly Ala
1               5

<210> SEQ ID NO 490
<211> LENGTH: 6
<212> TYPE: PRT
<213> ORGANISM: Homo sapiens

<400> SEQUENCE: 490

Gly Ala Arg Gly Asn Asp
1               5

<210> SEQ ID NO 491
<211> LENGTH: 6
<212> TYPE: PRT
<213> ORGANISM: Homo sapiens

<400> SEQUENCE: 491

Pro Gly Ala Pro Gly Gln
1               5

<210> SEQ ID NO 492
<211> LENGTH: 6
<212> TYPE: PRT
<213> ORGANISM: Homo sapiens

<400> SEQUENCE: 492

Gly Pro Pro Gly Pro Pro
1               5

<210> SEQ ID NO 493
<211> LENGTH: 6
<212> TYPE: PRT
<213> ORGANISM: Homo sapiens

<400> SEQUENCE: 493

Ile Ala Gly Ile Thr Gly
1               5

<210> SEQ ID NO 494
<211> LENGTH: 6
<212> TYPE: PRT
<213> ORGANISM: Homo sapiens

<400> SEQUENCE: 494

Gly Pro Ala Gly Ile Pro
1               5

<210> SEQ ID NO 495
<211> LENGTH: 6
<212> TYPE: PRT
```

<213> ORGANISM: Homo sapiens

<400> SEQUENCE: 495

Gly Pro Pro Gly Pro Pro
1               5

<210> SEQ ID NO 496
<211> LENGTH: 6
<212> TYPE: PRT
<213> ORGANISM: Homo sapiens

<400> SEQUENCE: 496

Arg Pro Gly Leu Pro Gly
1               5

<210> SEQ ID NO 497
<211> LENGTH: 6
<212> TYPE: PRT
<213> ORGANISM: Homo sapiens

<400> SEQUENCE: 497

Gly Pro Pro Gly Ser Asn
1               5

<210> SEQ ID NO 498
<211> LENGTH: 6
<212> TYPE: PRT
<213> ORGANISM: Homo sapiens

<400> SEQUENCE: 498

Pro Gly Phe Pro Gly Met
1               5

<210> SEQ ID NO 499
<211> LENGTH: 6
<212> TYPE: PRT
<213> ORGANISM: Homo sapiens

<400> SEQUENCE: 499

Gly Pro Pro Gly Glu Asn
1               5

<210> SEQ ID NO 500
<211> LENGTH: 6
<212> TYPE: PRT
<213> ORGANISM: Homo sapiens

<400> SEQUENCE: 500

Gly Leu Pro Gly Pro Pro
1               5

<210> SEQ ID NO 501
<211> LENGTH: 6
<212> TYPE: PRT
<213> ORGANISM: Homo sapiens

<400> SEQUENCE: 501

Pro Gly Pro Pro Gly Ile
1               5

<210> SEQ ID NO 502
<211> LENGTH: 6
<212> TYPE: PRT
<213> ORGANISM: Homo sapiens

```
<400> SEQUENCE: 502

Pro Gly Phe Arg Gly Pro
1               5

<210> SEQ ID NO 503
<211> LENGTH: 6
<212> TYPE: PRT
<213> ORGANISM: Homo sapiens

<400> SEQUENCE: 503

Gly Ile Ala Gly Ile Thr
1               5

<210> SEQ ID NO 504
<211> LENGTH: 6
<212> TYPE: PRT
<213> ORGANISM: Homo sapiens

<400> SEQUENCE: 504

Gly Ile Pro Gly Ala Pro
1               5

<210> SEQ ID NO 505
<211> LENGTH: 6
<212> TYPE: PRT
<213> ORGANISM: Homo sapiens

<400> SEQUENCE: 505

Gly Ile Thr Gly Ala Arg
1               5

<210> SEQ ID NO 506
<211> LENGTH: 6
<212> TYPE: PRT
<213> ORGANISM: Homo sapiens

<400> SEQUENCE: 506

Gly Ala Pro Gly Glu Lys
1               5

<210> SEQ ID NO 507
<211> LENGTH: 6
<212> TYPE: PRT
<213> ORGANISM: Homo sapiens

<400> SEQUENCE: 507

Ser Pro Gly Pro Gln Gly
1               5

<210> SEQ ID NO 508
<211> LENGTH: 6
<212> TYPE: PRT
<213> ORGANISM: Homo sapiens

<400> SEQUENCE: 508

Pro Pro Gly Pro Gln Gly
1               5

<210> SEQ ID NO 509
<211> LENGTH: 6
<212> TYPE: PRT
<213> ORGANISM: Homo sapiens

<400> SEQUENCE: 509
```

Glu Arg Gly Pro Pro Gly
1               5

<210> SEQ ID NO 510
<211> LENGTH: 6
<212> TYPE: PRT
<213> ORGANISM: Homo sapiens

<400> SEQUENCE: 510

Ala Pro Gly Leu Arg Gly
1               5

<210> SEQ ID NO 511
<211> LENGTH: 6
<212> TYPE: PRT
<213> ORGANISM: Homo sapiens

<400> SEQUENCE: 511

Gly Pro Ala Gly Pro Pro
1               5

<210> SEQ ID NO 512
<211> LENGTH: 6
<212> TYPE: PRT
<213> ORGANISM: Homo sapiens

<400> SEQUENCE: 512

Ser Pro Gly Pro Gln Gly
1               5

<210> SEQ ID NO 513
<211> LENGTH: 6
<212> TYPE: PRT
<213> ORGANISM: Homo sapiens

<400> SEQUENCE: 513

Leu Ala Gly Pro Pro Gly
1               5

<210> SEQ ID NO 514
<211> LENGTH: 6
<212> TYPE: PRT
<213> ORGANISM: Homo sapiens

<400> SEQUENCE: 514

Phe Pro Gly Pro Lys Gly
1               5

<210> SEQ ID NO 515
<211> LENGTH: 6
<212> TYPE: PRT
<213> ORGANISM: Homo sapiens

<400> SEQUENCE: 515

Pro Pro Gly Pro Ala Gly
1               5

<210> SEQ ID NO 516
<211> LENGTH: 6
<212> TYPE: PRT
<213> ORGANISM: Homo sapiens

<400> SEQUENCE: 516

Leu Pro Gly Ala Ala Gly
1               5

<210> SEQ ID NO 517
<211> LENGTH: 6
<212> TYPE: PRT
<213> ORGANISM: Homo sapiens

<400> SEQUENCE: 517

Ile Pro Gly Gln Pro Gly
1               5

<210> SEQ ID NO 518
<211> LENGTH: 6
<212> TYPE: PRT
<213> ORGANISM: Homo sapiens

<400> SEQUENCE: 518

Gly Ala Pro Gly Pro Ala
1               5

<210> SEQ ID NO 519
<211> LENGTH: 6
<212> TYPE: PRT
<213> ORGANISM: Homo sapiens

<400> SEQUENCE: 519

Gly His Arg Gly Phe Asp
1               5

<210> SEQ ID NO 520
<211> LENGTH: 6
<212> TYPE: PRT
<213> ORGANISM: Homo sapiens

<400> SEQUENCE: 520

Pro Gly Pro Lys Gly Asp
1               5

<210> SEQ ID NO 521
<211> LENGTH: 6
<212> TYPE: PRT
<213> ORGANISM: Homo sapiens

<400> SEQUENCE: 521

Gly Pro Pro Gly Pro Ser
1               5

<210> SEQ ID NO 522
<211> LENGTH: 6
<212> TYPE: PRT
<213> ORGANISM: Homo sapiens

<400> SEQUENCE: 522

Pro Pro Gly Ala Pro Gly
1               5

<210> SEQ ID NO 523
<211> LENGTH: 6
<212> TYPE: PRT
<213> ORGANISM: Homo sapiens

<400> SEQUENCE: 523

Gly Glu Val Gly Pro Ala
1               5

```
<210> SEQ ID NO 524
<211> LENGTH: 6
<212> TYPE: PRT
<213> ORGANISM: Homo sapiens

<400> SEQUENCE: 524

Gly Ala Pro Gly Leu Arg
1               5

<210> SEQ ID NO 525
<211> LENGTH: 6
<212> TYPE: PRT
<213> ORGANISM: Homo sapiens

<400> SEQUENCE: 525

Gly Pro Gln Gly Val Lys
1               5

<210> SEQ ID NO 526
<211> LENGTH: 6
<212> TYPE: PRT
<213> ORGANISM: Homo sapiens

<400> SEQUENCE: 526

Gly Met Pro Gly Pro Arg
1               5

<210> SEQ ID NO 527
<211> LENGTH: 6
<212> TYPE: PRT
<213> ORGANISM: Homo sapiens

<400> SEQUENCE: 527

Gly Ala Ala Gly Ile Lys
1               5

<210> SEQ ID NO 528
<211> LENGTH: 6
<212> TYPE: PRT
<213> ORGANISM: Homo sapiens

<400> SEQUENCE: 528

Pro Gly Ala Ala Gly Phe
1               5

<210> SEQ ID NO 529
<211> LENGTH: 6
<212> TYPE: PRT
<213> ORGANISM: Homo sapiens

<400> SEQUENCE: 529

Gly Pro Ala Gly Glu Arg
1               5

<210> SEQ ID NO 530
<211> LENGTH: 6
<212> TYPE: PRT
<213> ORGANISM: Homo sapiens

<400> SEQUENCE: 530

Gly Ile Ala Gly Pro Arg
1               5

<210> SEQ ID NO 531
<211> LENGTH: 6
```

```
<212> TYPE: PRT
<213> ORGANISM: Homo sapiens

<400> SEQUENCE: 531

Thr Gly Ala Arg Gly Leu
1               5

<210> SEQ ID NO 532
<211> LENGTH: 6
<212> TYPE: PRT
<213> ORGANISM: Homo sapiens

<400> SEQUENCE: 532

Val Lys Gly Glu Ser Gly
1               5

<210> SEQ ID NO 533
<211> LENGTH: 6
<212> TYPE: PRT
<213> ORGANISM: Homo sapiens

<400> SEQUENCE: 533

Thr Gly Glu Arg Gly Ala
1               5

<210> SEQ ID NO 534
<211> LENGTH: 6
<212> TYPE: PRT
<213> ORGANISM: Homo sapiens

<400> SEQUENCE: 534

Glu Arg Gly Leu Pro Gly
1               5

<210> SEQ ID NO 535
<211> LENGTH: 6
<212> TYPE: PRT
<213> ORGANISM: Homo sapiens

<400> SEQUENCE: 535

Ile Thr Gly Ala Arg Gly
1               5

<210> SEQ ID NO 536
<211> LENGTH: 6
<212> TYPE: PRT
<213> ORGANISM: Homo sapiens

<400> SEQUENCE: 536

Glu Arg Gly Leu Pro Gly
1               5

<210> SEQ ID NO 537
<211> LENGTH: 6
<212> TYPE: PRT
<213> ORGANISM: Homo sapiens

<400> SEQUENCE: 537

Pro Gly Ala Pro Gly Gly
1               5

<210> SEQ ID NO 538
<211> LENGTH: 6
<212> TYPE: PRT
<213> ORGANISM: Homo sapiens
```

```
<400> SEQUENCE: 538

Gly Pro Pro Gly Val Ala
1               5

<210> SEQ ID NO 539
<211> LENGTH: 6
<212> TYPE: PRT
<213> ORGANISM: Homo sapiens

<400> SEQUENCE: 539

Gly Leu Ala Gly Pro Pro
1               5

<210> SEQ ID NO 540
<211> LENGTH: 6
<212> TYPE: PRT
<213> ORGANISM: Homo sapiens

<400> SEQUENCE: 540

Val Gly Gly Leu Ala Gly
1               5

<210> SEQ ID NO 541
<211> LENGTH: 6
<212> TYPE: PRT
<213> ORGANISM: Homo sapiens

<400> SEQUENCE: 541

Ser Pro Gly Ala Gln Gly
1               5

<210> SEQ ID NO 542
<211> LENGTH: 6
<212> TYPE: PRT
<213> ORGANISM: Homo sapiens

<400> SEQUENCE: 542

Gln Pro Gly Val Met Gly
1               5

<210> SEQ ID NO 543
<211> LENGTH: 6
<212> TYPE: PRT
<213> ORGANISM: Homo sapiens

<400> SEQUENCE: 543

Ile Pro Gly Ala Pro Gly
1               5

<210> SEQ ID NO 544
<211> LENGTH: 6
<212> TYPE: PRT
<213> ORGANISM: Homo sapiens

<400> SEQUENCE: 544

Val Lys Gly Glu Arg Gly
1               5

<210> SEQ ID NO 545
<211> LENGTH: 6
<212> TYPE: PRT
<213> ORGANISM: Homo sapiens

<400> SEQUENCE: 545
```

Gly Pro Pro Gly Ile Asn
1               5

<210> SEQ ID NO 546
<211> LENGTH: 6
<212> TYPE: PRT
<213> ORGANISM: Homo sapiens

<400> SEQUENCE: 546

Gly Ile Asn Gly Ser Pro
1               5

<210> SEQ ID NO 547
<211> LENGTH: 6
<212> TYPE: PRT
<213> ORGANISM: Homo sapiens

<400> SEQUENCE: 547

Leu Arg Gly Gly Ala Gly
1               5

<210> SEQ ID NO 548
<211> LENGTH: 6
<212> TYPE: PRT
<213> ORGANISM: Homo sapiens

<400> SEQUENCE: 548

Tyr Gln Gly Pro Pro Gly
1               5

<210> SEQ ID NO 549
<211> LENGTH: 6
<212> TYPE: PRT
<213> ORGANISM: Homo sapiens

<400> SEQUENCE: 549

Gly Ile Pro Gly Phe Pro
1               5

<210> SEQ ID NO 550
<211> LENGTH: 6
<212> TYPE: PRT
<213> ORGANISM: Homo sapiens

<400> SEQUENCE: 550

Phe Pro Gly Met Lys Gly
1               5

<210> SEQ ID NO 551
<211> LENGTH: 6
<212> TYPE: PRT
<213> ORGANISM: Homo sapiens

<400> SEQUENCE: 551

Gly Pro Pro Gly Glu Asn
1               5

<210> SEQ ID NO 552
<211> LENGTH: 6
<212> TYPE: PRT
<213> ORGANISM: Homo sapiens

<400> SEQUENCE: 552

Ala Ala Gly Phe Pro Gly 1               5

<210> SEQ ID NO 553
<211> LENGTH: 6
<212> TYPE: PRT
<213> ORGANISM: Homo sapiens

<400> SEQUENCE: 553

Pro Gly Val Ser Gly Pro
1               5

<210> SEQ ID NO 554
<211> LENGTH: 6
<212> TYPE: PRT
<213> ORGANISM: Homo sapiens

<400> SEQUENCE: 554

Gly Phe Pro Gly Ala Pro
1               5

<210> SEQ ID NO 555
<211> LENGTH: 6
<212> TYPE: PRT
<213> ORGANISM: Homo sapiens

<400> SEQUENCE: 555

Gly Leu Ser Gly Glu Arg
1               5

<210> SEQ ID NO 556
<211> LENGTH: 6
<212> TYPE: PRT
<213> ORGANISM: Homo sapiens

<400> SEQUENCE: 556

Gly Gly Ala Gly Pro Pro
1               5

<210> SEQ ID NO 557
<211> LENGTH: 6
<212> TYPE: PRT
<213> ORGANISM: Homo sapiens

<400> SEQUENCE: 557

Val Gly Gly Leu Ala Gly
1               5

<210> SEQ ID NO 558
<211> LENGTH: 6
<212> TYPE: PRT
<213> ORGANISM: Homo sapiens

<400> SEQUENCE: 558

Gly Leu Ala Gly Pro Pro
1               5

<210> SEQ ID NO 559
<211> LENGTH: 6
<212> TYPE: PRT
<213> ORGANISM: Homo sapiens

<400> SEQUENCE: 559

Pro Gly Pro Pro Gly Ile
1               5

```
<210> SEQ ID NO 560
<211> LENGTH: 6
<212> TYPE: PRT
<213> ORGANISM: Homo sapiens

<400> SEQUENCE: 560

Gly Ala Pro Gly Pro Met
1               5

<210> SEQ ID NO 561
<211> LENGTH: 6
<212> TYPE: PRT
<213> ORGANISM: Homo sapiens

<400> SEQUENCE: 561

Gly Ala Arg Gly Leu Ala
1               5

<210> SEQ ID NO 562
<211> LENGTH: 6
<212> TYPE: PRT
<213> ORGANISM: Homo sapiens

<400> SEQUENCE: 562

Gly Leu Ala Gly Pro Pro
1               5

<210> SEQ ID NO 563
<211> LENGTH: 6
<212> TYPE: PRT
<213> ORGANISM: Homo sapiens

<400> SEQUENCE: 563

Pro Gly Phe Arg Gly Pro
1               5

<210> SEQ ID NO 564
<211> LENGTH: 6
<212> TYPE: PRT
<213> ORGANISM: Homo sapiens

<400> SEQUENCE: 564

Gly Pro Val Gly Pro Ser
1               5

<210> SEQ ID NO 565
<211> LENGTH: 6
<212> TYPE: PRT
<213> ORGANISM: Homo sapiens

<400> SEQUENCE: 565

Ala Gly Gln Pro Gly Glu
1               5

<210> SEQ ID NO 566
<211> LENGTH: 6
<212> TYPE: PRT
<213> ORGANISM: Homo sapiens

<400> SEQUENCE: 566

Gly Ala Pro Gly Phe Arg
1               5

<210> SEQ ID NO 567
```

```
<211> LENGTH: 6
<212> TYPE: PRT
<213> ORGANISM: Homo sapiens

<400> SEQUENCE: 567

Pro Gly Phe Pro Gly Met
1               5

<210> SEQ ID NO 568
<211> LENGTH: 6
<212> TYPE: PRT
<213> ORGANISM: Homo sapiens

<400> SEQUENCE: 568

Gly Leu Ala Gly Pro Pro
1               5

<210> SEQ ID NO 569
<211> LENGTH: 6
<212> TYPE: PRT
<213> ORGANISM: Homo sapiens

<400> SEQUENCE: 569

Ser Gly Asp Arg Gly Glu
1               5

<210> SEQ ID NO 570
<211> LENGTH: 6
<212> TYPE: PRT
<213> ORGANISM: Homo sapiens

<400> SEQUENCE: 570

Ala Gly Ile Pro Gly Phe
1               5

<210> SEQ ID NO 571
<211> LENGTH: 6
<212> TYPE: PRT
<213> ORGANISM: Homo sapiens

<400> SEQUENCE: 571

Glu Arg Gly Ala Ala Gly
1               5

<210> SEQ ID NO 572
<211> LENGTH: 6
<212> TYPE: PRT
<213> ORGANISM: Homo sapiens

<400> SEQUENCE: 572

Pro Gly Pro Pro Gly Thr
1               5

<210> SEQ ID NO 573
<211> LENGTH: 6
<212> TYPE: PRT
<213> ORGANISM: Homo sapiens

<400> SEQUENCE: 573

His Pro Gly Ser Pro Gly
1               5

<210> SEQ ID NO 574
<211> LENGTH: 6
<212> TYPE: PRT
```

<213> ORGANISM: Homo sapiens

<400> SEQUENCE: 574

Ser Pro Gly Pro Gln Gly
1               5

<210> SEQ ID NO 575
<211> LENGTH: 6
<212> TYPE: PRT
<213> ORGANISM: Homo sapiens

<400> SEQUENCE: 575

Gly Leu Ala Gly Thr Ala
1               5

<210> SEQ ID NO 576
<211> LENGTH: 6
<212> TYPE: PRT
<213> ORGANISM: Homo sapiens

<400> SEQUENCE: 576

Gly Pro Pro Gly Pro Gln
1               5

<210> SEQ ID NO 577
<211> LENGTH: 6
<212> TYPE: PRT
<213> ORGANISM: Homo sapiens

<400> SEQUENCE: 577

Gly Phe Pro Gly Met Lys
1               5

<210> SEQ ID NO 578
<211> LENGTH: 6
<212> TYPE: PRT
<213> ORGANISM: Homo sapiens

<400> SEQUENCE: 578

Glu Lys Gly Pro Ala Gly
1               5

<210> SEQ ID NO 579
<211> LENGTH: 6
<212> TYPE: PRT
<213> ORGANISM: Homo sapiens

<400> SEQUENCE: 579

Pro Gly Pro Gln Gly Leu
1               5

<210> SEQ ID NO 580
<211> LENGTH: 6
<212> TYPE: PRT
<213> ORGANISM: Homo sapiens

<400> SEQUENCE: 580

Phe Pro Gly Ala Pro Gly
1               5

<210> SEQ ID NO 581
<211> LENGTH: 6
<212> TYPE: PRT
<213> ORGANISM: Homo sapiens

```
<400> SEQUENCE: 581

Ala Pro Gly Pro Leu Gly
1               5

<210> SEQ ID NO 582
<211> LENGTH: 6
<212> TYPE: PRT
<213> ORGANISM: Homo sapiens

<400> SEQUENCE: 582

Gly Phe Pro Gly Met Lys
1               5

<210> SEQ ID NO 583
<211> LENGTH: 6
<212> TYPE: PRT
<213> ORGANISM: Homo sapiens

<400> SEQUENCE: 583

Pro Gly Leu Pro Gly Ile
1               5

<210> SEQ ID NO 584
<211> LENGTH: 6
<212> TYPE: PRT
<213> ORGANISM: Homo sapiens

<400> SEQUENCE: 584

Gly His Arg Gly Phe Asp
1               5

<210> SEQ ID NO 585
<211> LENGTH: 6
<212> TYPE: PRT
<213> ORGANISM: Homo sapiens

<400> SEQUENCE: 585

Pro Gly Pro Lys Gly Asn
1               5

<210> SEQ ID NO 586
<211> LENGTH: 6
<212> TYPE: PRT
<213> ORGANISM: Homo sapiens

<400> SEQUENCE: 586

Gly Glu Val Gly Pro Ala
1               5

<210> SEQ ID NO 587
<211> LENGTH: 6
<212> TYPE: PRT
<213> ORGANISM: Homo sapiens

<400> SEQUENCE: 587

Gly Pro Pro Gly Pro Ser
1               5

<210> SEQ ID NO 588
<211> LENGTH: 6
<212> TYPE: PRT
<213> ORGANISM: Homo sapiens

<400> SEQUENCE: 588
```

Gly Leu Pro Gly Leu Ala
1               5

<210> SEQ ID NO 589
<211> LENGTH: 6
<212> TYPE: PRT
<213> ORGANISM: Homo sapiens

<400> SEQUENCE: 589

Gly Ser Pro Gly Tyr Gln
1               5

<210> SEQ ID NO 590
<211> LENGTH: 6
<212> TYPE: PRT
<213> ORGANISM: Homo sapiens

<400> SEQUENCE: 590

Glu Met Gly Pro Ala Gly
1               5

<210> SEQ ID NO 591
<211> LENGTH: 6
<212> TYPE: PRT
<213> ORGANISM: Homo sapiens

<400> SEQUENCE: 591

Gly Lys Pro Gly Ala Asn
1               5

<210> SEQ ID NO 592
<211> LENGTH: 6
<212> TYPE: PRT
<213> ORGANISM: Homo sapiens

<400> SEQUENCE: 592

Gly Met Pro Gly Pro Arg
1               5

<210> SEQ ID NO 593
<211> LENGTH: 6
<212> TYPE: PRT
<213> ORGANISM: Homo sapiens

<400> SEQUENCE: 593

Gly Ile Thr Gly Ala Arg
1               5

<210> SEQ ID NO 594
<211> LENGTH: 6
<212> TYPE: PRT
<213> ORGANISM: Homo sapiens

<400> SEQUENCE: 594

Ala Gly Pro Arg Gly Ala
1               5

<210> SEQ ID NO 595
<211> LENGTH: 6
<212> TYPE: PRT
<213> ORGANISM: Homo sapiens

<400> SEQUENCE: 595

Gly Pro Ala Gly Ala Asn
1               5

<210> SEQ ID NO 596
<211> LENGTH: 6
<212> TYPE: PRT
<213> ORGANISM: Homo sapiens

<400> SEQUENCE: 596

Gly Lys Pro Gly Ala Asn
1               5

<210> SEQ ID NO 597
<211> LENGTH: 6
<212> TYPE: PRT
<213> ORGANISM: Homo sapiens

<400> SEQUENCE: 597

Gly Phe Pro Gly Ala Arg
1               5

<210> SEQ ID NO 598
<211> LENGTH: 6
<212> TYPE: PRT
<213> ORGANISM: Homo sapiens

<400> SEQUENCE: 598

Ile Ala Gly Ile Thr Gly
1               5

<210> SEQ ID NO 599
<211> LENGTH: 6
<212> TYPE: PRT
<213> ORGANISM: Homo sapiens

<400> SEQUENCE: 599

Ile Thr Gly Ala Arg Gly
1               5

<210> SEQ ID NO 600
<211> LENGTH: 6
<212> TYPE: PRT
<213> ORGANISM: Homo sapiens

<400> SEQUENCE: 600

Leu Arg Gly Gly Ala Gly
1               5

<210> SEQ ID NO 601
<211> LENGTH: 6
<212> TYPE: PRT
<213> ORGANISM: Homo sapiens

<400> SEQUENCE: 601

Val Gly Gly Leu Ala Gly
1               5

<210> SEQ ID NO 602
<211> LENGTH: 6
<212> TYPE: PRT
<213> ORGANISM: Homo sapiens

<400> SEQUENCE: 602

Ala Gly Pro Pro Gly Met
1               5

<210> SEQ ID NO 603
<211> LENGTH: 6
<212> TYPE: PRT
<213> ORGANISM: Homo sapiens

<400> SEQUENCE: 603

Pro Gln Gly Pro Pro Gly
1               5

<210> SEQ ID NO 604
<211> LENGTH: 6
<212> TYPE: PRT
<213> ORGANISM: Homo sapiens

<400> SEQUENCE: 604

Ser Pro Gly Gly Lys Gly
1               5

<210> SEQ ID NO 605
<211> LENGTH: 6
<212> TYPE: PRT
<213> ORGANISM: Homo sapiens

<400> SEQUENCE: 605

Gly Ala Pro Gly Glu Lys
1               5

<210> SEQ ID NO 606
<211> LENGTH: 6
<212> TYPE: PRT
<213> ORGANISM: Homo sapiens

<400> SEQUENCE: 606

Ile Lys Gly Pro Ala Gly
1               5

<210> SEQ ID NO 607
<211> LENGTH: 6
<212> TYPE: PRT
<213> ORGANISM: Homo sapiens

<400> SEQUENCE: 607

Phe Arg Gly Pro Ala Gly
1               5

<210> SEQ ID NO 608
<211> LENGTH: 6
<212> TYPE: PRT
<213> ORGANISM: Homo sapiens

<400> SEQUENCE: 608

Asp Ala Gly Ala Pro Gly
1               5

<210> SEQ ID NO 609
<211> LENGTH: 6
<212> TYPE: PRT
<213> ORGANISM: Homo sapiens

<400> SEQUENCE: 609

Gly Leu Pro Gly Pro Pro
1               5

<210> SEQ ID NO 610
<211> LENGTH: 6

<212> TYPE: PRT
<213> ORGANISM: Homo sapiens

<400> SEQUENCE: 610

Pro Gly Glu Asn Gly Lys
1               5

<210> SEQ ID NO 611
<211> LENGTH: 6
<212> TYPE: PRT
<213> ORGANISM: Homo sapiens

<400> SEQUENCE: 611

Gln Gln Gly Ala Ile Gly
1               5

<210> SEQ ID NO 612
<211> LENGTH: 6
<212> TYPE: PRT
<213> ORGANISM: Homo sapiens

<400> SEQUENCE: 612

Val Ala Gly Pro Pro Gly
1               5

<210> SEQ ID NO 613
<211> LENGTH: 6
<212> TYPE: PRT
<213> ORGANISM: Homo sapiens

<400> SEQUENCE: 613

Pro Gly Met Lys Gly His
1               5

<210> SEQ ID NO 614
<211> LENGTH: 6
<212> TYPE: PRT
<213> ORGANISM: Homo sapiens

<400> SEQUENCE: 614

Pro Gly Asp Lys Gly Glu
1               5

<210> SEQ ID NO 615
<211> LENGTH: 6
<212> TYPE: PRT
<213> ORGANISM: Homo sapiens

<400> SEQUENCE: 615

Gly Ser Asp Gly Gln Pro
1               5

<210> SEQ ID NO 616
<211> LENGTH: 6
<212> TYPE: PRT
<213> ORGANISM: Homo sapiens

<400> SEQUENCE: 616

Gly Ala Arg Gly Asn Asp
1               5

<210> SEQ ID NO 617
<211> LENGTH: 6
<212> TYPE: PRT
<213> ORGANISM: Homo sapiens

<400> SEQUENCE: 617

Gly Ala Arg Gly Pro Pro
1               5

<210> SEQ ID NO 618
<211> LENGTH: 6
<212> TYPE: PRT
<213> ORGANISM: Homo sapiens

<400> SEQUENCE: 618

Gly Pro Lys Gly Asp Ala
1               5

<210> SEQ ID NO 619
<211> LENGTH: 6
<212> TYPE: PRT
<213> ORGANISM: Homo sapiens

<400> SEQUENCE: 619

Pro Gly Pro Gln Gly His
1               5

<210> SEQ ID NO 620
<211> LENGTH: 6
<212> TYPE: PRT
<213> ORGANISM: Homo sapiens

<400> SEQUENCE: 620

Gly Ile Thr Gly Ala Arg
1               5

<210> SEQ ID NO 621
<211> LENGTH: 6
<212> TYPE: PRT
<213> ORGANISM: Homo sapiens

<400> SEQUENCE: 621

Gly Ser Arg Gly Ala Pro
1               5

<210> SEQ ID NO 622
<211> LENGTH: 6
<212> TYPE: PRT
<213> ORGANISM: Homo sapiens

<400> SEQUENCE: 622

Gly Ala Pro Gly Glu Lys
1               5

<210> SEQ ID NO 623
<211> LENGTH: 6
<212> TYPE: PRT
<213> ORGANISM: Homo sapiens

<400> SEQUENCE: 623

Pro Gln Gly Leu Gln Gly
1               5

<210> SEQ ID NO 624
<211> LENGTH: 6
<212> TYPE: PRT
<213> ORGANISM: Homo sapiens

<400> SEQUENCE: 624

Lys Gly Ser Pro Gly Ala
1               5

<210> SEQ ID NO 625
<211> LENGTH: 6
<212> TYPE: PRT
<213> ORGANISM: Homo sapiens

<400> SEQUENCE: 625

Pro Gly Pro Gln Gly Pro
1               5

<210> SEQ ID NO 626
<211> LENGTH: 6
<212> TYPE: PRT
<213> ORGANISM: Homo sapiens

<400> SEQUENCE: 626

Gly Pro Thr Gly Pro Ile
1               5

<210> SEQ ID NO 627
<211> LENGTH: 6
<212> TYPE: PRT
<213> ORGANISM: Homo sapiens

<400> SEQUENCE: 627

Gly Ser Pro Gly Glu Arg
1               5

<210> SEQ ID NO 628
<211> LENGTH: 6
<212> TYPE: PRT
<213> ORGANISM: Homo sapiens

<400> SEQUENCE: 628

Gly Ser Pro Gly Ala Gln
1               5

<210> SEQ ID NO 629
<211> LENGTH: 6
<212> TYPE: PRT
<213> ORGANISM: Homo sapiens

<400> SEQUENCE: 629

Gly Leu Ala Gly Pro Pro
1               5

<210> SEQ ID NO 630
<211> LENGTH: 6
<212> TYPE: PRT
<213> ORGANISM: Homo sapiens

<400> SEQUENCE: 630

Gly Ala Pro Gly Glu Lys
1               5

<210> SEQ ID NO 631
<211> LENGTH: 6
<212> TYPE: PRT
<213> ORGANISM: Homo sapiens

<400> SEQUENCE: 631

Gly Met Pro Gly Pro Arg

```
<210> SEQ ID NO 632
<211> LENGTH: 6
<212> TYPE: PRT
<213> ORGANISM: Homo sapiens

<400> SEQUENCE: 632

Pro Gly Pro Leu Gly Ile
1               5

<210> SEQ ID NO 633
<211> LENGTH: 6
<212> TYPE: PRT
<213> ORGANISM: Homo sapiens

<400> SEQUENCE: 633

Gly Asn Arg Gly Glu Arg
1               5

<210> SEQ ID NO 634
<211> LENGTH: 6
<212> TYPE: PRT
<213> ORGANISM: Homo sapiens

<400> SEQUENCE: 634

Pro Ser Gly Pro Pro Gly
1               5

<210> SEQ ID NO 635
<211> LENGTH: 6
<212> TYPE: PRT
<213> ORGANISM: Homo sapiens

<400> SEQUENCE: 635

Gly Leu Pro Gly Leu Ala
1               5

<210> SEQ ID NO 636
<211> LENGTH: 6
<212> TYPE: PRT
<213> ORGANISM: Homo sapiens

<400> SEQUENCE: 636

Pro Gly Pro Pro Gly Thr
1               5

<210> SEQ ID NO 637
<211> LENGTH: 6
<212> TYPE: PRT
<213> ORGANISM: Homo sapiens

<400> SEQUENCE: 637

Gly Pro Pro Gly Pro Gln
1               5

<210> SEQ ID NO 638
<211> LENGTH: 6
<212> TYPE: PRT
<213> ORGANISM: Homo sapiens

<400> SEQUENCE: 638

Phe Pro Gly Met Lys Gly
1               5
```

<210> SEQ ID NO 639
<211> LENGTH: 6
<212> TYPE: PRT
<213> ORGANISM: Homo sapiens

<400> SEQUENCE: 639

Gly Pro Pro Gly Ile Cys
1               5

<210> SEQ ID NO 640
<211> LENGTH: 6
<212> TYPE: PRT
<213> ORGANISM: Homo sapiens

<400> SEQUENCE: 640

Gly Pro Pro Gly Ile Cys
1               5

<210> SEQ ID NO 641
<211> LENGTH: 6
<212> TYPE: PRT
<213> ORGANISM: Homo sapiens

<400> SEQUENCE: 641

Gly Ala Pro Gly Leu Met
1               5

<210> SEQ ID NO 642
<211> LENGTH: 6
<212> TYPE: PRT
<213> ORGANISM: Homo sapiens

<400> SEQUENCE: 642

Glu Pro Gly Pro Arg Gly
1               5

<210> SEQ ID NO 643
<211> LENGTH: 6
<212> TYPE: PRT
<213> ORGANISM: Homo sapiens

<400> SEQUENCE: 643

Gly His Arg Gly Phe Asp
1               5

<210> SEQ ID NO 644
<211> LENGTH: 6
<212> TYPE: PRT
<213> ORGANISM: Homo sapiens

<400> SEQUENCE: 644

Gly Ala Ala Gly Ile Lys
1               5

<210> SEQ ID NO 645
<211> LENGTH: 6
<212> TYPE: PRT
<213> ORGANISM: Homo sapiens

<400> SEQUENCE: 645

Gly Glu Pro Gly Pro Arg
1               5

<210> SEQ ID NO 646

```
<211> LENGTH: 6
<212> TYPE: PRT
<213> ORGANISM: Homo sapiens

<400> SEQUENCE: 646

Gly Ile Pro Gly Ala Pro
1               5

<210> SEQ ID NO 647
<211> LENGTH: 6
<212> TYPE: PRT
<213> ORGANISM: Homo sapiens

<400> SEQUENCE: 647

Gly Ala Pro Gly Leu Met
1               5

<210> SEQ ID NO 648
<211> LENGTH: 6
<212> TYPE: PRT
<213> ORGANISM: Homo sapiens

<400> SEQUENCE: 648

Thr Gly Ala Arg Gly Leu
1               5

<210> SEQ ID NO 649
<211> LENGTH: 6
<212> TYPE: PRT
<213> ORGANISM: Homo sapiens

<400> SEQUENCE: 649

Met Pro Gly Pro Arg Gly
1               5

<210> SEQ ID NO 650
<211> LENGTH: 6
<212> TYPE: PRT
<213> ORGANISM: Homo sapiens

<400> SEQUENCE: 650

Gly Met Lys Gly His Arg
1               5

<210> SEQ ID NO 651
<211> LENGTH: 6
<212> TYPE: PRT
<213> ORGANISM: Homo sapiens

<400> SEQUENCE: 651

Gly Pro Gln Gly Val Lys
1               5

<210> SEQ ID NO 652
<211> LENGTH: 6
<212> TYPE: PRT
<213> ORGANISM: Homo sapiens

<400> SEQUENCE: 652

Pro Gly Ala Asn Gly Leu
1               5

<210> SEQ ID NO 653
<211> LENGTH: 6
<212> TYPE: PRT
```

```
<213> ORGANISM: Homo sapiens

<400> SEQUENCE: 653

Gly Thr Gly Gly Pro Pro
1               5

<210> SEQ ID NO 654
<211> LENGTH: 6
<212> TYPE: PRT
<213> ORGANISM: Homo sapiens

<400> SEQUENCE: 654

Gly Pro Pro Gly Pro Arg
1               5

<210> SEQ ID NO 655
<211> LENGTH: 6
<212> TYPE: PRT
<213> ORGANISM: Homo sapiens

<400> SEQUENCE: 655

Gly Gly Lys Gly Glu Arg
1               5

<210> SEQ ID NO 656
<211> LENGTH: 6
<212> TYPE: PRT
<213> ORGANISM: Homo sapiens

<400> SEQUENCE: 656

Pro Gln Gly Val Lys Gly
1               5

<210> SEQ ID NO 657
<211> LENGTH: 6
<212> TYPE: PRT
<213> ORGANISM: Homo sapiens

<400> SEQUENCE: 657

Pro Gly Ala Asn Gly Leu
1               5

<210> SEQ ID NO 658
<211> LENGTH: 161
<212> TYPE: PRT
<213> ORGANISM: Homo sapiens

<400> SEQUENCE: 658
```

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
                20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
        50                  55                  60

Arg Gly Thr Val Phe Ser Arg Met Pro Pro Arg Asp Lys Thr Met Arg
65                  70                  75                  80

Phe Phe Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
                100                 105                 110

His Ile Cys Thr Ser Trp Glu Ser Ala Ser Gly Ile Val Glu Phe Trp
            115                 120                 125

Val Asp Gly Lys Pro Arg Val Arg Lys Ser Leu Lys Lys Gly Tyr Thr
        130                 135                 140

Val Gly Ala Glu Ala Ser Ile Ile Leu Gly Gln Glu Gln Asp Ser Phe
145                 150                 155                 160

Gly

<210> SEQ ID NO 659
<211> LENGTH: 317
<212> TYPE: PRT
<213> ORGANISM: Homo sapiens

<400> SEQUENCE: 659

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
            260                 265                 270

Glu Ala Phe Gln Ala Arg Leu Lys Ser Trp Phe Glu Pro Leu Val Glu
        275                 280                 285

Asp Met Gln Arg Gln Trp Ala Gly Leu Val Glu Lys Val Gln Ala Ala
    290                 295                 300

Val Gly Thr Ser Ala Ala Pro Val Pro Ser Asp Asn His
305                 310                 315

<210> SEQ ID NO 660
<211> LENGTH: 17
<212> TYPE: PRT
<213> ORGANISM: Homo sapiens

<400> SEQUENCE: 660

Ala Lys Val Glu Gln Ala Val Glu Thr Glu Pro Glu Pro Glu Leu Arg
1               5                   10                  15

Gln

<210> SEQ ID NO 661
<211> LENGTH: 17
<212> TYPE: PRT
<213> ORGANISM: Homo sapiens

<400> SEQUENCE: 661

Ala Lys Val Glu Gln Ala Val Glu Thr Glu Pro Glu Pro Glu Leu Arg
1               5                   10                  15

Gln

<210> SEQ ID NO 662
<211> LENGTH: 16
<212> TYPE: PRT
<213> ORGANISM: Homo sapiens

<400> SEQUENCE: 662

Val Ala Glu Val Arg Ala Lys Leu Glu Glu Gln Ala Gln Gln Ile Arg
1               5                   10                  15

<210> SEQ ID NO 663
<211> LENGTH: 17
<212> TYPE: PRT
<213> ORGANISM: Homo sapiens

<400> SEQUENCE: 663

Ala Lys Val Glu Gln Ala Val Glu Thr Glu Pro Glu Pro Glu Leu Arg
1               5                   10                  15

Gln

<210> SEQ ID NO 664
<211> LENGTH: 13
<212> TYPE: PRT
<213> ORGANISM: Homo sapiens

<400> SEQUENCE: 664

Ala Met Leu Gly Gln Ser Thr Glu Glu Leu Arg Val Arg
1               5                   10

<210> SEQ ID NO 665
<211> LENGTH: 14
<212> TYPE: PRT
<213> ORGANISM: Homo sapiens

<400> SEQUENCE: 665

Glu Gln Ala Val Glu Thr Glu Pro Glu Pro Glu Leu Arg Gln
1               5                   10

<210> SEQ ID NO 666
<211> LENGTH: 14
<212> TYPE: PRT
<213> ORGANISM: Homo sapiens

```
<400> SEQUENCE: 666

Arg Gln Gln Thr Glu Trp Gln Ser Gly Gln Arg Trp Glu Leu
1               5                   10

<210> SEQ ID NO 667
<211> LENGTH: 18
<212> TYPE: PRT
<213> ORGANISM: Homo sapiens

<400> SEQUENCE: 667

Leu Ala Val Tyr Gln Ala Gly Ala Arg Glu Gly Ala Glu Arg Gly Leu
1               5                   10                  15

Ser Ala

<210> SEQ ID NO 668
<211> LENGTH: 13
<212> TYPE: PRT
<213> ORGANISM: Homo sapiens

<400> SEQUENCE: 668

Arg Ala Lys Leu Glu Glu Gln Ala Gln Gln Ile Arg Leu
1               5                   10

<210> SEQ ID NO 669
<211> LENGTH: 14
<212> TYPE: PRT
<213> ORGANISM: Homo sapiens

<400> SEQUENCE: 669

Ala Lys Leu Glu Glu Gln Ala Gln Gln Ile Arg Leu Gln Ala
1               5                   10

<210> SEQ ID NO 670
<211> LENGTH: 17
<212> TYPE: PRT
<213> ORGANISM: Homo sapiens

<400> SEQUENCE: 670

Ala Lys Val Glu Gln Ala Val Glu Thr Glu Pro Glu Pro Glu Leu Arg
1               5                   10                  15

Gln

<210> SEQ ID NO 671
<211> LENGTH: 16
<212> TYPE: PRT
<213> ORGANISM: Homo sapiens

<400> SEQUENCE: 671

Lys Val Glu Gln Ala Val Glu Thr Glu Pro Glu Pro Glu Leu Arg Gln
1               5                   10                  15

<210> SEQ ID NO 672
<211> LENGTH: 14
<212> TYPE: PRT
<213> ORGANISM: Homo sapiens

<400> SEQUENCE: 672

Glu Gln Ala Val Glu Thr Glu Pro Glu Pro Glu Leu Arg Gln
1               5                   10

<210> SEQ ID NO 673
<211> LENGTH: 16
<212> TYPE: PRT
```

<213> ORGANISM: Homo sapiens

<400> SEQUENCE: 673

Asp Glu Val Lys Glu Gln Val Ala Glu Val Arg Ala Lys Leu Glu Glu
1               5                   10                  15

<210> SEQ ID NO 674
<211> LENGTH: 16
<212> TYPE: PRT
<213> ORGANISM: Homo sapiens

<400> SEQUENCE: 674

Lys Glu Ser Asp Thr Ser Tyr Val Ser Leu Lys Ala Pro Leu Thr Lys
1               5                   10                  15

<210> SEQ ID NO 675
<211> LENGTH: 16
<212> TYPE: PRT
<213> ORGANISM: Homo sapiens

<400> SEQUENCE: 675

Gly Gly Asn Phe Glu Gly Ser Gln Ser Leu Val Gly Asp Ile Gly Asn
1               5                   10                  15

<210> SEQ ID NO 676
<211> LENGTH: 16
<212> TYPE: PRT
<213> ORGANISM: Homo sapiens

<400> SEQUENCE: 676

Ala Leu Lys Tyr Glu Val Gln Gly Glu Val Phe Thr Lys Pro Gln Leu
1               5                   10                  15

<210> SEQ ID NO 677
<211> LENGTH: 14
<212> TYPE: PRT
<213> ORGANISM: Homo sapiens

<400> SEQUENCE: 677

Gly Ile Val Glu Phe Trp Val Asp Gly Lys Pro Arg Val Arg
1               5                   10

<210> SEQ ID NO 678
<211> LENGTH: 10
<212> TYPE: PRT
<213> ORGANISM: Homo sapiens

<400> SEQUENCE: 678

Arg Lys Ala Phe Val Phe Pro Lys Glu Ser
1               5                   10

<210> SEQ ID NO 679
<211> LENGTH: 16
<212> TYPE: PRT
<213> ORGANISM: Homo sapiens

<400> SEQUENCE: 679

Lys Tyr Glu Val Gln Gly Glu Val Phe Thr Lys Pro Gln Leu Trp Pro
1               5                   10                  15

<210> SEQ ID NO 680
<211> LENGTH: 13
<212> TYPE: PRT
<213> ORGANISM: Homo sapiens

```
<400> SEQUENCE: 680

Asp Ser Phe Gly Gly Asn Phe Glu Gly Ser Gln Ser Leu
1               5                   10

<210> SEQ ID NO 681
<211> LENGTH: 12
<212> TYPE: PRT
<213> ORGANISM: Homo sapiens

<400> SEQUENCE: 681

Asp Phe Val Leu Ser Pro Asp Glu Ile Asn Thr Ile
1               5                   10

<210> SEQ ID NO 682
<211> LENGTH: 13
<212> TYPE: PRT
<213> ORGANISM: Homo sapiens

<400> SEQUENCE: 682

Ser Leu Lys Lys Gly Tyr Thr Val Gly Ala Glu Ala Ser
1               5                   10

<210> SEQ ID NO 683
<211> LENGTH: 12
<212> TYPE: PRT
<213> ORGANISM: Homo sapiens

<400> SEQUENCE: 683

Ala Phe Gly Gln Thr Asp Met Ser Arg Lys Ala Phe
1               5                   10

<210> SEQ ID NO 684
<211> LENGTH: 14
<212> TYPE: PRT
<213> ORGANISM: Homo sapiens

<400> SEQUENCE: 684

Ser Leu Lys Lys Gly Tyr Thr Val Gly Ala Glu Ala Ser Ile
1               5                   10

<210> SEQ ID NO 685
<211> LENGTH: 11
<212> TYPE: PRT
<213> ORGANISM: Homo sapiens

<400> SEQUENCE: 685

Gly Glu Val Phe Thr Lys Pro Gln Leu Trp Pro
1               5                   10

<210> SEQ ID NO 686
<211> LENGTH: 15
<212> TYPE: PRT
<213> ORGANISM: Homo sapiens

<400> SEQUENCE: 686

Ser Ile Ile Leu Gly Gln Glu Gln Asp Ser Phe Gly Gly Asn Phe
1               5                   10                  15

<210> SEQ ID NO 687
<211> LENGTH: 14
<212> TYPE: PRT
<213> ORGANISM: Homo sapiens

<400> SEQUENCE: 687
```

Lys Tyr Glu Val Gln Gly Glu Val Phe Thr Lys Pro Gln Leu
1               5                   10

<210> SEQ ID NO 688
<211> LENGTH: 6
<212> TYPE: PRT
<213> ORGANISM: Homo sapiens

<400> SEQUENCE: 688

Lys Val Glu Gln Ala Val
1               5

<210> SEQ ID NO 689
<211> LENGTH: 6
<212> TYPE: PRT
<213> ORGANISM: Homo sapiens

<400> SEQUENCE: 689

Ala Glu Val Arg Ala Lys
1               5

<210> SEQ ID NO 690
<211> LENGTH: 6
<212> TYPE: PRT
<213> ORGANISM: Homo sapiens

<400> SEQUENCE: 690

Met Leu Gly Gln Ser Thr
1               5

<210> SEQ ID NO 691
<211> LENGTH: 6
<212> TYPE: PRT
<213> ORGANISM: Homo sapiens

<400> SEQUENCE: 691

Gln Ala Val Glu Thr Glu
1               5

<210> SEQ ID NO 692
<211> LENGTH: 6
<212> TYPE: PRT
<213> ORGANISM: Homo sapiens

<400> SEQUENCE: 692

Gln Gln Thr Glu Trp Gln
1               5

<210> SEQ ID NO 693
<211> LENGTH: 6
<212> TYPE: PRT
<213> ORGANISM: Homo sapiens

<400> SEQUENCE: 693

Ala Val Tyr Gln Ala Gly
1               5

<210> SEQ ID NO 694
<211> LENGTH: 6
<212> TYPE: PRT
<213> ORGANISM: Homo sapiens

<400> SEQUENCE: 694

Ala Lys Leu Glu Glu Gln
1               5

```
<210> SEQ ID NO 695
<211> LENGTH: 6
<212> TYPE: PRT
<213> ORGANISM: Homo sapiens

<400> SEQUENCE: 695

Lys Leu Glu Glu Gln Ala
1               5

<210> SEQ ID NO 696
<211> LENGTH: 6
<212> TYPE: PRT
<213> ORGANISM: Homo sapiens

<400> SEQUENCE: 696

Val Glu Gln Ala Val Glu
1               5

<210> SEQ ID NO 697
<211> LENGTH: 6
<212> TYPE: PRT
<213> ORGANISM: Homo sapiens

<400> SEQUENCE: 697

Gln Ala Val Glu Thr Glu
1               5

<210> SEQ ID NO 698
<211> LENGTH: 6
<212> TYPE: PRT
<213> ORGANISM: Homo sapiens

<400> SEQUENCE: 698

Glu Val Lys Glu Gln Val
1               5

<210> SEQ ID NO 699
<211> LENGTH: 6
<212> TYPE: PRT
<213> ORGANISM: Homo sapiens

<400> SEQUENCE: 699

Ala Phe Val Phe Pro Lys
1               5

<210> SEQ ID NO 700
<211> LENGTH: 6
<212> TYPE: PRT
<213> ORGANISM: Homo sapiens

<400> SEQUENCE: 700

Tyr Glu Val Gln Gly Glu
1               5

<210> SEQ ID NO 701
<211> LENGTH: 6
<212> TYPE: PRT
<213> ORGANISM: Homo sapiens

<400> SEQUENCE: 701

Lys Ala Phe Val Phe Pro
1               5
```

```
<210> SEQ ID NO 702
<211> LENGTH: 6
<212> TYPE: PRT
<213> ORGANISM: Homo sapiens

<400> SEQUENCE: 702

Ser Phe Gly Gly Asn Phe
1               5

<210> SEQ ID NO 703
<211> LENGTH: 6
<212> TYPE: PRT
<213> ORGANISM: Homo sapiens

<400> SEQUENCE: 703

Phe Val Leu Ser Pro Asp
1               5

<210> SEQ ID NO 704
<211> LENGTH: 6
<212> TYPE: PRT
<213> ORGANISM: Homo sapiens

<400> SEQUENCE: 704

Leu Lys Lys Gly Tyr Thr
1               5

<210> SEQ ID NO 705
<211> LENGTH: 6
<212> TYPE: PRT
<213> ORGANISM: Homo sapiens

<400> SEQUENCE: 705

Phe Gly Gln Thr Asp Met
1               5

<210> SEQ ID NO 706
<211> LENGTH: 6
<212> TYPE: PRT
<213> ORGANISM: Homo sapiens

<400> SEQUENCE: 706

Leu Lys Lys Gly Tyr Thr
1               5

<210> SEQ ID NO 707
<211> LENGTH: 6
<212> TYPE: PRT
<213> ORGANISM: Homo sapiens

<400> SEQUENCE: 707

Ile Ile Leu Gly Gln Glu
1               5

<210> SEQ ID NO 708
<211> LENGTH: 6
<212> TYPE: PRT
<213> ORGANISM: Homo sapiens

<400> SEQUENCE: 708

Tyr Glu Val Gln Gly Glu
1               5

<210> SEQ ID NO 709
<211> LENGTH: 6
```

<212> TYPE: PRT
<213> ORGANISM: Homo sapiens

<400> SEQUENCE: 709

Leu Lys Tyr Glu Val Gln
1               5

<210> SEQ ID NO 710
<211> LENGTH: 6
<212> TYPE: PRT
<213> ORGANISM: Homo sapiens

<400> SEQUENCE: 710

Ile Val Glu Phe Trp Val
1               5

<210> SEQ ID NO 711
<211> LENGTH: 6
<212> TYPE: PRT
<213> ORGANISM: Homo sapiens

<400> SEQUENCE: 711

Glu Ser Asp Thr Ser Tyr
1               5

<210> SEQ ID NO 712
<211> LENGTH: 6
<212> TYPE: PRT
<213> ORGANISM: Homo sapiens

<400> SEQUENCE: 712

Gly Asn Phe Glu Gly Ser
1               5

<210> SEQ ID NO 713
<211> LENGTH: 6
<212> TYPE: PRT
<213> ORGANISM: Homo sapiens

<400> SEQUENCE: 713

Thr Glu Pro Glu Pro Glu
1               5

<210> SEQ ID NO 714
<211> LENGTH: 6
<212> TYPE: PRT
<213> ORGANISM: Homo sapiens

<400> SEQUENCE: 714

Thr Glu Pro Glu Pro Glu
1               5

<210> SEQ ID NO 715
<211> LENGTH: 6
<212> TYPE: PRT
<213> ORGANISM: Homo sapiens

<400> SEQUENCE: 715

Glu Gln Ala Gln Gln Ile
1               5

<210> SEQ ID NO 716
<211> LENGTH: 6
<212> TYPE: PRT
<213> ORGANISM: Homo sapiens

<400> SEQUENCE: 716

Thr Glu Glu Leu Arg Val
1               5

<210> SEQ ID NO 717
<211> LENGTH: 6
<212> TYPE: PRT
<213> ORGANISM: Homo sapiens

<400> SEQUENCE: 717

Pro Glu Pro Glu Leu Arg
1               5

<210> SEQ ID NO 718
<211> LENGTH: 6
<212> TYPE: PRT
<213> ORGANISM: Homo sapiens

<400> SEQUENCE: 718

Ser Gly Gln Arg Trp Glu
1               5

<210> SEQ ID NO 719
<211> LENGTH: 6
<212> TYPE: PRT
<213> ORGANISM: Homo sapiens

<400> SEQUENCE: 719

Glu Gly Ala Glu Arg Gly
1               5

<210> SEQ ID NO 720
<211> LENGTH: 6
<212> TYPE: PRT
<213> ORGANISM: Homo sapiens

<400> SEQUENCE: 720

Gln Ala Gln Gln Ile Arg
1               5

<210> SEQ ID NO 721
<211> LENGTH: 6
<212> TYPE: PRT
<213> ORGANISM: Homo sapiens

<400> SEQUENCE: 721

Gln Gln Ile Arg Leu Gln
1               5

<210> SEQ ID NO 722
<211> LENGTH: 6
<212> TYPE: PRT
<213> ORGANISM: Homo sapiens

<400> SEQUENCE: 722

Glu Pro Glu Pro Glu Leu
1               5

<210> SEQ ID NO 723
<211> LENGTH: 6
<212> TYPE: PRT
<213> ORGANISM: Homo sapiens

<400> SEQUENCE: 723

Pro Glu Pro Glu Leu Arg
1               5

<210> SEQ ID NO 724
<211> LENGTH: 6
<212> TYPE: PRT
<213> ORGANISM: Homo sapiens

<400> SEQUENCE: 724

Glu Val Arg Ala Lys Leu
1               5

<210> SEQ ID NO 725
<211> LENGTH: 7
<212> TYPE: PRT
<213> ORGANISM: Homo sapiens

<400> SEQUENCE: 725

Lys Ala Phe Val Phe Pro Lys
1               5

<210> SEQ ID NO 726
<211> LENGTH: 6
<212> TYPE: PRT
<213> ORGANISM: Homo sapiens

<400> SEQUENCE: 726

Ala Phe Val Phe Pro Lys
1               5

<210> SEQ ID NO 727
<211> LENGTH: 6
<212> TYPE: PRT
<213> ORGANISM: Homo sapiens

<400> SEQUENCE: 727

Lys Pro Gln Leu Trp Pro
1               5

<210> SEQ ID NO 728
<211> LENGTH: 6
<212> TYPE: PRT
<213> ORGANISM: Homo sapiens

<400> SEQUENCE: 728

Phe Val Phe Pro Lys Glu
1               5

<210> SEQ ID NO 729
<211> LENGTH: 6
<212> TYPE: PRT
<213> ORGANISM: Homo sapiens

<400> SEQUENCE: 729

Pro Asp Glu Ile Asn Thr
1               5

<210> SEQ ID NO 730
<211> LENGTH: 6
<212> TYPE: PRT
<213> ORGANISM: Homo sapiens

<400> SEQUENCE: 730

Asp Met Ser Arg Lys Ala

```
1               5

<210> SEQ ID NO 731
<211> LENGTH: 6
<212> TYPE: PRT
<213> ORGANISM: Homo sapiens

<400> SEQUENCE: 731

Val Gly Ala Glu Ala Ser
1               5

<210> SEQ ID NO 732
<211> LENGTH: 6
<212> TYPE: PRT
<213> ORGANISM: Homo sapiens

<400> SEQUENCE: 732

Lys Pro Gln Leu Trp Pro
1               5

<210> SEQ ID NO 733
<211> LENGTH: 6
<212> TYPE: PRT
<213> ORGANISM: Homo sapiens

<400> SEQUENCE: 733

Asp Ser Phe Gly Gly Asn
1               5

<210> SEQ ID NO 734
<211> LENGTH: 6
<212> TYPE: PRT
<213> ORGANISM: Homo sapiens

<400> SEQUENCE: 734

Val Phe Thr Lys Pro Gln
1               5

<210> SEQ ID NO 735
<211> LENGTH: 757
<212> TYPE: PRT
<213> ORGANISM: Homo sapiens

<400> SEQUENCE: 735

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
```

```
                130                 135                 140
Gly Leu Pro Gly Val Tyr Pro Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
        210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
        290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Val Gly Thr Pro Ala Ala Ala Ala Lys Ala
    450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
            500                 505                 510

Val Gly Val Ala Pro Gly Ile Gly Pro Gly Gly Val Ala Ala Ala Ala
        515                 520                 525

Lys Ser Ala Ala Lys Val Ala Ala Lys Ala Gln Leu Arg Ala Ala Ala
    530                 535                 540

Gly Leu Gly Ala Gly Ile Pro Gly Leu Gly Val Gly Val Gly Val Pro
545                 550                 555                 560
```

```
Gly Leu Gly Val Gly Ala Gly Val Pro Gly Leu Gly Val Gly Ala Gly
            565                 570                 575
Val Pro Gly Phe Gly Ala Gly Ala Asp Glu Gly Val Arg Arg Ser Leu
            580                 585                 590
Ser Pro Glu Leu Arg Glu Gly Asp Pro Ser Ser Ser Gln His Leu Pro
            595                 600                 605
Ser Thr Pro Ser Ser Pro Arg Val Pro Gly Ala Leu Ala Ala Ala Lys
            610                 615                 620
Ala Ala Lys Tyr Gly Ala Ala Val Pro Gly Val Leu Gly Gly Leu Gly
625                 630                 635                 640
Ala Leu Gly Gly Val Gly Ile Pro Gly Gly Val Val Gly Ala Gly Pro
                645                 650                 655
Ala Ala Ala Ala Ala Ala Lys Ala Ala Lys Ala Ala Gln Phe
                660                 665                 670
Gly Leu Val Gly Ala Ala Gly Leu Gly Leu Gly Val Gly Gly Leu
                675                 680                 685
Gly Val Pro Gly Val Gly Gly Leu Gly Gly Ile Pro Pro Ala Ala Ala
            690                 695                 700
Ala Lys Ala Ala Lys Tyr Gly Ala Ala Gly Leu Gly Gly Val Leu Gly
705                 710                 715                 720
Gly Ala Gly Gln Phe Pro Leu Gly Gly Val Ala Ala Arg Pro Gly Phe
                725                 730                 735
Gly Leu Ser Pro Ile Phe Pro Gly Gly Ala Cys Leu Gly Lys Ala Cys
                740                 745                 750
Gly Arg Lys Arg Lys
            755

<210> SEQ ID NO 736
<211> LENGTH: 20
<212> TYPE: PRT
<213> ORGANISM: Homo sapiens

<400> SEQUENCE: 736

Ala Arg Pro Gly Val Gly Val Gly Gly Ile Pro Thr Tyr Gly Val Gly
1               5                   10                  15

Ala Gly Gly Phe
            20

<210> SEQ ID NO 737
<211> LENGTH: 17
<212> TYPE: PRT
<213> ORGANISM: Homo sapiens

<400> SEQUENCE: 737

Gly Leu Pro Tyr Thr Thr Gly Lys Leu Pro Tyr Gly Tyr Gly Pro Gly
1               5                   10                  15

Gly

<210> SEQ ID NO 738
<211> LENGTH: 25
<212> TYPE: PRT
<213> ORGANISM: Homo sapiens

<400> SEQUENCE: 738

Gly Val Ala Pro Gly Val Gly Val Ala Pro Gly Val Gly Val Ala Pro
1               5                   10                  15

Gly Ile Gly Pro Gly Gly Val Ala Ala
```

20                  25

<210> SEQ ID NO 739
<211> LENGTH: 23
<212> TYPE: PRT
<213> ORGANISM: Homo sapiens

<400> SEQUENCE: 739

Gly Gly Ala Gly Val Pro Gly Val Pro Gly Ala Ile Pro Gly Ile Gly
1               5                   10                  15

Gly Ile Ala Gly Val Gly Thr
            20

<210> SEQ ID NO 740
<211> LENGTH: 23
<212> TYPE: PRT
<213> ORGANISM: Homo sapiens

<400> SEQUENCE: 740

Gly Gly Ala Gly Val Pro Gly Val Pro Gly Ala Ile Pro Gly Ile Gly
1               5                   10                  15

Gly Ile Ala Gly Val Gly Thr
            20

<210> SEQ ID NO 741
<211> LENGTH: 16
<212> TYPE: PRT
<213> ORGANISM: Homo sapiens

<400> SEQUENCE: 741

Gly Val Gly Ile Ser Pro Glu Ala Gln Ala Ala Ala Ala Ala Lys Ala
1               5                   10                  15

<210> SEQ ID NO 742
<211> LENGTH: 16
<212> TYPE: PRT
<213> ORGANISM: Homo sapiens

<400> SEQUENCE: 742

Gly Val Gly Ile Ser Pro Glu Ala Gln Ala Ala Ala Ala Ala Lys Ala
1               5                   10                  15

<210> SEQ ID NO 743
<211> LENGTH: 6
<212> TYPE: PRT
<213> ORGANISM: Homo sapiens

<400> SEQUENCE: 743

Arg Pro Gly Val Gly Val
1               5

<210> SEQ ID NO 744
<211> LENGTH: 6
<212> TYPE: PRT
<213> ORGANISM: Homo sapiens

<400> SEQUENCE: 744

Leu Pro Tyr Thr Thr Gly
1               5

<210> SEQ ID NO 745
<211> LENGTH: 6
<212> TYPE: PRT
<213> ORGANISM: Homo sapiens

<400> SEQUENCE: 745

Val Ala Pro Gly Val Gly
1               5

<210> SEQ ID NO 746
<211> LENGTH: 6
<212> TYPE: PRT
<213> ORGANISM: Homo sapiens

<400> SEQUENCE: 746

Gly Ala Gly Val Pro Gly
1               5

<210> SEQ ID NO 747
<211> LENGTH: 6
<212> TYPE: PRT
<213> ORGANISM: Homo sapiens

<400> SEQUENCE: 747

Val Gly Ile Ser Pro Glu
1               5

<210> SEQ ID NO 748
<211> LENGTH: 6
<212> TYPE: PRT
<213> ORGANISM: Homo sapiens

<400> SEQUENCE: 748

Arg Pro Gly Val Gly Val
1               5

<210> SEQ ID NO 749
<211> LENGTH: 6
<212> TYPE: PRT
<213> ORGANISM: Homo sapiens

<400> SEQUENCE: 749

Leu Pro Tyr Thr Thr Gly
1               5

<210> SEQ ID NO 750
<211> LENGTH: 6
<212> TYPE: PRT
<213> ORGANISM: Homo sapiens

<400> SEQUENCE: 750

Gly Val Gly Ala Gly Gly
1               5

<210> SEQ ID NO 751
<211> LENGTH: 6
<212> TYPE: PRT
<213> ORGANISM: Homo sapiens

<400> SEQUENCE: 751

Tyr Gly Tyr Gly Pro Gly
1               5

<210> SEQ ID NO 752
<211> LENGTH: 6
<212> TYPE: PRT
<213> ORGANISM: Homo sapiens

<400> SEQUENCE: 752

```
Gly Pro Gly Gly Val Ala
1               5

<210> SEQ ID NO 753
<211> LENGTH: 6
<212> TYPE: PRT
<213> ORGANISM: Homo sapiens

<400> SEQUENCE: 753

Gly Ile Ala Gly Val Gly
1               5

<210> SEQ ID NO 754
<211> LENGTH: 13
<212> TYPE: PRT
<213> ORGANISM: Homo sapiens

<400> SEQUENCE: 754

Lys Asn Gly Glu Thr Gly Pro Gln Gly Pro Gly Gly Cys
1               5                   10

<210> SEQ ID NO 755
<211> LENGTH: 13
<212> TYPE: PRT
<213> ORGANISM: Homo sapiens

<400> SEQUENCE: 755

Lys Asn Gly Glu Thr Gly Pro Gln Gly Pro Pro Gly Lys
1               5                   10

<210> SEQ ID NO 756
<211> LENGTH: 13
<212> TYPE: PRT
<213> ORGANISM: Homo sapiens

<400> SEQUENCE: 756

Lys Asp Gly Glu Thr Gly Ala Ala Gly Pro Pro Gly Lys
1               5                   10

<210> SEQ ID NO 757
<211> LENGTH: 13
<212> TYPE: PRT
<213> ORGANISM: Homo sapiens

<400> SEQUENCE: 757

Lys Asp Gly Glu Ala Gly Ala Gln Gly Pro Pro Gly Lys
1               5                   10

<210> SEQ ID NO 758
<211> LENGTH: 14
<212> TYPE: PRT
<213> ORGANISM: Homo sapiens

<400> SEQUENCE: 758

Pro Gly Lys Asn Gly Glu Thr Pro Gly Pro Gln Gly Pro Lys
1               5                   10

<210> SEQ ID NO 759
<211> LENGTH: 13
<212> TYPE: PRT
<213> ORGANISM: Homo sapiens

<400> SEQUENCE: 759

Ile Ala Gly Ile Thr Gly Ala Arg Gly Leu Gly Gly Cys
```

<210> SEQ ID NO 760
<211> LENGTH: 13
<212> TYPE: PRT
<213> ORGANISM: Homo sapiens

<400> SEQUENCE: 760

Ile Ala Gly Ile Thr Gly Ala Arg Gly Leu Ala Gly Lys
1               5                   10

<210> SEQ ID NO 761
<211> LENGTH: 13
<212> TYPE: PRT
<213> ORGANISM: Homo sapiens

<400> SEQUENCE: 761

Ile Ala Gly Leu Thr Gly Ala Arg Gly Leu Ala Gly Lys
1               5                   10

<210> SEQ ID NO 762
<211> LENGTH: 15
<212> TYPE: PRT
<213> ORGANISM: Homo sapiens

<400> SEQUENCE: 762

Leu Gly Ile Ala Gly Ile Thr Gly Ala Arg Gly Leu Ala Gly Lys
1               5                   10                  15

<210> SEQ ID NO 763
<211> LENGTH: 6
<212> TYPE: PRT
<213> ORGANISM: Homo sapiens

<400> SEQUENCE: 763

Lys Asp Gly Thr Ser Gly
1               5

<210> SEQ ID NO 764
<211> LENGTH: 13
<212> TYPE: PRT
<213> ORGANISM: Homo sapiens

<400> SEQUENCE: 764

Lys Asp Gly Thr Ser Gly His Pro Gly Pro Gly Gly Cys
1               5                   10

<210> SEQ ID NO 765
<211> LENGTH: 13
<212> TYPE: PRT
<213> ORGANISM: Homo sapiens

<400> SEQUENCE: 765

Lys Asp Gly Thr Ser Gly His Pro Gly Pro Ile Gly Lys
1               5                   10

<210> SEQ ID NO 766
<211> LENGTH: 13
<212> TYPE: PRT
<213> ORGANISM: Homo sapiens

<400> SEQUENCE: 766

Lys Asp Gly Ser Ser Gly His Pro Gly Pro Ile Gly Lys
1               5                   10

```
<210> SEQ ID NO 767
<211> LENGTH: 13
<212> TYPE: PRT
<213> ORGANISM: Homo sapiens

<400> SEQUENCE: 767

Pro Gly Lys Asp Gly Thr Ser Gly His Pro Gly Pro Lys
1               5                   10

<210> SEQ ID NO 768
<211> LENGTH: 13
<212> TYPE: PRT
<213> ORGANISM: Homo sapiens

<400> SEQUENCE: 768

Cys Gly Gly Gly Pro Pro Gly Ala Pro Gly Pro Leu Gly
1               5                   10

<210> SEQ ID NO 769
<211> LENGTH: 12
<212> TYPE: PRT
<213> ORGANISM: Homo sapiens

<400> SEQUENCE: 769

Ala Gln Gly Pro Pro Gly Ala Pro Gly Pro Leu Gly
1               5                   10

<210> SEQ ID NO 770
<211> LENGTH: 12
<212> TYPE: PRT
<213> ORGANISM: Homo sapiens

<400> SEQUENCE: 770

Ala Gln Gly Pro Pro Gly Ser Pro Gly Pro Leu Gly
1               5                   10

<210> SEQ ID NO 771
<211> LENGTH: 12
<212> TYPE: PRT
<213> ORGANISM: Homo sapiens

<400> SEQUENCE: 771

Asp Asp Gly Pro Ser Gly Ala Glu Gly Pro Pro Gly
1               5                   10

<210> SEQ ID NO 772
<211> LENGTH: 12
<212> TYPE: PRT
<213> ORGANISM: Homo sapiens

<400> SEQUENCE: 772

Gly Pro Pro Gly Ala Pro Gly Pro Leu Gly Ile Ala
1               5                   10

<210> SEQ ID NO 773
<211> LENGTH: 13
<212> TYPE: PRT
<213> ORGANISM: Homo sapiens

<400> SEQUENCE: 773

Asn Thr Gly Ala Pro Gly Ser Pro Gly Val Cys Gly Gly
1               5                   10

<210> SEQ ID NO 774
```

```
<211> LENGTH: 13
<212> TYPE: PRT
<213> ORGANISM: Homo sapiens

<400> SEQUENCE: 774

Asn Thr Gly Ala Pro Gly Ser Pro Gly Val Ser Gly Lys
1               5                   10

<210> SEQ ID NO 775
<211> LENGTH: 13
<212> TYPE: PRT
<213> ORGANISM: Homo sapiens

<400> SEQUENCE: 775

Asn Ser Gly Ser Pro Gly Asn Pro Gly Val Ala Gly Lys
1               5                   10

<210> SEQ ID NO 776
<211> LENGTH: 12
<212> TYPE: PRT
<213> ORGANISM: Homo sapiens

<400> SEQUENCE: 776

Ala Gly Asn Thr Gly Ala Pro Gly Ser Pro Gly Val
1               5                   10

<210> SEQ ID NO 777
<211> LENGTH: 13
<212> TYPE: PRT
<213> ORGANISM: Homo sapiens

<400> SEQUENCE: 777

Ala Ile Gly Pro Ser Gly Pro Ala Gly Lys Gly Gly Cys
1               5                   10

<210> SEQ ID NO 778
<211> LENGTH: 13
<212> TYPE: PRT
<213> ORGANISM: Homo sapiens

<400> SEQUENCE: 778

Ala Ile Gly Pro Ser Gly Pro Ala Gly Lys Asp Gly Lys
1               5                   10

<210> SEQ ID NO 779
<211> LENGTH: 13
<212> TYPE: PRT
<213> ORGANISM: Homo sapiens

<400> SEQUENCE: 779

Ala Ile Gly Pro Ala Gly Pro Ala Gly Lys Asp Gly Lys
1               5                   10

<210> SEQ ID NO 780
<211> LENGTH: 13
<212> TYPE: PRT
<213> ORGANISM: Homo sapiens

<400> SEQUENCE: 780

Pro Gly Ala Ile Gly Pro Ser Gly Pro Ala Gly Lys Asp
1               5                   10

<210> SEQ ID NO 781
<211> LENGTH: 6
<212> TYPE: PRT
```

<213> ORGANISM: Homo sapiens

<400> SEQUENCE: 781

Ala Gly Gly Phe Ala Pro
1               5

<210> SEQ ID NO 782
<211> LENGTH: 11
<212> TYPE: PRT
<213> ORGANISM: Homo sapiens

<400> SEQUENCE: 782

Cys Gly Gly Glu Lys Ala Gly Gly Phe Ala Pro
1               5                   10

<210> SEQ ID NO 783
<211> LENGTH: 10
<212> TYPE: PRT
<213> ORGANISM: Homo sapiens

<400> SEQUENCE: 783

Cys Gly Glu Lys Ala Gly Gly Phe Ala Pro
1               5                   10

<210> SEQ ID NO 784
<211> LENGTH: 10
<212> TYPE: PRT
<213> ORGANISM: Homo sapiens

<400> SEQUENCE: 784

Cys Gly Glu Lys Ser Gly Gly Phe Ser Pro
1               5                   10

<210> SEQ ID NO 785
<211> LENGTH: 12
<212> TYPE: PRT
<213> ORGANISM: Homo sapiens

<400> SEQUENCE: 785

Gly Gly Glu Lys Ala Gly Gly Phe Ala Pro Tyr Tyr
1               5                   10

<210> SEQ ID NO 786
<211> LENGTH: 6
<212> TYPE: PRT
<213> ORGANISM: Homo sapiens

<400> SEQUENCE: 786

Gln Asn Gly Asn Ile Lys
1               5

<210> SEQ ID NO 787
<211> LENGTH: 13
<212> TYPE: PRT
<213> ORGANISM: Homo sapiens

<400> SEQUENCE: 787

Ile Val Ile Glu Leu Gly Thr Asn Pro Leu Gly Gly Cys
1               5                   10

<210> SEQ ID NO 788
<211> LENGTH: 13
<212> TYPE: PRT
<213> ORGANISM: Homo sapiens

```
<400> SEQUENCE: 788

Ile Val Ile Glu Leu Gly Thr Asn Pro Leu Lys Ser Lys
1               5                   10

<210> SEQ ID NO 789
<211> LENGTH: 13
<212> TYPE: PRT
<213> ORGANISM: Homo sapiens

<400> SEQUENCE: 789

Leu Val Ile Glu Leu Gly Gly Asn Pro Leu Lys Asn Lys
1               5                   10

<210> SEQ ID NO 790
<211> LENGTH: 13
<212> TYPE: PRT
<213> ORGANISM: Homo sapiens

<400> SEQUENCE: 790

Ile Val Val Glu Leu Gly Gly Asn Pro Leu Thr Asn Lys
1               5                   10

<210> SEQ ID NO 791
<211> LENGTH: 14
<212> TYPE: PRT
<213> ORGANISM: Homo sapiens

<400> SEQUENCE: 791

Gln Met Ile Val Ile Glu Leu Gly Thr Asn Pro Leu Lys Lys
1               5                   10

<210> SEQ ID NO 792
<211> LENGTH: 13
<212> TYPE: PRT
<213> ORGANISM: Homo sapiens

<400> SEQUENCE: 792

Asn Val Leu Val Ile Glu Leu Gly Gly Asn Pro Leu Lys
1               5                   10

<210> SEQ ID NO 793
<211> LENGTH: 13
<212> TYPE: PRT
<213> ORGANISM: Homo sapiens

<400> SEQUENCE: 793

Cys Gly Gly Leu Asp Leu Gln Asn Asn Asp Ile Ser Glu
1               5                   10

<210> SEQ ID NO 794
<211> LENGTH: 12
<212> TYPE: PRT
<213> ORGANISM: Homo sapiens

<400> SEQUENCE: 794

Thr Leu Leu Asp Leu Gln Asn Asn Asp Ile Ser Glu
1               5                   10

<210> SEQ ID NO 795
<211> LENGTH: 12
<212> TYPE: PRT
<213> ORGANISM: Homo sapiens

<400> SEQUENCE: 795
```

```
Leu Asp Leu Gln Asn Asn Asp Ile Ser Glu Leu Arg
1               5                   10
```

<210> SEQ ID NO 796
<211> LENGTH: 16
<212> TYPE: PRT
<213> ORGANISM: Homo sapiens

<400> SEQUENCE: 796

```
Gln Asn Gly Asn Ile Lys Ile Gly Gln Asp Gly Gly Cys Lys Leu His
1               5                   10                  15
```

<210> SEQ ID NO 797
<211> LENGTH: 12
<212> TYPE: PRT
<213> ORGANISM: Homo sapiens

<400> SEQUENCE: 797

```
Gln Asn Gly Asn Ile Lys Ile Gly Gln Asp Tyr Lys
1               5                   10
```

<210> SEQ ID NO 798
<211> LENGTH: 12
<212> TYPE: PRT
<213> ORGANISM: Homo sapiens

<400> SEQUENCE: 798

```
Gln Asp Gly Asn Ile Lys Ile Gly Gln Asp Tyr Lys
1               5                   10
```

<210> SEQ ID NO 799
<211> LENGTH: 13
<212> TYPE: PRT
<213> ORGANISM: Homo sapiens

<400> SEQUENCE: 799

```
Val Ala Gln Asn Gly Asn Ile Lys Ile Gly Gln Asp Lys
1               5                   10
```

<210> SEQ ID NO 800
<211> LENGTH: 13
<212> TYPE: PRT
<213> ORGANISM: Homo sapiens

<400> SEQUENCE: 800

```
Val Ala Gln Asp Gly Asn Ile Lys Ile Gly Gln Asp Lys
1               5                   10
```

<210> SEQ ID NO 801
<211> LENGTH: 13
<212> TYPE: PRT
<213> ORGANISM: ARTIFICIAL
<220> FEATURE:
<223> OTHER INFORMATION: Human sequence with synthetic extension

<400> SEQUENCE: 801

```
Lys Asn Gly Glu Thr Gly Pro Gln Gly Pro Gly Gly Cys
1               5                   10
```

<210> SEQ ID NO 802
<211> LENGTH: 13
<212> TYPE: PRT
<213> ORGANISM: artificial
<220> FEATURE:
<223> OTHER INFORMATION: Human sequence with synthetic extension

```
<400> SEQUENCE: 802

Lys Asn Gly Glu Thr Gly Pro Gln Gly Pro Pro Gly Lys
1               5                   10

<210> SEQ ID NO 803
<211> LENGTH: 13
<212> TYPE: PRT
<213> ORGANISM: artificial
<220> FEATURE:
<223> OTHER INFORMATION: Deselection peptide

<400> SEQUENCE: 803

Lys Asp Gly Glu Thr Gly Ala Ala Gly Pro Pro Gly Lys
1               5                   10

<210> SEQ ID NO 804
<211> LENGTH: 13
<212> TYPE: PRT
<213> ORGANISM: artificial
<220> FEATURE:
<223> OTHER INFORMATION: Deselection peptide

<400> SEQUENCE: 804

Lys Asp Gly Glu Ala Gly Ala Gln Gly Pro Pro Gly Lys
1               5                   10

<210> SEQ ID NO 805
<211> LENGTH: 14
<212> TYPE: PRT
<213> ORGANISM: Artificial
<220> FEATURE:
<223> OTHER INFORMATION: Deselection sequence

<400> SEQUENCE: 805

Pro Gly Lys Asn Gly Glu Thr Pro Gly Pro Gln Gly Pro Lys
1               5                   10

<210> SEQ ID NO 806
<211> LENGTH: 13
<212> TYPE: PRT
<213> ORGANISM: Artificial
<220> FEATURE:
<223> OTHER INFORMATION: Human with synthetic extension

<400> SEQUENCE: 806

Ile Ala Gly Ile Thr Gly Ala Arg Gly Leu Gly Gly Cys
1               5                   10

<210> SEQ ID NO 807
<211> LENGTH: 13
<212> TYPE: PRT
<213> ORGANISM: Artificial
<220> FEATURE:
<223> OTHER INFORMATION: Human with synthetic extension

<400> SEQUENCE: 807

Ile Ala Gly Ile Thr Gly Ala Arg Gly Leu Ala Gly Lys
1               5                   10

<210> SEQ ID NO 808
<211> LENGTH: 13
<212> TYPE: PRT
<213> ORGANISM: Artificial
<220> FEATURE:
<223> OTHER INFORMATION: Human with synthetic extension

<400> SEQUENCE: 808
```

```
Ile Ala Gly Leu Thr Gly Ala Arg Gly Leu Ala Gly Lys
1               5                   10
```

<210> SEQ ID NO 809
<211> LENGTH: 15
<212> TYPE: PRT
<213> ORGANISM: Artificial
<220> FEATURE:
<223> OTHER INFORMATION: Deselection peptide

<400> SEQUENCE: 809

```
Leu Gly Ile Ala Gly Ile Thr Gly Ala Arg Gly Leu Ala Gly Lys
1               5                   10                  15
```

<210> SEQ ID NO 810
<211> LENGTH: 13
<212> TYPE: PRT
<213> ORGANISM: Artificial
<220> FEATURE:
<223> OTHER INFORMATION: Human with synthetic extension

<400> SEQUENCE: 810

```
Lys Asp Gly Thr Ser Gly His Pro Gly Pro Gly Gly Cys
1               5                   10
```

<210> SEQ ID NO 811
<211> LENGTH: 13
<212> TYPE: PRT
<213> ORGANISM: Artificial
<220> FEATURE:
<223> OTHER INFORMATION: Human with synthetic extension

<400> SEQUENCE: 811

```
Lys Asp Gly Thr Ser Gly His Pro Gly Pro Ile Gly Lys
1               5                   10
```

<210> SEQ ID NO 812
<211> LENGTH: 13
<212> TYPE: PRT
<213> ORGANISM: Artificial
<220> FEATURE:
<223> OTHER INFORMATION: Human with synthetic extension

<400> SEQUENCE: 812

```
Lys Asp Gly Ser Ser Gly His Pro Gly Pro Ile Gly Lys
1               5                   10
```

<210> SEQ ID NO 813
<211> LENGTH: 13
<212> TYPE: PRT
<213> ORGANISM: Artificial
<220> FEATURE:
<223> OTHER INFORMATION: Deselection peptide

<400> SEQUENCE: 813

```
Lys Asp Gly Ser Ser Gly His Pro Gly Pro Ile Gly Lys
1               5                   10
```

<210> SEQ ID NO 814
<211> LENGTH: 13
<212> TYPE: PRT
<213> ORGANISM: Artificial
<220> FEATURE:
<223> OTHER INFORMATION: Human with synthetic extension

<400> SEQUENCE: 814

```
Cys Gly Gly Gly Pro Pro Gly Ala Pro Gly Pro Leu Gly
1               5                   10
```

<210> SEQ ID NO 815
<211> LENGTH: 12
<212> TYPE: PRT
<213> ORGANISM: Artificial
<220> FEATURE:
<223> OTHER INFORMATION: Human with synthetic extension

<400> SEQUENCE: 815

```
Ala Gln Gly Pro Pro Gly Ala Pro Gly Pro Leu Gly
1               5                   10
```

<210> SEQ ID NO 816
<211> LENGTH: 12
<212> TYPE: PRT
<213> ORGANISM: Artificial
<220> FEATURE:
<223> OTHER INFORMATION: Human with synthetic extension

<400> SEQUENCE: 816

```
Ala Gln Gly Pro Pro Gly Ser Pro Gly Pro Leu Gly
1               5                   10
```

<210> SEQ ID NO 817
<211> LENGTH: 12
<212> TYPE: PRT
<213> ORGANISM: Artificial
<220> FEATURE:
<223> OTHER INFORMATION: Deselection peptide

<400> SEQUENCE: 817

```
Asp Asp Gly Pro Ser Gly Ala Glu Gly Pro Pro Gly
1               5                   10
```

<210> SEQ ID NO 818
<211> LENGTH: 12
<212> TYPE: PRT
<213> ORGANISM: Artificial
<220> FEATURE:
<223> OTHER INFORMATION: Deselection peptide

<400> SEQUENCE: 818

```
Gly Pro Pro Gly Ala Pro Gly Pro Leu Gly Ile Ala
1               5                   10
```

<210> SEQ ID NO 819
<211> LENGTH: 13
<212> TYPE: PRT
<213> ORGANISM: Artificial
<220> FEATURE:
<223> OTHER INFORMATION: Human with synthetic extension

<400> SEQUENCE: 819

```
Asn Thr Gly Ala Pro Gly Ser Pro Gly Val Cys Gly Gly
1               5                   10
```

<210> SEQ ID NO 820
<211> LENGTH: 13
<212> TYPE: PRT
<213> ORGANISM: Artificial
<220> FEATURE:
<223> OTHER INFORMATION: Human with synthetic extension

<400> SEQUENCE: 820

```
Asn Thr Gly Ala Pro Gly Ser Pro Gly Val Ser Gly Lys
```

```
1               5                  10
```

<210> SEQ ID NO 821
<211> LENGTH: 13
<212> TYPE: PRT
<213> ORGANISM: Artificial
<220> FEATURE:
<223> OTHER INFORMATION: Human with synthetic extension

<400> SEQUENCE: 821

```
Asn Ser Gly Ser Pro Gly Asn Pro Gly Val Ala Gly Lys
1               5                   10
```

<210> SEQ ID NO 822
<211> LENGTH: 12
<212> TYPE: PRT
<213> ORGANISM: Artificial
<220> FEATURE:
<223> OTHER INFORMATION: Deselection peptide

<400> SEQUENCE: 822

```
Ala Gly Asn Thr Gly Ala Pro Gly Ser Pro Gly Val
1               5                   10
```

<210> SEQ ID NO 823
<211> LENGTH: 13
<212> TYPE: PRT
<213> ORGANISM: Artificial
<220> FEATURE:
<223> OTHER INFORMATION: Human with synthetic extension

<400> SEQUENCE: 823

```
Ala Ile Gly Pro Ser Gly Pro Ala Gly Lys Gly Gly Cys
1               5                   10
```

<210> SEQ ID NO 824
<211> LENGTH: 13
<212> TYPE: PRT
<213> ORGANISM: Artificial
<220> FEATURE:
<223> OTHER INFORMATION: Human with synthetic extension

<400> SEQUENCE: 824

```
Ala Ile Gly Pro Ser Gly Pro Ala Gly Lys Asp Gly Lys
1               5                   10
```

<210> SEQ ID NO 825
<211> LENGTH: 13
<212> TYPE: PRT
<213> ORGANISM: Artificial
<220> FEATURE:
<223> OTHER INFORMATION: Human with synthetic extension

<400> SEQUENCE: 825

```
Ala Ile Gly Pro Ala Gly Pro Ala Gly Lys Asp Gly Lys
1               5                   10
```

<210> SEQ ID NO 826
<211> LENGTH: 13
<212> TYPE: PRT
<213> ORGANISM: Artificial
<220> FEATURE:
<223> OTHER INFORMATION: Deselection peptide

<400> SEQUENCE: 826

```
Pro Gly Ala Ile Gly Pro Ser Gly Pro Ala Gly Lys Asp
1               5                   10
```

<210> SEQ ID NO 827
<211> LENGTH: 11
<212> TYPE: PRT
<213> ORGANISM: Artificial
<220> FEATURE:
<223> OTHER INFORMATION: Human with synthetic extension

<400> SEQUENCE: 827

Cys Gly Gly Glu Lys Ala Gly Gly Phe Ala Pro
1               5                   10

<210> SEQ ID NO 828
<211> LENGTH: 10
<212> TYPE: PRT
<213> ORGANISM: Artificial
<220> FEATURE:
<223> OTHER INFORMATION: Human with synthetic extension

<400> SEQUENCE: 828

Cys Gly Glu Lys Ala Gly Gly Phe Ala Pro
1               5                   10

<210> SEQ ID NO 829
<211> LENGTH: 10
<212> TYPE: PRT
<213> ORGANISM: Artificial
<220> FEATURE:
<223> OTHER INFORMATION: Human with synthetic extension

<400> SEQUENCE: 829

Cys Gly Glu Lys Ser Gly Gly Phe Ser Pro
1               5                   10

<210> SEQ ID NO 830
<211> LENGTH: 12
<212> TYPE: PRT
<213> ORGANISM: Artificial
<220> FEATURE:
<223> OTHER INFORMATION: Deselection peptide

<400> SEQUENCE: 830

Gly Gly Glu Lys Ala Gly Gly Phe Ala Pro Tyr Tyr
1               5                   10

<210> SEQ ID NO 831
<211> LENGTH: 13
<212> TYPE: PRT
<213> ORGANISM: Artificial
<220> FEATURE:
<223> OTHER INFORMATION: Human with synthetic extension

<400> SEQUENCE: 831

Ile Val Ile Glu Leu Gly Thr Asn Pro Leu Gly Gly Cys
1               5                   10

<210> SEQ ID NO 832
<211> LENGTH: 13
<212> TYPE: PRT
<213> ORGANISM: Artificial
<220> FEATURE:
<223> OTHER INFORMATION: Human with synthetic extension

<400> SEQUENCE: 832

Ile Val Ile Glu Leu Gly Thr Asn Pro Leu Lys Ser Lys
1               5                   10

<210> SEQ ID NO 833
<211> LENGTH: 13
<212> TYPE: PRT
<213> ORGANISM: Artificial
<220> FEATURE:
<223> OTHER INFORMATION: Human with synthetic extension

<400> SEQUENCE: 833

Leu Val Ile Glu Leu Gly Gly Asn Pro Leu Lys Asn Lys
1               5                   10

<210> SEQ ID NO 834
<211> LENGTH: 13
<212> TYPE: PRT
<213> ORGANISM: Artificial
<220> FEATURE:
<223> OTHER INFORMATION: Human with synthetic extension

<400> SEQUENCE: 834

Ile Val Val Glu Leu Gly Gly Asn Pro Leu Thr Asn Lys
1               5                   10

<210> SEQ ID NO 835
<211> LENGTH: 14
<212> TYPE: PRT
<213> ORGANISM: Artificial
<220> FEATURE:
<223> OTHER INFORMATION: Deselection peptide

<400> SEQUENCE: 835

Gln Met Ile Val Ile Glu Leu Gly Thr Asn Pro Leu Lys Lys
1               5                   10

<210> SEQ ID NO 836
<211> LENGTH: 13
<212> TYPE: PRT
<213> ORGANISM: Artificial
<220> FEATURE:
<223> OTHER INFORMATION: Deselection peptide

<400> SEQUENCE: 836

Asn Val Leu Val Ile Glu Leu Gly Gly Asn Pro Leu Lys
1               5                   10

<210> SEQ ID NO 837
<211> LENGTH: 13
<212> TYPE: PRT
<213> ORGANISM: Artificial
<220> FEATURE:
<223> OTHER INFORMATION: Human with synthetic extension

<400> SEQUENCE: 837

Cys Gly Gly Leu Asp Leu Gln Asn Asn Asp Ile Ser Glu
1               5                   10

<210> SEQ ID NO 838
<211> LENGTH: 12
<212> TYPE: PRT
<213> ORGANISM: Artificial
<220> FEATURE:
<223> OTHER INFORMATION: Human with synthetic extension

<400> SEQUENCE: 838

Thr Leu Leu Asp Leu Gln Asn Asn Asp Ile Ser Glu
1               5                   10

```
<210> SEQ ID NO 839
<211> LENGTH: 12
<212> TYPE: PRT
<213> ORGANISM: Artificial
<220> FEATURE:
<223> OTHER INFORMATION: Deselection peptide

<400> SEQUENCE: 839

Leu Asp Leu Gln Asn Asn Asp Ile Ser Glu Leu Arg
1               5                   10

<210> SEQ ID NO 840
<211> LENGTH: 13
<212> TYPE: PRT
<213> ORGANISM: Artificial
<220> FEATURE:
<223> OTHER INFORMATION: Human with synthetic extension

<400> SEQUENCE: 840

Gln Asn Gly Asn Ile Lys Ile Gly Gln Asp Gly Gly Cys
1               5                   10

<210> SEQ ID NO 841
<211> LENGTH: 12
<212> TYPE: PRT
<213> ORGANISM: Artificial
<220> FEATURE:
<223> OTHER INFORMATION: Human with synthetic extension

<400> SEQUENCE: 841

Gln Asn Gly Asn Ile Lys Ile Gly Gln Asp Tyr Lys
1               5                   10

<210> SEQ ID NO 842
<211> LENGTH: 12
<212> TYPE: PRT
<213> ORGANISM: Artificial
<220> FEATURE:
<223> OTHER INFORMATION: Human with synthetic extension

<400> SEQUENCE: 842

Gln Asp Gly Asn Ile Lys Ile Gly Gln Asp Tyr Lys
1               5                   10

<210> SEQ ID NO 843
<211> LENGTH: 13
<212> TYPE: PRT
<213> ORGANISM: Artificial
<220> FEATURE:
<223> OTHER INFORMATION: Deselection peptide

<400> SEQUENCE: 843

Val Ala Gln Asn Gly Asn Ile Lys Ile Gly Gln Asp Lys
1               5                   10

<210> SEQ ID NO 844
<211> LENGTH: 13
<212> TYPE: PRT
<213> ORGANISM: Artificial
<220> FEATURE:
<223> OTHER INFORMATION: Deselection peptide

<400> SEQUENCE: 844

Val Ala Gln Asn Gly Asn Ile Lys Ile Gly Gln Asp Lys
1               5                   10
```

BIOCHEMICAL MARKERS FOR CVD RISK ASSESSMENT

The present invention relates to assays for detection of biochemical markers valuable for diagnostic purposes in cardiovascular disease and prognosis of disease development, including biochemical markers indicative of the risk of cardiovascular events resulting from atherosclerotic development and plaque instability.

Worldwide, cardiovascular disease (CVD) is the leading cause of morbidity and mortality. At present, there are no effective and non-invasive diagnostic methods that allow for diagnosis and classification of patients into different risk-groups and for the diagnosis of low risk patients. Diagnostic and prognostic tools are composed mainly of multivariate analysis of simple markers, such as age, smoking and various lipid and lipoprotein concentrations.

CVD covers several clinical syndromes, primarily, angina pectoris, myocardial infarction (coronary thrombosis) and stroke. All of these syndromes are usually the sequelae of complicated atherosclerosis.

Atherosclerosis begins with intimal thickening in childhood and progresses to fatty streaks in the intima of arteries—these lesions are characterized as type I and II, respectively. Fatty streaks are the earliest macroscopically visible lesions in the development of atherosclerosis and occur among almost all human beings of all races and societies. In the non pathogenic state, endothelial cells (EC) resist adhesive interactions with leukocytes. However, the actions of proinflammatory cytokines and accumulated oxidized lipoprotein in the arterial wall during atherogenesis, initiate expression of adhesion molecules, such as intercellular adhesion molecules (ICAM)-1 and vascular cell adhesion molecules (VCAM)-1, on the surface of aortic ECs. This allows for capturing and transmigration of leukocytes through the endothelial surface, into the intimal part of the vessel wall. The development of plaques involves an increasing number of smooth muscle cells (SMC) that undergo displacement and apoptosis, which results in increased matrix turnover. The impaired collagen synthesis can result in a weakened fibrous cap and an atherosclerotic plaque that is more prone to rupture; however, most investigators believe that the actions of a proteolytic enzymes such as matrix metallo-proteases (MMPs) and other proteases importantly contribute to the risk of plaque rupture (Clarkson and Kaplan 509-28).

Plaques are divisible into two different types: 'vulnerable' and 'stabilized' plaques. However, for detailed histological analyses and molecular understanding, a more detailed classification is often used. There are three major stages in development of plaque: initiation, fatty streaks and the complex/advanced plaque (Stary H. C.).

Atherosclerotic plaques develop within the intima of arteries, and may be classified depending on their composition and structure. This classification divides lesions into eight types (Stary H. C.):

I. Macrophages loaded with and enlarged by lipid droplets (macrophage foam cells) are increased in the intima.

II. Macrophage foam cells accumulate in the deep part of the proteoglycan layer along with lipid droplets within the intimal SMC. The layers of foam cells are visible as fatty streaks. In type II lesions monocytes penetrate the endothelial lining by monocyte chemo attractant proteins (mainly MCP-1), which are over expressed in human atheroma. The early types of lesion (type I and II) can start in infancy and do not necessarily lead to plaque rupture. Furthermore, the development of atherosclerosis may end after the formation of type III lesion, and the formation of plaque is not predictable (Stary H. C.).

III. The type III lesion is determined as the intermediate lesion between the fatty streaks (type II) and the atheroma (type IV). These lesions contain pools of extracellular lipid and thereby expand the spaces between the normally closely adjoining SMCs of the deep musculoelastic layer of the intima. The pools of material may replace proteoglycans and collagen fibres that normally reside here, but this occurs with little impact at this stage of atherogenesis.

IV. The atheroma is the first clinical sign of atherosclerosis. Displacement of SMCs in the intima of arteries by accumulating extracellular pools of lipids and disruption of the intimal architecture is a hallmark of a type IV lesion. The formation of the lipid cores is the end result of this SMC displacement. Formation of a lipid core accounts for the increased wall thickening. The lipid core is a large and well delineated region of the deep intima where the normal structural elements of this part of the arterial wall have been replaced by densely packed foam cell remnants, free lipids droplets, cholesterol crystals and calcium particles. SMCs normally resident in this area are decreased or completely absent at this stage of atherosclerosis progression. Any remnant SMCs become widely dispersed and have developed elongated cell bodies and very often unusually thick basement membranes. At this stage, the development of a layer overlying the lipid core begins. This layer consists of collagen and proteoglycan-rich intercellular matrix, SMCs with and without lipid droplets, macrophages, and foam cells.

V. The response to type IV lesion is the formation of a reparative fibrous tissue matrix, forming a fibrous "cap". Typically, these lesions will consist of layers of lipid cores and reparative tissue irregularly stacked on top of each other. Events such as hematoma and thrombus formation may additionally complicate these types of lesions. If not fatal, these lesion complications are integrated into the lesion and overgrown by a thin layer of reparative matrix tissue, consisting of collagens and proteoglycans. The content of extracellular matrix proteins collagen and proteoglycans increases in the atherosclerotic plaque during formation of the cap.

VI. The defects of the endothelium such as fissures, erosions, ulcerations, hematoma, thrombus, haemorrhage can if combined lead to more complicated lesion type designated type VI lesion.

VII. The lesion is often referred to as calcified lesion, where more than 50% of the lesion consists of mineral. In addition to calcifications, these lesions contain abundance of reparative fibrous connective tissue. When the SMCs trapped in this undergo apoptosis and disintegrate; their mineralized organelles become a part of the calcification.

VIII. The fibrotic lesion follows the calcific lesion. The fibrotic lesion may consist entirely of collagen and no lipid. (Stary H. C.)

Cardiovascular events are often the result of plaque rupture, in which inflammation and the release of proteases weaken the shoulder regions of the fibrous cap and allow the fatty materials in the plaque to come into contact with the blood precipitating a mural thrombus (Clarkson and Kaplan). Thinning of the fibrous cap by increased protease activity in the combination with decreased matrix production, is considered a hallmark of plaque instability increasing the risk of rupture. Vulnerability of plaques and their risk of rupture is an area of clinical interest. Definition of a vulnerable plaque (VP) is not standardized, but there is a general agreement stating existence of three histological hallmarks compared to stable plaque:
1) A larger lipid core (>40 percent of total lesion).
2) A thinner fibrous cap (65-150 micrometers).
3) Large amount of acute inflammatory cells.

Major criteria for defining VP include: active inflammation (presence of monocytes, macrophages and T cells), thin cap with large lipid core, endothelial denudation with superficial platelet aggregation, fissured plaque, and >90% stenosis of the artery. Other minor criteria include: superficial calcified nodule, intraplaque haemorrhage, endothelial dysfunction, and outward remodelling (Shin, Edelberg, and Hong).

Plaque complications, instability and rupture may be inhibited by medical treatment and/or lifestyle modification. In some cases, however, more invasive methods may be needed, i.e. angioplasty or bypass surgery.

Presently, diagnostic tools are based on either static image analyses still under development or low-technology methods such as systolic and diastolic blood pressure levels related to the risk of CVD. The field has devoted much attention to the development of multivariate analysis that may better identify patients at high risk. One such model is the SCORE-model (Systematic Coronary Risk Evaluation model). In 1994, with a revision in 2003, The European Atherosclerosis Society, The European Society of Cardiology and The European Society of Hypertension issued a set of recommendations regarding prevention of coronary heart diseases. This guideline is based on several assessment techniques, which have been developed to assess the risk of CVD in asymptomatic subjects, i.e. identification of asymptomatic high-risk patients. The SCORE-model integrates gender, age, smoking, systolic blood pressure and either total cholesterol or the cholesterol/HDL ratio as risk factors (Graham et al.).

In order to make a more detailed diagnosis, the SCORE model is not sufficient and imaging techniques are used. Imaging methods are therefore used mostly on patients in the high-risk group or during research.

Imaging Techniques

Coronary angiography (CAG) is currently the gold standard imaging technique for defining the degree of stenosis. CAG images the lumen of the vessel in two dimensions, but is restricted only to the lumen and not the vessel wall thereby CAG can not distinguish between an artery with a stable plaque and an artery with a vulnerable plaque. CAG is often used to determine whether a patient needs surgery; angioplasty or bypass. In order to determine if a point of luminal narrowing is an advanced plaque, other techniques are needed i.e. intravascular coronary ultrasound (IVUS) or angioscopy.

IVUS provides two-dimensional cross-sectional images of the plaque and vessel wall, and is considered as a method good for characterization of vessel wall and morphology and the degree of calcification, but poor for assessing the lipids in the lesion. However, IVUS is invasive and requires expertise and expense: therefore, its use is not wide spread. Angioscopy is another useful method in understanding and identifying atherosclerosis. Angioscopy is a direct visualization of plaque surface and has the capability of detecting colour of plaque and thrombosis. Angioscopy is, however, invasive and technically difficult, and so far it is has not been able to detect the degree of plaque extension. Another imaging technique that currently is receiving much attention is Magnetic Resonance imaging (MRI). MRI is non-invasive and able to identify carotid plaque at high risk of stroke. On the other hand, MRI is not the best technique to image coronary arteries, because of small plaque sizes and location of the coronary arteries. Other imaging techniques are under development, i.e. elastography, thermography and optical coherence tomography (Schaar et al.).

The imaging techniques mentioned are all under development and alone, none can identify a vulnerable plaque, but they are useful tools in understanding both the molecular events and plaque turnover prior to rupture. Presently, the only opportunity to diagnose CVD at an early stage is to utilize a range of risk factors for established coronary heart disease, peripheral artery disease and cerebrovascular atherosclerotic disease of the patient in question, as well as close relatives of the patient.

Present Biochemical Markers

At present, several biochemical markers are known as risk factors for atherosclerosis. Recently much attention has been directed to the measurement of biochemical marker concentrations in serum; both lipids such as total cholesterol, low-density lipoprotein cholesterol (LDL-C) and the high-density lipoprotein cholesterol (HDL-C) and inflammatory markers such as C-Reactive Protein (CRP), Interleukin-6 (IL-6), Interleukin-18 (IL-18), Tumor Necrosis Factor-alpha (TNFα), CD40, CD40 ligand (CD40L) and others.

Among lipoprotein markers, there have been at least two noteworthy advances. The size of LDL particles seems to predict the degree of atherosclerosis progression. Increased concentrations of small LDL particles are more related to CVD risk than increased concentrations of large particles (Gardner, Fortmann, and Krauss).

The level of HDL-C is strongly related to triglyceride, and high triglyceride level is correlated to a higher risk of CHD. A cohort study by Jeppesen et al (2003) found high TG/low HDL-C as the strongest risk factors of IHD (ischemic heart disease)(Jeppesen et al.).

Lipid profiles are important for evaluation of risk factors, but do not allow understanding and measurement of the molecular events associated with plaque turnover. A number of biochemical markers have been suggested as risk factors for CVD, although not specific product of the disease. These include CRP and Bone natriuretic peptide (BNP). Table 1 summarizes some of the known markers of CVD.

TABLE 1

A selection of present biochemical markers in CVD.

| Marker | Type | Description |
| --- | --- | --- |
| C-reactive protein (CRP) | Inflammatory | Produced in the liver, increases during inflammatory states. |
| Pregnancy-associated plasma protein (PAPP-A) | Inflammatory | Zinc-binding protein that acts as an enzyme, specifically a metallopeptidase. |
| Interleukin-6 (IL-6) | Inflammatory cytokine | Elevated level in heart failure and myocardial infarction. |
| Inteleukin-8 (IL-8) | Inflammatory cytokine | Elevated in myocardial infarctions. |
| Interleukin-18 | Inflammatory cytokine | Elevated in myocardial infarction. |

TABLE 1-continued

A selection of present biochemical markers in CVD.

| Marker | Type | Description |
| --- | --- | --- |
| TNF-α (Tumor Necrosis Factor) | Cytokine | Conc. Elevated in the settings of heart failure. |
| MCP-1 | Chemokine | Recruits monocytes from the blood into early atherosclerotic lesion. |
| Intercellular adhesion molecule-1 (ICAM-1) | Adhesion molecule | Elevated in myocardial infarctions and stroke. |
| Vascular cellular adhesion molecule-1 (VCAM-1) | Adhesion molecule | Elevated in myocardial infarctions and stroke. |
| Brain natriuretic peptide (BNP) | Neurohormonal activity | Produced in atria and ventricles of normal healthy heart. |
| Lipoprotein-associated phospholipase A2 (Lp-PLA$_2$) | Phospholipase | LDL-associated Lp-PLA$_2$ has proatherogenic effects. |
| Creatine phospokinase (CK-MB) | Enzyme | Useful as early detection of myocardial infarction. |
| Myeloperoxidase (MPO) | Heme enzyme | Activates metallo-proteases and promotes destabilization of plaque. |
| Myoglobulin | Heme protein | Released upon tissue necrosis. |
| CD40L | Protein | Released in the early stages of atherogenesis through to plaque rupture. Elevated in stroke. |
| Troponin T (TnT) | Protein | Tool for risk stratification. |
| Heart-Type Fatty Acid-binding protein (H-FABP) | Protein | H-FARB is released from the heart immediately after infarction. |
| Microalbuminurea | Protein | Marker of vascular endothelial dysfunction. |
| Low density lipoprotein cholesterol (LDL-C) | Lipoprotein | Transport cholesterol in the blood. |
| High Density lipoprotein cholersterol (HDL-C) | Lipoprotein | Holds antioxidant and antiinflammatory properties. |
| Triglyceride | Lipid | |
| PIIINP | Procollagen | Marker of type III collagen turnover. |

Thus, a range of different biochemical markers have been suggested as markers of cardiovascular events. Wang et al (2006) have measured 10 different biochemical markers in 3200 patients participating in the Framingham study, described in Table 1. The conclusion was that the measurement of 10 biochemical markers only contributes moderately to diagnosis over and above standard risk factors. Of the 10 biochemical markers, B-type natriuretic peptide level, C-reactive protein level and the urinary albumin-to-creatinine ratio showed the best correlation between marker and death/cardiovascular events (Wang et al.).

C-Reactive Protein

C-reactive protein (CRP) is an acute phase serum protein produced by the liver in response to different clinical conditions such as, inflammation, infection, or trauma (Gabay & Kushner 1999). The production of CRP is induced by cytokines such as IL-6, released from the affected or damaged tissues. The physiological role of CRP is yet unknown and discussions on its pro- or anti-inflammatory actions are ongoing.

There is accumulating evidence that the CRP is a risk factor for CVD in humans. In a study by Ridker et al. 2002, CRP was shown to be a better predictor of future cardiovascular events than LDL cholesterol, in a large population consisting of 28,000 healthy women followed for eight years for the occurrences of acute myocardial infarction, stroke, coronary revascularization, or death from CVD. Many other studies have also reported that baseline CRP levels constitute an independent risk factor for cardiovascular events (Thompson et al. 1995, Mendell et al. 1996, Kuller et al. 1996, Ridker et al. 1997, Tracy et al. 1997, Ridker et al. 2000).

It has been speculated that circulating CRP only reflects the general inflammation occurring in the atherosclerotic process and is not an active component in the pathogenesis of the disease. However, several lines of evidence also support the view that CRP has a role in atherogenesis. First, chronic infections giving rise to CRP are also associated with increased risk for CVD (Leinonen & Saikku 2002). Secondly, we and others have identified CRP is in different levels of atherosclerotic lesions (Reynolds & Vance 1987, Hatanaka et al. 1995). Finally, CRP has been shown to have proatherogenic properties in vitro: CRP may activate endothelial cells to produce adhesion molecules (Pasceri et al. 2000). It may also decrease the production of eNOS in endothelial cells (Venugopal et al. 2002) and enhance the uptake of LDL by macrophages (Zwaka et al. 2001).

Brain Natriuretic Peptide

Brain (B-type) natriuretic peptide (BNP) is a peptide hormone secreted by the ventricles of the heart in response to excessive stretching of cardiac myocytes in the ventricles. T-proBNP (the inactive N-terminal fragment) is, along with the active hormone (BNP), released to the blood stream upon cleavage of proBNP. Both BNP and NT-proBNP have been suggested as potential biochemical markers of cardiovascular events (Wang et al.).

Chemokines

Chemokines are also potential markers of CVD; chemokines are low molecular weight cytokines produced in inflammation. One major chemokine in relation to CVD is monocyte chemo attractant protein 1 (MCP-1). MCP-1 appears to play an early and important role in the recruitment of monocytes to atherosclerotic lesions. In a study using a monkey model of atherosclerosis, plasma concentrations of MCP-1 were highly associated with plaque size and plaque complications (Register et al.).

Lipids Including Cholesterol

Recently much attention has been directed to the measurement of cholesterol concentrations in serum; both total cholesterol, as well as the concentrations of low-density lipoprotein cholesterol (LDL-C) and the high-density lipoprotein cholesterol (HDL-C). Among lipoprotein markers, there have been at least two noteworthy advances. First, LDL particle size seems to predict the degree of atherosclerosis progression. Increased concentrations of small LDL particles are more related to CVD risk than increased concentrations of large particles (Gardner et al). Secondly, the cholesteryl oleate content of LDL particles may become a particularly important marker of CVD risk. In monkeys, enrichment of lipoprotein particle cores with cholesteryl oleate was strongly and positively associated with more severe coronary artery atherosclerosis (Rudel et al) and was additive to the contributions of LDL and HDL cholesterol concentrations. These findings in experimental animals are further supported by earlier human studies (Lawrie et al) that showed plasma lipoproteins with lower proportions of cholesteryl linoleate (and conversely higher proportions of cholesteryl oleate) are typical of patients with complications of CHD (coronary heart disease) compared to normal controls.

The level of HDL-C is strongly related to triglyceride, and high triglyceride level is correlated to a higher risk of CHD. A cohort study by Jeppesen et al) found high TG/low HDL-C as the strongest risk factors of IHD (ischemic heart disease).

These lipid profiles are important for evaluation of risk factors, but do not allow understanding and measurement of the molecular events associated with plaque turnover. A number of biochemical markers have been suggested as risk factors for CVD, although these are not the specific products of the disease. These include CRP and ApoE.

Lipoproteins

The biomarker most commonly used to predict CVD is cholesterol concentration (both total and the cholesterol/HDL ratio). These are used along with other risk factors, such as blood pressure and level of LDL. Both factors are used in the previously mentioned SCORE-model. The level of LDL is important as LDL transports cholesterol in the blood and accumulation of oxidized LDL can promote atherosclerosis (Graham et al). In addition, a significant association between CHD and triglyceride (TG) levels are found, in which an increased risk of CHD was associated with increasing TG levels, independent of both LDL-C and HDL-C levels, although the level of cholesterol is viewed as one of the major risk factors of CVD (Jeppeson et al).

Apo-E

Apolipoprotein E is found in chylomicrons, VLDL, and HDL. It is mainly synthesised in the liver, but also in many other organs such as brain, spleen, kidney (Siest et al. 1995). ApoE plays an essential role in lipoprotein metabolism by acting as a ligand for two receptors: the LDL receptor and Apo E specific chylomicron remnant receptor. The interaction between ApoE with these receptors gives a basis for the metabolic regulation of cholesterol. Polymorphism at the apoE gene locus results in three alleles found in most populations: ε2, ε3 and ε4 that determine six apoE phenotypes. Isoforms differ from each other by one aminoacid at positions 112 and 158. Apo E2 has cysteine on both residues and E4 has arginine at both positions. Apo E3 contains cysteine at position 112 and arginine at 158. Allele frequencies differ in different populations. Some studies have assessed the possible relationship between apoE polymorphism and atherosclerosis. A meta-analysis of 14 observation studies demonstrated ε4 allele as associated with coronary disease among both men and women (Wilson et al. 1996). Furthermore, ε4 allele has been associated with carotid artery atherosclerosis (Terry et al. 1996, Cattin et al. 1997, Haraki et al. 2002).

ApoE is 299 amino acids long and transports lipoprotein, fat soluble vitamins, and cholesterol into the lymph system and further into the blood circulation. ApoE is primarily synthesized in the liver. Currently, there are seven mammalian receptors for ApoE which belong to conserved low density lipoprotein receptor gene family.

Additional Biochemical Markers

Microalbuminurea (albumin to creatinine level) is also a potential and independent marker. The urinary albumin excretion rate is a marker of changes in the kidney and, when compared with a small creatinine elevation, it may indicate atherosclerosis (Wang et al.).

Of the procollagen markers, the marker for type III collagen turnover rate (PIIINP) has been investigated as a prognostic marker for hypertension and has been associated with myocardial infarction. Satta et al. examined the correlation between abdominal aortic aneurysm (AAA) and the concentration of the procollagen (PIIINP) in blood. They showed that the turnover of collagen type III is increased in patients with AAA and may be due to enhanced synthesis, enhanced degradation or a combination of both. In the same experiment, the carboxyterminal propeptide of type I procollagen (PICP) was measured, and there was no accelerated synthesis of type I collagen in the aneurysm sac.

Protein Profile of Plaque

Human arteries can be divided into larger or elastic arteries, medium or muscular arteries, and small arteries. The walls of arteries are composed of intima, media and adventitia, separated by the internal elastic lamina and external elastic lamina. The intima consists of connective tissue, smooth muscle cells and a few isolated macrophages. The boundaries of the intima can be defined as a layer between the luminal surface of the endothelium and the internal elastic lamina.

The arterial intima can further be divided into two layers. The inner layer, called a proteoglycan layer, composed of abundant proteoglycans, smooth muscle cells and macrophages. The lower layer, musculoelastic layer, is composed of abundant smooth muscle cells and elastic fibers. In the normal conditions, the two layers of the intima are barely visible by light microscopy, but are distinct and prominent when intimal thickening occurs. The media is the muscular part of the arterial wall, composed of smooth muscle cells, elastin, collagen fibrils.

The adventitia, outer layer, is highly microvascular and contains collagens, elastic fibrils, smooth muscle cells, and lymphatic channels.

Human atherosclerotic plaques are characterized by a lipid-rich core covered by a fibrous cap composed of fibrillar collagens, elastin, proteoglycans and SMC. Proteoglycans hyaluronan are major nonfibrillar components of the extracellular matrix that have the potential to affect lesion development by regulating events such as lipid accumulation, thrombosis, and cell proliferation and migration and by affecting the material properties of the tissue (Wight 1995). Infiltrating ApoE and CRP are also present and we have demonstrated localisation of both in atherosclerotic plaques of coronary arteries at different stages of the atherosclerotic disease.

ApoE and CRP Distribution in Human Beings

Table 2 below shows the distribution of ApoE and CRP in the human body.

TABLE 2

| Protein | Sites of expression |
|---|---|
| APOE | Blood, Serum, Plasma, Liver, Saliva, Monocyte, Cerebellum, Cerebrospinal Fluid, Frontal Cortex, Hippocampus, Temporal Cortex |
| CRP | Blood, Kidney, Liver, Peritoneal Fluid, Plasma, Serum |

Table 3 below illustrates known interactions of ApoE and CRP with proteins demonstrated in vivo and/or in vitro.

TABLE 3

| Protein | Interactions with proteins |
|---|---|
| ApoE | Albumin, Amyloid beta A4 protein, Macroglobulin, Microtubule associated protein tau, LDL receptor, Cathepsin B, Neurofilament 3, Phospholipid transfer protein, Prion protein, VLDL receptors, Scavenger receptors class B, |
| CRP | Serum amyloid P, Complement factor H, Fibronectin 1, Histone 1, FC gamma RI, FC gamma RIIb, CD32, Platelet glycoprotein VI, Leptin. Non protein interaction: Calcium, Cholesterol |

Collagen Distribution in Human Beings

Collagen is widely distributed in the human body, i.e. ~30% of the protein mass in the human body is composed of collagen. In Table 4, the major collagen types are listed with their major tissue distribution.

TABLE 4

| Collagen type | Tissue distribution |
|---|---|
| I | Skin, bone, tendon, ligament, cornea |
| II | Cartilage, vitreous |
| III | Skin, vessel, intestine, uterus |
| IV | Basement membranes |
| V | Bone, skin, cornea, placenta |
| VI | Bone, cartilage, cornea, skin, vessel |
| VII | Skin, bladder, oral mucosa, umbilical cord, amnion |
| VIII | Descemet's membrane, vessel, bone, brain, heart, kidney, skin, cartilage |
| XIII | Endothelial cells, skin, eye, heart, skeletal muscle |
| XIV | Vessel, bone, skin, cartilage, eye, nerve, tendon, uterus |
| XXI | Vessel, heart, stomach, kidney, skeletal muscle, placenta |

Type I collagen is the most abundant collagen and is found in most connective tissue. It is especially important for the structure of bone and skin. The major content of collagen in the human body is distributed in the skin and bone, where the major collagenous components are type I and III collagens. Collagen type III is a major component of large arteries, and is also found in smaller amounts in tissues rich type I collagen. In addition, collagen type IV is found in the basement membrane and around blood vessels and nerves. The most common localization of type V collagen is within the characteristic collagen fibrils, in association with the collagen type I and III (Garrone et al).

Some collagens have a restricted tissue distribution: for example, type II, which are found almost exclusively in cartilage (Mayne R.).

Collagen fibrils often consist of more than one collagen type. For example, the type I collagen fibrils often contain small amounts of types III, V and XII, whereas the type II collagen fibrils of cartilage also contain types IX and XI.

Collagens in Arteries

In arteries, six types of collagen are found (types I, III, IV, V, VI and VIII), where type I and III are the most abundant, 80-90% of collagen content. Type I and III are also predominant in the vessel wall. They appear to be co-distributed in different amounts within all three layers of the artery wall, synthesis of collagen type I and III tends to be located in the intima (Mayne R).

Collagens and Other Structural Proteins in Plaque—Turnover

During development of atherosclerotic plaques collagen is accumulated in the fibrous cap (Stary H. C.). In a study by Katsuda et al (1992) collagen types I, III and IV were found in the thickening intima at all stages of the lesion in aortic human tissues. Collagen type VI was distributed in the basement membrane in the region of intimal cells and in advanced lesions also detected around the elongated SMC. Earlier studies of type I and III have provided evidence of an equal distribution in atherosclerotic arterial wall (Shekhonin et al). According to McCullagh et al (1980) type III is the predominant collagen in normal human aortic media (appr. 70% of the extractable collagen). A recent study by Eriksen et al (2006) found a decrease of total collagen content in human aortic valve depending on the degree of stenosis. The molecular mechanism of stenosis is thought to be similar to atherosclerosis. In healthy aortic valves, the collagen content is mainly type I and III. During stenosis, the total content of collagen decreases, which is presumably caused by an increased turnover of collagen type I. Type I collagen accounted for approximately 60-70% of total collagen; whereas the proportion of type III collagen was 30-40% both in healthy valves and in calcified valves.

Type V collagen also increases in advanced atherosclerotic lesions and is distributed throughout the extracellular matrix in both aortic media and in the subendothelial region of the plaques (McCullagh et al).

There seems to be a consensus that the main collagen types to be found in atherosclerotic plaque are type I and III, whether they are equally distributed in healthy and atherosclerotic vessel remains to be further investigated.

In the study by Katsuda et al (1992) no collagen was detected in the center of the atheroma of more advanced lesions.

Elastin

Elastin is one of the most stable proteins in the body and is found in most connective tissue caused by its elasticity and resilience. Elastin dominates the protein content of the arterial wall, where it is the major extracellular matrix protein.

Elastin is the main component in elastic fibers and is related to calcification. Vascular calcification occurs at two distinct sites within the vessel wall: the intima and the media. Intimal calcification is related to atherosclerosis, mainly within the necrotic core. Calcified elastic fiber constitutes the plaque shoulder where the plaques are most prone to rupture; suggesting that calcification of elastic fiber may affect plaque stability (Bobryshev Y. V.). In atherosclerosis, the content of elastic fibers decreases along with lipid deposition, this generates an enhanced susceptibility to elastin degrading enzymes. Thereby the content of elastin in contrast to collagen decreases as the lesion develops.

Distribution of Elastin in Human Beings

Table 5 shows the distribution of Elastin in the human body.

TABLE 5

| Protein | Sites of expression |
|---|---|
| Elastin | Aorta and other Blood vessels, Lung, Skin Fibroblasts |

Table 6 illustrates known interactions of Elastin with proteins demonstrated in vivo and/or in vitro.

TABLE 6

| Protein | Interactions with proteins |
|---|---|
| Elastin | Decorin, Elastase, Fibrillin, Fibulin, Lysozyme, Lysyl Oxidase, Galectin, Biglycan, Nidogen, Ficolin, Proteinase3. |

Proteoglycans as Matrix Components

Proteoglycans (PG) are polysaccharide-protein macromolecules localized predominately in the intercellular matrix of vessel wall (Salisbury and Wagner 1981). PGs are macromolecules characterized by the presence of one, or more, long un-branched and highly polyanionic sugar side chains called GAGs, covalently attached to a core protein through a link region. The repeating unit of the GAG consists of an amino sugar, either N-acetyl-glucosamine (GlcNAc) or N-acetyl-galactosamine (GalNAc), and a hexuronic acid, either glucouronic acid (GlcA) or iduronic acid (IdoA). One or both of the sugars in the repeating unit contain one or more sulfate groups (Rodriguez-Lee 2007). In addition to the GAG chains, most core proteins carry N- and/or O-linked oligosaccharides.

Classification and Nomenclature of PGs

PGs are a very heterogeneous group of macromolecules. A single type of core protein can vary in the number and type of attached GAG chains. The length of the chains and the arrangement of the sulfated residues along the chains vary also.

Four main classes of GAGs are distinguished according to the structure of the repeating disaccharide unit: chondroitin sulfate (CS) and dermatan sulfate (DS), heparin sulfate (HS) and heparin, hyaluronan, and keratin sulfate (KS).

Hyaluronan is the simplest of GAGs. In contrast to all of the others, it does not contain any sulfated sugars. All of its disaccharide units are identical, its chain length is enormous and it is not linked to any core protein.

KS is a sulfated polylactosamine chain. KS-I has originally been described in cornea, and is N-linked to aspargine residues in the core protein, whereas KS-II or cartilage KS, is 0-linked to serine or threonine residues (Funderburgh 2000).

PGs can be classified according to several parameters:
  Attached GAG chain (CS/DS- or HS containing PGs),
  Topographic distribution in relation to the cell (extracellular and basement membrane PGs, cell-associated PGs or intracellular PGs),
  Core protein homology (hyalectans, small leucine-rich PGs (SLRPs).

Chondroitin/dermatan sulfate PGs (Versican, aggrecan, neurocan, and brevican) belong to the family of hyaluronan-binding proteoglycans. This gene family is collectively termed hyalectans. Each family member has a characteristic distribution, with aggrecan prominent in cartilage, neurocan and brevican prominent in the central nervous system, and versican present in a variety of soft tissues, including arterial walls. The gene and protein structure of versican follows a domain template. The amino-terminal globular end (G1) binds to GAG hyaluronan, and the carboxy-terminal globular domain (G3) resembles the selectin family of proteins, consisting of a C-type lectin adjacent to two epidermal growth factor (EGF) domains and a complement regulatory region. The middle region of versican core protein is encoded by two large exons that specify the CS attachment regions of versican. The region encoded by exon 7 is called aGAG, whereas the region encoded by exon 8 is called βGAG. Four mRNA transcripts arise from alternative splicing of versican, giving rise to V0, V1, V2, and V3 which differ in the length of the core protein and the number of attached GAGs (Dours-Zimmermann and Zimmermann). The number of potential GAG attachment sites in human versican is: 17-23 for V0, 12-15 for V1, 5-8 for V2, and none for V3 (Wight 617-23).

Decorin and biglycan are members of SLRP-family that comprises at least nine members grouped into three classes (I, II, and III) and different subfamilies. They are all characterized by the presence of a central domain containing leucine-rich repeats to achieve strong presence of a central domain containing leucine-rich repeats to achieve strong protein-protein interactions. Decorin and biglycan are members of class I, and show highest amino-acid homology of the family (~57%) and are the only SLRPs with a propeptide. The propeptide is highly conserved across species and may function as a recognition sequence for xylosyltransferase, the first enzyme involved in synthesis of the GAG chain.

Versican, decorin, and biglycan are the major CS/DS PGs in the matrix of the mammalian arterial wall (Wight et al. 1986). The size of Versican V0 core protein is 370 kDa, which makes it roughly 10 times larger than decorin 36 kDa and biglycan 38 kDa. Side-chains show a wide range of sizes, but generally average around 40-90 kDa each.

Heparan sulfate proteoglycans: HSPGs are divided into five distinct classes of cell-associated and pericellular PGs and they account for at least 95% of the HS of mammalian cell surfaces, basement membranes and ECMs. The cell-associated HSPGs include integral membrane syndecans and anchored glypicans. Pericellular HSPGs include mainly perlecan, agrin. These PGs are termed pericellular because of their close association with the plasmamembrane via integrins (Whitelock and lozzo).

Perlecan is a modular HSPG that is expressed in nearly all basement membranes as well as mesenchymal organs and connective tissues and is one of the largest single-chain polypeptides found in vertebrate and invertebrate animals. The five modules of perlecan and its HS side-chains take part in a large number of molecular interactions such as with fibroblast growth factor-2, vascular endothelial growth factor (VEGF), platelet-derived growth factor (PDGF), and other matrix proteins. The core protein of human perlecan is ~470 kDa and, together with numerous O-linked oligosaccharides and four HS side chains, it can reach a molecular weight of over 800 kDa (Knox and Whitelock).

Proteoglycan Distribution

Proteoglycans (PGs) are macromolecules distributed almost everywhere in the human body. The structure and size of PGs vary extremely. The basic structure of all PGs includes a core protein and at least one, but often many carbohydrate chains-glycosaminoglycans (GAGs). PGs can be found intracellularly, on the surface of cells, and in the extracellular matrix. The structural diversity of PGs suggests numerous biological functions. Table 7 above gives an overview of PG distribution and function.

TABLE 7

| Proteoglycan family | Proteoglycan | Distribution | Function |
|---|---|---|---|
| Keratan sulphate- Small leucine rich PG | Lumican | Cornea | Collagen fibril organization and growth. Corneal transparency. Epithelial cell migration and tissue repair. |
| Chondroitin sulphate | Versican | Smooth muscle cells of blood vessels. Epithelial cells of skin. Cells of central and peripheral nervous system. | Cell adhesion, migration and proliferation. |
| Dermatan Sulphate (Small leucine rich PGs) | Decorin | Connective tissue. Artery wall. | Plays a role in matrix assembly. |
| | Biglycan | Extracellular matrix tissue: bone, cartilage, tendon, arteries. | Role in mineralization of the bone. |
| Heparan sulphate | Perlecan | Extracellular matrix of blood vessels. | Binds to and cross-links many extracellular matrix components and cell-surface molecules. |
| Chondroitin sulphate- Large aggregating PG | Aggrecan | Cartilage. Extracellular matrix. | Gives tissues ability to resist compressive loads. |

Proteoglycans in Arteries

At least five types of PGs are present in the extracellular matrix of the artery wall; versican—which interacts with hyaluronan to form large aggregates; small-leucine rich decorin and biglycan, which interact with fibrillar matrix components like collagen and elastin; heparan sulphate—perlecan, which is a component of basal lamina and keratin sulphate—lumican (Talusan et al.).

Versican is one of several ECM molecules that accumulate in lesions of atherosclerosis. Although a number of studies indicate that versican is clearly capable of binding to LDL, versican is generally not detected in the lipid-rich center of the necrotic core (Evanko et al.).

Lumican has been shown to directly bind to macrophages and to enhance macrophage migration. Lumican may therefore directly influence macrophage behavior in the vascular intima as well as stimulate the formation of the necrotic core, characteristic of advanced atherosclerotic lesions (Funderburgh et al. 1997).

Biglycan is found in the fibrous cap. Versican and biglycan have affinity for LDL and form insoluble complexes, which accelerates oxidation of LDL. Biglycan may contribute to the pathogenesis of atherosclerosis by trapping lipoproteins in the artery wall. Changes in the proteoglycan metabolism of the intima of arteries constitute the initial lesions of atherosclerosis and the accumulation of proteoglycans play a fundamental role in the progression of atherosclerosis (Kunz J.).

Perlecan was reported in human intimal hyperplasia as one of the central components of intimal extracellular matrix, by mass spectrometry-based analysis and by immunohistochemistry.

Table 8 illustrates distribution of some PGs in immunohistochemical stainings of PGs in normal and atherosclerotic arteries (Evanko et al).

TABLE 8

| | Normal Vessel | | Fibrous Core | | | | |
|---|---|---|---|---|---|---|---|
| PG or GAG | Endothelial cells | SMCs | Endothelial cells | SMC's | Macrophages | Fibrous Cap | Plaque core |
| Perlecan | +++ | ++ | +++ | +++ | ++ | + | +++ |
| Decorin | + | ++ | + | + | +++ | + | +++ |
| Biglycan | −/+ | ++ | ++ | +++ | + | +++ | −/+ |
| Versican | − | ++ | −/+ | +++ | − | +++ | − |
| Hyaluronan | ++ | + | ++ | +++ | +++ | +++ | +++ |

Staining results:
− undetectable;
−/+ variably detectable;
+ detectable;
++ moderate;
+++ strong Proteoglycan Involvement in Matrix Remodelling A study of atherosclerosis progression in nonhuman primates has demonstrated that accumulation of specific PGs varies with lesion severity and with the distribution of cells and growth factors, suggesting that different PGs play distinct roles during progression of atherosclerosis. Different levels of specific PGs may directly affect material properties of the tissue via their contribution to altering structural arrangements of fibrous matrix components such as elastin and collagen.

Versican and hyaluronan show similar localization in the matrix, suggesting aggregate formation between the two in the atherogenesis. The marked increase in versican and hyaluronan in early lesions could suggest that they play a role in early atherosclerotic lesions, such as proliferation and migration of SMCs and leukocytes. Furthermore, versican and hyaluronan are principal matrix components of human restenotic lesions and have been shown to contribute to neo-intimal thickening after vascular injury in vitro. An abundance of versican early in atherogenesis could also predispose the extracellular matrix to increase lipid entrapment due to the binding of lipoproteins to chondroitin sulphate chains of versican. This idea is supported by co-localization of versican with apoprotein (a) and apolipoprotein E in transplant arteriopathy (Evanko et al). Loss of versican from the plaque may result in matrix instability.

This is further evidenced by upregulation of versican gene observed after vascular injury. Versican was also here identified in all stages of atherogenesis; in the intima of early developing plaques, but also throughout advanced lesions and at the borders of lipid-filled necrotic cores as well as at the plaque-thrombus interface (Wight and Merrilees 2005). These observations implicate versican in lipid accumulation, inflammation, and thrombosis. Furthermore, versican plays an important role in the assembly of ECM and in control of elastic fiber fibrillogenesis, which is of fundamental importance in ECM remodelling during vascular disease (Wight and Merrilees 2005).

The role of biglycan in arterial cell biology is unclear. Some immunohistochemical studies have showen biglycan association with collagen I and III staining in human restenotic lesions (Evanko et al.).

The importance of biglycan as matrix protein was further stated by the generation of BALB/cA mice homozygous for a null mutation of the biglycan gene, where 50% of biglycan-deficient male mice died suddenly within the first 3 months of life as a result of from aortic rupture. This observation suggests biglycan to be essential for the structural and functional integrity of the aortic wall, as well as a potential role of biglycan gene defects in the pathogenesis of aortic dissection and rupture in humans. (Heegaard et al. 2007)

Other studies indicate that biglycan is a major PG associated with elastin in primate arteries; these observations are similar to those of in human coronary arteriopathy (Evanko et al).

Decorin has been shown to bind to collagen and regulate collagen fibril formation (Brown and Vogel) (Danielson et al.).

Protease Profiles

Proteases hydrolyse peptide bonds and are responsible for the degradation of extracellular matrix proteins such as collagen, proteoglycans and elastin in atheroma, see Table 9. In atherosclerotic plaques three main types are found: metallo-proteinases (i.e. MMPs), serine proteases and cysteine proteases (i.e. cathepsins). Cathepsins and MMPs are responsible for degradation of all extracellular matrix proteins. As matrix is essential for plaque stability, its removal from the fibrous cap by proteases may invoke plaque rupture (Stary H. C.).

In Table 9 a variety of proteases found in atherosclerotic plaque are listed.

TABLE 9

Proteases detected in atherosclerotic plaques.

| Protease | Degradation substrates |
| --- | --- |
| Cathepsin K | Proteoglycans, elastin, collagen |
| Cathepsin S | Proteoglycans, elastin, collagen |
| Cathepsin L | Proteoglycans, Collagen type I |
| Cathepsin B | Proteoglycans |
| MMP-1 | Collagen type I, II and III |
| MMP-2 | Proteoglycans, elastin |
| MMP-3 | Proteoglycans, collagen type III, elastin |
| MMP-8 | Proteoglycans, collagen type I, II and III |
| MMP-9 | Elastin, collagen type I and III |
| MMP-13 | Proteoglycans, collagen type I, II and III |
| MMP-18 | Collagen type I |

The main source of MMP expression in the plaque is suspected to be related to macrophage and SMC activity. Macrophages in plaques contain abundant MMP-1, -8, -9, and -13 and co-localize with sites of collagen and proteoglycan degradation in situ (Kunz J.). Furthermore, own data suggest localization of MMP-8 and Cathepsin K in atherosclerotic plaques.

Matrix Metalloproteinases (MMP)

MMP is a large group of endopeptidases, capable of degrading most components of the ECM. Presently, more than 25 MMPs have been identified. Metallo-proteinases are characterized by an active site containing a metal atom, typically zinc, and are secreted as zymogens. Specific tissue inhibitors, TIMPs, regulate the activity of MMPs. A great variety of MMPs are found in the atherosclerotic plaques. They are most often located in macrophages bordering the fibrous cap, within plaque shoulders in SMC and macrophages and are rarely identified within the fibrous cap (Kunz J.).]

MMPs are classified in different groups according to their substrate specificity: Collagenases, which degrade fibrillar collagen, like collagen type I, II, III and V but also proteoglycans; Gelatinases, which degrade proteoglycans, collagen type IV, V, VII and elastin; Stromelysin that is active against proteoglycans and elastin (Rouis M). These three subgroups are of particular interest with regards to matrix remodelling in atherosclerotic plaques.

Gelatinases

Insoluble elastin is digested by MMP-2 and -9, both belonging to the gelatinase-family of MMPs. MMP-9 has an important role affecting the size and composition of atherosclerotic plaque. In unstable human atherosclerotic plaques and in vulnerable regions of plaques, greater expression and concentration of MMP-9 have been observed. Moreover, MMP-9 is found intracellularly (indicating active synthesis) in coronary plaques more often in patients with unstable angina compared with those with stable angina. Blood MMP-9 level increases in association with coronary atherosclerosis and predicts adverse cardiovascular events (Sundstrom and Vasan). A recent study by Kuzuya et al (2006) indicates that MMP-2 is responsible for accumulation of SMC in the fibrous cap and thereby inducing plaque instability.

Stromelysin

MMP-3 belongs to the stromelysin proteases and is capable of degrading both elastin and proteoglycans. A study by Yamada et al (2002) indicates that MMP-3 may prove to be a reliable mean of predicting the genetic risk of myocardial infarction in women.

Collagenases

MMP-1, -8 and -13 have all been identified in atherosclerotic plaques where they degrade proteoglycans and collagen types I and III.

MMP-1, -8 and -13 are collagenases, which cleave collagen into two fragments that are further degraded by MMP-2, -3 or -9.

MMP-8 is expressed by neutrophils, not commonly found in human atheroma but has been identified in atherosclerotic plaques. MMP-8 may be partly responsible for degradation of the fibrous cap as MMP-8 has a preference for collagen type I (Herman et al), having a three fold greater activity in degradation of collagen I than MMP-1 and 13. This is supported by Turu et al (2006), in this study the content of MMP-8 in the plasma are significantly higher for patients with vulnerable plaques, than patients with stable plaques.

MMP-13 has been reported to cleave SLRPS, with high specificity for biglycan. Degradation of biglycan by MMP-13 at a specific cleavage site ( . . . $G_{177}/V_{178}$) has previously been demonstrated by Monfort et al. (2005) and proposed to play a important role in early detection of cartilage degradation in osteoarthritis.)

Cathepsins

Human cysteine cathepsins consist of 11 members, including cathepsins B, K, L, and S, and are predominantly expressed within the endosomal/lysosomal compartments of cells. Cathepsins are capable of catalysing the hydrolytic breakdown of proteoglycans, collagen and elastin.

In abdominal aortic aneurysm (AAA) high levels of cathepsins S, K, and L were found compared to normal aorta. Normal human vascular SMC contain no detectable cathepsin K by immunostaining, but cells within atherosclerotic plaques are clearly positive. Cathepsin K is localized in rupture-prone areas such as the fibrous cap, plaque shoulders and at the actual site of plaque ruptures (Chapman et al). Cathepsin S is found to co-localize with regions of increased elastin breakdown in atherosclerotic plaques, and reduced atherosclerosis is observed in cathepsin S- and K-deficient mice (Liu et al).

Both cathepsin L and K degrade several proteoglycans and collagen type I and II, cathepsin K degrades within covalently cross-linked triple helices, while cathepsin L cleaves only in the nonhelical telopeptide regions. Cathepsin K is localized in the fibrous cap and plaque shoulder. Cathepsin K expression in normal arteries is very low. Early human atherosclerotic lesions showed cathepsin K expression in the intimal and medial SMCs. In advanced atherosclerotic plaques, cathepsin K was localized mainly in macrophages and SMCs of the fibrous cap (Lutgens et al). Cathepsin K protein levels were increased in atherosclerotic lesions when compared with normal arteries, whereas cathepsin K mRNA levels were similar in both atherosclerotic and normal arteries. Furthermore, it was shown that cathepsin K mRNA and protein levels were highest in advanced but stable human atherosclerotic plaques compared with early atherosclerotic lesions and lesions containing thrombus (Chapman et al).

Cathepsin S is only sparsely expressed in intimal and medial SMCs in early human atherosclerotic lesion and fatty streaks. In advanced human atherosclerotic plaques cathepsin S was localized in macrophages and SMCs of the fibrous cap. EC lining the lumen of the vessel itself and the plaque microvessels also expressed cathepsin S. Furthermore, cathepsin S mRNA and protein levels were increased in human atheroma compared with normal arteries (Lutgens et al). Cathepsin S can degrade proteoglycans, elastin and collagen (Liu et al). Presently, the determination of CVD risk is occurring at a late stage in atherosclerosis progression; a point in which there is a significant risk of fibrous plaque rupture. There is a need for diagnostic or prognostic assays that will provide information regarding atherosclerosis or CVD risk at both earlier stage and late stages. The findings of Katsuda et al (1992) suggest that there are enzymatic mechanisms for removal of collagens from advanced lesions, suggesting indeed a major role of neo-epitopes in arteriosclerosis.

The invention will be further explained and illustrated with reference to the accompanying drawings, in which.

Figure 1:
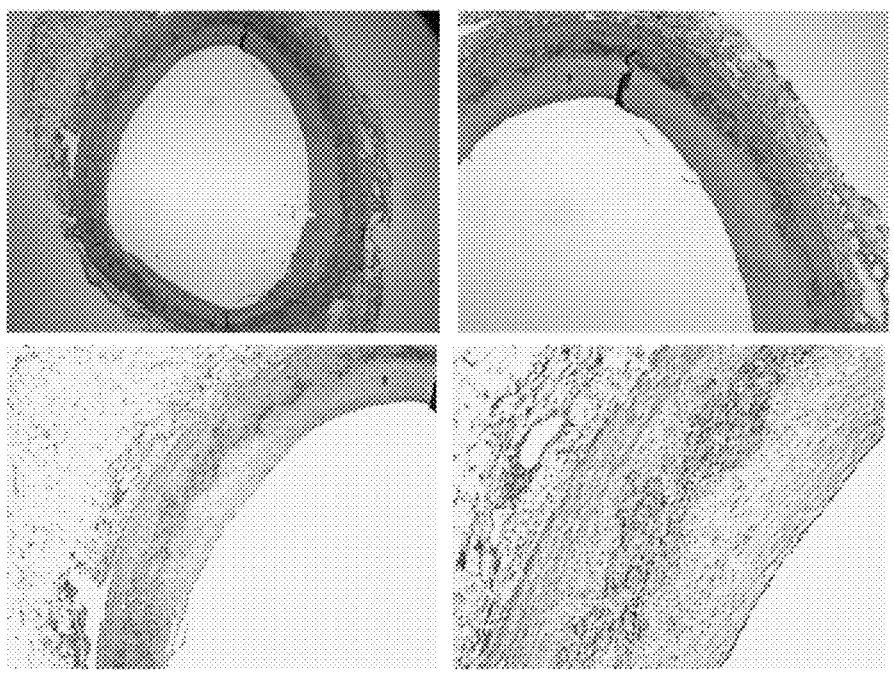
FIG. 1 shows Biglycan staining (magnifications 2, 4, 4 and 10× respectively) using a monoclonal mouse antibody on an aortic sample with type III lesion.

The present invention provides a method of bioassay for the quantification of peptide fragments comprising a neo-epitope formed by cleavage of a protein of an atherosclerotic plaque by a proteinase, said method comprising contacting a sample comprising said peptide fragments with an immunological binding partner having specific binding affinity for a said neo-epitope and determining the level of binding of said immunological binding partner to peptide fragments in said sample.

The result of said assay may produce an index indicative of the degree of risk in a particular patient of rupture of an atherosclerotic plaque or of the vulnerable status of the atherosclerotic plaques of a patient.

Patients having a value for said index above a threshold level may be recommended for further investigation by plaque imaging methods (including those discussed above) or for the prescribing of medication for treatment of atherosclerosis or for surgical treatment of atherosclerosis, and such follow up investigations or treatment may form part of the method of the invention.

Proteins of the atherosclerotic plaque include lumican, versican, perlecan, decorin, biglycan, collagen type III, CRP, ApoE and elastin. Collagen type I is not considered to be proteins of the atherosclerotic plaque. Proteins present in the atherosclerotic plaque which are exposed there to proteases to a higher degree than elsewhere in the body are of particular interest.

The immunological binding partner may have specific binding affinity for peptide fragments comprising a C-terminal neo-epitope or an N-terminal neo-epitope.

Proteoglycan Assays

The peptide fragments may be fragments of proteoglycans versican (SEQ ID NO 1), lumican (SEQ ID NO 2), perlecan (SEQ ID NO 3), biglycan (SEQ ID NO 4) and decorin (SEQ ID NO 5), which are all identified in normal and atherosclerotic arteries. Proteoglycans are some of the main proteins constituting atherosclerotic plaques and plaque cap together with elastin and collagens. The content of proteoglycans varies during the progression of atherosclerosis, which makes the potential neo-epitopes of proteoglycans a good marker of disease staging and disease progression. Since especially versican and lumican are not abundant in many other organs, this makes them more specific biochemical marker candidates.

Several candidate proteases may be responsible for the digestion of proteoglycans in the plaque, as the literature reports many different proteases in the atherosclerotic plaques. Most likely, this is the result of a large range of complicated processes eventually leading to plaque rupture. However, in our assessment, early phases may consist of a range of MMPs, whereas later stages may rely more on cathepsin degradation of the matrix, resulting in different neo-epitope profiles dependent on the stages of the disease. We have determined that the enzymes listed in table 10 generate lumican, versican, biglycan, perlecan and decorin resulting in at least following cleavage products:

TABLE 10

Protease generated peptides-cleavage products of proteoglycans

| Protease | | SEQ ID NO |
|---|---|---|
| Biglycan | | |
| MMP-3 | K*SVPKEISPDTTLLDLQNNDISE*L | 6 |
| MMP-3 | L*KSVPKEISPDTTLLDLQNNDISE*L | 7 |
| MMP-9 | E*NSGFEPGAFDGLKLNYLRISEAK*L | 8 |
| MMP-9 | G*LKSVPKEISPDTTLLDLQNNDISE*L | 9 |
| MMP-12 | Y*LRISEAKLTGIPKDLPET*L | 10 |
| MMP-13 | G*LKSVPKEISPDTTLLDLQNNDISE*L | 11 |
| MMP-13 | *LTGIPKDLPETLNELHLDHNKIQAIE* | 12 |
| ADAMTS4 | K*RISEAKLTGIPKDLPETLNE*L | 13 |
| ADAMTS4 | Q*AIELEDLLRYSK*L | 14 |
| ADAMTS4 | Q*AIELEDLLRY*S | 15 |
| ADAMTS4 | S*EAKLTGIPKDLPETLNE*L | 16 |
| ADAMTS4 | -*LKAVPKEISPDTTLLDLQNNDISE*L | 17 |
| MMP-8 | T*LLDLQNNDISELRKDD*F | 18 |
| MMP-8 | A*IELEDLLRYS*K | 19 |
| CathepsinS | E*NSGFEPGAFDGLK*L | 20 |
| Decorin | | |
| MMP-12 | M*IVIELGTNPLK*S | 21 |
| MMP-3 | E*DEASGIGPEVPDDR*D | 22 |
| MMP-3 | E*LHLDGNKISRVDAAS*L | 23 |
| MMP-3 | L*VNNKISKVSPGAFTPL*V | 24 |
| MMP-3 | A*LILVNNKISKVSPGAFTPLVKLER*L | 25 |
| MMP-9 | F*SNPVQYWEIQPSTFR*C | 26 |
| CathepsinK | K*SSGIENGAFQGMK*K | 27 |
| CathepsinK | K*SSGIENGAFQGMKKLS*Y | 28 |

TABLE 10-continued

Protease generated peptides-cleavage products of proteoglycans

| Protease | | SEQ ID NO |
|---|---|---|
| ADAMTS1 | N*KITEIKDGDFK*N | 29 |
| ADAMTS1 | Q*GLPPSLTELHLDGNK*I | 30 |
| Versican | | |
| Unknown | K*LLASDAGLYR*C | 31 |
| Unknown | *LATVGELQAAWR*N | 32 |
| Unknown | K*ETTVLVAQNGNIK*I | 33 |
| Lumican | | |
| Unknown | -*SLEDLQLTHNK*I | 34 |
| Unknown | R*LKEDAVSAAFK*G | 35 |
| Perlecan | | |
| Unknown | R*SIEYSPQLEDAGSR*E | 36 |
| Unknown | R*LEGDTLIIPR*V | 37 |
| ADAMTS4 | E*VSEAVVEKLEPEYR*- | 38 |
| ADAMTS4 | R*EVSEAVVEKLEPEYR*- | 39 |
| ADAMTS4 | R*SIEYSPQLED*A | 40 |

*indicates a site of cleavage

Accordingly, in a method of the invention, said peptide fragments preferably comprise a neo-epitope formed by cleavage of versican, lumican, perlecan, decorin or biglycan by a protease at a site marked by the sign * in any one of the above partial sequences thereof.

Also, in a method of the invention, said peptide fragments preferably comprise a neo-epitope formed by cleavage of following proteoglycans: versican, lumican, perlecan, decorin and biglycan; by a (or more) protease(s) at a site in any one of the following partial sequences of versican, lumican, decorin, perlecan, and biglycan, or the immunological binding partner is specifically reactive with one of the following sequences:

TABLE 11

Peptide fragments of proteoglycan cleavage

| Sequence | SEQ ID NO |
|---|---|
| SVPKEISPDTTLLDLQNNDISE | 41 |
| KSVPKEISPDTTLLDLQNNDISE | 42 |
| NSGFEPGAFDGLKLNYLRISEAK | 43 |
| LKSVPKEISPDTTLLDLQNNDISE | 44 |
| LRISEAKLTGIPKDLPET | 45 |
| LKSVPKEISPDTTLLDLQNNDISE | 46 |
| LTGIPKDLPETLNELHLDHNKIQAIE | 47 |
| IVIELGTNPLK | 48 |
| LLASDAGLYR | 49 |

TABLE 11-continued

Peptide fragments of proteoglycan cleavage

| Sequence | SEQ ID NO |
|---|---|
| LATVGELQAAWR | 50 |
| ETTVLVAQNGNIK | 51 |
| SLEDLQLTHNK | 52 |
| LKEDAVSAAFK | 53 |
| SIEYSPQLEDAGSR | 54 |
| LEGDTLIIPR | 55 |
| RISEAKLTGIPKDLPETLNE | 56 |
| AIELEDLLRYSK | 57 |
| AIELEDLLRY | 58 |
| EAKLTGIPKDLPETLNE | 59 |
| LKAVPKEISPDTTLLDLQNNDISE | 60 |
| LLDLQNNDISELRKDD | 61 |
| IELEDLLRYS | 62 |
| NSGFEPGAFDGLK | 63 |
| DEASGIGPEVPDDR | 64 |
| LHLDGNKISRVDAAS | 65 |
| VNNKISKVSPGAFTPL | 66 |
| LILVNNKISKVSPGAFTPLVKLER | 67 |
| SNPVQYWEIQPSTFR | 68 |
| SSGIENGAFQGMK | 69 |
| SSGIENGAFQGMKKLS | 70 |
| KITEIKDGDFK | 71 |
| GLPPSLTELHLDGNK | 72 |
| VSEAVVEKLEPEYR | 73 |
| EVSEAVVEKLEPEYR | 74 |
| SIEYSPQLEDASAKEFR | 75 |

Preferably, said immunological binding partner is not reactive with intact versican, lumican, decorin, perlecan, and biglycan. Preferably, said immunological binding partner is not reactive with a said sequence listed above if prolonged past the respective c-terminal and N-terminal ends of generated fragments.

The immunological binding partner may be one specifically reactive with a C-terminal or N-terminal neo-epitope formed by cleavage of type versican, lumican, decorin, perlecan, and biglycan.

Suitable immunological binding partners may therefore be specifically reactive with any of the following sequences in Table 12 at the N terminal of a peptide.

TABLE 12

N-terminal sequences of protease generated peptide fragments of proteoglycans

| | | SEQ ID NO |
|---|---|---|
| Biglycan | SVPKEI | 76 |
| | NSGFEP | 77 |
| | LKSVPK | 78 |
| | LRISEA | 79 |
| | GLKLNY | 80 |
| | LKSVPK | 81 |
| | QCSDLG | 82 |
| | LTGIPK | 83 |
| | RISEAK | 84 |
| | AIELED | 85 |
| | EAKLTG | 86 |
| | LKAVPK | 87 |
| | LLDLQN | 88 |
| | IELEDL | 89 |
| | NSGFEP | 90 |
| Decorin | IVIELG | 91 |
| | NGLNQM | 92 |
| | DEASGI | 93 |
| | LHLDGN | 94 |
| | VNNKIS | 95 |
| | LILVNN | 96 |
| | SNPVQY | 97 |
| | SSGIEN | 98 |
| | KITEIK | 99 |
| | GLPPSL | 100 |
| Versican | LLASDA | 101 |
| | LATVGE | 102 |
| | ETTVLV | 103 |
| | SLTVVK | 104 |
| | ENQDAR | 105 |
| | NGFDQC | 106 |
| Lumican | SLEDLQ | 107 |
| | LKEDAV | 108 |
| | HLQHNR | 109 |
| | LQHNRL | 110 |
| Perlecan | SIEYSP | 111 |
| | LVNFTR | 112 |
| | VSEAVV | 113 |
| | EVSEAV | 114 |
| | SIEYSP | 115 | or with any of the following sequences in Table 13, at the C-terminal of a peptide.

TABLE 13

C-terminal fragments of protease generated peptide fragments of proteoglycans

| | | SEQ ID NO |
|---|---|---|
| Biglycan | NNDISE | 116 |
| | RISEAK | 117 |
| | LRKDDF | 118 |
| | KDLPET | 119 |
| | LNELHL | 120 |
| | YWEVQP | 121 |
| | KIQAIE | 122 |
| | PETLNE | 123 |
| | LLRYSK | 124 |
| | EDLLRY | 125 |
| | NNDISE | 126 |
| | ELRKDD | 127 |
| | DLLRYS | 128 |
| | AFDGLK | 129 |
| Decorin | GTNPLK | 130 |
| | SSGIEN | 131 |
| | EVPDDR | 132 |

TABLE 13-continued

C-terminal fragments of protease generated peptide fragments of proteoglycans

|  |  | SEQ ID NO |
|---|---|---|
|  | RVDAAS | 133 |
|  | GAFTPL | 134 |
|  | LVKLER | 135 |
|  | QPSTFR | 136 |
|  | AFQGMK | 137 |
|  | GMKKLS | 138 |
|  | KDGDFK | 139 |
|  | HLDGNK | 140 |
| Versican | CDVMYG | 141 |
|  | NGFDQC | 142 |
|  | QNGNIK | 143 |
|  | IGQDYK | 144 |
| Lumican | QLTHNK | 145 |
|  | VSAAFK | 146 |
|  | GLKSLE | 147 |
| Perlecan | EDAGSR | 148 |
|  | EFREVS | 149 |
|  | VAQQDS | 150 |
|  | LEPEYR | 151 |
|  | SAKEFR | 152 |

Further cleavage sites defining neo-epitopes that may be assayed in a similar manner can be identified by exposing proteoglycans or other atherosclerotic plaque proteins to any of the enzymes described herein and isolating and sequencing peptides thereby produced.

Collagen Assays

The peptide fragments may be fragments of Type III collagen (SEQ ID NO 153), preferably of mature Type III collagen, i.e. not of collagen type III propeptide. The main proteins in the atherosclerotic plaques are collagen type I and III as well as elastin, whereas proteoglycan contributes only to a minor extent to the matrix of the plaque. Of the three major proteins found in atherosclerotic plaques collagen type I and III are dominant, whereas elastin dominates the protein profile in arteries, but not the main protein component in the plaque. Collagen type I is abundant throughout the human body, whereas type III has a more restricted tissue location, and thereby in our view constitutes a more specific candidate as biochemical marker.

Several candidate proteases may be responsible for the digestion of collagen in the plaque as the literature reports many different proteases in the atherosclerotic plaque. Most likely, this is the result of the large range of complicated processes eventually leading to plaque rupture. However, in our assessment, early phases may consist of a range of MMPs, whereas later stages may rely more on cathepsin K degradation of the matrix, resulting in different neo-epitope profiles dependent on the levels of disease. We have determined that the enzymes listed in the following table cleave type III collagen at least at the following cleavage sites marked *:

| Protease | Neo-Epitope | SEQ ID NO |
|---|---|---|
| MMP-1 | A*GIPGAPGLMGARGPPGPA*G | 154 |
| MMP-1 | K*GDPGPPGIPGRNGDPGI*P | 155 |
| MMP-1 | G*LAGPPGMPGPRGSPGPQG*V | 156 |
| MMP-1 | G*ERGLPGPPGIKGPAGIPGF*P | 157 |
| MMP-1 | G*IAGITGARGLAGPPGMPGPR*G | 158 |
| MMP-1 | G*IKGHRGFPGNPGAPGSPGPAG*Q | 159 |
| MMP-1 | A*RGLAGPPGMPGPRGSPGPQGV*K | 160 |
| MMP-1 | I*TGARGLAGPPGMPGPRGSPGPQG*V | 161 |
| MMP-1 | I*TGARGLAGPPGMPGPRGSPGPQGV*K | 162 |
| MMP-1 | G*ITGARGLAGPPGMPGPRGSPGPQG*V | 163 |
| MMP-1 | G*VKGESGKPGANGLSGERGPPGPQG*L | 164 |
| MMP-1 | G*SRGAPGPQGPRGDKGETGERGAAG*I | 165 |
| MMP-1 | P*KGDAGQPGEKGSPGAQGPPGAPGPLG*I | 166 |
| MMP-1 | G*ITGARGLAGPPGMPGPRGSPGPQGV*K | 167 |
| MMP-1 | G*LRGGAGPPGPEGGKGAAGPPGPPGAAGTPG*L | 168 |
| MMP-1 | G*HAGAQGPPGPPGINGSPGGKGEMGPAGIPGAPG*L | 169 |
| MMP-1 | A*GKSGDRGESGPAGPAGAPGPAGSRGAPGPQGPRGDKGETGERGAAG*I | 170 |
| MMP-1 | G*LQGLPGTGGPPGENGKPGEPGPKGDAGAPGAPGGKGDAGAPGERGPPG*L | 171 |
| MMP-3 | G*ERGLPGPPGIKGPAGIPGF*P | 172 |
| MMP-3 | A*VGGLAGYPGPAGPPGPPGPPGT*S | 173 |

-continued

| Protease | Neo-Epitope | SEQ ID NO |
|---|---|---|
| MMP-3 | K*DGTSGHPGPIGPPGPRGNRGER*G | 174 |
| MMP-3 | A*VGGLAGYPGPAGPPGPPGPPGTSGHPG*S | 175 |
| MMP-3 | G*IAGITGARGLAGPPGMPGPRGSPGPQG*V | 176 |
| MMP-3 | A*PGAPGGKGDAGAPGERGPPGLAGAPGLRG*G | 177 |
| MMP-3 | A*VGGLAGYPGPAGPPGPPGPPGTSGHPGSPG*S | 178 |
| MMP-2 | A*IGSPGPAGPRGPVGPSGPPG*K | 179 |
| MMP-3 and -8 | G*AIGSPGPAGPRGPVGPSGPPG*K | 180 |
| MMP-8 | P*AGQQGAIGSPGPA*G | 181 |
| MMP-8 | G*GPPGVAGPPGGSGPAGPP*G | 182 |
| MMP-8 | L*AGPPGMPGPRGSPGPQG*V | 183 |
| MMP-8 | G*LSGERGPPGPQGLPGLA*G | 184 |
| MMP-8 | R*GLAGPPGMPGPRGSPGPQG*V | 185 |
| MMP-8 | G*LAGPPGMPGPRGSPGPQGV*K | 186 |
| MMP-8 | R*GLAGPPGMPGPRGSPGPQGV*K | 187 |
| MMP-8 | G*PQGPPGKNGETGPQGPPGP*T | 188 |
| MMP-8 | G*VKGERGSPGGPGAAGFPGAR*G | 189 |
| MMP-8 | A*RGLAGPPGMPGPRGSPGPQG*V | 190 |
| MMP-8 | N*GLSGERGPPGPQGLPGLAGTA*G | 191 |
| MMP-8 | A*VGGLAGYPGPAGPPGPPGPPGT*S | 192 |
| MMP-8 | G*SPGGKGEMGPAGIPGAPGLMGA*R | 193 |
| MMP-8 | T*GARGLAGPPGMPGPRGSPGPQG*V | 194 |
| MMP-8 | V*KGESGKPGANGLSGERGPPGPQG*L | 195 |
| MMP-8 | G*VKGERGSPGGPGAAGFPGARGLPGPPGSNGNPGPPGPSGSPGKDGPPGPAG*N | 196 |
| MMP-8 | G*SPGAQGPPGAPGPLGIAGITGARGLAGPPG*M | 197 |
| MMP-8 | R*GAPGEKGEGGPPGVAGPPGGSGPAGPPGPQ*G | 198 |
| MMP-8 | R*GAPGEKGEGGPPGVAGPPGGSGPAGPPGPQ*G | 199 |
| MMP-8 | G*IAGITGARGLAGPPGMPGPRGSPGPQG*V | 200 |
| MMP-9 | G*IKGPAGIPGFPG*M | 201 |
| MMP-9 | G*QPGVMGFPGPKG*N | 202 |
| MMP-9 | G*IKGPAGIPGFPGMK*G | 203 |
| MMP-9 | G*IKGPAGIPGFPGMKG*H | 204 |
| MMP-9 | I*PGAPGLMGARGPPGPAG*A | 205 |
| MMP-9 | G*ERGLPGPPGIKGPAGIP*G | 206 |
| MMP-9 | G*IPGAPGLMGARGPPGPAG*A | 207 |
| MMP-9 | G*FRGPAGPNGIPGEKGPAG*E | 208 |
| MMP-9 | P*GIPGQPGSPGSPGPPGIC*E | 209 |
| MMP-9 | G*ERGLPGPPGIKGPAGIPGF*P | 210 |

-continued

| Protease | Neo-Epitope | SEQ ID NO |
|---|---|---|
| MMP-9 | A*VGGLAGYPGPAGPPGPPGPPG*T | 211 |
| MMP-9 | G*VKGERGSPGGPAAGFPGARG*L | 212 |
| MMP-9 | G*DAGAPGAPGGKGDAGAPGERGPPG*L | 213 |
| MMP-9 | Q*GPPGPTGPGGDKGDTGPPGPQGL*Q | 214 |
| MMP-9 | G*INGSPGGKGEMGPAGIPGAPGLM*G | 215 |
| MMP-9 | Q*GPPGEPGQAGPSGPPGPPGAIGPS*G | 216 |
| MMP-9 | P*GPPGINGSPGGKGEMGPAGIPGAP*G | 217 |
| MMP-9 | R*GLPGPPGSNGNPGPPGPSGSPGKDGPPGPAG*N | 218 |
| MMP-9 | G*KNGETGPQGPPGPTGPGGDKGDTGPPGPQG*L | 219 |
| MMP-9 | G*LPGIAGPRGSPGERGETGPPGPAGFPGAPG*Q | 220 |
| MMP-9 | G*INGSPGGKGEMGPAGIPGAPGLMGARGPPGPAG*A | 221 |
| MMP-9 | P*GINGSPGGKGEMGPAGIPGAPGLMGARGPPGPAG*A | 222 |
| MMP-9 | P*PGENGKPGEPGPKGDAGAPGAPGGKGDAGAPGERGPPG*L | 223 |
| MMP-9 | G*LKGENGLPGENGAPGPMGPRGAPGERGRPGLPGAAG*A | 224 |
| MMP-9 | G*NTGAPGSPGVSGPKGDAGQPGEKGSPGAQGPPGAPGPLG*I | 225 |
| MMP-9 | G*LMGARGPPGPAGANGAPGLRGGAGEPGKNGAKGEPGPRG*E | 226 |
| MMP-9 | G*LRGGAGPPGPEGGKGAAGPPGPPGAAGTPGLQGMPGERGGLGSPGPKG*D | 227 |
| MMP-8 and -9 | G*QQGAIGSPGPAGPRGPVGPSGPPG*K | 228 |
| MMP-9 | K*GDPGPPGIPGRNGDPGIPGQPG*S | 229 |
| MMP-9 | G*LRGGAGPPGPEGGKGAAGPPGPPG*A | 230 |
| MMP-9 | G*KNGETGPQGPPGPTGPGGDKGDTGPPGPQG*L | 231 |
| MMP-9 | G*YQGPPGEPGQAGPSGPPGPPG*A | 232 |
| MMP-9 | G*VAGPPGGSGPAGPPGPQG*V | 233 |
| MMP-8, -9 and -13 | G*DKGEPGGPGADGVPGKDGPRGPTGPIGPPGPAG*Q | 234 |
| ADAMTS-5 | Q*GHAGAQGPPGPPGIN*G | 235 |
| CathepsinK | A*GERGAPGPA*G | 236 |
| CathepsinK | A*GIPGFPGMK*G | 237 |
| CathepsinK | F*PGMKGHRGFD*G | 238 |
| CathepsinK | G*FPGARGLPGPPG*S | 239 |
| CathepsinK | A*GFPGARGLPGPPG*S | 240 |
| CathepsinK | P*PGPPGPPGTSGHP*G | 241 |
| CathepsinK | G*FPGMKGHRGFD*G | 242 |
| CathepsinK | Q*PGDKGEGGAPGLPGI*A | 243 |
| CathepsinK | R*GDKGETGERGAAGIK*G | 244 |

-continued

| Protease | Neo-Epitope | SEQ ID NO |
|---|---|---|
| CathepsinK | D*GRNGEKGETGAPGLK*G | 245 |
| CathepsinK | A*GQPGDKGEGGAPGLPGIA*G | 246 |
| CathepsinK | G*GPPGENGKPGEPGPKGD*A | 247 |
| CathepsinK | A*GIPGFPGMKGHRGFD*G | 248 |
| CathepsinK | R*GGAGEPGKNGAKGEPGPR*G | 249 |
| CathepsinK | K*GERGSPGGPGAAGFPGARGLPGPP*G | 250 |
| CathepsinK | I*PGVPGAKGEDGKDGSPGEPGANGLP*G | 251 |
| CathepsinK | G*AAGFPGARGLPGPPGSNGNPGPPGPS*G | 252 |
| CathepsinK | R*PGPPGPSGPRGQPGVMGFPGPKGN*D | 253 |
| CathepsinK | Q*GPPGPPGINGSPGGKGEMGPAGIPGAP*G | 254 |
| CathepsinK | A*GKDGESGRPGRPGERGLPGPPGIK*G | 255 |
| CathepsinK | A*GARGNDGARGSDGQPGPPGPPGTAGFPG*S | 256 |
| CathepsinK | S*PGVSGPKGDAGQPGEKGSPGAQGPPGAPG*P | 257 |
| CathepsinK | R*GSDGQPGPPGPPGTAGFPGSPGAKGEVGPA*G | 258 |
| CathepsinK | Q*GPPGPPGINGSPGGKGEMGPAGIPGAPGLM*G | 259 |
| CathepsinK | A*GPPGPPGPPGTSGHPGSPGSPGYQGPPGEPG*Q | 260 |
| CathepsinK | F*PGAPGQNGEPGGKGERGAPGEKGEGGPPGVA*G | 261 |
| CathepsinK | A*GFPGAPGQNGEPGGKGERGAPGEKGEGGPPG*V | 262 |
| CathepsinK | A*GARGNDGARGSDGQPGPPGPPGTAGFPGSPGAKGEVGPA*G | 263 |
| CathepsinK | R*GAAGEPGRDGVPGGPGMRGMPGSPGGPGSDGKPGPPGSQGESGRPGPPGPS*G | 264 |
| CathepsinS | G*IAGITGARGL*A | 265 |
| CathepsinS | AGPPGPPGAAGTPGLQGM | 266 |
| CathepsinS | N*GLSGERGPPGPQGLPG*L | 267 |
| CathepsinS | M*GARGPPGPAGANGAPGLR*G | 268 |
| CathepsinS | N*GLSGERGPPGPQGLPGLA*G | 269 |
| CathepsinS | G*IAGITGARGLAGPPGMPGPRG*S | 270 |
| CathepsinS | G*IAGITGARGLAGPPGMPGPRGSPGPQG*V | 271 |
| CathepsinS | R*GGAGPPGPEGGKGAAGPPGPPGAAGTPGLQ*G | 272 |
| CathepsinS | S*GPKGDAGQPGEKGSPGAQGPPGAPGPLG*I | 273 |
| CathepsinS | G*IAGITGARGLAGPPGMPGPRGSPGPQGVK*G | 274 |
| CathepsinS | A*VGGLAGYPGPAGPPGPPGPPGTSGHPGSPGSPGYQ*G | 275 |
| CathepsinS | E*PGPQGHAGAQGPPGPPGINGSPGGKGEMGPAGIPGAPG*L | 276 |
| ADAMTS1 | I*PGFPGMKGHR*G | 277 |
| ADAMTS1 | R*GSPGGPGAAGFPGAR*G | 278 |
| ADAMTS1 | K*GPAGIPGFPGMKGHR*G | 279 |
| ADAMTS1 | R*GLAGPPGMPGPRGSPGPQ*G | 280 |
| ADAMST1 | A*GITGARGLAGPPGMPGPR*G | 281 |

-continued

| Protease | Neo-Epitope | SEQ ID NO |
|---|---|---|
| ADAMST1 | L*GIAGITGARGLAGPPGMPGPR*G | 282 |
| ADAMST1 | T*GARGLAGPPGMPGPRGSPGPQ*G | 283 |
| ADAMST1 | Q*GPPGPPGINGSPGGKGEMGPAG*I | 284 |
| ADAMST1 | L*PGPPGIKGPAGIPGFPGMKGHR*G | 285 |
| ADAMST1 | A*GITGARGLAGPPGMPGPRGSPGPQ*G | 286 |
| ADAMST1 | T*GARGLAGPPGMPGPRGSPGPQGVK*G | 287 |
| ADAMST1 | R*GLPGPPGIKGPAGIPGFPGMKGHR*G | 288 |
| ADAMST1 | G*RPGLPGAAGARGNDGARGSDGQPGPPG*P | 289 |
| ADAMST1 | N*GAPGPMGPRGAPGERGRPGLPGAAGAR*G | 290 |
| ADAMST1 | A*GSRGAPGPQGPRGDKGETGERGAAGIK*G | 291 |
| ADAMST1 | R*GLAGPPGMPGPRGSPGPQGVKGESGKPGAN*G | 292 |
| ADAMST1 | R*GLAGPPGMPGPRGSPGPQGVKGESGKPGANGL*S | 293 |
| ADAMST1 | P*GPPGSNGNPGPPGPSGSPGKDGPPGPAGNTGAPGS*P | 294 |
| ADAMST1 | T*GARGLAGPPGMPGPRGSPGPQGVKGESGKPGAN*G | 295 |
| ADAMST1 | R*GAPGEKGEGGPPGVAGPPGGSGPAGPPGPQGVKGER*G | 296 |
| ADAMST1 | G*PPGVAGPPGGSGPAGPPGPQGVKGERGSPGGPGAAGF*P | 297 |
| ADAMST1 | K*SGDRGESGPAGPAGAPGPAGSRGAPGPQGPRGDKGETGERGAAGIK*G | 298 |
| ADAMTS4 | I*PGFPGMKGHR*G | 299 |
| ADAMTS4 | R*GLAGPPGMPGPR*G | 300 |
| ADAMTS4 | G*PQGLQGLPGTGGPP*G | 301 |
| ADAMTS4 | K*GPAGIPGFPGMKGHR*G | 302 |
| ADAMTS4 | R*GLAGPPGMPGPRGSPGPQG*V | 303 |
| ADAMTS4 | G*PPGENGKPGEPGPKGDAGAP*G | 304 |
| ADAMTS4 | A*PGFRGPAGPNGIPGEKGPAGER*G | 305 |
| ADAMTS4 | E*KGSPGAQGPPGAPGPLGIAGITGAR*G | 306 |
| ADAMTS4 | L*PGPPGIKGPAGIPGFPGMKGHR*G | 307 |
| ADAMTS4 | R*GAPGFRGPAGPNGIPGEKGPAGER*G | 308 |
| ADAMTS4 | R*GLPGPPGIKGPAGIPGFPGMKGHR*G | 309 |
| ADAMTS4 | R*GPVGPSGPPGKDGTSGHPGPIGPPGPR*G | 310 |
| ADAMTS4 | A*PGPQGPRGDKGETGERGAAGIKGHR*G | 311 |
| ADAMTS4 | R*GAPGPQGPRGDKGETGERGAAGIKGHR*G | 312 |
| ADAMTS4 | R*GFPGNPGAPGSPGPAGQQGAIGSPGPAGPR*G | 313 |
| ADAMTS4 | L*PGPPGIKGPAGIPGFPGMKGHRGFDGR*N | 314 |
| ADAMTS4 | D*AGQPGEKGSPGAQGPPGAPGPLGIAGITGAR*G | 315 |
| ADAMTS4 | R*GPTGPIGPPGPAGQPGDKGEGGAPGLPGIAGPR*G | 316 |
| ADAMTS4 | K*GDAGQPGEKGSPGAQGPPGAPGPLGIAGITGAR*G | 317 |
| ADAMTS4 | R*NGEKGETGAPGLKGENGLPGENGAPGPMGPR*G | 318 |

-continued

| Protease | Neo-Epitope | SEQ ID NO |
|---|---|---|
| ADAMTS4 | A*PGFRGPAGPNGIPGEKGPAGERGAPGPAGPRGA*A | 319 |
| ADAMTS4 | R*GAPGFRGPAGPNGIPGEKGPAGERGAPGPAGPR*G | 320 |
| ADAMTS4 | R*GSPGERGETGPPGPAGFPGAPGQNGEPGGKGER*G | 321 |
| ADAMTS4 | G*HAGAQGPPGPPGINGSPGGKGEMGPAGIPGAPGLMG*A | 322 |
| ADAMTS4 | R*GLAGPPGMPGPRGSPGPQGVKGESGKPGANGLSGER*G | 323 |
| ADAMTS8 | L*GIAGITGARGL*A | 324 |
| ADAMTS8 | I*PGFPGMKGHR*G | 325 |
| ADAMTS8 | R*GLAGPPGMPGPR*G | 326 |
| ADAMTS8 | Q*GPPGAPGPLGIAGITGAR*G | 327 |
| ADAMTS8 | A*GITGARGLAGPPGMPGPR*G | 328 |
| ADAMTS8 | A*GIPGAPGLMGARGPPGPAGAN*G | 329 |
| ADAMTS8 | R*GLAGPPGMPGPRGSPGPQGVKG*E | 330 |
| ADAMTS8 | K*GSPGAQGPPGAPGPLGIAGITGAR*G | 331 |
| ADAMTS8 | L*PGPPGIKGPAGIPGFPGMKGHR*G | 332 |
| ADAMTS8 | K*DGTSGHPGPIGPPGPRGNRGER*G | 333 |
| ADAMTS8 | A*GITGARGLAGPPGMPGPRGSPGPQ*G | 334 |
| ADAMTS8 | R*GLAGPPGMPGPRGSPGPQGVKGESG*K | 335 |
| ADAMTS8 | R*GLAGPPGMPGPRGSPGPQGVKGESGKPGAN*G | 336 |
| ADAMTS8 | R*GLAGPPGMPGPRGSPGPQGVKGESGKPGANGL*S | 337 |
| ADAMTS8 | P*GPPGSNGNPGPPGPSGSPGKDGPPGPAGNTGAPGS*P | 338 |
| ADAMTS8 | R*GAPGEKGEGGPPGVAGPPGGSGPAGPPGPQGVKGER*G | 339 |
| ADAMTS8 | K*SGDRGESGPAGPAGAPGPAGSRGAPGPQGPRGDKGETGERGA*A | 340 |
| ADAMTS8 | R*GAPGEKGEGGPPGVAGPPGGSGPAGPPGPQGVKGERGSPGGPGAAGFPGAR*G | 341 |
| MMP9 | _*AIGPSG_*_ | 342 |
| unknown | -AGGFAP* | 781 |

Accordingly, in a method of the invention, said peptide fragments preferably comprise a neo-epitope formed by cleavage of Type III collagen by a protease at a site marked by the sign * in any one of the above partial sequences of Type III collagen.

Also, in a method of the invention, said peptide fragments preferably comprise a neo-epitope formed by cleavage of collagen type III by a (or more) protease(s) at a site in any one of the above partial sequences of collagen type III between the *s, or the immunological binding partner is specifically reactive with a sequence extending between the *s in any entry in the above table.

Preferably, said immunological binding partner is not reactive with intact type III collagen. Preferably, said immunological binding partner is not reactive with a said sequence listed above if prolonged past the respective cleavage site.

The immunological binding partner may be one specifically reactive with a C-terminal or N-terminal neoepitope formed by cleavage of type III collagen.

Suitable immunological binding partners may therefore be specifically reactive with any of the following sequences at the N terminal of a peptide: (Sequence ID Nos follow each sequence).

| | | | | |
|---|---|---|---|---|
| GIPGAP 343 | GDPGPP 408 | LAGPPG 470 | ERGLPG 534 | IAGITG 598 |
| IKGHRG 344 | RGLAGP 409 | TGARGL 471 | | ITGARG 599 |

-continued

| | | | | |
|---|---|---|---|---|
| VKGESG 345 | SRGAPG 410 | KGDAGQ 472 | ITGARG 535 | LRGGAG 600 |
| HAGAQG 346 | GKSGDR 411 | LQGLPG 473 | ERGLPG 536 | KDGTSG 763 |
| DGTSGH 347 | VGGLAG 412 | IAGITG 474 | PGAPGG 537 | VGGLAG 601 |
| IGSPGP 348 | AIGSPG 413 | AGQQGA 475 | GPPGVA 538 | AGPPGM 602 |
| LSGERG 349 | GLAGPP 414 | LAGPPG 476 | GLAGPP 539 | PQGPPG 603 |
| VKGERG 350 | RGLAGP 415 | GLSGER 477 | VGGLAG 540 | SPGGKG 604 |
| GARGLA 351 | KGESGK 416 | VKGERG 478 | SPGAQG 541 | GAPGEK 605 |
| GAPGEK 352 | IAGITG 417 | IKGPAG 479 | QPGVMG 542 | IKGPAG 606 |
| IKGPAG 353 | PGAPGL 418 | ERGLPG 480 | IPGAPG 543 | FRGPAG 607 |
| GIPGQP 354 | ERGLPG 419 | VGGLAG 481 | VKGERG 544 | DAGAPG 608 |
| GPPGPT 355 | INGSPG 420 | GPPGEP 482 | GPPGIN 545 | GLPGPP 609 |
| KNGETG 356 | LPGIAG 421 | INGSPG 483 | GINGSP 546 | PGENGK 610 |
| LKGENG 357 | NTGAPG 422 | LMGARG 484 | LRGGAG 547 | QQGAIG 611 |
| GDPGPP 358 | LRGGAG 423 | 000 485 | YQGPPG 548 | VAGPPG 612 |
| DKGEPG 359 | GHAGAQ 424 | GERGAP 486 | GIPGFP 549 | PGMKGH 613 |
| FPGARG 360 | GFPGAR 425 | PGPPGP 487 | FPGMKG 550 | PGDKGE 614 |
| GDKGET 361 | GRNGEK 426 | GQPGDK 488 | GPPGEN 551 | |
| GGAGEP 362 | GERGSP 427 | PGVPGA 489 | AAGFPG 552 | |
| GPPGPP 363 | GKDGES 428 | GARGND 490 | PGVSGP 553 | GSDGQP 615 |
| | | PGAPGQ 491 | GFPGAP 554 | GARGND 616 |
| GAAGEP 365 | IAGITG 429 | GPPGPP 492 | GLSGER 555 | GARGPP 617 |
| GLSGER 366 | | IAGITG 493 | GGAGPP 556 | GPKGDA 618 |
| IAGITG 367 | GPKGDA 430 | | VGGLAG 557 | PGPQGH 619 |
| PGFPGM 368 | GSPGGP 431 | GPAGIP 494 | GLAGPP 558 | |
| GIAGIT 369 | | GPPGPP 495 | PGPPGI 559 | GITGAR 620 |
| GARGLA 370 | GLPGPP 432 | RPGLPG 496 | GAPGPM 560 | GSRGAP 621 |
| GLAGPP 371 | | GPPGSN 497 | GARGLA 561 | GAPGEK 622 |
| GPPGVA 372 | SGDRGE 433 | PGFPGM 498 | GLAGPP 562 | PQGLQG 623 |
| GPAGIP 373 | GLAGPP 434 | GPPGEN 499 | PGFRGP 563 | KGSPGA 624 |
| PGPPGI 374 | GAPGFR 435 | GLPGPP 500 | GPVGPS 564 | PGPQGP 625 |
| GAPGPQ 375 | GFPGNP 436 | PGPPGI 501 | AGQPGE 565 | GPTGPI 626 |
| GDAGQP 376 | NGEKGE 437 | PGFRGP 502 | GAPGFR 566 | GSPGER 627 |
| HAGAQG 377 | GLAGPP 438 | GIAGIT 503 | PGFPGM 567 | |
| GPPGAP 378 | GITGAR 439 | GIPGAP 504 | GLAGPP 568 | GSPGAQ 628 |
| | DGTSGH 440 | GITGAR 505 | | GLAGPP 629 |
| GLAGPP 379 | GPPGSN 441 | GAPGEK 506 | SGDRGE 569 | GAPGEK 630 |
| AIGPSG 380 | | | | | or with any of the following sequences at the C-terminal of a peptide:

| | | | | |
|---|---|---|---|---|
| GPPGPA 381 | NGDPGI 442 | SPGPQG 507 | AGIPGF 570 | GMPGPR 631 |
| SPGPAG 382 | PGPQGV 443 | PPGPQG 508 | ERGAAG 571 | PGPLGI 632 |
| AAGTPG 383 | IPGAPG 444 | ERGPPG 509 | PGPPGT 572 | GNRGER 633 |
| TSGHPG 384 | SPGPQG 445 | APGLRG 510 | HPGSPG 573 | PSGPPG 634 |
| PSGPPG 385 | GPPGPA 446 | GPAGPP 511 | SPGPQG 574 | GLPGLA 635 |
| | QGPPGP 447 | SPGPQG 512 | GLAGTA 575 | PGPPGT 636 |
| PGLMGA 386 | | LAGPPG 513 | GPPGPQ 576 | GPPGPQ 637 |
| SPGPQG 387 | IPGFPG 448 | FPGPKG 514 | GFPGMK 577 | FPGMKG 638 |
| | GPAGIP 449 | PPGPAG 515 | EKGPAG 578 | GPPGIC 640 |
| PPGPPG 388 | FPGARG 450 | | PGPQGL 579 | GAPGLM 641 |
| GAIGPS 389 | GIPGAP 451 | | FPGAPG 580 | |
| PPGPAG 390 | ERGPPG 452 | LPGAAG 516 | APGPLG 581 | EPGPRG 642 |
| SPGPKG 391 | PSGPPG 453 | IPGAPG 517 | | |
| PPGPAG 392 | GPPGIN 454 | GAPGPA 518 | GFPGMK 582 | GHRGFD 643 |
| LPGPPG 393 | GTSGHP 455 | GHRGFD 519 | PGLPGI 583 | GAAGIK 644 |
| GAPGLK 394 | GLPGIA 456 | PGPKGD 520 | GHRGFD 584 | GEPGPR 645 |
| GLPGPP 395 | GANGLP 457 | GPPGPS 521 | PGPKGN 585 | GIPGAP 646 |
| GPPGIK 396 | TAGFPG 458 | PPGAPG 522 | GEVGPA 586 | GAPGLM 647 |
| GPPGVA 397 | EGGPPG 459 | GEVGPA 523 | GPPGPS 587 | TGARGL 648 |
| TPGLQG 398 | PQGLPG 460 | GAPGLR 524 | GLPGLA 588 | MPGPRG 649 |
| GTPGLQ 399 | APGPLG 461 | GPQGVK 525 | GSPGYQ 589 | GMKGHR 650 |
| GFPGAR 400 | GSPGPQ 462 | GMPGPR 526 | EMGPAG 590 | GPQGVK 651 |
| QPGPPG 401 | GAAGAR 463 | GAAGIK 527 | GKPGAN 591 | PGANGL 652 |
| TGAPGS 402 | GVKGER 464 | PGAAGF 528 | GMPGPR 592 | GTGGPP 653 |
| SPGPQG 403 | GDAGAP 465 | GPAGER 529 | GITGAR 593 | GPPGPR 654 |
| GPAGPR 404 | RGFDGR 466 | GIAGPR 530 | AGPRGA 594 | GGKGER 655 |
| APGLMG 405 | GLSGER 467 | TGARGL 531 | GPAGAN 595 | PQGVKG 656 |
| GNRGER 406 | GSPGPQ 468 | VKGESG 532 | GKPGAN 596 | PGANGL 657 |
| TGAPGS 407 | GVKGER 469 | TGERGA 533 | | |
| | | | GFPGAR 597 | |

Further cleavage sites defining neoepitopes that may be assayed in a similar manner can be identified by exposing collagen type III or another atherosclerotic plaque protein to any of the enzymes described herein and isolating and sequencing peptides thereby produced.

CRP and ApoE ASSAYS

Said peptide fragments may be fragments of CRP (SEQ ID NO 658) or ApoE (SEQ ID NO 659). For ApoE, preferably the chosen fragments occur in all of the identified isotypes of ApoE, ε2, ε3 and ε4.

Even though both CRP and ApoE are abundant throughout the human body, their localization in the atherosclerotic tissue exposes them to the action of local proteases. These molecules are thereby good and specific candidates as biochemical markers.

Several candidate proteases may be responsible for the digestion of CRP and ApoE in the plaque as the literature reports many different proteases in the atherosclerotic plaque. Most likely, this is the result of the large range of complicated processes eventually leading to plaque rupture. However, early phases may consist of a range of MMPs, whereas later stages may rely more on cathepsin K degradation of the matrix, resulting in different neo-epitope profiles dependent on the levels of disease. We have through a range of in vitro cleavages of pure native proteins determined that the enzymes listed in the following table cleave CRP and ApoE at at least following cleavage sites (marked *):

TABLE 14

CRP and APOE fragments generated by specific proteases

| Protease/Protein | Neo-epitope | SEQ ID NO |
|---|---|---|
| APOE + MMP3 | A*KVEQAVETEPEPELR*Q | 660 |
| APOE + MMP9 | A*KVEQAVETEPEPELR*Q | 661 |
| APOE + MMP1 | V*AEVRAKLEEQAQQI*R | 662 |
| APOE + MMP3 | A*KVEQAVETEPEPELR*Q | 663 |
| APOE + MMP3 | A*MLGQSTEELRV*R (M-oxidized) | 664 |
| APOE + ADAMTS1 | E*QAVETEPEPELR*Q | 665 |
| APOE + ADAMTS1 | R*QQTEWQSGQRWE*L | 666 |
| APOE + ADAMTS1 | L*AVYQAGAREGAERGLS*A | 667 |
| APOE + ADAMTS1 | R*AKLEEQAQQIR*L | 668 |
| APOE + ADAMTS1 | A*KLEEQAQQIRLQ*A | 669 |
| APOE + CathepsinK | A*KVEQAVETEPEPELR*Q | 670 |
| APOE + CathepsinK | K*VEQAVETEPEPELR*Q | 671 |
| APOE + CathepsinK | E*QAVETEPEPELR*Q | 672 |
| APOE + CathepsinK | D*EVKEQVAEVRAKLE*E | 673 |
| CRP + CatK | K*ESDTSYVSLKAPLT*K | 674 |
| CRP + CatK | G*GNFEGSQSLVGDIG*N | 675 |
| CRP + MMP9 | A*LKYEVQGEVFTKPQ*L | 676 |
| CRP + MMP9 | G*IVEFWVDGKPRV*R | 677 |
| CRP + MMP1/MMP3 | R*KAFVFPKE*S | 678 |
| CRP + MMP3 | K*YEVQGEVFTKPQLWP*- | 679 |
| CRP + MMP3 | D*SFGGNFEGSQS*L | 680 |
| CRP + MMP3 | D*FVLSPDEINT*I | 681 |
| CRP + MMP3 | S*LKKGYTVGAEA*S | 682 |
| CRP + MMP3 | A*FGQTDMSRKA*F | 683 |
| CRP + MMP3 | S*LKKGYTVGAEAS*I | 684 |
| CRP + MMP3 | G*EVFTKPQLWP*- | 685 |
| CRP + MMP3 | S*IILGQEQDSFGGN*F | 686 |
| CRP + MMP3 | K*YEVQGEVFTKPQ*L | 687 |

Accordingly, in a method of the invention, said peptide fragments preferably comprise a neo-epitope formed by cleavage of CRP and ApoE by a protease at a site marked by the sign * in any one of the following partial sequences of CRP and APOE, or the immunological binding partner is specifically reactive with a sequence defined between the *s in one of the following sequences:

TABLE 15

Cleavage fragments of CRP and APOE.

ApoE fragments

A*KVEQAVETEPEPELR*Q

A*KVEQAVETEPEPELR*Q

V*AEVRAKLEEQAQQI*R

A*KVEQAVETEPEPELR*Q

A*MLGQSTEELRV*R (M-oxidized)

E*QAVETEPEPELR*Q

R*QQTEWQSGQRWE*L

L*AVYQAGAREGAERGLS*A

R*AKLEEQAQQIR*L

A*KLEEQAQQIRLQ*A

A*KVEQAVETEPEPELR*Q

K*VEQAVETEPEPELR*Q

E*QAVETEPEPELR*Q

D*EVKEQVAEVRAKLE*E

CRP fragments

K*ESDTSYVSLKAPLT*K

G*GNFEGSQSLVGDIG*N

A*LKYEVQGEVFTKPQ*L

G*IVEFWVDGKPRV*R

R*KAFVFPKE*S

K*YEVQGEVFTKPQLWP*-

D*SFGGNFEGSQS*L

D*FVLSPDEINT*I

S*LKKGYTVGAEA*S

A*FGQTDMSRKA*F

S*LKKGYTVGAEAS*I

G*EVFTKPQLWP*-

S*IILGQEQDSFGGN*F

K*YEVQGEVFTKPQ*L

Suitable immunological binding partners may therefore be specifically reactive with any of the following sequences at the N terminal of a peptide:

| APOE | SEQ ID NO | CRP | SEQ ID NO |
|---|---|---|---|
| KVEQAV | 688 | AFVFPK | 699 |
| AEVRAK | 689 | YEVQGE | 700 |
| MLGQST | 690 | KAFVFP | 701 |
| QAVETE | 691 | SFGGNF | 702 |
| QQTEWQ | 692 | FVLSPD | 703 |
| AVYQAG | 693 | LKKGYT | 704 |

-continued

| APOE | SEQ ID NO | CRP | SEQ ID NO |
|---|---|---|---|
| AKLEEQ | 694 | FGQTDM | 705 |
| KLEEQA | 695 | LKKGYT | 706 |
| VEQAVE | 696 | IILGQE | 707 |
| QAVETE | 697 | YEVQGE | 708 |
| EVKEQV | 698 | LKYEVQ | 709 |
|  |  | IVEFWV | 710 |
|  |  | ESDTSY | 711 |
|  |  | GNFEGS | 712 | or with any of the following sequences at the C-terminal of a peptide:

| APOE | SEQ ID NO | CRP | SEQ ID NO |
|---|---|---|---|
| TEPEPE | 714 | KAFVFPK | 725 |
| EQAQQI | 715 | AFVFPK | 726 |
| TEELRV | 716 | KPQLWP | 727 |
| PEPELR | 717 | FVFPKE | 728 |
| SGQRWE | 718 | PDEINT | 729 |
| EGAERG | 719 | DMSRKA | 730 |
| QAQQIR | 720 | VGAEAS | 731 |
| QQIRLQ | 721 | KPQLWP | 732 |
| EPEPEL | 722 | DSFGGN | 733 |
| PEPELR | 723 | VFTKPQ | 734 |
| EVRAKL | 724 |  |  |

Further cleavage sites defining neo-epitopes that may be assayed in a similar manner can be identified by exposing CRP and AppoE or another atherosclerotic plaque protein to any of the enzymes described herein and isolating and sequencing peptides thereby produced.

Elastin Assays

Said peptide fragments may be fragments of elastin (SEQ ID NO 735). Even though elastin is abundant throughout the human body, its localization in the atherosclerotic tissue exposes it to the action of local proteases, which is why these molecules are good and specific candidates as biochemical markers of atherosclerotic plaque turnover.

Several candidate proteases may be responsible for the digestion of elastin in the plaque as the literature reports many different proteases in the atherosclerotic plaque. Most likely, this is the result of the large range of complicated processes eventually leading to plaque rupture. However, early phases may consist of a range of MMPs, whereas later stages may rely more on cathepsin K degradation of the matrix, resulting in different neo-epitope profiles dependent on the levels of disease. We have through a range of in vitro cleavages of pure native proteins determined that the enzymes listed in the following table cleave elastin at at least following cleavage sites (marked *):

TABLE 16

Elastin fragments generated by specific proteases.

| Protease/Protein | Neo-epitope | SEQ ID NO |
|---|---|---|
| ADAMTS4 | A*RPGVGVGGIPTYGVGAGG*F | 736 |
| Cat K | G*LPYTTGKLPYGYGPG*G | 737 |
| Cat S | G*VAPGVGVAPGVGVAPGIGPGGVA*A | 738 |
| Cat S | G*GAGVPGVPGAIPGIGGIAGVG*T | 739 |
| ADAMTS4 | G*GAGVPGVPGAIPGIGGIAGVG*T | 740 |
| Cat K | G*VGISPEAQAAAAAK*A | 741 |
| ADAMTS1 | G*VGISPEAQAAAAAK*A | 742 |

Accordingly, in a method of the invention, said peptide fragments preferably comprise a neo-epitope formed by cleavage of elastin by a protease at a site marked by the sign * in any one of the following partial sequences of Elastin, or the immunological binding partner is specifically reactive with a sequence defined between the *s in one of the following sequences:

TABLE 17

Cleavage fragments of Elastin

Elastin fragments

A*RPGVGVGGIPTYGVGAGG*F

G*LPYTTGKLPYGYGPG*G

G*VAPGVGVAPGVGVAPGIGPGGVA*A

G*GAGVPGVPGAIPGIGGIAGVG*T

G*GAGVPGVPGAIPGIGGIAGVG*T

G*VGISPEAQAAAAAK*A

G*VGISPEAQAAAAAK*A

A*RPGVGVGGIPTYGVGAGG*F

G*LPYTTGKLPYGYGPG*G

Suitable immunological binding partners may therefore be specifically reactive with any of the following sequences at the N terminal of a peptide:

| Elastin | SEQ ID NO |
|---|---|
| RPGVGV | 743 |
| LPYTTG | 744 |
| VAPGVG | 745 |
| GAGVPG | 746 |
| VGISPE | 747 |
| RPGVGV | 748 |
| LPYTTG | 749 | or with any of the following sequences at the C-terminal of a peptide:

| Elastin | SEQ ID NO |
|---------|-----------|
| GVGAGG  | 750       |
| YGYGPG  | 751       |
| GPGGVA  | 752       |
| GIAGVG  | 753       |

Further cleavage sites defining neo-epitopes that may be assayed in a similar manner can be identified by exposing elastin or another atherosclerotic plaque protein to any of the enzymes described herein and isolating and sequencing peptides thereby produced.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

The term 'protein' used herein includes lipoproteins and proteoglycans and other protein-(non-protein) naturally occurring conjugates.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be a synthetic peptide or a purified native peptide formed by cleavage of the protein to which the neo-epitope belongs to reveal said neo-epitope. Thus, the peptide may be derived from any of versican, lumican, perlecan, decorin, biglycan, collagen type III, ApoE, CRP or elastin. One suitable method could be a competition immunoassay using monoclonal antibodies or antibody binding fragments binding to neo-epitopes of fragments of any of these proteins or neo-epitopes on peptide fragments from other proteins derived from atherosclerotic plaques. Appropriately selected synthetic peptides coated onto the solid surface of a microtitre plate could compete with the sample for binding to the monoclonal antibodies or binding fragments. Alternatively, purified, native fragments from one or more of these proteins carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin. The sample may be a sample of urine, serum, blood, plasma or other, e.g. atherosclerotic plaque biopsy.

In certain preferred methods, the sample is a patient derived sample, and the method further comprises comparing the determined level of said binding of said peptide fragments with values characteristic of (a) comparable healthy individuals and/or (b) a pathological atherosclerotic condition and optionally associating a higher level of the measured peptide (normally indicated by a higher level of binding) with a more severe degree of a said condition.

An aspect of the present invention relates to the development of monoclonal antibodies recognising neo-epitopes as described above. This can be achieved by immunising mice with synthetic peptides originating from the amino acid sequence of the protein molecule concerned (including the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-prolongated form of the immunising peptide (for a C-terminal neo-epitope) or an N-terminal prolongated form of the immunising peptide (for an N-terminal neo-epitope). Antibodies for neo-epitopes may also be evaluated to establish a lack of binding capacity to native protein. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of a said protein by a protease at an end-site in any one of the partial sequences set out above, and may be for instance a monoclonal antibody or a binding fragment thereof.

The invention includes a cell line producing a monoclonal antibody against a C-terminal or N-terminal neo-epitope formed by cleavage of an atherosclerotic plaque protein at the end-sites of sequences in any one of the partial sequences o set out above.

The invention further provides a peptide comprising a C-terminal or N-terminal neo-epitope formed by cleavage of a said protein in any one of the partial sequences of these proteins set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of a said protein in any one of the partial sequences set out above.

The invention further comprises a vector comprising a nucleic acid sequence comprising an expression signal and a coding sequence which codes for the expression of a peptide comprising a C-terminal or N-terminal neo-epitope formed by cleavage of a said protein in any one of the partial sequences set out above and further includes a host cell transformed with such a vector and expressing a said peptide.

Yet another aspect of the invention relates to kits, which can be used conveniently for carrying out the methods described above. Such kits may include (1) a microtitre plate coated with synthetic peptide; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native protein fragments; (2) a monoclonal antibody recognising a neo-epitope on fragments of any one of said proteins, and reactive with said purified fragments; and (3) a labelled anti-mouse IgG immunoglobulin. Alternatively, such kits may include (1) a microtitre plate coated with streptavidin; (2) a synthetic peptide linked to biotin; (3) a monoclonal antibody recognising a neo-epitope on said protein fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin; (3) a monoclonal antibody recognising a neo-epitope on said protein fragments (and reactive with said synthetic peptide) and conjugated to horseradish peroxidase.

Thus, the invention includes an immunoassay kit comprising an immunological binding partner as described herein, and a competition agent which binds said immunological binding partner, and optionally one or more of a wash reagent, a buffer, a stopping reagent, an enzyme label, an enzyme label substrate, calibration standards, an anti-mouse antibody and instructions for conducting a said immunoassay.

The assays described herein are useful in the diagnosis of atherosclerotic disease in patients. In addition, the tests are useful for the assessment of disease progression, and the monitoring of response to therapy. The immunological binding partners of the invention may also be used in immunostaining to show the presence or location of cleavage products of any atherosclerotic plaque protein described herein.

EXAMPLE 1

For analysis of localization of proteoglycans and proteases we performed immunohistochemical stainings of human arterial samples derived from left coronary descending arteries (LAD).

Figure 2:
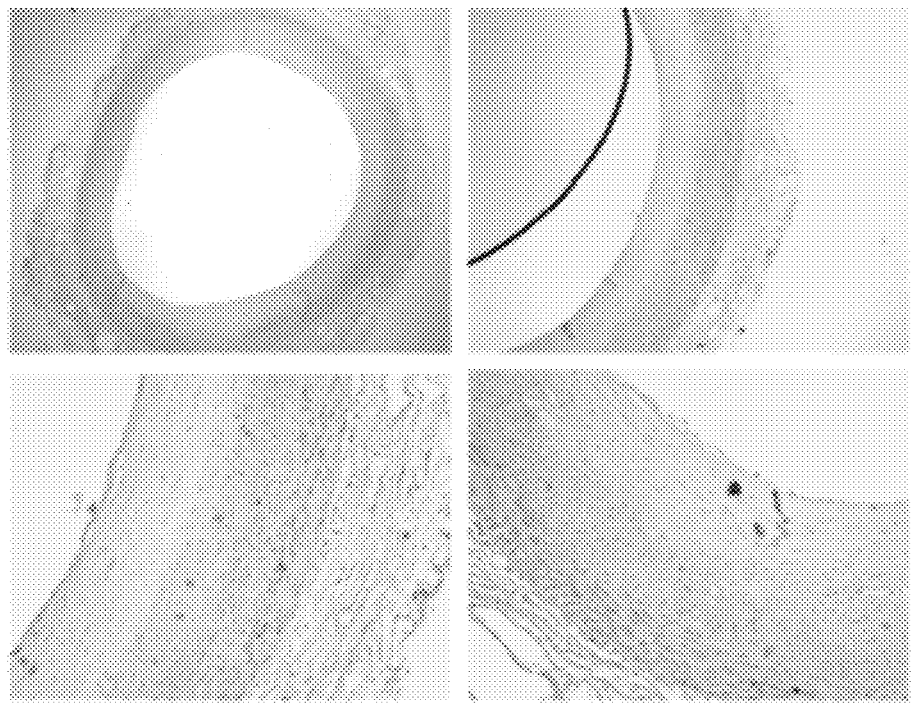
FIG. 2 shows Cathepsin K staining (magnifications 2, 4, 10 and 10× respectively) using a monoclonal mouse antibody on an aortic sample with type III lesion.
Figure 3:
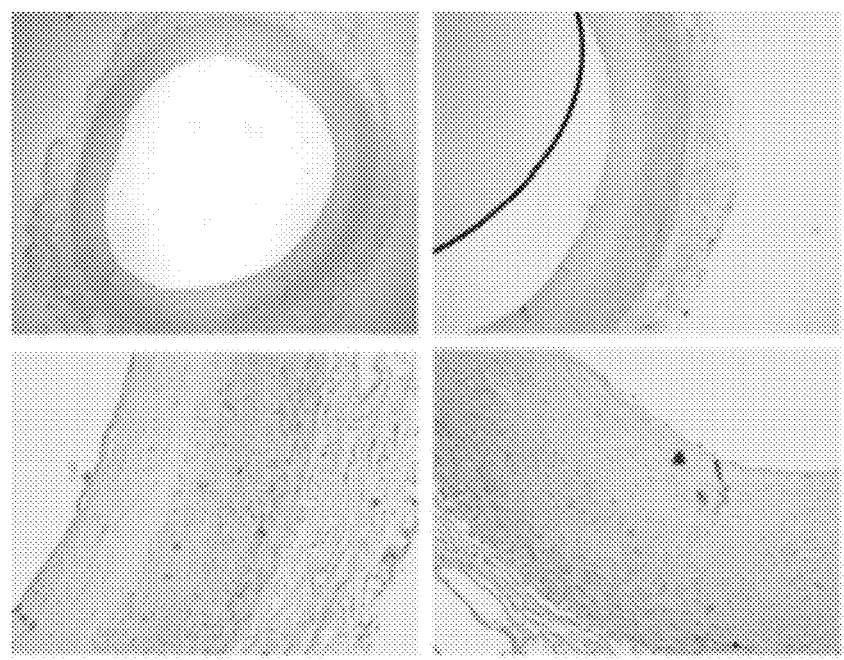
FIG. 3 shows Biglycan staining (magnifications 2, 4, 10 and 10× respectively) using a monoclonal mouse antibody on an aortic sample with type V lesion.
Figure 4:
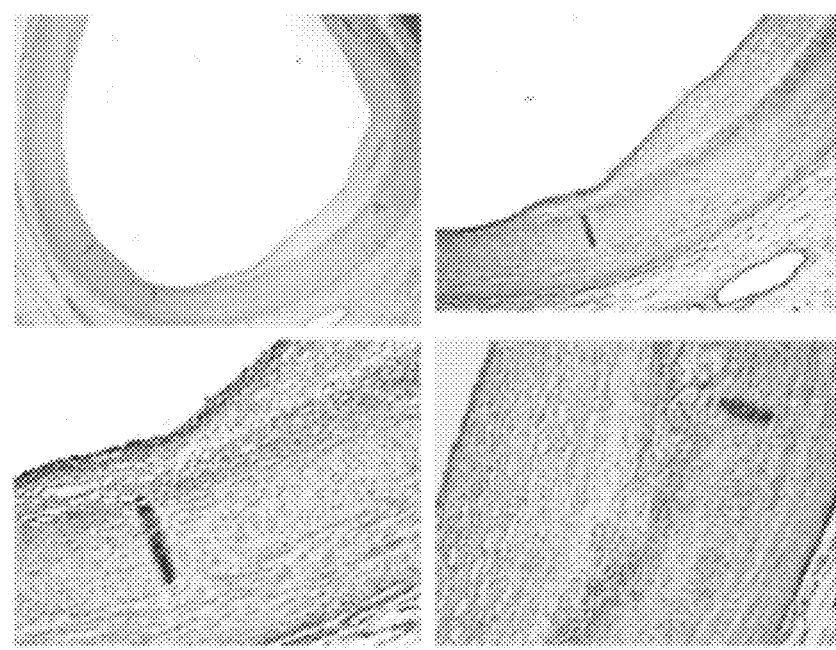
FIG. 4 shows Cathepsin K staining (magnifications 2, 4, 10 and 10× respectively) using a monoclonal mouse antibody on an aortic sample containing type V lesion.

In the following, co-localization of Cathepsin K protease and biglycan is demonstrated. Immunohistochemical staining as seen in FIGS. 1 and 2 revealed a co-localization of biglycan and cathepsin K. This may suggest that biglycan is a preferred substrate of cathepsin K. The same immunohistochemical staining was performed on the aortic samples, where the atherosclerotic plaque was formed and as a result of this normal aortic architecture was replaced by macrophage foam cell infiltrates and calcifications. The results of these immunostainings are collected in FIGS. 3 and 4.

Immunohistochemical staining of biglycan and cathepsin K were shown to co-localize in a progressed atherosclerotic lesion. These results together generate hypothesis of specific cathepsin K cleavage sites in biglycan, resulting in increased neo-epitope generation in atherosclerotic lesions. To test this hypothesis, we cleaved biglycan with different proteases.

EXAMPLE 2

Figure 5:
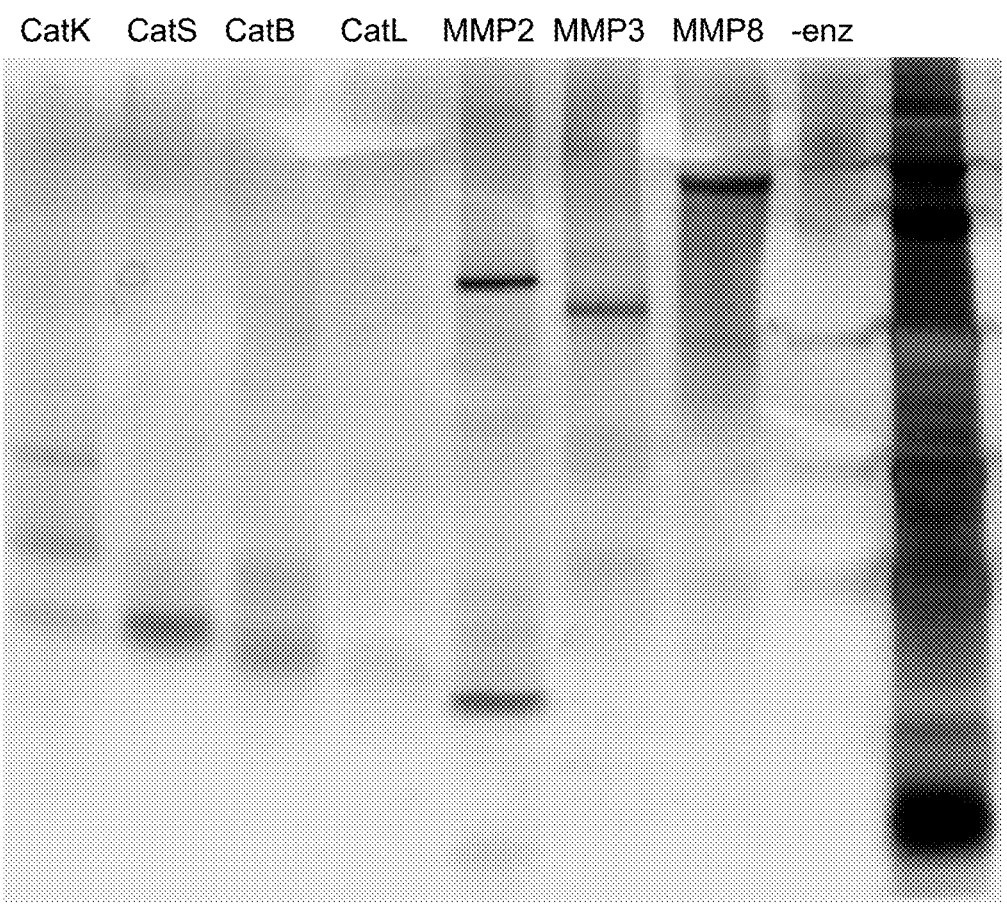
FIG. 5 shows cleavage products of biglycan generated by proteases: MMP2, MMP3, MMP8, cathepsin K, cathepsin S, cathepsin B, and cathepsin L. M=Rainbow marker. −enz=no enzyme digestion, run on a gel in Example 2.

Degradation of biglycan for assessment of degradation fragments. Biglycan from bovine articular cartilage (B8041—Sigma-Aldrich) was cleaved by following proteases: MMP2, MMP3, MMP8, Cathepsin K, Cathepsin S, Cathepsin B, and Cathepsin L. Fragments of proteoglycans generated by enzymatic cleavage of above mentioned proteases were separated on 10% NuPage® Bis-Tris gels and afterwards silver-stained by "Silver Express"—silver staining kit (Invitrogen cat.nr. LC6100, lot.nr.341099). Results of separation of proteolytically derived and biglycan and silver-stainings are represented by FIG. 5.

EXAMPLE 3

Mice were immunised with collagen type III derived peptides conjugated with ovalbumin. Sera were screened for reactivity with screening peptide sequences conjugated to biotin. Monoclonal antibody secreting clones were produced and screened using the screening sequences. Clones were checked for lack of reactivity with elongated versions of the target peptide which are continued with the adjacent sequences from collagen type III (deselection peptide) and for lack of reactivity with a nonsense peptide. None of the clones positive for the target sequences reacted with either the elongated or the nonsense sequences.

The target sequences, immunogens, screening sequences and deselection sequences were as follows:

| No: | Target sequence | Immunogen | Screening Sequence | De-selection sequence | Mouse No. |
|---|---|---|---|---|---|
| NB51 | KNGETG 356 | KNGETGPQGP GGC-OVA | KNGETGPQG P-PG-K-Biotin | KDGETGAAGPPG K-Biotin KDGEAGAQGPPG K-Biotin PGKNGETPGPQ- GP-K-Biotin | 278; 279; 289; 345; 346; 347 |
| NB26 | IAGITG 429 | IAGITGARGLG GC-KLH | IAGITGARGL- AG-K-Biotin IAGLTGARGL- AG-K-Biotin | LGIAGITGARGL- AG-K-Biotin | 146; 147; 148; 149; 156; 157; |
| NB52 | IAGITG | IAGITGARGLG GC-OVA | IAGITGARGL- AG-K-Biotin IAGLTGARGL- AG-K-Biotin | LGIAGITGARGL- AG-K-Biotin | 348; 349; 357; 358; 359; |
| NB27 | KDGTSG 763 | KDGTSGHPGP GGC-OVA | KDGTSGHPGP- IG-K-Biotin KDGSSGHPG P-IG-K-Biotin | PGKDGTSGHP- GP-K-Biotin | 158; 159; 167; 168; 169; 178; |
| NB67 | APGPLG 581 | OVA-CGG- GPPGAPGPLG | Biotin-AQ- GPPGAPGPLG Biotin-AQ- GPPGSPGPLG | Biotin-DD- GPSGAEGPPG Biotin-GP- PGAPGPLGIA | 167; 168; 169; 178; 179; 189; |

-continued

| No: | Target sequence | Immunogen | Screening Sequence | De-selection sequence | Mouse No. |
|---|---|---|---|---|---|
| NB68 | NTGAPG 422 | NTGAPGSPGV-CGG-OVA | NTGAPGSPGV-SG-K-Biotin NSGSPGNPG VAG-K-Biotin | AGNTGAPGSP-GV-Biotin | 234; 235; 236; 237; 238; 239; |
| NB69 | AIGPSG 380 | AIGPSGPAGK-GGC-OVA (808680) | AIGPSGPAGK DG-K-Biotin AIGPAGPAGK DG-K-Biotin | PGAIGPSGPAG-KD-Biotin | 245; 246; 247; 248; 249; 256; |
| NB57 | AGGFAP 781 | KLH-CGG-EKAGGFAP | Biotin-CG-EKAGGFAP Biotin-CG-EKSGGFSP | Biotin-GG-EKAGGFAPYY | 1; 2; 3; 4; 5; 6; |

EXAMPLE 4

Reactivity of Collagen Type III Neo-Epitope Monoclonal Antibodies with Human Urine The reactivity of selected monoclonal antibody clones from example 3 with human urine was determined in a competition assay format using the immunising peptides as competition agent. In a typical procedure, 96 well streptavidin coated plates were coated for 30 min with 10 ng/mL Biotin-peptide in PBS-BTE at 20° C. with shaking and washed 5× in washing buffer. 20 μl of diluted sample was added (either urine or peptide solution). 100 μL of unpurified antibody solution (supernatant from cell culture) diluted as detailed below was added. The plates were incubated for 1 hr at 20° C. with shaking at 300 rpm and were then washed 5× in washing buffer. 100 μL secondary antibody-POD (1:5000) was added and incubated for 1 hr at 20° C. with shaking at 300 rpm before washing 5× in washing buffer. 100 μL TMB was added and incubated for 15 min in darkness shaking at 300 rpm before adding 100 μL stopping solution. The plates were read at 450 nm on an ELISA reader with 650 nm as reference. Competition therefore occurred between the peptide on the plate and peptide in solution for the antibody and the amount of plate bound antibody was determined by the peroxidase colour forming reaction.

Figure 6:
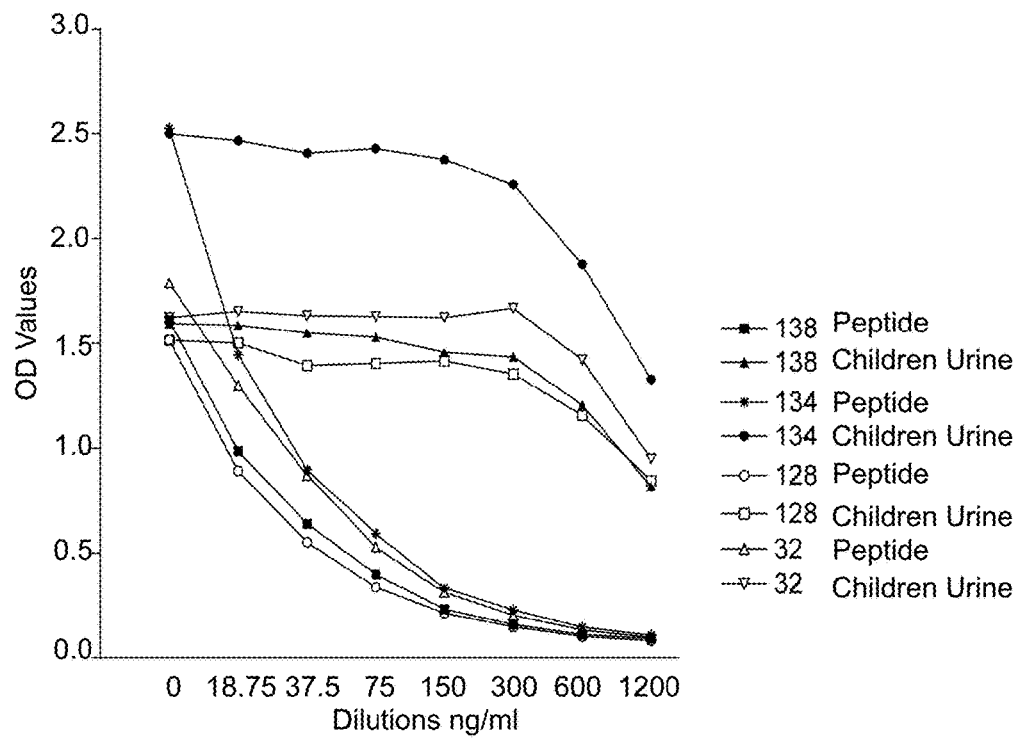
FIGS. 6 to 8 show competition study results obtained in Example 4.

Results are seen in FIG. 6 for four different clones. It can be seen that the antibodies each detect relevant sequences in urine.

Figure 7:
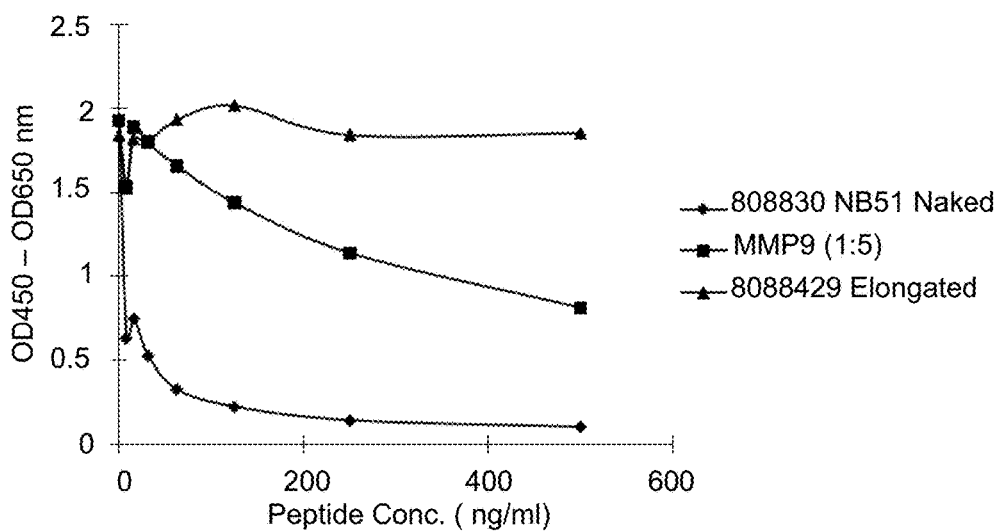

Further competition studies were performed on one selected clone to test competition for antibody binding between the immunizing peptide and native collagen type III cleaved in vitro by MMP9. Results are shown in FIG. 7 for the cleaved collagen, the peptide KNGETG (SEQ ID NO: 356) and an elongated version of that sequence. It can be seen that the antibody binds the immunizing peptide and the enzyme cleaved collagen, but not the extended sequence.

Figure 8:
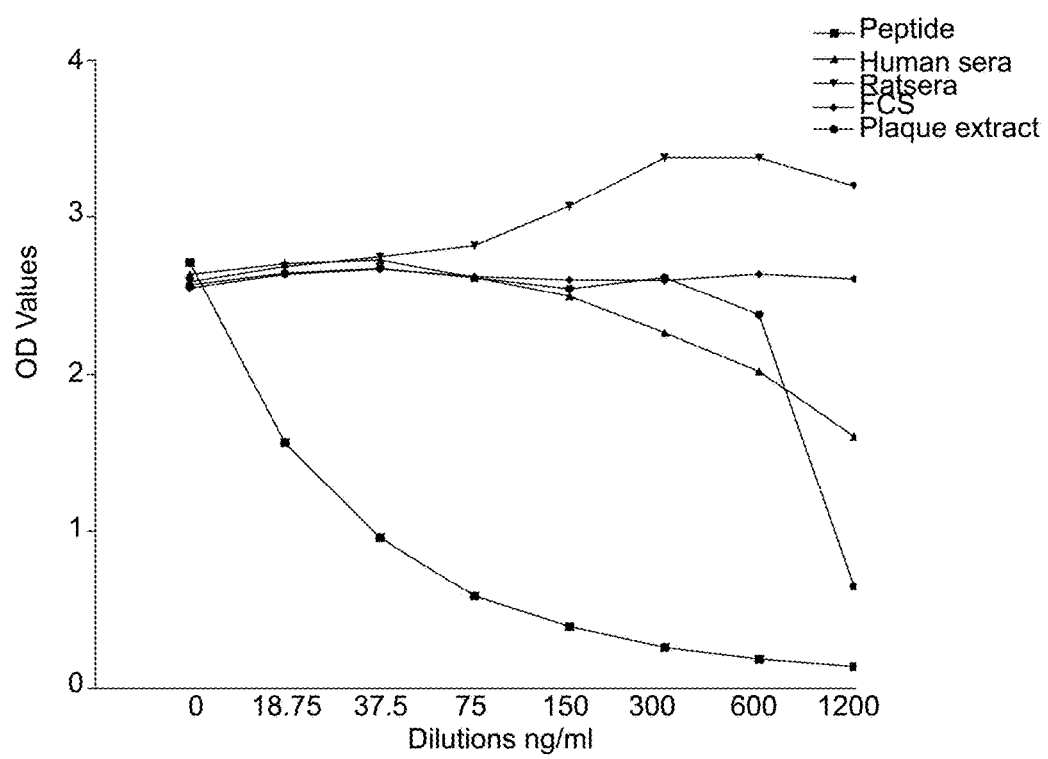

Further competition studies on the same clone are seen in FIG. 8 where the competition agents were the peptide KNGETG (SEQ ID NO: 356), human serum, rat serum, FCS (fetal calf serum), and atherosclerotic plaque extracts respectively. It is seen that the antibody is reactive with the peptide, the plaque extract and human serum, but not the rat serum or FCS.

EXAMPLE 5

Raising of Anti-Sera to Decorin, Biglycan and Versican Sequences

Anti-sera were raised and monoclonal antibodies were obtained as in Example 3, but using the following immunogens, screening sequences and deselection sequences:

| No: | Epitope | Target sequence | Immunogen | Screening Sequence | De-selection sequence | Mouse No. |
|---|---|---|---|---|---|---|
| NB62 | Decorin-176N | IVIELG 91 | IVIELGTNPL-GGC-KLH | IVIELGTNPL-KS-K-Biotin LVIELGGNPL-KN-K-Biotin IVVELGGNPL-TN-K-Biotin | QMIVIELGTNP LK-K-Biotin NVLVIELGGNP L-K-Biotin | 7; 8; 9; 10; 12; 13 |
| NB63 | Biglycan-108C | NNDISE 116 | OVA-CGG-LDLQNNDISE | Biotin-TL-LDLQNNDISE | Biotin-LDLQ NNDISELR | 14; 15; 16; 17; 18; 19 |
| NB64 | Versican-87N | QNGNIK 143 | QNGNIKIGQD-GGC-KLH | QNGNIKIGQD-YK-Biotin QDGNIKIGQD-YK-Biotin | VAQNGNIKIGQ D-K-Biotin VAQDGNIKIGQ D-K-Biotin | 23; 24 25; 26; 27; 28; |

EXAMPLE 6

Reactivity of Decorin Neo-Epitope Monoclonal Antibody with Human Urine

A competition ELISA was carried out generally as in Example 5 using one anti-decorin unpurified monoclonal antibody (NB62)

Figure 9:
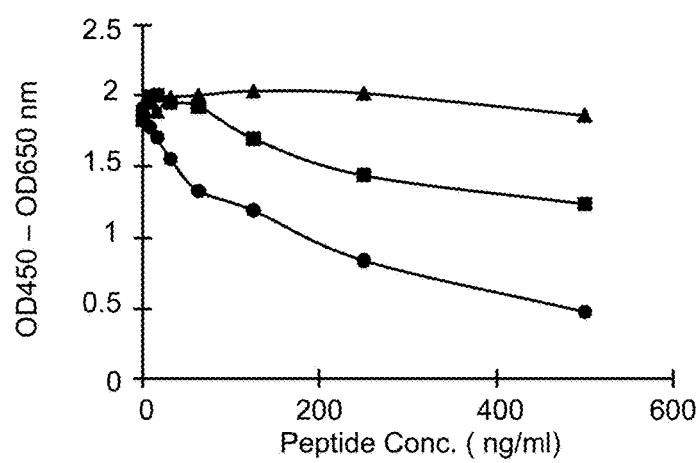
FIG. 9 shows competition study results obtained in Example 6.

Results are shown in FIG. 9. Reactivity is seen against the peptide sequence against which the antibody was raised and selected and against urine, but not against the irrelevant peptide sequence NB18.

EXAMPLE 7

Reactivity of Versican Neo-Epitope Monoclonal Antibody with Human Urine

A competition ELISA was carried out generally as in Example 5 using two anti-versican unpurified monoclonal antibody clones raised against sequence (NB64).

Figure 10:
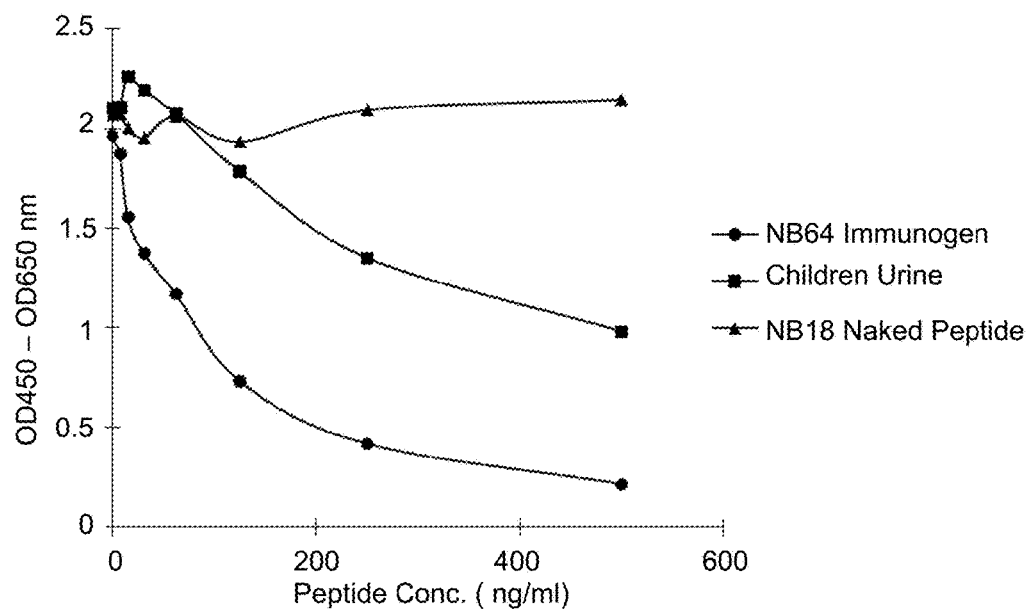
FIGS. 10 and 11 show competition study results obtained in Example 7.
Figure 11:
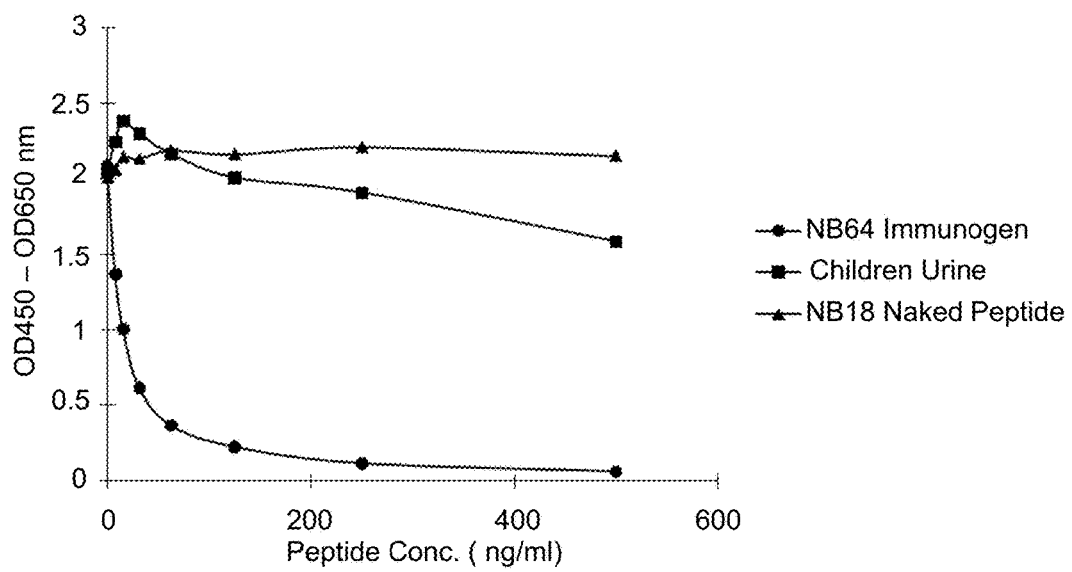

Results are shown in FIGS. 10 and 11 for the respective clones. In each case reactivity is seen against the peptide sequence against which the antibody was raised and selected and against urine, but not against the irrelevant peptide sequence NB18.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

The following references are cited herein.

Bobryshev Y V. Calcification of elastic fibers in human atherosclerotic plaque. Atherosclerosis 2005; 180:293-303.

Brown, D. C. and K. G. Vogel. "Characteristics of the in vitro interaction of a small proteoglycan (PGII) of bovine tendon with type I collagen." Matrix. 9.6 (1989): 468-78.

Cattin L, Fisicaro M, Tonizzo M, Valenti M, Danek G M, Fonda M, Da Col P G, Casagrande S, Pincetri E, Bovenzi M, and Baralle F. Polymorphism of the apolipoprotein E gene and early carotid atherosclerosis defined by ultrasonography in asymptomatic adults. Arterioscler Thromb Vasc Biol. 1997 January; 17(1):91-4.

Chapman H A, Riese R J, Shi G P. Emerging roles for cysteine proteases in human biology. Annu. Rev. Physiol 1997; 59:63-88.

Clarkson T B, Kaplan J R. Stage of Reproductive Life, Atherosclerosis Progression and Estrogen Effects on Coronary Artery Atherosclerosis, In: Lobo R A, editor. Treatment of the Postmenopausal Woman: Basic and Clinical Aspects, 3 ed. San Diego: Elsevier; 2007. p. 509-28.

Danielson, K. G., et al. "Targeted disruption of decorin leads to abnormal collagen fibril morphology and skin fragility." J. Cell Biol. 136.3 (1997): 729-43.

Dours-Zimmermann, M. T. and D. R. Zimmermann. "A novel glycosaminoglycan attachment domain identified in two alternative splice variants of human versican." J. Biol. Chem. 269.52 (1994): 32992-98.

Eriksen H A, Satta J, Risteli J, Veijola M, Vare P, Soini Y. Type I and type III collagen synthesis and composition in the valve matrix in aortic valve stenosis. Atherosclerosis 2006; 189:91-98.

Evanko, S. P., et al. "Proteoglycan distribution in lesions of atherosclerosis depends on lesion severity, structural characteristics, and the proximity of platelet-derived growth factor and transforming growth factor-beta." Am. J. Pathol. 152.2 (1998): 533-46.

Funderburgh, J. L. "Keratan sulfate: structure, biosynthesis, and function." Glycobiology 10.10 (2000): 951-58.

Funderburgh, J. L., et al. "Macrophage receptors for lumican. A corneal keratan sulfate proteoglycan." Invest Ophthalmol. Vis. Sci. 38.6 (1997): 1159-67.

Gabay C and Kushner I. Acute-phase proteins and other systemic responses to inflammation. N Engl J Med. 1999 Feb. 11; 340(6):448-54.

Gardner C D, Fortmann S P, Krauss R M. Association of small low-density lipoprotein particles with the incidence of coronary artery disease in men and women. JAMA 1996; 276:875-81.

Garrone R, Lethias C, Le Guellec D. Distribution of minor collagens during skin development. Microsc. Res Tech. 1997; 38:407-12.

Graham I, Atar D, Borch-Johnsen K, Boysen G, Burell G, Cifkova R et al. European guidelines on cardiovascular disease prevention in clinical practice: executive summary. Atherosclerosis 2007; 194:1-45.

Haraki T, Takegoshi T, Kitoh C, Wakasugi T, Saga T, Hirai J I, Aoyama T, Inazu A and Mabuchi H, Carotid artery intima-media thickness and brachial artery flow-mediated vasodilation in asymptomatic Japanese male subjects amongst apolipoprotein E phenotypes. J Intern Med. 2002 August; 252(2):114-20.

Hatanaka K, Li X A, Masuda K, Yutani C and Yamamoto A, Immunohistochemical localization of C-reactive proteinbinding sites in human atherosclerotic aortic lesions by a modified streptavidin-biotin-staining method. Pathol Int. 1995 September; 45(9):635-41.

Heegaard A M, Corsi A, Danielsen C C, Nielsen K L, Jorgensen H L, Riminucci M, Young M F and Bianco P, Biglycan deficiency causes spontaneous aortic dissection and rupture in mice. Circulation. 2007 May 29; 115(21): 2731-8. Epub 2007 May 14.

Herman M P, Sukhova G K, Libby P, Gerdes N, Tang N, Horton D B et al. Expression of neutrophil collagenase (matrix metalloproteinase-8) in human atheroma: a novel collagenolytic pathway suggested by transcriptional profiling. Circulation 2001; 104:1899-904.

Jeppesen J, Hein H O, Suadicani P, Gyntelberg F. High triglycerides/low high-density lipoprotein cholesterol, ischemic electrocardiogram changes, and risk of ischemic heart disease. Am Heart J 2003; 145:103-08.

Lawrie T D, Mcalpine S G, Rifkind B M, Robinson J F. Serum fatty-acid patterns in coronary-artery disease. Lancet 1961; 1:421-24.

Katsuda S, Okada Y, Minamoto T, Oda Y, Matsui Y, Nakanishi I. Collagens in human atherosclerosis. Immunohistochemical analysis using collagen type-specific antibodies. Arterioscler. Thromb. 1992; 12:494-502.

Knox, S. M. and J. M. Whitelock. "Perlecan: how does one molecule do so many things?" Cell Mol. Life Sci. 63.21 (2006): 2435-45.

Kuller L H, Tracy R P, Shaten J and Meilahn E N, Relation of C-reactive protein and coronary heart disease in the MRFIT nested case-control study. Multiple Risk Factor Intervention Trial. Am J Epidemiol. 1996 Sep. 15; 144 (6):537-47.

Kunz J. Matrix metalloproteinases and atherogenesis in dependence of age. Gerontology. 2007; 53:63-73.

Kuzuya M, Nakamura K, Sasaki T, Cheng X W, Itohara S, Iguchi A. Effect of MMP-2 deficiency on atherosclerotic lesion formation in apoE-deficient mice. Arterioscler. Thromb. Vasc. Biol 2006; 26:1120-25.

Leinonen M and Saikku P, Evidence for infectious agents in cardiovascular disease and atherosclerosis. Lancet Infect Dis. 2002 January; 2(1):11-7.

Liu J, Sukhova G K, Sun J S, Xu W H, Libby P, Shi G P. Lysosomal cysteine proteases in atherosclerosis. Arterioscler. Thromb. Vasc. Biol 2004; 24:1359-66.

Lutgens, S. P., et al. "Cathepsin cysteine proteases in cardiovascular disease." FASEB J. 21.12 (2007): 3029-41.

Mayne R. Collagenous proteins of blood vessels. Arteriosclerosis. 1986; 6:585-93.

McCullagh K G, Duance V C, Bishop K A. The distribution of collagen types I, III and V (AB) in normal and atherosclerotic human aorta. J Pathol 1980; 130:45-55.

Mendall M A, Patel P, Ballam L, Strachan D and Northfield T C. C reactive protein and its relation to cardiovascular risk factors: a population based cross sectional study., BMJ. 1996 Apr. 27; 312(7038):1061-5.

Monfort J, Nacher M, Montell E, Vila J, Verges J and Benito P, Chondroitin sulfate and hyaluronic acid (500-730 kda) inhibit stromelysin-1 synthesis in human osteoarthritic chondrocytes. Drugs Exp Clin Res. 2005; 31(2):71-6.

Pasceri V, Willerson J T and Yeh E T, Direct proinflammatory effect of C-reactive protein on human endothelial cells. Circulation. 2000 Oct. 31; 102(18):2165-8.

Register T C, Cann J A, Kaplan J R, Williams J K, Adams M R, Morgan T M et al. Effects of soy isoflavones and conjugated equine estrogens on inflammatory markers in atherosclerotic, ovariectomized monkeys. J Clin Endocrinol Metab 2005; 90:1734-40.

Reynolds G D and Vance R P. C-reactive protein immunohistochemical localization in normal and atherosclerotic human aortas. Arch Pathol Lab Med. 1987 March; 111(3):265-9.

Ridker P M, Intrinsic fibrinolytic capacity and systemic inflammation: novel risk factors for arterial thrombotic disease. Haemostasis. 1997; 27 Suppl 1:2-11.

Ridker P M, Hennekens C H, Buring J E and Rifai N. C-reactive protein and other markers of inflammation in the prediction of cardiovascular disease in women. N Engl J Med. 2000 Mar. 23; 342(12):836-43.

Rodriguez-Lee M, Bondjers G and Camejo G, Fatty acid-induced atherogenic changes in extracellular matrix proteoglycans. Curr Opin Lipidol. 2007 October; 18(5):546-53

Rouis M. Matrix metalloproteinases: a potential therapeutic target in atherosclerosis. Curr Drug Targets. Cardiovasc Haematol Disord. 2005; 5:541-48.

Rudel L L, Haines J, Sawyer J K, Shah R, Wilson M S, Carr T P. Hepatic origin of cholesteryl oleate in coronary artery atherosclerosis in African green monkeys. Enrichment by dietary monounsaturated fat. J Clin Invest 1997; 100:74-83.

Salisbury B G and Wagner, W D J Biol Chem. 1981 Aug. 10; 256(15):8050-7, 'Isolation and preliminary characterization of proteoglycans dissociatively extracted from human aorta'.

Satta J, Juvonen T, Haukipuro K, Juvonen M, Kairaluoma M I. Increased turnover of collagen in abdominal aortic aneurysms, demonstrated by measuring the concentration of the aminoterminal propeptide of type III procollagen in peripheral and aortal blood samples. J Vasc. Surg. 1995; 22:155-60.

Schaar J A, Mastik F, Regar E, den Uil C A, Gijsen F J, Wentzel J J et al. Current diagnostic modalities for vulnerable plaque detection. Curr Pharm Des. 2007; 13:995-1001.

Siest G, Pillot T, Regis-Bailly A, Leininger-Muller B, Steinmetz J, Galteau M M and Visvikis S, Apolipoprotein E: an important gene and protein to follow in laboratory medicine. Clin Chem. 1995 August; 41(8 Pt 1):1068-86.

Shin, J., J. E. Edelberg, and M. K. Hong. "Vulnerable atherosclerotic plaque: clinical implications." Curr. Vasc. Pharmacol. 1.2 (2003): 183-204.

Shekhonin B V, Domogatsky S P, Muzykantov V R, Idelson G L, Rukosuev V S. Distribution of type I, III, I V and V collagen in normal and atherosclerotic human arterial wall: immunomorphological characteristics. Coll. Relat Res 1985; 5:355-68.

Stary H C. Composition and classification of human atherosclerotic lesions. Virchows Arch A. Pathol Anat. Histopathol. 1992; 421:277-90.

Sundstrom J, Vasan R S. Circulating biomarkers of extracellular matrix remodeling and risk of atherosclerotic events. Curr Opin Lipidol. 2006; 17:45-53.

Talusan, P., et al. "Analysis of intimal proteoglycans in atherosclerosis-prone and atherosclerosis-resistant human arteries by mass spectrometry." Mol. Cell Proteomics. 4.9 (2005): 1350-57.

Thompson D, Banks R E, Forbes M A, Storr M, Higginson J, Raynes J, Illingworth J M, Perren T J, Selby P J and Whicher J T, The acute phase protein response in patients receiving subcutaneous IL-6. Clin Exp Immunol. 1995 October; 102(1):217-23.

Terry J G, Howard G, Mercuri M, Bond M G and Crouse J R 3rd. Apolipoprotein E polymorphism is associated with segment-specific extracranial carotid artery intima-media thickening., Stroke. 1996 October; 27(10):1755-9.

Tracy R P, Lemaitre R N, Psaty B M, Ives D G, Evans R W, Cushman M, Meilahn E N and Kuller L H, Relationship of C-reactive protein to risk of cardiovascular disease in the elderly. Results from the Cardiovascular Health Study and the Rural Health Promotion Project. Arterioscler Thromb Vasc Biol. 1997 June; 17(6):1121-7.

Turu M M, Krupinski J, Catena E, Rosell A, Montaner J, Rubio F et al. Intraplaque MMP-8 levels are increased in asymptomatic patients with carotid plaque progression on ultrasound. Atherosclerosis 2006; 187:161-69.

Venugopal S K, Devaraj S, Yuhanna I, Shaul P and Jialal I. Demonstration that C-reactive protein decreases eNOS expression and bioactivity in human aortic endothelial cells., Circulation. 2002 Sep. 17; 106(12):1439-41.

Wang T J, Gona P, Larson M G, Tofler G H, Levy D, Newton-Cheh C et al. Multiple biomarkers for the prediction of first major cardiovascular events and death. N Engl J Med 2006; 355:2631-39.

Whitelock, J. M. and R. V. lozzo. "Heparan sulfate: a complex polymer charged with biological activity." Chem. Rev. 105.7 (2005): 2745-64.

Wight, T. N. "The extracellular matrix and atherosclerosis." Curr. Opin. Lipidol. 6.5 (1995): 326-34.

Wight, T. N., et al. "Vascular cell proteoglycans: evidence for metabolic modulation." Ciba Found. Symp. 124 (1986): 241-59.

Wight T N, Versican: a versatile extracellular matrix proteoglycan in cell biology. Curr Opin Cell Biol. 2002 October; 14(5):617-23.

Wight T N and Merrilees M J, Proteoglycans in atherosclerosis and restenosis: key roles for versican. Circ Res. 2004 May 14; 94(9):1158-67.

Wilson P W, Schaefer E J, Larson M G and Ordovas J M. Apolipoprotein E alleles and risk of coronary disease. A meta-analysis. Arterioscler Thromb Vasc Biol. 1996 October; 16(10):1250-5.

Yamada Y, Izawa H, Ichihara S, Takatsu F, Ishihara H, Hirayama H et al. Prediction of the risk of myocardial infarction from polymorphisms in candidate genes. N Engl J Med 2002; 347:1916-23.

Zwaka T P, Hombach V and Torzewski J. C-reactive protein-mediated low density lipoprotein uptake by macrophages: implications for atherosclerosis., Circulation. 2001 Mar. 6; 103(9):1194-7.

What is claimed is:

1. A method of detecting an N- or C-terminal neo-epitope formed by cleavage of C-reactive protein (CRP), Apolipoprotein E (ApoE), lumican, versican, perlecan, decorin, biglycan or elastin by a proteinase in a patient, said method comprising:
  a. obtaining a biofluid sample from a human patient;
  b. detecting whether said N- or C-terminal neo-epitope is present in the biofluid sample by contacting the biofluid sample with an antibody and detecting binding between the N- or C-terminal neo-epitope and the antibody;
  wherein said antibody is raised against a synthetic peptide corresponding to a said N- or C-terminal neo-epitope and has specific binding affinity for said N- or C-terminal neo-epitope amino acid sequence, wherein the antibody does not specifically bind intact CRP, ApoE, lumican, versican, perlecan, decorin, biglycan or elastin, and
  wherein said antibody specifically binds said N-terminal neo epitope amino acid sequence formed by cleavage of CRP by a proteinase, said N-terminal amino acid sequence selected from the group consisting of:

| CRP | SEQ ID NO |
|---|---|
| AFVFPK | 699 |
| YEVQGE | 700 |
| KAFVFP | 701 |
| SFGGNF | 702 |
| FVLSPD | 703 |
| LKKGYT | 704 |
| FGQTDM | 705 |
| LKKGYT | 706 |
| IILGQE | 707 |
| YEVQGE | 708 |
| LKYEVQ | 709 |
| IVEFWV | 710 |
| ESDTSY | 711 |
| GNFEGS | 712 | or wherein said antibody specifically binds a said C-terminal neo epitope amino acid sequence formed by cleavage of CRP by a proteinase, said C-terminal amino acid sequence selected from the group consisting of:

| CRP | SEQ ID NO |
|---|---|
| KAFVFPK | 725 |
| AFVFPK | 726 |
| KPQLWP | 727 |
| FVFPKE | 728 |
| PDEINT | 729 |
| DMSRKA | 730 |
| VGAEAS | 731 |
| KPQLWP | 732 |
| DSFGGN | 733 |
| VFTKPQ | 734 | or wherein said antibody specifically binds a said N-terminal neo epitope amino acid sequence formed by cleavage of ApoE by a proteinase, said N-terminal amino acid sequence selected from the group consisting of:

| ApoE | SEQ ID NO |
|---|---|
| KVEQAV | 688 |
| AEVRAK | 689 |
| MLGQST | 690 |
| QAVETE | 691 |
| QQTEWQ | 692 |
| AVYQAG | 693 |
| AKLEEQ | 694 |
| KLEEQA | 695 |
| VEQAVE | 696 |
| QAVETE | 697 |
| EVKEQV | 698 | or wherein said antibody specifically binds a said C-terminal neo epitope amino acid sequence formed by cleavage of ApoE by a proteinase, said C-terminal amino acid sequence selected from the group consisting of:

| ApoE | SEQ ID NO |
|---|---|
| TEPEPE | 714 |
| EQAQQI | 715 |
| TEELRV | 716 |
| PEPELR | 717 |
| SGQRWE | 718 |
| EGAERG | 719 |
| QAQQIR | 720 |
| QQIRLQ | 721 |
| EPEPEL | 722 |
| PEPELR | 723 |
| EVRAKL | 724 | or wherein said antibody specifically binds a said N-terminal neo epitope amino acid sequence formed by cleavage of lumican, versican, perlecan, decorin, or biglycan by a proteinase, said N-terminal amino acid sequence selected from the group consisting of:

| Protein | | SEQ ID NO |
|---|---|---|
| Biglycan | SVPKEI | 76 |
| | NSGFEP | 77 |
| | LKSVPK | 78 |
| | LRISEA | 79 |
| | GLKLNY | 80 |
| | LKSVPK | 81 |
| | QCSDLG | 82 |
| | LTGIPK | 83 |
| | RISEAK | 84 |
| | AIELED | 85 |

| Protein | | SEQ ID NO |
|---|---|---|
| | EAKLTG | 86 |
| | LKAVPK | 87 |
| | LLDLQN | 88 |
| | IELEDL | 89 |
| | NSGFEP | 90 |
| Decorin | IVIELG | 91 |
| | NGLNQM | 92 |
| | DEASGI | 93 |
| | LHLDGN | 94 |
| | VNNKIS | 95 |
| | LILVNN | 96 |
| | SNPVQY | 97 |
| | SSGIEN | 98 |
| | KITEIK | 99 |
| | GLPPSL | 100 |
| Versican | LLASDA | 101 |
| | LATVGE | 102 |
| | ETTVLV | 103 |
| | SLTVVK | 104 |
| | ENQDAR | 105 |
| | NGFDQC | 106 |
| Lumican | SLEDLQ | 107 |
| | LKEDAV | 108 |
| | HLQHNR | 109 |
| | LQHNRL | 110 |
| Perlecan | SIEYSP | 111 |
| | LVNFTR | 112 |
| | VSEAVV | 113 |
| | EVSEAV | 114 |
| | SIEYSP | 115 | or wherein said antibody specifically binds a said C-terminal neo epitope amino acid sequence formed by cleavage of lumican, versican, perlecan, decorin, or biglycan by a proteinase, said C-terminal amino acid sequence selected from the group consisting of:

| Protein | | SEQ ID NO |
|---|---|---|
| Biglycan | NNDISE | 116 |
| | RISEAK | 117 |
| | LRKDDF | 118 |
| | KDLPET | 119 |
| | LNELHL | 120 |
| | YWEVQP | 121 |
| | KIQAIE | 122 |
| | PETLNE | 123 |
| | LLRYSK | 124 |
| | EDLLRY | 125 |
| | NNDISE | 126 |
| | ELRKDD | 127 |
| | DLLRYS | 128 |
| | AFDGLK | 129 |
| Decorin | GTNPLK | 130 |
| | SSGIEN | 131 |
| | EVPDDR | 132 |
| | RVDAAS | 133 |
| | GAFTPL | 134 |
| | LVKLER | 135 |
| | QPSTFR | 136 |
| | AFQGMK | 137 |
| | GMKKLS | 138 |
| | KDGDFK | 139 |
| | HLDGNK | 140 |
| Versican | CDVMYG | 141 |
| | NGFDQC | 142 |
| | QNGNIK | 143 |
| | IGQDYK | 144 |

| Protein | | SEQ ID NO |
|---|---|---|
| Lumican | QLTHNK | 145 |
| | VSAAFK | 146 |
| | GLKSLE | 147 |
| Perlecan | EDAGSR | 148 |
| | EFREVS | 149 |
| | VAQQDS | 150 |
| | LEPEYR | 151 |
| | SAKEFR | 152 | or wherein said antibody specifically binds a said N-terminal neo epitope amino acid sequence formed by cleavage of elastin by a proteinase, said N-terminal amino acid sequence selected from the group consisting of:

| Elastin | SEQ ID NO |
|---|---|
| RPGVGV | 743 |
| LPYTTG | 744 |
| VAPGVG | 745 |
| GAGVPG | 746 |
| VGISPE | 747 |
| RPGVGV | 748 |
| LPYTTG | 749 | or wherein said antibody specifically binds a said C-terminal neo epitope amino acid sequence formed by cleavage of elastin by a proteinase, said C-terminal amino acid sequence selected from the group consisting of:

| Elastin | SEQ ID NO |
|---|---|
| GVGAGG | 750 |
| YGYGPG | 751 |
| GPGGVA | 752 |
| GIAGVG | 753. |

2. The method of claim 1, wherein said antibody has specific binding affinity for a said C-terminal neo-epitope.

3. The method of claim 1, wherein said antibody has specific binding affinity for a said N-terminal neo-epitope.

4. The method of claim 1, wherein said antibody is a monoclonal antibody or a fragment of a monoclonal antibody having specific binding affinity.

5. The method of claim 1, wherein said method is conducted as a competition immunoassay in which said antibody and a competition agent are incubated in the presence of said sample and the competition agent competes with the N- or C-terminal neo-epitope in the sample to bind to the antibody.

6. The method of claim 5, wherein said competition agent is a synthetic peptide or is a purified native peptide formed by cleavage of CRP, ApoE, lumican, versican, perlecan, decorin, biglycan or elastin by a proteinase so as to reveal said N- or C-terminal neo-epitope.

7. The method of claim 1, wherein the sample is a sample of urine, serum, blood, or plasma.

8. The method of claim 1, wherein said antibody specifically binds the N-terminal neo-epitope amino acid sequence formed by cleavage of CRP by a proteinase, said N-terminal neo-epitope amino acid sequence being KAFVFP (SEQ ID NO: 701).

* * * * *